(12) United States Patent
De Corte et al.

(10) Patent No.: US 7,879,881 B2
(45) Date of Patent: Feb. 1, 2011

(54) PIPERIDINYL COMPOUNDS THAT SELECTIVELY BIND INTEGRINS

(75) Inventors: Bart De Corte, South Hampton, PA (US); William A. Kinney, Newtown, PA (US); Bruce E. Maryanoff, Forest Grove, PA (US); Shyamali Ghosh, Norristown, PA (US); Li Liu, Doylestown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 215 days.

(21) Appl. No.: 11/897,484

(22) Filed: Aug. 30, 2007

(65) Prior Publication Data
US 2008/0058359 A1 Mar. 6, 2008

Related U.S. Application Data

(63) Continuation of application No. 10/782,060, filed on Feb. 18, 2004, now abandoned, which is a continuation-in-part of application No. 10/641,964, filed on Aug. 15, 2003, now abandoned.

(60) Provisional application No. 60/404,239, filed on Aug. 16, 2002.

(51) Int. Cl.
*A61K 31/452* (2006.01)
*C07D 211/32* (2006.01)
(52) U.S. Cl. ...................... 514/319; 546/205
(58) Field of Classification Search .............. 514/300, 514/319; 546/122, 205
See application file for complete search history.

(56) References Cited

U.S. PATENT DOCUMENTS

| | | | |
|---|---|---|---|
| 4,289,772 | A | 9/1981 | Campbell et al. |
| 5,474,765 | A | 12/1995 | Thorpe et al. |
| 5,753,659 | A | 5/1998 | Mills |
| 5,762,918 | A | 6/1998 | Thorpe et al. |
| 5,855,866 | A | 1/1999 | Thorpe et al. |
| 5,902,795 | A | 5/1999 | Toole et al. |
| 5,919,792 | A | 7/1999 | Duggan et al. |
| 6,211,191 | B1 | 4/2001 | Duggan et al. |
| 6,342,219 | B1 | 1/2002 | Thorpe et al. |
| 2002/0016625 | A1 | 2/2002 | Falotico et al. |
| 2004/0009465 | A1 | 1/2004 | Luckanatinvong |

FOREIGN PATENT DOCUMENTS

| | | |
|---|---|---|
| WO | WO 94/09029 A1 | 4/1994 |
| WO | WO 96/32907 A1 | 10/1996 |
| WO | WO 99/31061 A1 | 6/1999 |
| WO | WO 99/58162 A2 | 11/1999 |
| WO | WO 00/35488 A2 | 6/2000 |
| WO | WO 00/35492 A2 | 6/2000 |
| WO | WO 00/35887 A2 | 6/2000 |
| WO | WO 00/72801 A2 | 12/2000 |
| WO | WO 01/23376 A1 | 4/2001 |
| WO | WO 01/96334 A2 | 12/2001 |
| WO | WO 2004/020435 A1 | 3/2004 |
| WO | 2005/082889 | 9/2005 |

OTHER PUBLICATIONS

Hoekstra et al, Current Medicinal Chemistry, 1998, 5, 195.
Miller, W. H. et al, Drug Discovery Today, 2000, 5 (9) 397-407.
Samanen et al, Current Pharmaceutical Design, 1997, 3, 545-584.
Gould, Philip, "Salt selection for basic drugs," International J. Pharm., 1986, 33, 201-217.
Berge et al, "Pharmaceutical Salts," J. Pharm Sci., Jan. 1997, 66, 1, 1-19.
Mousa, S.A. et al., Emerging Theraupeutic Targets, 2000, 4 (2), 143-153.
Mousa, S.A. et al, Exp. Opin. Ther. Patents, 1999, 9 (9), 1237-1248.
Varon et al, thromb. Haemostasis, 1993, 70 (6) 1030-1036.
S. B. Rodan and G. A. Rodan, Integrin Function in Osteoclasts, Journal of Endocriminology, 1997, 154: S47-S56.
Brooks et al, Cell, 1994, 79, 1157-1164.
Storgard, C. M. et al, Decreased Angiogenesis and Arthritic Disease in Rabbits Treated with an avB3 Antagonist, J. Clin. Invest. 1999, 103, 47-54.
Friendlander et al, Science, 1995, 270, 1500-1502.
Melpo Christofidou-Solomidou et al, Expression and Funciton of Endothelial Cell on Integrin Receptors in Wound-Induced Human Angiogenesis in Human Skin/SCID25 Mice Chimerase, American Journal of Pathology, 1997, 151, 975-83.
Huang, Xiao-Zhu et al, Inactivation of the Integrin 6 Subunit Gene Reveals a Role of Epithelial Integrins in Regulating Inflammation in the Lungs and Skin, Journal of Cell Biology, 1996, 133, 921-28.
Hood, J.D. et al, Tumor Regression by Targeted Gene Delivery to the Neovasculature, Science, Jun. 28, 2002, 296, 2404-2407.
Ross et al, Nature, 1993, 362, 801-809.
Amon et al, Monoclonal Antibodies for Immunotargeting of Drugs in Cancer Therapy, Monoclonal Antibodies and Cancer Therapy, Reisfeld et al (eds) pp. 243-256 (Alan R. Lis, Inc. 1985).
Hellstrom et al, Antibodies for Drug Delivery, Controlled Drug Delivery (2nd ed) Robinson et al (eds) pp. 623-653 (Marcel Dekker, Inc. 1987).
Mehta et al, Biochem. J., 1998, 330, 861.
Mousa et al, Anti-integrin as novel drug-discovery targets: potential therapeutic and diagnostic implications, Curr Opin Chem Biol., Aug. 2002, 6 (4), pp. 534-541.
Yin et al, Correlation of cell apoptosis induction with expression of human beta 5 integrin on hematopoietic cells, Zhongua Xue Ye Xue Za Zhi, Jan. 2001, 22 (1) pp. 13-16.

(Continued)

*Primary Examiner*—Taofiq A Solola
(74) *Attorney, Agent, or Firm*—Yuriy P. Stercho

(57) ABSTRACT

The invention is directed to piperidinyl compounds that selectively bind integrin receptors and methods for treating an integrin mediated disorder.

41 Claims, No Drawings

OTHER PUBLICATIONS

De Groot et al, Design, synthesis, and biological evaluation of a dual tumor-specific motive containing integrin-targeted plasmin-cleavaable doxorubicin prodrug, Mol. Cancer Ther., Sep. 2002, (11) pp. 901-911.

Hynes, R.O. et al, A reevaluation of integrins as regulators of angiogenesis, Nature Medicine, vol. 8 No. 9, Sep. 2002, pp. 918-921.

Zhang et al, p21 activated kinase 4 interacts with integrin avB5-mediated cell migration, The Journal of Cell Biology, vol. 158, No. 7, Sep. 30, 2002, pp. 1287-1297.

Lafrenie, R.M. et al, Involvement of Integrin avB3 in the Patnhogenesis of Nhuman Immunodeficiency Virus Type 1 Infection in Monocytes, Virology 297, 2002, pp. 31-38.

Bishop G. G., Selective avB3-Receptor Blockage Reduces Macrophase Infiltration and Restenosis after Balloon Angioplasty in the Atherosclerotic Rabbit, Circulation, Apr. 10, 2001, 1906-1911.

F.A.L.M. Eskens, Phase I and pharmacokinetic study of continuous twice weekly intravenous administration of Cliengitide (EMD 121974) a novel inhibitor of the integrins avB3 and avB5 in patiensts with advanced solid tumors, European Journal of Cancer 39, 2003, pp. 917-926.

Kerr, J.S. The alpha v integrin antagonists as novel anticancer agents: an update, Expert Opin Investig Drugs, Dec. 11, 2002 (12) 1765-74.

Hoekstra et al, "Potent, Orally Active GPIIb/IIIa Antagonists Containing a Nipecotic Acid Subunit, Structure—Activity Studies Leading to the Discovery of RWJ-53308," J. Med Chem, 1999, vol. 42, pp. 5254-5265.

Lawson et al, "1,2,4 Triazolo [3,4-a] pyridine as a Novel, Constrained Template for Fibrinogen Receptor (GPIIb/IIIa) Antagonists," Bioorganic Medicinal Chemistry Letters, 2001, vol. 11, 2619-2622.

Su et al, "Fibrinogen Receptor (GPIIb-IIIa) Antagaonists Derived from 5,6 Bicyclic Templates. Amidinoindoles, Amidinoindazoles, and Amidinobenzofurans Containing the N-a-Sulfonamide Carboxylic Acid Function as Potent Platelet Aggregation Inhibitors," J. Med Chem, 1997, vol. 40, 4308-4318.

Katano et al, "Tetrahydrothienopyridine Derivatives as Novel GPIIB/IIIA Antagonists," Bioorganic & Medicinal Chemistry Letters, 1996, vol. 6, No. 21, 2601-2606.

Klein, et al. "Design of a New Class of Orally Active Fibringen receptor Antagonists", Journal of Medicinal Chemistry, 1998, pp. 2492-2502, 41 (14).

Grumbel, et al., "Synthesis of substituted oxazolo [4,5-b] pyridine derivatives", Heterocycles, 2001, pp. 1329-1345, 55(7).

Fisher, et al., Fused bicyclic Gly-Asp. Beta.-turn mimics with potent affinity for GPIIb-IIIa. Exploration of the Arginine Isostere: Bioorganic & Medicinal Chemistry Letters, 2000, pp. 385-389, 10(4).

Alabaster, et al., 2,4-Diamino-6,7-dimethoxyquianozolines. 2.2-(4-Carbamoylpiperidino) Derivatives as alphaII-Adrenoceptor Antagonists and Antihypertensive Agents: Journal of Medicinal Chemistry, American Chemical Society. Washington, US, 1987, pp. 999-1003, vol. 30.

Ishihara, et al, "Regioselective Friedel-Crafts Acylation of 2,3,4,5-Tetrahydro-1H-2-Be Nzazepine and related Nitrogen Heterocycles", Journal of the Chemical Society, Perkin Transactions 1, Chemical Society. Letchworth, GB, 1994, pp. 2993-2999, vol. 20.

PIPERIDINYL COMPOUNDS THAT SELECTIVELY BIND INTEGRINS

This application is a continuation of non-provisional application Ser. No. 10/782,060, filed on Feb. 18, 2004 now abandoned which is a continuation-in-part of non-provisional application Ser. No. 10/641,964, filed Aug. 15, 2003, now abandoned, and claims benefit of provisional patent application Ser. No. 60/404,239, filed on Aug. 16, 2002, which are all hereby incorporated by reference herein.

FIELD OF THE INVENTION

This invention relates to novel compounds and methods for use in treating an integrin mediated disorder. More particularly, this invention relates to piperidinyl compounds that selective bind integrin receptors and methods for treating an integrin mediated disorder.

BACKGROUND OF THE INVENTION

Integrins are a family of transmembrane receptors, each of which is composed of a pair of heterodimeric, noncovalently associated glycoproteins, designated as α and β chains. The α subunit contains heavy and light chains as part of its extracellular domain, with 3-4 divalent-cation binding sites; the light chain also contains transmembrane and intracellular domains. The β-subunit contains a large extracellular domain, as well as transmembrane and intracellular domains. Integrins are cell surface receptors, which bind to extracellular matrix adhesive proteins such as fibrinogen, fibronectin, vitronectin and osteopontin. These transmembrane glycoproteins are classified by the β subunits. The β3 class of integrin family has received the most attention in recent drug discovery efforts (W. J. Hoekstra, Current Medicinal Chemistry, 1998, 5, 195), however, the β5 class has also become a focus of attention. Some of the disease states that have been associated with a strong β3 and β5 integrin component in their etiologies are thrombosis (integrin α2bβ3 also called GPIIb/IIIa); unstable angina (GPIIb/IIIa); restenosis (GPIIb/IIIa and integrin αvβ3); arthritis, vascular disorders or osteoporosis (αvβ3); tumor angiogenesis, multiple sclerosis, neurological disorders, asthma, vascular injury or diabetic retinopathy (αvβ3 or αvβ5) and tumor metastasis (αvβ3). See S. A. Mousa, et al., *Emerging Therapeutic Targets*, 2000, 4(2) 148-149; and W. H. Miller, et al., *Drug Discovery Today*, 2000, 5(9), 397-40. Antibodies and/or low-molecular weight compound antagonists of αvβ3 have shown efficacy against these respective disease states in animal models (J. Samanen, *Current Pharmaceutical Design*, 1997, 3 545-584) and thereby offer promise as therapeutic agents. Several patents have described compounds that could interact with these integrins. For example, U.S. Pat. No. 5,919,792 B1, U.S. Pat. No. 6,211,191 B1, and WO 01/96334 and WO 01/23376 describe αvβ3 and αvβ5 integrin receptor antagonists.

The present invention provides a new class of piperidinyl compounds, which selective bind to β3, β5 or dual integrin receptors (e.g. αvβ3 and αvβ5) for the treatment of a wide variety of integrin mediated disease states.

SUMMARY OF THE INVENTION

The present invention is directed to piperidinyl compounds of Formula (I):

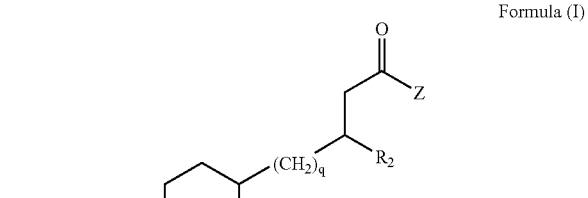

Formula (I)

and Formula (II)

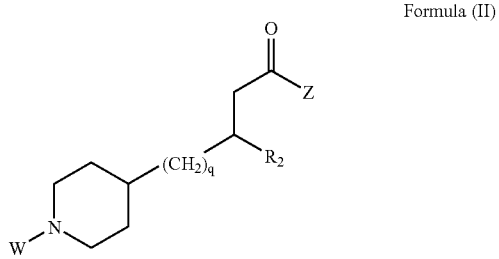

Formula (II)

wherein

W is selected from the group consisting of —$C_{0-6}$alkyl($R_1$), —$C_{1-6}$alkyl($R_{1a}$), —$C_{0-6}$alkyl-aryl($R_1$,$R_8$), —$C_{0-6}$alkyl-heterocyclyl($R_1$,$R_8$), —$C_{0-6}$alkoxy($R_1$), —$C_{0-6}$alkoxy-aryl($R_1$,$R_8$), and —$C_{0-6}$alkoxy-heterocyclyl($R_1$,$R_8$), $R_1$ is selected from the group consisting of hydrogen, —N($R_4$)$_2$, —N($R_4$)($R_5$), —N($R_4$)($R_6$), -heterocyclyl($R_8$) and -heteroaryl($R_8$);

$R_{1a}$ is selected from the group consisting of —C($R_4$)(=N—$R_4$), —C(=N—$R_4$)—N($R_4$)$_2$, —C(=N—$R_4$)—N($R_4$)($R_6$), —C(=N—$R_4$)—N($R_4$)—C(=O)—$R_4$, —C(=N—$R_4$)—N($R_4$)—C(=O)—N($R_4$)$_2$, —C(=N—$R_4$)—N($R_4$)—CO$_2$—$R_4$, —C(=N—$R_4$)—N($R_4$)—SO$_2$—$C_{1-8}$alkyl($R_7$) and —C(=N—$R_4$)—N($R_4$)—SO$_2$—N($R_4$)$_2$;

$R_4$ is selected from the group consisting of hydrogen and —$C_{1-8}$alkyl($R_7$);

$R_5$ is selected from the group consisting of —C(=O)—$R_4$, —C(=O)—N($R_4$)$_2$, —C(=O)-cycloalkyl($R_8$), —C(=O)-heterocyclyl($R_8$), —C(=O)-aryl($R_8$), —C(=O)-heteroaryl($R_8$), —C(=O)—N($R_4$)-cycloalkyl($R_8$), —C(=O)—N($R_4$)-aryl($R_8$), —CO$_2$—$R_4$, —CO$_2$-cycloalkyl($R_8$), —CO$_2$-aryl($R_8$), —C($R_4$)(=N—$R_4$), —C(=N—$R_4$)—N($R_4$)$_2$, —C(=N—$R_4$)—N($R_4$)($R_6$), —C(=N—$R_4$)—N($R_4$)—C(=O)—$R_4$, —C(=N—$R_4$)—N($R_4$)—C(=O)—N($R_4$)$_2$, —C(=N—$R_4$)—N($R_4$)—CO$_2$—$R_4$, —C(=N—$R_4$)—N($R_4$)—SO$_2$—$C_{1-8}$alkyl($R_7$), —C(=N—$R_4$)—N($R_4$)—SO$_2$—N($R_4$)$_2$, —N($R_4$)—C($R_4$)(=N—$R_4$), —N($R_4$)—C(=N—$R_4$)—N($R_4$)$_2$, —N($R_4$)—C(=N—$R_4$)—N($R_4$)($R_6$), —N($R_4$)—C(=N—$R_4$)—N($R_4$)—C(=O)—$R_4$, —N($R_4$)—C(=N—$R_4$)—N($R_4$)—C(=O)—N($R_4$)$_2$, —N($R_4$)—C(=N—$R_4$)—N($R_4$)—CO$_2$—$R_4$, —N($R_4$)—C(=N—$R_4$)—N($R_4$)—SO$_2$—$C_{1-8}$alkyl($R_7$), —N($R_4$)—C(=N—$R_4$)—N($R_4$)—SO$_2$—N($R_4$)$_2$, —SO$_2$—$C_{1-8}$alkyl($R_7$), —SO$_2$—N($R_4$)$_2$, —SO$_2$-cycloalkyl($R_8$) and —SO$_2$-aryl($R_8$);

$R_6$ is selected from the group consisting of -cycloalkyl($R_8$), -heterocyclyl($R_8$), -aryl($R_8$) and -heteroaryl($R_8$);

$R_7$ is one to two substituents independently selected from the group consisting of hydrogen, —$C_{1-8}$alkoxy($R_9$), —$NH_2$, —NH—$C_{1-8}$alkyl($R_9$), —N($C_{1-8}$alkyl($R_9$))$_2$, —C(=O)H, —C(=O)—$C_{1-8}$alkyl($R_9$), —C(=O)—$NH_2$, —C(=O)—NH—$C_{1-8}$alkyl($R_9$), —C(=O)—N($C_{1-8}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —$CO_2$H, —$CO_2$—$C_{1-8}$alkyl($R_9$), —$CO_2$-aryl($R_{10}$), —C(=NH)—$NH_2$, —SH, —S—$C_{1-8}$alkyl($R_9$), —S—$C_{1-8}$alkyl-S—$C_{1-8}$alkyl($R_9$), —S—$C_{1-8}$alkyl-$C_{1-8}$alkoxy($R_9$), —S—$C_{1-8}$alkyl-NH—$C_{1-8}$alkyl($R_9$), —$SO_2$—$C_{1-8}$alkyl($R_9$), —$SO_2$—$NH_2$, —$SO_2$—NH—$C_{1-8}$alkyl($R_9$), —$SO_2$—N($C_{1-8}$alkyl($R_9$))$_2$, —$SO_2$-aryl($R_{10}$), cyano, (halo)$_{1-3}$, hydroxy, nitro, oxo, -cycloalkyl($R_{10}$), -heterocyclyl($R_{10}$), -aryl($R_{10}$) and -heteroaryl($R_{10}$);

$R_8$ is one to four substituents independently selected from the group consisting of hydrogen, —$C_{1-8}$alkyl($R_9$), —C(=O)H, —C(=O)—$C_{1-8}$alkyl($R_9$), —C(=O)—$NH_2$, —C(=O)—NH—$C_{1-8}$alkyl($R_9$), —C(=O)—N($C_{1-8}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —$CO_2$H, —$CO_2$—$C_{1-8}$alkyl($R_9$), —$CO_2$-aryl($R_{10}$), —C(=NH)—$NH_2$, —$SO_2$—$C_{1-8}$alkyl($R_9$), —$SO_2$—$NH_2$, —$SO_2$—NH—$C_{1-8}$alkyl($R_9$), —$SO_2$—N($C_{1-8}$alkyl($R_9$))$_2$, —$SO_2$-aryl($R_{10}$), -cycloalkyl($R_{10}$) and -aryl($R_{10}$) when attached to a nitrogen atom; and, wherein $R_8$ is one to four substituents independently selected from the group consisting of hydrogen, —$C_{1-8}$alkyl($R_9$), —$C_{1-8}$alkoxy($R_9$), —O-cycloalkyl($R_{10}$), —O-aryl($R_{10}$), —C(=O)H, —C(=O)—$C_{1-8}$alkyl($R_9$), —C(=O)—$NH_2$, —C(=O)—NH—$C_{1-8}$alkyl($R_9$), —C(=O)—N($C_{1-8}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —$CO_2$H, —$CO_2$—$C_{1-8}$alkyl($R_9$), —$CO_2$-aryl($R_{10}$), —C(=NH)—$NH_2$, —$SO_2$—$C_{1-8}$alkyl($R_9$), —$SO_2$—$NH_2$, —$SO_2$—NH—$C_{1-8}$alkyl($R_9$), —$SO_2$—N($C_{1-8}$alkyl($R_9$))$_2$, —$SO_2$-aryl($R_{10}$), —SH, —S—$C_{1-8}$alkyl($R_9$), —S—$C_{1-8}$alkyl-S—$C_{1-8}$alkyl($R_9$), —S—$C_{1-8}$alkyl-$C_{1-8}$alkoxy($R_9$), —S—$C_{1-8}$alkyl-NH—$C_{1-8}$alkyl($R_9$), —$NH_2$, —NH—$C_{1-8}$alkyl($R_9$), —N($C_{1-8}$alkyl($R_9$))$_2$, cyano, halo, hydroxy, nitro, oxo, -cycloalkyl($R_{10}$), -heterocyclyl($R_{10}$), -aryl($R_{10}$) and -heteroaryl($R_{10}$) when attached to a carbon atom;

$R_9$ is selected from the group consisting of hydrogen, —$C_{1-8}$alkoxy, —$NH_2$, —NH—$C_{1-8}$alkyl, —N($C_{1-8}$alkyl)$_2$, —C(=O)H, —C(=O)—$NH_2$, —C(=O)—NH—$C_{1-8}$alkyl, —C(=O)—N($C_{1-8}$alkyl)$_2$, —$CO_2$H, —$CO_2$—$C_{1-8}$alkyl, —$SO_2$—$C_{1-8}$alkyl, —$SO_2$—$NH_2$, —$SO_2$—NH—$C_{1-8}$alkyl, —$SO_2$—N($C_{1-8}$alkyl)$_2$, cyano, (halo)$_{1-3}$, hydroxy, nitro and oxo;

$R_{10}$ is one to four substituents independently selected from the group consisting of hydrogen, —$C_{1-8}$alkyl, —C(=O)H, —C(=O)—$C_{1-8}$alkyl, —C(=O)—$NH_2$, —C(=O)—NH—$C_{1-8}$alkyl, —C(=O)—N($C_{1-8}$alkyl)$_2$, —$CO_2$H, —$CO_2$—$C_{1-4}$alkyl, —$SO_2$—$C_{1-8}$alkyl, —$SO_2$—$NH_2$, —$SO_2$—NH—$C_{1-8}$alkyl and —$SO_2$—N($C_{1-8}$alkyl)$_2$ when attached to a nitrogen atom; and, wherein $R_{10}$ is one to four substituents independently selected from the group consisting of hydrogen, —$C_{1-8}$alkyl, —$C_{1-8}$alkoxy, —C(=O)H, —C(=O)—$C_{1-8}$alkyl, —C(=O)—$NH_2$, —C(=O)—NH—$C_{1-8}$alkyl, —C(=O)—N($C_{1-8}$alkyl)$_2$, —$CO_2$H, —$CO_2$—$C_{1-4}$alkyl, —$SO_2$—$C_{1-8}$alkyl, —$SO_2$—$NH_2$, —$SO_2$—NH—$C_{1-8}$alkyl, —$SO_2$—N($C_{1-8}$alkyl)$_2$, —$NH_2$, —NH—$C_{1-8}$alkyl, —N($C_{1-8}$alkyl)$_2$, cyano, halo, hydroxy, nitro and oxo when attached to a carbon atom;

$R_2$ is selected from the group consisting of hydrogen, —$C_{1-8}$alkyl($R_7$), —$C_{2-8}$alkenyl($R_7$), —$C_{2-8}$alkynyl($R_7$), -cycloalkyl($R_8$), -heterocyclyl($R_8$), -aryl($R_8$) and -heteroaryl($R_8$);

q is 0, 1, 2 or 3;

Z is selected from the group consisting of hydroxy, —$NH_2$, —NH—$C_{1-8}$alkyl, —N($C_{1-8}$alkyl)$_2$, —O—$C_{1-8}$alkyl, —O—$C_{1-8}$alkyl-OH, —O—$C_{1-8}$alkyl$C_{1-8}$alkoxy, —O—$C_{1-8}$alkylcarbonyl$C_{1-8}$alkyl, —O—$C_{1-8}$alkyl-$CO_2$H, —O—$C_{1-8}$alkyl-C(O)O—$C_{1-8}$alkyl, —O—$C_{1-8}$alkyl-O—C(O)$C_{1-8}$alkyl, —O—$C_{1-8}$alkyl-$NH_2$, —O—$C_{1-8}$alkyl-NH—$C_{1-8}$alkyl, —O—$C_{1-8}$alkyl-N($C_{1-8}$alkyl)$_2$, —O—$C_{1-8}$alkylamide, —O—$C_{1-8}$alkyl-C(O)—NH—$C_{1-8}$alkyl, —O—$C_{1-8}$alkyl-C(O)—N($C_{1-8}$alkyl)$_2$ and —NHC(O)$C_{1-8}$alkyl.

and pharmaceutically acceptable salts, racemic mixtures and enantiomers thereof.

The present invention is also directed to methods for producing the instant piperidinyl compounds and pharmaceutical compositions and medicaments thereof.

The present invention is further directed to a method for treating or ameliorating an integrin receptor mediated disorder.

DETAILED DESCRIPTION OF THE INVENTION

Another aspect of the present invention includes compounds of Formula (I) and Formula (II) wherein W is preferably is selected from the group consisting of —$C_{0-4}$alkyl($R_1$), —$C_{1-4}$alkyl($R_{1a}$), —$C_{0-4}$alkyl-aryl($R_1,R_8$), —$C_{0-4}$alkyl-heterocyclyl($R_1,R_8$), —$C_{0-4}$alkoxy($R_1$), —$C_{0-4}$alkoxy-aryl($R_1,R_8$), and —$C_{0-4}$alkoxy-heterocyclyl($R_1,R_8$).

Aspects of the present invention include compounds of Formula (I) and Formula (II) wherein W is preferably —$C_{0-4}$alkyl($R_1$) or —$C_{0-4}$alkyl-aryl($R_1,R_8$).

Another aspect of the present invention includes compounds of Formula (I) and Formula (II) wherein W is preferably —$C_{0-4}$alkyl($R_1$) or —$C_{0-4}$alkyl-phenyl($R_1,R_8$).

Aspects of the present invention include compounds of Formula (I) and Formula (II) wherein $R_1$ is —N($R_4$)($R_6$), -heterocyclyl($R_8$) or -heteroaryl($R_8$).

Another aspect of the present invention includes compounds of Formula (I) and Formula (II) wherein $R_1$ is —N($R_4$)($R_6$), -dihydro-1H-pyrrolo[2,3-b]pyridinyl($R_8$), -tetrahydropyrimidinyl($R_8$), -tetrahydro-1,8-naphthyridinyl($R_8$), -tetrahydro-1H-azepino[2,3-b]pyridinyl($R_8$) or -pyridinyl($R_8$).

Another aspect of the present invention includes compounds of Formula (I) and Formula (II) wherein $R_1$ is —N($R_4$)($R_6$), -tetrahydropyrimidinyl($R_8$) or -tetrahydro-1,8-naphthyridinyl($R_8$).

Aspects of the present invention include compounds of Formula (I) and Formula (II) wherein $R_{1a}$ is —C($R_4$)(=N—$R_4$), —C(=N—$R_4$)—N($R_4$)$_2$, —C(=N—$R_4$)—N($R_4$)($R_6$), —C(=N—$R_4$)—N($R_4$)—C(=O)—$R_4$, —C(=N—$R_4$)—N($R_4$)—C(=O)—N($R_4$)$_2$, —C(=N—$R_4$)—N($R_4$)—$CO_2$—$R_4$, —C(=N—$R_4$)—N($R_4$)—$SO_2$—$C_{1-4}$alkyl($R_7$) or —C(=N—$R_4$)—N($R_4$)—$SO_2$—N($R_4$)$_2$.

Aspects of the present invention include compounds of Formula (I) and Formula (II) wherein $R_4$ is hydrogen or —$C_{1-4}$alkyl($R_7$).

Another aspect of the present invention includes compounds of Formula (I) and Formula (II) wherein $R_4$ is hydrogen.

Aspects of the present invention include compounds of Formula (I) and Formula (II) wherein $R_5$ is —C(=O)—$R_4$, —C(=O)—N($R_4$)$_2$, —C(=O)-cycloalkyl($R_8$), —C(=O)-heterocyclyl($R_8$), —C(=O)-aryl($R_8$), —C(=O)-heteroaryl($R_8$), —C(=O)—N($R_4$)-cycloalkyl($R_8$), —C(=O)—N($R_4$)-aryl($R_8$), —CO$_2$—$R_4$, —CO$_2$-cycloalkyl($R_8$), —CO$_2$-aryl($R_8$), —C($R_4$)(=N—$R_4$), —C(=N—$R_4$)—N($R_4$)$_2$, —C(=N—$R_4$)—N($R_4$)($R_6$), —C(=N—$R_4$)—N($R_4$)—C(=O)—$R_4$, —C(=N—$R_4$)—N($R_4$)—C(=O)—N($R_4$)$_2$, —C(=N—$R_4$)—N($R_4$)—CO$_2$—$R_4$, —C(=N—$R_4$)—N($R_4$)—SO$_2$—C$_{1-4}$alkyl($R_7$), —C(=N—$R_4$)—N($R_4$)—SO$_2$—N($R_4$)$_2$, —N($R_4$)—C($R_4$)(=N—$R_4$), —N($R_4$)—C(=N—$R_4$)—N($R_4$)$_2$, —N($R_4$)—C(=N—$R_4$)—N($R_4$)($R_6$), —N($R_4$)—C(=N—$R_4$)—N($R_4$)—C(=O)—$R_4$, —N($R_4$)—C(=N—$R_4$)—N($R_4$)—C(=O)—N($R_4$)$_2$, —N($R_4$)—C(=N—$R_4$)—N($R_4$)—CO$_2$—$R_4$, —N($R_4$)—C(=N—$R_4$)—N($R_4$)—SO$_2$—C$_{1-4}$alkyl($R_7$), —N($R_4$)—C(=N—$R_4$)—N($R_4$)—SO$_2$—N($R_4$)$_2$, —SO$_2$—C$_{1-4}$alkyl($R_7$), —SO$_2$—N($R_4$)$_2$, —SO$_2$-cycloalkyl($R_8$) or —SO$_2$-aryl($R_8$).

Another aspect of the present invention includes compounds of Formula (I) and Formula (II) wherein $R_5$ is —C(=O)—$R_4$, —C(=O)—N($R_4$)$_2$, —CO$_2$—$R_4$, —C($R_4$)(=N—$R_4$), —C(=N—$R_4$)—N($R_4$)$_2$, —C(=N—$R_4$)—N($R_4$)($R_6$), —N($R_4$)—C($R_4$)(=N—$R_4$), —N($R_4$)—C(=N—$R_4$)—N($R_4$)$_2$, —N($R_4$)—C(=N—$R_4$)—N($R_4$)($R_6$), —SO$_2$—C$_{1-4}$alkyl($R_7$) or —SO$_2$—N($R_4$)$_2$.

Aspects of the present invention include compounds of Formula (I) and Formula (II) wherein $R_6$ is -heterocyclyl($R_8$) or -heteroaryl($R_8$).

Another aspect of the present invention includes compounds of Formula (I) and Formula (II) wherein $R_6$ is -dihydroimidazolyl($R_8$), -tetrahydropyridinyl($R_8$), -tetrahydropyrimidinyl($R_8$) or -pyridinyl($R_8$).

Aspects of the present invention include compounds of Formula (I) and Formula (II) wherein $R_7$ is one to two substituents independently selected from hydrogen, —C$_{1-4}$alkoxy($R_9$), —NH$_2$, —NH—C$_{1-4}$alkyl($R_9$), —N(C$_{1-4}$alkyl($R_9$))$_2$, —C(=O)H, —C(=O)—C$_{1-4}$alkyl($R_9$), —C(=O)—NH$_2$, —C(=O)—NH—C$_{1-4}$alkyl($R_9$), —C(=O)—N(C$_{1-4}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —CO$_2$H, —CO$_2$—C$_{1-4}$alkyl($R_9$), —CO$_2$-aryl($R_{10}$), —C(=NH)—NH$_2$, —SH, —S—C$_{1-4}$alkyl($R_9$), —S—C$_{1-4}$alkyl-S—C$_{1-4}$alkyl($R_9$), —S—C$_{1-4}$alkyl-C$_{1-4}$alkoxy($R_9$), —S—C$_{1-4}$alkyl-NH—C$_{1-4}$alkyl($R_9$), —SO$_2$—C$_{1-4}$alkyl($R_9$), —SO$_2$—NH$_2$, —SO$_2$—NH—C$_{1-4}$alkyl($R_9$), —SO$_2$—N(C$_{1-4}$alkyl($R_9$))$_2$, —SO$_2$-aryl($R_{10}$), cyano, (halo)$_{1-3}$, hydroxy, nitro, oxo, -cycloalkyl($R_{10}$), -heterocyclyl($R_{10}$), -aryl($R_{10}$) or -heteroaryl($R_{10}$).

Another aspect of the present invention includes compounds of Formula (I) and Formula (II) wherein $R_7$ is one to two substituents independently selected from hydrogen, —C$_{1-4}$alkoxy($R_9$), —NH$_2$, —NH—C$_{1-4}$alkyl($R_9$), —N(C$_{1-4}$alkyl($R_9$))$_2$, (halo)$_{1-3}$, hydroxy or oxo.

A further aspect of the present invention includes compounds of Formula (I) and Formula (II) wherein $R_7$ is hydrogen.

Aspects of the present invention include compounds of Formula (I) and Formula (II) wherein $R_8$ is one to four substituents independently selected from hydrogen, —C$_{1-4}$alkyl($R_9$), —C(=O)H, —C(=O)—C$_{1-4}$alkyl($R_9$), —C(=O)—NH$_2$, —C(=O)—NH—C$_{1-4}$alkyl($R_9$), —C(=O)—N(C$_{1-4}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —CO$_2$H, —CO$_2$—C$_{1-4}$alkyl($R_9$), —CO$_2$-aryl($R_{10}$), —C(=NH)—NH$_2$, —SO$_2$—C$_{1-4}$alkyl($R_9$), —SO$_2$—NH$_2$, —SO$_2$—NH—C$_{1-4}$alkyl($R_9$), —SO$_2$—N(C$_{1-4}$alkyl($R_9$))$_2$, —SO$_2$-aryl($R_{10}$), -cycloalkyl($R_{10}$) or -aryl($R_{10}$) when attached to a nitrogen atom; and, wherein $R_8$ is one to four substituents independently selected from hydrogen, —C$_{1-4}$alkyl($R_9$), —C$_{1-4}$alkoxy($R_9$), —O-cycloalkyl($R_{10}$), —O-aryl($R_{10}$), —C(=O)H, —C(=O)—C$_{1-4}$alkyl($R_9$), —C(=O)—NH$_2$, —C(=O)—NH—C$_{1-4}$alkyl($R_9$), —C(=O)—N(C$_{1-4}$alkyl-$R_{11}$)$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —CO$_2$H, —CO$_2$—C$_{1-4}$alkyl($R_9$), —CO$_2$-aryl($R_{10}$), —C(=NH)—NH$_2$, —SO$_2$—C$_{1-4}$alkyl($R_9$), —SO$_2$—NH$_2$, —SO$_2$—NH—C$_{1-4}$alkyl($R_9$), —SO$_2$—N(C$_{1-4}$alkyl($R_9$))$_2$, —SO$_2$-aryl($R_{10}$), —SH, —S—C$_{1-4}$alkyl($R_9$), —S—C$_{1-4}$alkyl-S—C$_{1-4}$alkyl($R_9$), —S—C$_{1-4}$alkyl-C$_{1-4}$alkoxy($R_9$), —S—C$_{1-4}$alkyl-NH—C$_{1-4}$alkyl($R_9$), —NH$_2$, —NH—C$_{1-4}$alkyl($R_9$), —N(C$_{1-4}$alkyl($R_9$))$_2$, cyano, halo, hydroxy, nitro, oxo, -cycloalkyl($R_{10}$), -heterocyclyl($R_{10}$), -aryl($R_{10}$) or -heteroaryl($R_{10}$) when attached to a carbon atom.

Another aspect of the present invention includes compounds of Formula (I) and Formula (II) wherein $R_8$ is one to four substituents independently selected from hydrogen, —C$_{1-4}$alkyl($R_9$), —C(=O)H, —C(=O)—NH$_2$, —C(=O)—NH—C$_{1-4}$alkyl($R_9$), —C(=O)—N(C$_{1-4}$alkyl($R_9$))$_2$, —CO$_2$H, —CO$_2$—C$_{1-4}$alkyl($R_9$) or —SO$_2$—NH$_2$ when attached to a nitrogen atom; and, wherein $R_8$ is one to four substituents independently selected from hydrogen, —C$_{1-4}$alkyl($R_9$), —C$_{1-4}$alkoxy($R_9$), —O-aryl($R_{10}$), —C(=O)H, —C(=O)—NH$_2$, —C(=O)—NH—C$_{1-4}$alkyl($R_9$), —C(=O)—N(C$_{1-4}$alkyl($R_9$))$_2$, —CO$_2$H, —CO$_2$—C$_{1-4}$alkyl($R_9$), —SO$_2$—NH$_2$, —NH$_2$, —NH—C$_{1-4}$alkyl($R_9$), —N(C$_{1-4}$alkyl($R_9$))$_2$, cyano, halo, hydroxy, nitro or oxo when attached to a carbon atom.

Another aspect of the present invention includes compounds of Formula (I) and Formula (II) wherein $R_8$ is one to four substituents independently selected from hydrogen or —C$_{1-4}$alkyl($R_9$) when attached to a nitrogen atom; and, wherein $R_8$ is one to four substituents independently selected from hydrogen, —C$_{1-4}$alkyl($R_9$), —C$_{1-4}$alkoxy($R_9$), —O-aryl($R_{10}$), —NH$_2$, —NH—C$_{1-4}$alkyl($R_9$), —N(C$_{1-4}$alkyl($R_9$))$_2$, halo, hydroxy or oxo when attached to a carbon atom.

A further aspect of the present invention includes compounds of Formula (I) and Formula (II) wherein $R_8$ is one to four substituents independently selected from hydrogen or —C$_{1-4}$alkyl($R_9$) when attached to a nitrogen atom; and, wherein $R_8$ is one to four substituents independently selected from hydrogen, —C$_{1-4}$alkyl($R_9$), —C$_{1-4}$alkoxy($R_9$)—O-aryl($R_{10}$) or hydroxy when attached to a carbon atom.

Aspects of the present invention include compounds of Formula (I) and Formula (II) wherein $R_9$ is hydrogen, —C$_{1-4}$alkoxy, —NH$_2$, —NH—C$_{1-4}$alkyl, —N(C$_{1-4}$alkyl)$_2$, —C(=O)H, —C(=O)—NH$_2$, —C(=O)—NH—C$_{1-4}$alkyl, —C(=O)—N(C$_{1-4}$alkyl)$_2$, —CO$_2$H, —CO$_2$—C$_{1-4}$alkyl, —SO$_2$—C$_{1-4}$alkyl, —SO$_2$—NH$_2$, —SO$_2$—NH—C$_{1-4}$alkyl, —SO$_2$—N(C$_{1-4}$alkyl)$_2$, cyano, (halo)$_{1-3}$, hydroxy, nitro or oxo.

Another aspect of the present invention includes compounds of Formula (I) and Formula (II) wherein $R_9$ is hydrogen, —C$_{1-4}$alkoxy, —NH$_2$, —NH—C$_{1-4}$alkyl, —N(C$_{1-4}$alkyl)$_2$, —C(=O)H, —CO$_2$H, —C(=O)—C$_{1-4}$alkoxy, (halo)$_{1-3}$, hydroxy or oxo.

A further aspect of the present invention includes compounds of Formula (I) wherein $R_9$ is hydrogen, —C$_{1-4}$alkoxy, —NH$_2$, —NH—C$_{1-4}$alkyl, —N(C$_{1-4}$alkyl)$_2$, (halo)$_{1-3}$ or hydroxy.

Aspects of the present invention include compounds of Formula (I) and Formula (II) wherein $R_{10}$ is one to four substituents independently selected from hydrogen, —$C_{1-4}$alkyl, —C(=O)H, —C(=O)—$C_{1-4}$alkyl, —C(=O)—$NH_2$, —C(=O)—NH—$C_{1-4}$alkyl, —C(=O)—N($C_{1-4}$alkyl)$_2$, —$CO_2$H, —$CO_2$—$C_{1-4}$alkyl, —$SO_2$—$C_{1-4}$alkyl, —$SO_2$—$NH_2$, —$SO_2$—NH—$C_{1-4}$alkyl or —$SO_2$—N($C_{1-4}$alkyl)$_2$ when attached to a nitrogen atom; and, wherein $R_{10}$ is one to four substituents independently selected from hydrogen, —$C_{1-4}$alkyl, —$C_{1-4}$alkoxy, —C(=O)H, —C(=O)—$C_{1-4}$alkyl, —C(=O)—$NH_2$, —C(=O)—NH—$C_{1-4}$alkyl, —C(=O)—N($C_{1-4}$alkyl)$_2$, —$CO_2$H, —$CO_2$—$C_{1-4}$alkyl, —$SO_2$—$C_{1-4}$alkyl, —$SO_2$—$NH_2$, —$SO_2$—NH—$C_{1-4}$alkyl, —$SO_2$—N($C_{1-4}$alkyl)$_2$, —$NH_2$, —NH—$C_{1-4}$alkyl, —N($C_{1-4}$alkyl)$_2$, cyano, halo, hydroxy, nitro or oxo when attached to a carbon atom.

Another aspect of the present invention includes compounds of Formula (I) and Formula (II) wherein $(R_{10})_{1-4}$ is hydrogen, —$C_{1-4}$alkyl, —$C_{1-4}$alkoxy, —C(=O)H, —C(=O)—$C_{1-4}$alkyl, —$CO_2$H, —$CO_2$—$C_{1-4}$alkyl, —$NH_2$, —NH—$C_{1-4}$alkyl, —N($C_{1-4}$alkyl)$_2$, halo, hydroxy, nitro or oxo when attached to a carbon atom.

A further aspect of the present invention includes compounds of Formula (I) and Formula (II) wherein $R_{10}$ is hydrogen.

Aspects of the present invention include compounds of Formula (I) and Formula (II) wherein $R_2$ is hydrogen, —$C_{1-4}$alkyl($R_7$), —$C_{2-4}$alkenyl($R_7$), —$C_{2-4}$alkynyl($R_7$), -cycloalkyl($R_8$), -heterocyclyl($R_8$), -aryl($R_8$) or -heteroaryl($R_8$).

Another aspect of the present invention includes compounds of Formula (I) and Formula (II) wherein $R_2$ is hydrogen, -cycloalkyl($R_8$), -heterocyclyl($R_8$), -aryl($R_8$) or -heteroaryl($R_8$).

Another aspect of the present invention includes compounds of Formula (I) and Formula (II) wherein $R_2$ is hydrogen, -cycloalkyl($R_8$), -heterocyclyl($R_8$), -phenyl($R_8$), -naphthalenyl($R_8$) or -heteroaryl($R_8$).

Another aspect of the present invention includes compounds of Formula (I) and Formula (II) wherein $R_2$ is hydrogen, -tetrahydropyrimidinyl($R_8$), -1,3-benzodioxolyl($R_8$), -dihydrobenzofuranyl($R_8$), -tetrahydroquinolinyl($R_8$), -phenyl($R_8$), -naphthalenyl($R_8$), -pyridinyl($R_8$), -pyrimidinyl($R_8$) or -quinolinyl($R_8$).

Aspects of the present invention include a composition comprising a compound of Formula (I) and Formula (II) wherein q is 1, 2 or 3.

Aspects of the present invention include a composition comprising a compound of Formula (I) and Formula (II) wherein Z is selected from the group consisting of hydroxy, —$NH_2$, —NH—$C_{1-8}$alkyl, —N($C_{1-8}$alkyl)$_2$, —O—$C_{1-8}$alkyl, —O—$C_{1-8}$alkyl-OH, —O—$C_{1-8}$alkyl$C_{1-4}$alkoxy, —O—$C_{1-8}$alkylcarbonyl$C_{1-4}$alkyl, —O—$C_{1-8}$alkyl-$CO_2$H, —O—$C_{1-8}$alkyl-C(O)O—$C_{1-6}$alkyl, —O—$C_{1-8}$alkyl-O—C(O)$C_{1-8}$alkyl, —O—$C_{1-8}$alkyl-$NH_2$, —O—$C_{1-8}$alkyl-NH—$C_{1-8}$alkyl, —O—$C_{1-8}$alkyl-N($C_{1-8}$alkyl)$_2$, —O—$C_{1-8}$alkylamide —O—$C_{1-8}$alkyl-C(O)—NH—$C_{1-8}$alkyl, —O—$C_{1-8}$alkyl-C(O)—N($C_{1-8}$alkyl)$_2$ and —NHC(O)$C_{1-8}$alkyl.

Aspects of the present invention include a composition comprising compound of Formula (I)

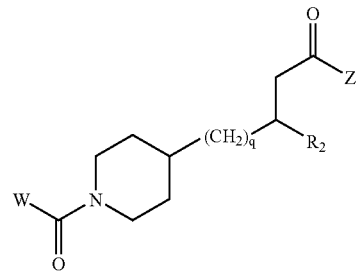

Formula (I)

wherein the compound is selected from the group consisting of:

| Cpd | W | $R_1$ | $R_2$ | q | Stereo chem | Z |
|---|---|---|---|---|---|---|
| 1 | —$CH_2$-Ph(3-$R_1$) | —NH-1,4,5,6-tetrahydro-pyrimidin-2-yl | H | 0 | | OH |
| 2 | —$(CH_2)_2$-Ph(3-$R_1$) | —NH-1,4,5,6-tetrahydro-pyrimidin-2-yl | H | 0 | | OH |
| 3 | —$CH_2$-Ph(3-$R_1$) | —NH-1,4,5,6-tetrahydro-5-OH-pyrimidin-2-yl | quinolin-3-yl | 0 | | OH |
| 4 | —$(CH_2)_3$—$R_1$ | 5,6,7,8-tetrahydro-[1,8]naphthyridin-2-yl | quinolin-3-yl | 0 | | OH |
| 5 | —$(CH_2)_3$—$R_1$ | 5,6,7,8-tetrahydro-[1,8]naphthyridin-2-yl | 1,2,3,4-tetrahydro-quinolin-3-yl | 0 | | OH |
| 5-1 | —$(CH_2)_3$—$R_1$ | 5,6,7,8-tetrahydro-[1,8]naphthyridin-2-yl | 1,2,3,4-tetrahydro-quinolin-3-yl | 0 | Isomer 1 | OH |
| 5-2 | —$(CH_2)_3$—$R_1$ | 5,6,7,8-tetrahydro-[1,8]naphthyridin-2-yl | 1,2,3,4-tetrahydro-quinolin-3-yl | 0 | Isomer 2 | OH |
| 5-3 | —$(CH_2)_3$—$R_1$ | 5,6,7,8-tetrahydro-[1,8]naphthyridin-2-yl | 1,2,3,4-tetrahydro-quinolin-3-yl | 0 | Isomer 3 | OH |
| 5-4 | —$(CH_2)_3$—$R_1$ | 5,6,7,8-tetrahydro-[1,8]naphthyridin-2-yl | 1,2,3,4-tetrahydro-quinolin-3-yl | 0 | Isomer 4 | OH |

-continued

| Cpd | W | $R_1$ | $R_2$ | q | Stereo chem | Z |
|---|---|---|---|---|---|---|
| 6 | Ph(3-$R_1$) | —NH-1,4,5,6-tetrahydro-pyrimidin-2-yl | pyridin-3-yl | 2 | | OH |
| 7 | Ph(3-$R_1$) | —NH-1,4,5,6-tetrahydro-5-OH-pyrimidin-2-yl | pyridin-3-yl | 2 | | OH |
| 8 | —(CH$_2$)$_2$—$R_1$ | 5,6,7,8-tetrahydro-[1,8]naphthyridin-2-yl | pyridin-3-yl | 2 | | OH |
| 9 | —(CH$_2$)$_3$—$R_1$ | —NH-pyridin-2-yl | pyridin-3-yl | 2 | | OH |
| 10 | Ph(3-$R_1$) | —NH-1,4,5,6-tetrahydro-5-OH-pyrimidin-2-yl | (6-OCH$_3$)-pyridin-3-yl | 2 | | OH |
| 11 | —(CH$_2$)$_2$—$R_1$ | 5,6,7,8-tetrahydro-[1,8]naphthyridin-2-yl | 1,3-benzodioxol-5-yl | 1 | | OH |
| 12 | Ph(3-$R_1$) | —NH-1,4,5,6-tetrahydro-pyrimidin-2-yl | quinolin-3-yl | 2 | | OH |
| 13 | —(CH$_2$)$_2$—$R_1$ | 5,6,7,8-tetrahydro-[1,8]naphthyridin-2-yl | phenyl | 1 | | OH |
| 14 | —(CH$_2$)$_2$—$R_1$ | 5,6,7,8-tetrahydro-[1,8]naphthyridin-2-yl | 1,3-benzodioxol-5-yl | 0 | | OH |
| 15 | —(CH$_2$)$_3$—$R_1$ | 5,6,7,8-tetrahydro-[1,8]naphthyridin-2-yl | 1,3-benzodioxol-5-yl | 0 | | OH |
| 16 | —CH$_2$—$R_1$ | 5,6,7,8-tetrahydro-[1,8]naphthyridin-2-yl | 1,3-benzodioxol-5-yl | 0 | | OH |
| 17 | —(CH$_2$)$_3$—$R_1$ | 5,6,7,8-tetrahydro-[1,8]naphthyridin-2-yl | (6-OCH$_3$)-pyridin-3-yl | 0 | | OH |
| 18 | —(CH$_2$)$_2$—$R_1$ | 5,6,7,8-tetrahydro-[1,8]naphthyridin-2-yl | 1,4,5,6-tetrahydro-2-Me-pyrimidin-5-yl | 1 | | OH |
| 19 | —(CH$_2$)$_2$—$R_1$ | 5,6,7,8-tetrahydro-[1,8]naphthyridin-2-yl | 1,2,3,4-tetrahydro-quinolin-3-yl | 1 | | OH |
| 19-1 | —(CH$_2$)$_2$—$R_1$ | 5,6,7,8-tetrahydro-[1,8]naphthyridin-2-yl | 1,2,3,4-tetrahydro-quinolin-3-yl | 1 | Isomer 1 | OH |
| 19-2 | —(CH$_2$)$_2$—$R_1$ | 5,6,7,8-tetrahydro-[1,8]naphthyridin-2-yl | 1,2,3,4-tetrahydro-quinolin-3-yl | 1 | Isomer 2 | OH |
| 19-3 | —(CH$_2$)$_2$—$R_1$ | 5,6,7,8-tetrahydro-[1,8]naphthyridin-2-yl | 1,2,3,4-tetrahydro-quinolin-3-yl | 1 | Isomer 3 | OH |
| 19-4 | —(CH$_2$)$_2$—$R_1$ | 5,6,7,8-tetrahydro-[1,8]naphthyridin-2-yl | 1,2,3,4-tetrahydro-quinolin-3-yl | 1 | Isomer 4 | OH |
| 20 | —(CH$_2$)$_2$—$R_1$ | 5,6,7,8-tetrahydro-[1,8]naphthyridin-2-yl | 1,3-benzodioxol-5-yl | 2 | | OH |
| 21 | —(CH$_2$)$_2$—$R_1$ | 5,6,7,8-tetrahydro-[1,8]naphthyridin-2-yl | (6-OCH$_3$)-pyridin-3-yl | 2 | | OH |
| 21a | —(CH$_2$)$_2$—$R_1$ | 5,6,7,8-tetrahydro-[1,8]naphthyridin-2-yl | (6-OCH$_3$)-pyridin-3-yl | 2 | Isomer a | OH |
| 21b | —(CH$_2$)$_2$—$R_1$ | 5,6,7,8-tetrahydro-[1,8]naphthyridin-2-yl | (6-OCH$_3$)-pyridin-3-yl | 2 | Isomer b | OH |
| 22 | —(CH$_2$)$_3$—$R_1$ | —NH-pyridin-2-yl | quinolin-3-yl | 2 | | OH |
| 23 | —(CH$_2$)$_3$—$R_1$ | —NH-pyridin-2-yl | 1,3-benzodioxol-5-yl | 2 | | OH |
| 24 | —(CH$_2$)$_3$—$R_1$ | —NH-pyridin-2-yl | 1,3-benzodioxol-5-yl | 0 | | OH |
| 25 | —(CH$_2$)$_3$—$R_1$ | —NH-pyridin-2-yl | (6-OCH$_3$)-pyridin-3-yl | 2 | | OH |
| 26 | —(CH$_2$)$_3$—$R_1$ | 5,6,7,8-tetrahydro-[1,8]naphthyridin-2-yl | 1,3-benzodioxol-5-yl | 1 | | OH |

-continued

| Cpd | W | R$_1$ | R$_2$ | q | Stereo chem | Z |
|---|---|---|---|---|---|---|
| 27 | Ph(3-R$_1$) | —NH-1,4,5,6-tetrahydro-5-OH-pyrimidin-2-yl | 1,3-benzodioxol-5-yl | 1 | | OH |
| 28 | —(CH$_2$)$_2$—R$_1$ | 5,6,7,8-tetrahydro-[1,8]naphthyridin-2-yl | (6-OCH$_3$)-pyridin-3-yl | 1 | | OH |
| 28a | —(CH$_2$)$_2$—R$_1$ | 5,6,7,8-tetrahydro-[1,8]naphthyridin-2-yl | (6-OCH$_3$)-pyridin-3-yl | 1 | Isomer a | OH |
| 28b | —(CH$_2$)$_2$—R$_1$ | 5,6,7,8-tetrahydro-[1,8]naphthyridin-2-yl | (6-OCH$_3$)-pyridin-3-yl | 1 | Isomer b | OH |
| 29 | —(CH$_2$)$_3$—R$_1$ | 5,6,7,8-tetrahydro-[1,8]naphthyridin-2-yl | quinolin-3-yl | 1 | | OH |
| 30 | —(CH$_2$)$_2$—R$_1$ | 5,6,7,8-tetrahydro-[1,8]naphthyridin-2-yl | (3-F)phenyl | 1 | | OH |
| 30a | —(CH$_2$)$_2$—R$_1$ | 5,6,7,8-tetrahydro-[1,8]naphthyridin-2-yl | (3-F)phenyl | 1 | Isomer a | OH |
| 30b | —(CH$_2$)$_2$—R$_1$ | 5,6,7,8-tetrahydro-[1,8]naphthyridin-2-yl | (3-F)phenyl | 1 | Isomer b | OH |
| 31 | —(CH$_2$)$_3$—R$_1$ | 5,6,7,8-tetrahydro-[1,8]naphthyridin-2-yl | (3-F)phenyl | 1 | | OH |
| 32 | —(CH$_2$)$_2$—R$_1$ | 5,6,7,8-tetrahydro-[1,8]naphthyridin-2-yl | quinolin-3-yl | 1 | | OH |
| 33 | —(CH$_2$)$_2$—R$_1$ | 5,6,7,8-tetrahydro-[1,8]naphthyridin-2-yl | (4-F)phenyl | 1 | | OH |
| 34 | —(CH$_2$)$_3$—R$_1$ | 5,6,7,8-tetrahydro-[1,8]naphthyridin-2-yl | (4-F)phenyl | 1 | | OH |
| 35 | —(CH$_2$)$_2$—R$_1$ | 5,6,7,8-tetrahydro-[1,8]naphthyridin-2-yl | (2-CH$_3$)pyrimidin-5-yl | 1 | | OH |
| 36 | —(CH$_2$)$_2$—R$_1$ | 5,6,7,8-tetrahydro-[1,8]naphthyridin-2-yl | 2,3-dihydro-benzofuran-6-yl | 1 | | OH |
| 36a | —(CH$_2$)$_2$—R$_1$ | 5,6,7,8-tetrahydro-[1,8]naphthyridin-2-yl | 2,3-dihydro-benzofuran-6-yl | 1 | Isomer a | OH |
| 36b | —(CH$_2$)$_2$—R$_1$ | 5,6,7,8-tetrahydro-[1,8]naphthyridin-2-yl | 2,3-dihydro-benzofuran-6-yl | 1 | Isomer b | OH |
| 37 | —(CH$_2$)$_2$—R$_1$ | 5,6,7,8-tetrahydro-[1,8]naphthyridin-2-yl | (3,5-difluoro)-phenyl | 1 | | OH |
| 38 | —(CH$_2$)$_3$—R$_1$ | 5,6,7,8-tetrahydro-[1,8]naphthyridin-2-yl | (3,5-difluoro)-phenyl | 1 | | OH |
| 39 | —(CH$_2$)$_2$—R$_1$ | 5,6,7,8-tetrahydro-[1,8]naphthyridin-2-yl | (3-CF$_3$)-phenyl | 1 | | OH |
| 40 | —(CH$_2$)$_2$—R$_1$ | 5,6,7,8-tetrahydro-[1,8]naphthyridin-2-yl | (4-OCF$_3$)-phenyl | 1 | | OH |
| 41 | —(CH$_2$)$_2$—R$_1$ | 5,6,7,8-tetrahydro-[1,8]naphthyridin-2-yl | (3-F-4-Ph)-phenyl | 1 | | OH |
| 42 | —(CH$_2$)$_2$—R$_1$ | 5,6,7,8-tetrahydro-[1,8]naphthyridin-2-yl | (3-F-4-OCH$_3$)-phenyl | 1 | | OH |
| 43 | —(CH$_2$)$_2$—R$_1$ | 5,6,7,8-tetrahydro-[1,8]naphthyridin-2-yl | (4-Oph)-phenyl | 1 | | OH |
| 44 | —(CH$_2$)$_2$—R$_1$ | 5,6,7,8-tetrahydro-[1,8]naphthyridin-2-yl | isoquinolin-4-yl | 1 | | OH |
| 45 | —(CH$_2$)$_2$—R$_1$ | 5,6,7,8-tetrahydro-[1,8]naphthyridin-2-yl | pyridin-3-yl | 1 | | OH |

-continued

| Cpd | W | R₁ | R₂ | q | Stereo chem | Z |
|---|---|---|---|---|---|---|
| 46 | —(CH₂)₂—R₁ | 5,6,7,8-tetrahydro-[1,8]naphthyridin-2-yl | dihydrobenzofuran-5-yl | 1 | | OH |
| 47 | —(CH₂)₂—R₁ | 5,6,7,8-tetrahydro-[1,8]naphthyridin-2-yl | (2,4-OCH₃)-pyrimidin-5-yl | 1 | | OH |
| 48 | —(CH₂)₂—R₁ | 5,6,7,8-tetrahydro-[1,8]naphthyridin-2-yl | (2-OCH₃)-pyrimidin-5-yl | 1 | | OH |
| 49 | Ph(3-R₁) | —NH-1,4,5,6-tetrahydro-5-OH-pyrimidin-2-yl | quinolin-3-yl | 2 | | OH |
| 50 | Ph(3-R₁) | —NH-1,4,5,6-tetrahydro-pyridin-2-yl | quinolin-3-yl | 2 | | OH |
| 51 | —(CH₂)₂—R₁ | 5,6,7,8-tetrahydro-[1,8]naphthyridin-2-yl | quinolin-3-yl | 2 | | OH |
| 52 | Ph(3-R₁) | —NH-3,4,5,6-tetrahydro-pyrimidin-2-yl | 1,3-benzodioxol-5-yl | 2 | | OH |
| 53 | Ph(3-R₁) | —NH-3,4,5,6-tetrahydro-pyridin-2-yl | 1,3-benzodioxol-5-yl | 2 | | OH |
| 54 | Ph(3-R₁) | NH-1,4,5,6-tetrahydro-5-OH-pyrimidin-2-yl | 1,3-benzodioxol-5-yl | 2 | | OH |
| 55 | —CH₂—R₁ | 5,6,7,8-tetrahydro-[1,8]naphthyridin-2-yl | 1,3-benzodioxol-5-yl | 2 | | OH |
| 56 | —(CH₂)₂—R₁ | 5,6,7,8-tetrahydro-[1,8]naphthyridin-2-yl | naphthalene-2-yl | 1 | | OH |
| 56a | —(CH₂)₂—R₁ | 5,6,7,8-tetrahydro-[1,8]naphthyridin-2-yl | naphthalen-2-yl | 1 | Isomer a | OH |
| 56b | —(CH₂)₂—R₁ | 5,6,7,8-tetrahydro-[1,8]naphthyridin-2-yl | naphthalen-2-yl | 1 | Isomer b | OH |
| 57 | —(CH₂)₂—R₁ | 5,6,7,8-tetrahydro-[1,8]naphthyridin-2-yl | 5,6,7,8-tetrahydro-quinolin-3-yl | 1 | racemic | OH |
| 58a | —(CH₂)₃—R₁ | 5,6,7,8-tetrahydro-[1,8]naphthyridin-2-yl | 5,6,7,8-tetrahydro-quinolin-3-yl | 0 | Isomer a | OH |
| 58b | —(CH₂)₃—R₁ | 5,6,7,8-tetrahydro-[1,8]naphthyridin-2-yl | 5,6,7,8-tetrahydro-quinolin-3-yl | 0 | Isomer b | OH |
| 59 | —(CH₂)₂—R | 5,6,7,8-tetrahydro-[1,8]naphthyridin-2-yl | (3-OCH₃)phenyl | 1 | racemic | OH |
| 60 | —(CH₂)₂—R₁ | 5,6,7,8-tetrahydro-[1,8]naphthyridin-2-yl | (4-OCH₃)phenyl | 1 | racemic | OH |
| 61 | —(CH₂)₂—R₁ | 5,6,7,8-tetrahydro-[1,8]naphthyridin-2-yl | H | 1 | | OH |
| 62 | —(CH₂)₂—R₁ | 5,6,7,8-tetrahydro-[1,8]naphthyridin-2-yl | tetrahydrofuran-3-yl | 1 | racemic | OH |
| 63 | —(CH₂)₂—R₁ | 5,6,7,8-tetrahydro-[1,8]naphthyridin-2-yl | thiophen-2-yl | 1 | racemic | OH |
| 64 | —(CH₂)₂—R₁ | 5,6,7,8-tetrahydro-[1,8]naphthyridin-2-yl | (3-F)phenyl | 1 | racemic | NH₂ |
| 65 | —(CH₂)₂—R₁ | 5,6,7,8-tetrahydro-[1,8]naphthyridin-2-yl | 2,3-dihydro-benzo[1,4]-dioxin-6-yl | 1 | racemic | OH |
| 66 | —(CH₂)₂—R₁ | 5,6,7,8-tetrahydro-[1,8]naphthyridin-2-yl | (3-SCH₃)phenyl | 1 | racemic | OH |
| 67 | —(CH₂)₂—R₁ | 5,6,7,8-tetrahydro-[1,8]naphthyridin-2-yl | N-methyl-1,2,3,4-tetrahydro-quinolin-3-yl | 1 | racemic | OH |

-continued

| Cpd | W | R₁ | R₂ | q | Stereo chem | Z |
|---|---|---|---|---|---|---|
| 68 | —(CH₂)₂—R₁ | 5,6,7,8-tetrahydro-[1,8]naphthyridin-2-yl | H | 1 | | —O-ethyl |
| 69 | —(CH₂)₂—R₁ | 5,6,7,8-tetrahydro-[1,8]naphthyridin-2-yl | H | 1 | | —O-2-propyl |
| 70 | —(CH₂)₂—R₁ | 5,6,7,8-tetrahydro-[1,8]naphthyridin-2-yl | H | 1 | | —O-t-butyl |
| 71 | —(CH₂)₂—R₁ | 5,6,7,8-tetrahydro-[1,8]naphthyridin-2-yl | H | 1 | | —O-n-octyl |
| 72 | —(CH₂)₂—R₁ | 5,6,7,8-tetrahydro-[1,8]naphthyridin-2-yl | H | 1 | | —O-s-butyl |
| 73 | —(CH₂)₂—R₁ | 5,6,7,8-tetrahydro-[1,8]naphthyridin-2-yl | H | 1 | | —O--methyl |
| 74 | —(CH₂)₂—R₁ | 5,6,7,8-tetrahydro-[1,8]naphthyridin-2-yl | H | 1 | racemic | —O—CH₂—OC(O)-t-butyl |
| 75 | —(CH₂)₂—R₁ | 5,6,7,8-tetrahydro-[1,8]naphthyridin-2-yl | (3-(NMe₂)phenyl | 1 | racemic | OH |
| 76 | —(CH₂)₂—R₁ | 5,6,7,8-tetrahydro-[1,8]naphthyridin-2-yl | (3-OMe-4-OH)phenyl | 1 | racemic | OH |
| 76a | —(CH₂)₂—R₁ | 5,6,7,8-tetrahydro-[1,8]naphthyridin-2-yl | (3-OMe-4-OH)phenyl | 1 | Isomer a | OH |
| 77 | Ph(3-R₁) | —NH-4,5-dihydro-1H-imidazol-2-yl | (3-F)phenyl | 1 | racemic | OH |
| 78 | —(CH₂)₂—R₁ | 5,6,7,8-tetrahydro-[1,8]naphthyridin-2-yl | (3-NHEt)phenyl | 1 | racemic | OH |
| 79 | —(CH₂)₂—R₁ | 5,6,7,8-tetrahydro-[1,8]naphthyridin-2-yl | (3-NHMe)phenyl | 1 | racemic | OH |
| 80 | —(CH₂)₃—R₁ | 5,6,7,8-tetrahydro-[1,8]naphthyridin-2-yl | dihydrobenzofuran-6-yl | 0 | | OH |

Aspects of the present invention include a composition comprising a compound of Formula (II)

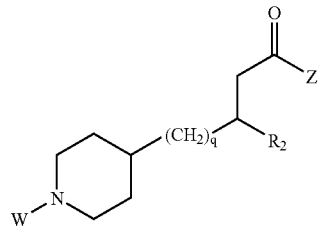

Formula (II)

wherein W, R₁, R₂, q and Z are as previously defined and preferably are

| Cpd | W | R₁ | R₂ | q | Stereo chem | Z |
|---|---|---|---|---|---|---|
| 81 | —(CH₂)₃—R₁ | 5,6,7,8-tetrahydro-[1,8]naphthyridin-2-yl | (3-F)phenyl | 1 | racemic | OH |

Aspects of the present invention include a composition comprising a compound of Formula (I) wherein the compound is selected from the group consisting of a compound of Formula (I) wherein W is —CH₂-Ph(3-R₁); R₁ is —NH-1,4,5,6-tetrahydro-pyrimidin-2-yl; R₂ is H, q is 0 and Z is OH;

a compound of Formula (I) wherein W is —(CH₂)₂-Ph(3-R₁); R₁ is —NH-1,4,5,6-tetrahydro-pyrimidin-2-yl; R₂ is H, q is 0 and Z is OH;

a compound of Formula (I) wherein W is —CH₂-Ph(3-R₁); R₁ is —NH-1,4,5,6-tetrahydro-5-OH-pyrimidin-2-yl; R₂ is -3-quinolinyl, q is 0 and Z is OH;

a compound of Formula (I) wherein W is —(CH₂)₃—R₁; R₁ is -5,6,7,8-tetrahydro-1,8-naphthyridin-2-yl; R₂ is -3-quinolinyl, q is 0 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -1,2,3,4-tetrahydro-3-quinolinyl, q is 0 and Z is OH a compound of Formula (I) wherein W is -Ph(3-R$_1$); R$_1$ is —NH-1,4,5,6-tetrahydro-pyrimidin-2-yl; R$_2$ is -3-pyridinyl, q is 2 and Z is OH;

a compound of Formula (I) wherein W is -Ph(3-R$_1$); R$_1$ is —NH-1,4,5,6-tetrahydro-5-OH-pyrimidin-2-yl; R$_2$ is -3-pyridinyl, q is 2 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-pyridinyl, q is 2 and Z is OH;

a compound of Formula (I) wherein W is —(CH$_2$)$_3$—R$_1$; R$_1$ is —NH-pyridin-2-yl; R$_2$ is -3-pyridinyl, q is 2, and Z is OH;

a compound of Formula (I) wherein W is -Ph(3-R$_1$); R$_1$ is —NH-1,4,5,6-tetrahydro-5-OH-pyrimidin-2-yl; R$_2$ is -(6-MeO)pyridin-3-yl, q is 2 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -1,3-benzodioxol-5-yl, q is 1 and Z is OH;

a compound of Formula (I) wherein W is -Ph(3-R$_1$); R$_1$ is —NH-1,4,5,6-tetrahydro-pyrimidin-2-yl; R$_2$ is -3-quinolinyl, q is 2 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -1,3-benzodioxol-5-yl, q is 0 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -1,3-benzodioxol-5-yl, q is 0 and Z is OH;

a compound of Formula (I) wherein W is —CH$_2$—R$_1$; R$_1$ is -5,6,7,8-tetrahydro-1,8-naphthyridin-2-yl; R$_2$ is -1,3-benzodioxol-5-yl, q is 0 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -(6-MeO)pyridin-3-yl, q is 0 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -1,4,5,6-tetrahydro-2-Me-pyrimidin-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -1,2,3,4-tetrahydro-3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -1,3-benzodioxol-5-yl, q is 2 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(6-MeO)pyridin-3-yl, q is 2 and Z is OH;

a compound of Formula (I) wherein W is —(CH$_2$)$_3$—R$_1$; R$_1$ is —NH-pyridin-2-yl; R$_2$ is -3-quinolinyl, q is 2 and Z is OH;

a compound of Formula (I) wherein W is —(CH$_2$)$_3$—R$_1$; R$_1$ is —NH-pyridin-2-yl; R$_2$ is -1,3-benzodioxol-5-yl, q is 2 and Z is OH;

a compound of Formula (I) wherein W is —(CH$_2$)$_3$—R$_1$; R$_1$ is —NH-pyridin-2-yl; R$_2$ is -1,3-benzodioxol-5-yl, q is 0 and Z is OH;

a compound of Formula (I) wherein W is —(CH$_2$)$_3$—R$_1$; R$_1$ is —NH-pyridin-2-yl; R$_2$ is -(6-MeO)pyridin-3-yl, q is 2 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -1,3-benzodioxol-5-yl, q is 1 and Z is OH;

a compound of Formula (I) wherein W is -Ph(3-R$_1$); R$_1$ is —NH-1,4,5,6-tetrahydro-5-OH-2-pyrimidinyl; R$_2$ is -1,3-benzodioxol-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(6-MeO)pyridin-3-yl, q is 1 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-F)Ph, q is 1 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -(3-F)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(4-F)Ph, q is 1 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -(4-F)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(2-Me)pyrimidin-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -2,3-dihydro-benzofuran-6-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3,5-F$_2$)Ph, q is 1 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -(3,5-F$_2$)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-CF$_3$)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(4-OCF$_3$)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-F-4-Ph)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-F-4-OMe)Ph, q is 1, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(4-OPh)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -4-isoquinolinyl, q is 1, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-pyridinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -5-dihydrobenzofuranyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -2,4-(OMe)$_2$-pyrimid-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(2-OMe)pyrimidin-5-yl, q is 1 and Z is OH;

a compound of Formula (I) wherein W is -Ph(3-R$_1$); R$_1$ is —NH-1,4,5,6-tetrahydro-5-OH-pyrimidin-2-yl; R$_2$ is -3-quinolinyl, q is 2 and Z is OH;

a compound of Formula (I) wherein W is -Ph(3-R$_1$); R$_1$ is —NH-3,4,5,6-tetrahydro-pyridin-2-yl; R$_2$ is -3-quinolinyl, q is 2 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-quinolinyl, q is 2 and Z is OH;

a compound of Formula (I) wherein W is -Ph(3-R$_1$); R$_1$ is —NH-3,4,5,6-tetrahydro-pyrimidin-2-yl; R$_2$ is -1,3-benzodioxol-5-yl, q is 2 and Z is OH;

a compound of Formula (I) wherein W is -Ph(3-R$_1$); R$_1$ is —NH-3,4,5,6-tetrahydro-pyridin-2-yl; R$_2$ is -1,3-benzodioxol-5-yl, q is 2 and Z is OH;

a compound of Formula (I) wherein W is -Ph(3-R$_1$); R$_1$ is —NH-1,4,5,6-tetrahydro-5-OH-pyrimidin-2-yl; R$_2$ is -1,3-benzodioxol-5-yl, q is 2 and Z is OH;

a compound of Formula (I) wherein W is —CH$_2$—R$_1$; R$_1$ is -5,6,7,8-tetrahydro-1,8-naphthyridin-2-yl; R$_2$ is -1,3-benzodioxol-5-yl, q is 2 and Z is OH; and, a compound of Formula (I) wherein W is —(CH$_2$)$_2$—R$_1$; R$_1$ is -5,6,7,8-tetrahydro-1,8-naphthyridin-2-yl; R$_2$ is -2-naphthalenyl, q is 1 and Z is OH.

Another aspect of the present invention includes a composition comprising a compound of Formula (I) wherein the compound is selected from the group consisting of:

a compound of Formula (I) wherein W is —(CH$_2$)$_3$—R$_1$; R$_1$ is -5,6,7,8-tetrahydro-1,8-naphthyridin-2-yl; R$_2$ is -1,2,3,4-tetrahydro-3-quinolinyl, q is 0 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -1,3-benzodioxol-5-yl, q is 0 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -1,2,3,4-tetrahydro-3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(6-MeO)pyridin-3-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-F)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(2-Me)pyrimidin-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -2,3-dihydro-benzofuran-6-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -4-isoquinolinyl, q is 1, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-pyridinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -2,4-(OMe)$_2$-pyrimid-5-yl, q is 1 and Z is OH; and, a compound of Formula (I) wherein W is —(CH$_2$)$_2$—R$_1$; R$_1$ is -5,6,7,8-tetrahydro-1,8-naphthyridin-2-yl; R$_2$ is -(2-OMe)pyrimidin-5-yl, q is 1 and Z is OH.

Another aspect of the present invention includes a compound of Formula (I) wherein W is —(CH$_2$)$_3$—R$_1$; R$_1$ is -5,6,7,8-tetrahydro-1,8-naphthyridin-2-yl; R$_2$ is -1,2,3,4-tetrahydro-3-quinolinyl, q is 0 and Z is OH.

Another aspect of the present invention includes a compound of Formula (I) wherein W is —(CH$_2$)$_3$—R$_1$; R$_1$ is -5,6,7,8-tetrahydro-1,8-naphthyridin-2-yl; R$_2$ is -1,3-benzodioxol-5-yl, q is 0 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -1,2,3,4-tetrahydro-3-quinolinyl, q is 1 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -(6-MeO)pyridin-3-yl, q is 1 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -(3-F)Ph, q is 1 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -3-quinolinyl, q is 1 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -(2-Me)pyrimidin-5-yl, q is 1 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -2,3-dihydro-benzofuran-6-yl, q is 1 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -4-isoquinolinyl, q is 1 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -3-pyridinyl, q is 1 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -2,4-(OMe)$_2$-pyrimid-5-yl, q is 1 and Z is OH.

Another aspect of the present invention includes a compound of Formula (I) wherein W is —(CH$_2$)$_2$—R$_1$; R$_1$ is -5,6,7,8-tetrahydro-1,8-naphthyridin-2-yl; R$_2$ is -(2-OMe)pyrimidin-5-yl, q is 1 and Z is OH.

Aspects of the present invention include a compound of Formula (I):

Formula (I)

wherein W, R$_1$, R$_2$, R$_6$, R$_8$, R$_9$, q and Z are as previously defined; and, preferably, wherein W is —C$_{0-4}$alkyl(R$_1$) or —C$_{0-4}$alkyl-phenyl(R$_1$,R$_8$);

R$_1$ is —NH(R$_6$);

R$_2$ is hydrogen, -tetrahydropyrimidinyl(R$_8$), -1,3-benzodioxolyl(R$_8$), -dihydrobenzofuranyl(R$_8$), -tetrahydroquinolinyl($R_8$), -phenyl($R_8$), -naphthalenyl($R_8$), -pyridinyl($R_8$), -pyrimidinyl($R_8$) or -quinolinyl($R_8$);

$R_6$ is -dihydroimidazolyl($R_8$), -tetrahydropyridinyl($R_8$), -tetrahydropyrimidinyl($R_8$) or -pyridinyl($R_8$);

$R_8$ is one to four substituents independently selected from hydrogen or —$C_{1-4}$alkyl($R_9$) when attached to a nitrogen atom; and, wherein $R_8$ is one to four substituents independently selected from hydrogen, —$C_{1-4}$alkyl($R_9$), —$C_{1-4}$alkoxy($R_9$), —O-aryl($R_{10}$) or hydroxy when attached to a carbon atom;

$R_9$ is hydrogen, —$C_{1-4}$alkoxy, —$NH_2$, —NH—$C_{1-4}$alkyl, —N($C_{1-4}$alkyl)$_2$, (halo)$_{1-3}$ or hydroxy; and, q is 1, 2 or 3;

Z is selected from the group consisting of hydroxy, —$NH_2$, —NH—$C_{1-8}$alkyl, —N($C_{1-8}$alkyl)$_2$, —O—$C_{1-8}$alkyl, —O—$C_{1-8}$alkyl-OH, —O—$C_{1-8}$alkyl$C_{1-8}$alkoxy, —O—$C_{1-8}$alkylcarbonyl$C_{1-8}$alkyl, —O—$C_{1-8}$alkyl-$CO_2H$, —O—$C_{1-8}$alkyl-C(O)O—$C_{1-8}$alkyl, —O—$C_{1-8}$alkyl-O—C(O)$C_{1-8}$alkyl, —O—$C_{1-8}$alkyl-$NH_2$, —O—$C_{1-8}$alkyl-NH—$C_{1-8}$alkyl, —O—$C_{1-8}$alkyl-N($C_{1-8}$alkyl)$_2$, —O—$C_{1-8}$alkylamide, —O—$C_{1-8}$alkyl-C(O)—NH—$C_{1-8}$alkyl, —O—$C_{1-8}$alkyl-C(O)—N($C_{1-8}$alkyl)$_2$ and —NHC(O)$C_{1-8}$alkyl;

and pharmaceutically acceptable salts, racemic mixtures and enantiomers thereof.

Aspects of the present invention include a compound of Formula (I) wherein the compound is a compound of Formula (I.2):

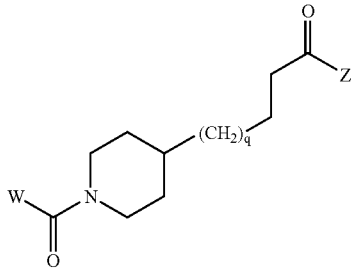

Formula (I.2)

wherein W, $R_1$, $R_6$, $R_8$, $R_9$, q and Z are as previously defined; and, preferably, wherein W is —$C_{0-4}$alkyl($R_1$) or —$C_{0-4}$alkyl-phenyl($R_1$,$R_8$);

$R_1$ is —NH($R_6$), -dihydro-1H-pyrrolo[2,3-b]pyridinyl($R_8$), -tetrahydropyrimidinyl($R_8$), -tetrahydro-1,8-naphthyridinyl($R_8$), -tetrahydro-1H-azepino[2,3-b]pyridinyl($R_8$) or -pyridinyl($R_8$);

$R_6$ is -dihydroimidazolyl($R_8$), -tetrahydropyridinyl($R_8$), -tetrahydropyrimidinyl($R_8$) or -pyridinyl($R_8$);

$R_8$ is one to four substituents independently selected from hydrogen or —$C_{1-4}$alkyl($R_9$) when attached to a nitrogen atom; and, wherein $R_8$ is one to four substituents independently selected from hydrogen, —$C_{1-4}$alkyl($R_9$), —$C_{1-4}$alkoxy($R_9$), —O-aryl($R_{10}$) or hydroxy when attached to a carbon atom;

$R_9$ is hydrogen, —$C_{1-4}$alkoxy, —$NH_2$, —NH—$C_{1-4}$alkyl, —N($C_{1-4}$alkyl)$_2$, (halo)$_{1-3}$ or hydroxy; and, q is 1, 2 or 3;

Z is selected from the group consisting of hydroxy, —$NH_2$, —NH—$C_{1-8}$alkyl, —N($C_{1-8}$alkyl)$_2$, —O—$C_{1-8}$alkyl, —O—$C_{1-8}$alkyl-OH, —O—$C_{1-8}$alkyl$C_{1-8}$alkoxy, —O—$C_{1-8}$alkylcarbonyl$C_{1-8}$alkyl, —O—$C_{1-8}$alkyl-$CO_2H$, —O—$C_{1-8}$alkyl-C(O)O—$C_{1-8}$alkyl, —O—$C_{1-8}$alkyl-O—C(O)$C_{1-8}$alkyl, —O—$C_{1-8}$alkyl-$NH_2$, —O—$C_{1-8}$alkyl-NH—$C_{1-8}$alkyl, —O—$C_{1-8}$alkyl-N($C_{1-8}$alkyl)$_2$, —O—$C_{1-8}$alkylamide, —O—$C_{1-8}$alkyl-C(O)—NH—$C_{1-8}$alkyl, —O—$C_{1-8}$alkyl-C(O)—N($C_{1-8}$alkyl)$_2$ and —NHC(O)$C_{1-8}$alkyl;

and pharmaceutically acceptable salts, racemic mixtures and enantiomers thereof.

Another aspect of the present invention includes compounds of Formula (I.2) wherein $R_1$ is —NH($R_6$), -tetrahydropyrimidinyl($R_8$) or -tetrahydro-1,8-naphthyridinyl($R_8$); and, all other variables are as previously defined.

Aspects of the present invention include a compound of Formula (I) wherein the compound is a compound of Formula (I.3):

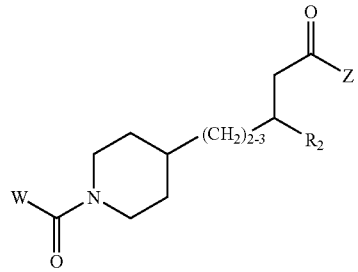

Formula (I.3)

wherein W, $R_1$, $R_2$, $R_6$, $R_8$, $R_9$ and Z are as previously defined; and, preferably, wherein W is —$C_{0-4}$alkyl($R_1$) or —$C_{0-4}$alkyl-phenyl($R_1$,$R_8$);

$R_1$ is —NH($R_6$), -dihydro-1H-pyrrolo[2,3-b]pyridinyl($R_8$), -tetrahydropyrimidinyl($R_8$), -tetrahydro-1,8-naphthyridinyl($R_8$), -tetrahydro-1H-azepino[2,3-b]pyridinyl($R_8$) or -pyridinyl($R_8$);

$R_2$ is hydrogen, -tetrahydropyrimidinyl($R_8$), -1,3-benzodioxolyl($R_8$), -dihydrobenzofuranyl($R_8$), -tetrahydroquinolinyl($R_8$), -phenyl($R_8$), -naphthalenyl($R_8$), -pyridinyl($R_8$), -pyrimidinyl($R_8$) or -quinolinyl($R_8$);

$R_6$ is -dihydroimidazolyl($R_8$), -tetrahydropyridinyl($R_8$), -tetrahydropyrimidinyl($R_8$) or -pyridinyl($R_8$);

$R_8$ is one to four substituents independently selected from hydrogen or —$C_{1-4}$alkyl($R_9$) when attached to a nitrogen atom; and, wherein $R_8$ is one to four substituents independently selected from hydrogen, —$C_{1-4}$alkyl($R_9$), —$C_{1-4}$alkoxy($R_9$), —O-aryl($R_{10}$) or hydroxy when attached to a carbon atom; and, $R_9$ is hydrogen, —$C_{1-4}$alkoxy, —$NH_2$, —NH—$C_{1-4}$alkyl, —N($C_{1-4}$alkyl)$_2$, (halo)$_{1-3}$ or hydroxy;

Z is selected from the group consisting of hydroxy, —$NH_2$, —NH—$C_{1-8}$alkyl, —N($C_{1-8}$alkyl)$_2$, —O—$C_{1-8}$alkyl, —O—$C_{1-8}$alkyl-OH, —O—$C_{1-8}$alkyl$C_{1-8}$alkoxy, —O—$C_{1-8}$alkylcarbonyl$C_{1-8}$alkyl, —O—$C_{1-8}$alkyl-$CO_2H$, —O—$C_{1-8}$alkyl-C(O)O—$C_{1-8}$alkyl, —O—$C_{1-8}$alkyl-O—C(O)$C_{1-8}$alkyl, —O—$C_{1-8}$alkyl-$NH_2$, —O—$C_{1-8}$alkyl-NH—$C_{1-8}$alkyl, —O—$C_{1-8}$alkyl-N($C_{1-8}$alkyl)$_2$, —O—$C_{1-8}$alkylamide, —O—$C_{1-8}$alkyl-C(O)—NH—$C_{1-8}$alkyl, —O—$C_{1-8}$alkyl-C(O)—N($C_{1-8}$alkyl)$_2$ and —NHC(O)$C_{1-8}$alkyl;

and pharmaceutically acceptable salts, racemic mixtures and enantiomers thereof.

Another aspect of the present invention includes compounds of Formula (I.3) wherein $R_1$ is —NH($R_6$), -tetrahydropyrimidinyl($R_8$) or -tetrahydro-1,8-naphthyridinyl($R_8$); and, all other variables are as previously defined.

Aspects of the present invention include a compound of Formula (I) wherein the compound is a compound of Formula (I.4):

Formula (I.4)

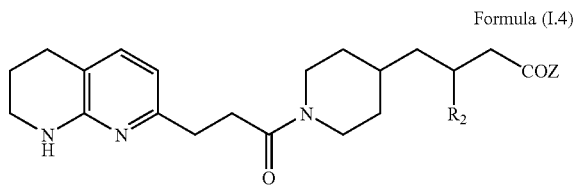

wherein $R_2$ and Z are as previously defined; and, further, $R_2$ is selected from the group consisting of -2-benzofuranyl, -3-benzofuranyl, -4-benzofuranyl, -5-benzofuranyl, -6-benzofuranyl, -7-benzofuranyl, -benzo[b]thien-2-yl, -benzo[b]thien-3-yl, -benzo[b]thien-4-yl, -benzo[b]thien-5-yl, -benzo[b]thien-6-yl, -benzo[b]thien-7-yl, -1H-indol-2-yl, -1H-indol-3-yl, -1H-indol-4-yl, -1H-indol-5-yl, -1H-indol-6-yl, -1H-indol-7-yl, -2-benzoxazolyl, -4-benzoxazolyl, -5-benzoxazolyl, -6-benzoxazolyl, -7-benzoxazolyl, -2-benzothiazolyl, -3-benzothiazolyl, -4-benzothiazolyl, -5-benzothiazolyl, -6-benzothiazolyl, -7-benzothiazolyl, -1H-benzimidazolyl-2-yl, -1H-benzimidazolyl-4-yl, -1H-benzimidazolyl-5-yl, -1H-benzimidazolyl-6-yl, -1H-benzimidazolyl-7-yl, -2-quinolinyl, -3-quinolinyl, -4-quinolinyl, -5-quinolinyl, -6-quinolinyl, -7-quinolinyl, -8-quinolinyl, -2H-1-benzopyran-2-yl, -2H-1-benzopyran-3-yl, -2H-1-benzopyran-4-yl, -2H-1-benzopyran-5-yl, -2H-1-benzopyran-6-yl, -2H-1-benzopyran-7-yl, -2H-1-benzopyran-8-yl, -4H-1-benzopyran-2-yl, -4H-1-benzopyran-3-yl, -4H-1-benzopyran-4-yl, -4H-1-benzopyran-5-yl, -4H-1-benzopyran-6-yl, -4H-1-benzopyran-7-yl, -4H-1-benzopyran-8-yl, -1H-2-benzopyran-1-yl, -1H-2-benzopyran-3-yl, -1H-2-benzopyran-3-yl, -1H-2-benzopyran-5-yl, -1H-2-benzopyran-6-yl, -1H-2-benzopyran-7-yl, -1H-2-benzopyran-8-yl, -1,2,3,4-tetrahydro-1-naphthalenyl, -1,2,3,4-tetrahydro-2-naphthalenyl, -1,2,3,4-tetrahydro-5-naphthalenyl, -1,2,3,4-tetrahydro-6-naphthalenyl, -2,3-dihydro-2-benzofuranyl, -2,3-dihydro-3-benzofuranyl, -2,3-dihydro-4-benzofuranyl, -2,3-dihydro-5-benzofuranyl, -2,3-dihydro-6-benzofuranyl, -2,3-dihydro-7-benzofuranyl, -2,3-dihydrobenzo[b]thien-2-yl, -2,3-dihydrobenzo[b]thien-3-yl, -2,3-dihydrobenzo[b]thien-4-yl, -2,3-dihydrobenzo[b]thien-5-yl, -2,3-dihydrobenzo[b]thien-6-yl, -2,3-dihydrobenzo[b]thien-7-yl, -2,3-dihydro-1H-indol-2-yl, -2,3-dihydro-1H-indol-3-yl, -2,3-dihydro-1H-indol-4-yl, -2,3-dihydro-1H-indol-5-yl, -2,3-dihydro-1H-indol-6-yl, -2,3-dihydro-1H-indol-7-yl, -2,3-dihydro-2-benzoxazolyl, -2,3-dihydro-4-benzoxazolyl, -2,3-dihydro-5-benzoxazolyl, -2,3-dihydro-6-benzoxazolyl, -2,3-dihydro-7-benzoxazolyl, -2,3-dihydro-1H-benzimidazol-2-yl, -2,3-dihydro-1H-benzimidazol-4-yl, -2,3-dihydro-1H-benzimidazol-5-yl, -2,3-dihydro-1H-benzimidazol-6-yl, -2,3-dihydro-1H-benzimidazol-7-yl, -3,4-dihydro-1(2H)-quinolinyl, -1,2,3,4-tetrahydro-2-quinolinyl, -1,2,3,4-tetrahydro-3-quinolinyl, -1,2,3,4-tetrahydro-4-quinolinyl, -1,2,3,4-tetrahydro-5-quinolinyl, -1,2,3,4-tetrahydro-6-quinolinyl, -1,2,3,4-tetrahydro-7-quinolinyl, -1,2,3,4-tetrahydro-8-quinolinyl, -3,4-dihydro-2H-1-benzopyran-2-yl, -3,4-dihydro-2H-1-benzopyran-3-yl, -3,4-dihydro-2H-1-benzopyran-4-yl, -3,4-dihydro-2H-1-benzopyran-5-yl, -3,4-dihydro-2H-1-benzopyran-6-yl, -3,4-dihydro-2H-1-benzopyran-7-yl, -3,4-dihydro-2H-1-benzopyran-8-yl, -3,4-dihydro-4H-1-benzopyran-2-yl, -3,4-dihydro-4H-1-benzopyran-3-yl, -3,4-dihydro-4H-1-benzopyran-4-yl, -3,4-dihydro-4H-1-benzopyran-5-yl, -3,4-dihydro-4H-1-benzopyran-6-yl, -3,4-dihydro-4H-1-benzopyran-7-yl, -3,4-dihydro-4H-1-benzopyran-8-yl, -3,4-dihydro-1H-2-benzopyran-2-yl, -3,4-dihydro-1H-2-benzopyran-3-yl, -3,4-dihydro-1H-2-benzopyran-4-yl, -3,4-dihydro-1H-2-benzopyran-5-yl, -3,4-dihydro-1H-2-benzopyran-6-yl, -3,4-dihydro-1H-2-benzopyran-7-yl and -3,4-dihydro-1H-2-benzopyran-8-yl optionally substituted when allowed by available valences with up to 7 substituents independently selected from methyl when attached to a nitrogen atom; and, independently selected from methyl, methoxy or fluoro when attached to a carbon atom;

Z is selected from the group consisting of hydroxy, —$NH_2$, —NH—$C_{1-8}$alkyl, —N($C_{1-8}$alkyl)$_2$, —O—$C_{1-8}$alkyl, —O—$C_{1-8}$alkyl-OH, —O—$C_{1-8}$alkyl$C_{1-8}$alkoxy, —O—$C_{1-8}$alkylcarbonyl$C_{1-8}$alkyl, —O—$C_{1-8}$alkyl-$CO_2H$, —O—$C_{1-8}$alkyl-C(O)O—$C_{1-8}$alkyl, —O—$C_{1-8}$alkyl-O—C(O)$C_{1-8}$alkyl, —O—$C_{1-8}$alkyl-$NH_2$, —O—$C_{1-8}$alkyl-NH—$C_{1-8}$alkyl, —O—$C_{1-8}$alkyl-N($C_{1-8}$alkyl)$_2$, —O—$C_{1-8}$alkylamide, —O—$C_{1-8}$alkyl-C(O)—NH—$C_{1-8}$alkyl, —O—$C_{1-8}$alkyl-C(O)—N($C_{1-8}$alkyl)$_2$ and —NHC(O)$C_{1-8}$alkyl;

pharmaceutically acceptable salts, racemic mixtures and enantiomers thereof.

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201-217; *J. Pharm. Sci.*, 1977 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may be resolved into their component enantiomers or diasteromers by standard techniques. It is to be understood that all stereoisomers, racemic mixtures, diastereomers and enantiomers thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

As used herein, the following underlined terms are intended to have the following meanings:

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-3}$ denotes a radical containing 1, 2 or 3 carbon atoms.

The term "alkyl" refers to an optionally substituted saturated or partially unsaturated, branched, straight-chain or cyclic monovalent hydrocarbon radicals derived by the removal of one hydrogen atom from a single carbon atom of an alkane molecule, thus forming the point of attachment. The term "alkenyl" refers to an optionally substituted partially unsaturated branched or straight-chain monovalent hydrocarbon radical having at least one carbon-carbon double bond and derived by the removal of one hydrogen atom from a single carbon atom of an alkene molecule, thus forming the point of attachment. The radical may be in either the cis or trans conformation about the double bond(s). The term "alkynyl" refers to an optionally substituted partially unsaturated branched or straight-chain monovalent hydrocarbon radical having at least one carbon-carbon triple bond and derived by the removal of one hydrogen atom from a single carbon atom of an alkyne molecule, thus forming the point of attachment. The term "alkoxy" refers to an optionally substituted saturated or partially unsaturated, branched, straight-chain monovalent hydrocarbon radical derived by the removal of the hydrogen atom from the single oxygen atom of an alkane, alkene or alkyne molecule, thus forming the point of attachment. An alkyl alkenyl, alkynyl or alkoxy radical is optionally substituted within the radical or on a terminal carbon atom (for a chain) with that amount of substituents allowed by available saturated valences.

The term "—$C_{1-8}$alkyl($R_x$)" (where x is an integer referring to a designated substituent group) refers to an $R_x$ substituent group which may be substituted within an alkyl chain, on a terminal carbon atom and may be similarly substituted on an alkenyl, alkynyl or alkoxy radical with a designated amount of substituents where allowed by available chemical bond valences. The term "—$C_{0-8}$alkyl($R_x$)" refers to an $R_x$ substituent group which may also be directly substituted on a point of attachment without an alkyl linking group (wherein $C_0$ is a placeholder for the $R_x$ substituent with a direct bond to the point of attachment).

The term "cycloalkyl" refers to saturated or partially unsaturated cyclic monovalent hydrocarbon radical consistent with the definitions of alkyl, alkanyl, alkenyl and alkynyl. Specifically included within the definition of cycloalkyl are fused polycyclic ring systems in which one or more rings are aromatic and one or more rings are saturated or partially unsaturated (it being understood that the radical may also occur on the aromatic ring). For example, the cycloalkyl groups are saturated or partially unsaturated or monocyclic alkyl radicals of from 3-8 carbon atoms (derived from a molecule such as cyclopropane, cyclobutane, cyclopentane, cyclohexane or cycloheptane); saturated or partially unsaturated fused or benzofused cyclic alkyl radicals of from 9 to 12 carbon atoms; or, saturated or partially unsaturated fused or benzofused tricyclic or polycyclic alkyl radicals of from 13 to 20 carbon atoms.

The term "heterocyclyl" refers to a saturated or partially unsaturated cyclic alkyl radical in which one or more carbon atoms are independently replaced with the same or different heteroatom. Specifically included within the definition of heterocyclyl are fused polycyclic ring systems in which one or more rings are aromatic and one or more rings are saturated or partially unsaturated (it being understood that the radical may also occur on the aromatic ring). Typical heteroatoms to replace the carbon atom(s) include, but are not limited to, N, O, S and the like. For example, the heterocyclyl group is a saturated or partially unsaturated five membered monocyclic alkyl ring of which at least one member is replaced by a N, O or S atom and which optionally contains one additional O atom replacing an additional member of the alkyl ring or one additional N atom replacing a member of the alkyl ring; a saturated or partially unsaturated six membered monocyclic alkyl ring of which one, two or three members of the alkyl ring are replaced by a N atom and optionally one member of the alkyl ring is replaced by a O or S atom or two members of the alkyl ring are replaced by O or S atoms; a saturated or partially unsaturated 5-6 membered heterocylic ring as previously defined fused to a heteroaryl as hereinafter defined; a saturated, partially unsaturated or benzofused nine or 10 membered bicyclic alkyl wherein at least one member of the ring is replaced by N, O, or S atom and which optionally one or two additional members of the bicyclic alkyl are replaced by N, O or S atoms; or, a saturated, partially unsaturated or benzofused 11 to 20 membered polycyclic alkyl of which at least one member is replaced by a N, O or S atom and which optionally one, two or three additional members of the polycyclic alkyl are replaced by N atoms. Examples of saturated or partially unsaturated heterocyclyl radicals include, but are not limited to, 2-pyrrolinyl, 3-pyrrolinyl, pyrrolidinyl, 1,3-dioxolanyl, 2-imidazolinyl, imidazolidinyl, dihydroimdazolyl, 2-pyrazolinyl, pyrazolidinyl, piperidinyl, morpholinyl, tetrahydropyrimidinyl, piperazinyl, dihydro-1H-pyrrolo[2,3-b]pyridinyl, tetrahydro-1,8-naphthyridinyl, tetrahydro-1H-azepino[2,3-b]pyridinyl, 1,3-benzodioxol-5-yl, 1,2,3,4-tetrahydro-3-quinolinyl or dihydrobenzofuranyl.

The term "aryl" refers to a monovalent aromatic hydrocarbon radical derived by the removal of one hydrogen atom from a single carbon atom of an aromatic ring system, thus forming the point of attachment for the radical. For example, the aryl group is derived from an unsaturated aromatic monocyclic ring system containing 5 to 6 carbon atoms (such as phenyl, derived from benzene); an unsaturated aromatic bicyclic ring system containing 9 to 10 carbon atoms (such as naphthyl, derived from naphthalene); or, an unsaturated aromatic tricyclic ring system containing 13 to 14 hydrogen carbon atoms (such as anthracenyl, derived from anthracene). The term "aromatic ring system" refers to an unsaturated cyclic or polycyclic ring system having an "aromatic" conjugated π electron system. Specifically excluded from the definition of aryl are fused ring systems in which one or more rings are saturated or partially unsaturated. Typical aryl groups include, but are not limited to, anthracenyl, naphthalenyl, azulenyl, benzenyl and the like The term "heteroaryl" refers to a monovalent heteroaromatic radical derived by the removal of one hydrogen atom from a single atom of a heteroaromatic ring system, thus forming the point of attachment for the radical. The term "heteroaromatic ring system" refers to an aromatic ring system in which one or more carbon atoms are each independently replaced with a heteroatom. Typical heteratoms to replace the carbon atoms include, but are not limited to, N, O, S, and the like. Specifically excluded from the definition of heteroaromatic ring system are fused ring systems in which one or more rings are saturated or partially unsaturated. For example, the heteroaryl group is derived from a heteroaromatic monocyclic ring system containing five members of which at least one member is a N, O or S atom and which optionally contains one, two or three additional N atoms; a heteroaromatic monocyclic ring system having six members of which one, two or three members are an N atom; a heteroaromatic fused bicyclic ring system having nine members of which at least one member is a N, O or S atom and which optionally contains one, two or three additional N atoms; a heteroaromatic fused bicyclic ring system having ten members of which one, two or three members are a N atom; a heteroaromatic fused tricyclic ring system containing 13 or 14 members of which at least one member is a N, O or S atom and which optionally contains one, two or three additional N atoms; or, a heteroaromatic fused polycyclic ring system containing 15 to 20 members of which at least one member is a N, O or S atom and which optionally contains one, two or three additional N atoms. Typical heteroaryls include, but are not limited to, cinnolinyl, furanyl, imidazolyl, indazolyl, indolyl, indolinyl, indolizinyl, isobenzofuranyl, isoquinolinyl, isothiazolyl, isoxazolyl, naphthyridinyl, oxazolyl, phenanthridinyl, phenanthrolinyl, purinyl, pyranyl, pyrazinyl, pyrazolyl, pyridazinyl, pyridinyl, pyrimidinyl, pyrrolyl, quinazolinyl, quinolinyl, quinoxalinyl, tetrazole, thiadiazole, thiazole, thiophene, triazole and the like.

The term "independently" means that when a group is substituted with more than one substituent that the substituents may be the same or different. The term "dependently" means that the substituents are specified in an indicated combination of structure variables.

Under standard nomenclature rules used throughout this disclosure, the terminal portion of the designated side chain is described first followed by the adjacent functionality toward the point of attachment. Thus, for example, a "phenyl $C_{1-6}$alkylamido$C_{1-6}$alkyl" substituent refers to a group of the formula:

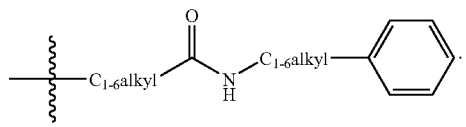

A substituent's point of attachment may also be indicated by a dashed line to indicate the point(s) of attachment, followed by the adjacent functionality and ending with the terminal functionality such as, for example, _—($C_{1-6}$)alkyl-carbonyl-NH—($C_{1-6}$)alkyl-phenyl.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Integrins are a widely expressed family of calcium or magnesium dependent α or β heterodimeric cell surface receptors, which bind to extracellular matrix adhesive proteins such as fibrinogen, fibronectin, vitronectin and osteopontin. The integrin receptors are transmembrane glycoproteins (GP's) known for their large extracellular domains and are classified by at least 8 known β subunits and 14α subunits (S. A. Mousa, et al., *Emerging Theraupeutic Targets*, 2000, 4, (2), 143-153).

For example, the β1 subfamily has the largest number of integrins wherein the various α subunits associate with various β subunits: β3, β5, β6 and β8 (S. A. Mousa, et al., *Emerging Theraupeutic Targets*, 2000, 4, (2), 144-147). Some of the disease states that have a strong αvβ3, αvβ5 and αIIbβ3 (also referred to as GPIIb/IIIa) integrin component in their etiologies are unstable angina, thromboembolic disorders or atherosclerosis (GPIIb/IIIa); thrombosis or restenosis (GPIIb/IIIa or αvβ3); restenosis (dual αvβ3/GPIIb/IIIa); rheumatoid arthritis, vascular disorders or osteoporosis (αvβ3); tumor angiogenesis, tumor metastasis, tumor growth, multiple sclerosis, neurological disorders, asthma, vascular injury or diabetic retinopathy (αvβ3 or αvβ5); and, angiogenesis (dual αvβ3/αvβ5) (S. A. Mousa, et al., *Emerging Theraupeutic Targets*, 2000, 4, (2), 148-149; W. H. Miller, et al., *Drug Discovery Today* 2000, 5 (9), 397-407; and, S. A. Mousa, et al., *Exp. Opin. Ther. Patents*, 1999, 9 (9), 1237-1248). The β3 subunit has received significant attention in recent drug discovery efforts. (W. J. Hoekstra, *Current Medicinal Chemistry* 1998, 5, 195). Antibodies and/or low-molecular weight compound antagonists of αvβ3 have shown efficacy in animal models (J. Samanen, *Current Pharmaceutical Design* 1997, 3, 545) and, thereby, offer promise as medicinal agents.

Integrin antagonists have typically been designed after the bioactive arginine-glycine-aspartate (RGD) conformation of peptides derived from the primary ligand vitronectin. The RGD motif is the general cell attachment sequence of many extracellular matrix, blood and cell surface proteins, as half of the approximately 20 known integrins bind the RGD-containing adhesion ligands. To discover RGD peptides with integrin selectivity, peptides with both restricted conformations and alterations of flanking residues have been studied. In particular, the structural requirements for interaction of the RGD sequence with GPIIb/IIIa and the inhibitory potential of a series of nonpeptidic mimetics on platelet aggregation and interactions with the extracellular matrix have been described (D. Varon, et al., *Thromb. Haemostasis*, 1993, 70(6), 1030-1036). Iterative synthesis of cyclic and alicyclic peptides and computer modelling have provided potent, selective agents as a platform for nonpeptide αv (as in αvβ3) integrin antagonist design.

Integrin antagonists have been implicated as useful for inhibiting bone resorption (S. B. Rodan and G. A. Rodan, Integrin Function In Osteoclasts, *Journal of Endocrinology*, 1997, 154: S47-S56). In vertebrates, bone resorption is mediated by the action of cells known as osteoclasts, large multinucleated cells of up to about 400 mm in diameter that resorb mineralized tissue, chiefly calcium carbonate and calcium phosphate. Osteoclasts are actively motile cells that migrate along the surface of bone and can bind to bone, secrete necessary acids and proteases, thereby causing the actual resorption of mineralized tissue from the bone. More specifically, osteoclasts are believed to exist in at least two physiological states, namely, the secretory state and the migratory or motile state. In the secretory state, osteoclasts are flat, attach to the bone matrix via a tight attachment zone (sealing zone), become highly polarized, form a ruffled border and secrete lysosomal enzymes and protons to resorb bone. The adhesion of osteoclasts to bone surfaces is an important initial step in bone resorption. In the migratory or motile state, osteoclasts migrate across bone matrix and do not take part in resorption until they again attach to bone.

Integrins are involved in osteoclast attachment, activation and migration. The most abundant integrin receptor on osteoclasts (e.g., on rat, chicken, mouse and human osteoclasts) is the αvβ3 integrin receptor, which is thought to interact in bone with matrix proteins that contain the RGD sequence. Antibodies to αvβ3 block bone resorption in vitro, indicating that this integrin plays a key role in the resorptive process. There is increasing evidence to suggest that αvβ3 ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia and glucocorticoid-induced osteoporosis. All of these conditions are characterized by bone loss, resulting from an imbalance between bone resorption, i.e. breakdown and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition that leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture. Individuals suffering from all the conditions listed above would benefit from treatment with agents that inhibit bone resorption.

Additionally, αvβ3 ligands have been found to be useful in treating and/or inhibiting restenosis (i.e. recurrence of stenosis after corrective surgery on the heart valve), atherosclerosis, diabetic retinopathy, macular degeneration and angiogenesis (i.e. formation of new blood vessels) and inhibiting viral disease.

Moreover, it has been postulated that the growth of tumors depends on an adequate blood supply, which in turn is dependent on the growth of new vessels into the tumor; thus, inhibition of angiogenesis can cause tumor regression in animal models (Harrison's Principles of Internal Medicine, 1991, 12*th* ed.). Therefore, αvβ3 antagonists, which inhibit angiogenesis can be useful in the treatment of cancer by inhibiting tumor growth (Brooks et al., *Cell,* 1994, 79, 1157-1164). Evidence has also been presented suggesting that angiogenesis is a central factor in the initiation and persistence of arthritic disease and that the vascular integrin αvβ3 may be a preferred target in inflammatory arthritis. Therefore, αvβ3 antagonists that inhibit angiogenesis may represent a novel therapeutic approach to the treatment of arthritic disease, such as rheumatoid arthritis (C. M. Storgard, et al., Decreased Angiogenesis and Arthritic Disease in Rabbits Treated with an αvβ3 Antagonist, *J. Clin. Invest.,* 1999, 103, 47-54).

Inhibition of the αvβ5 integrin receptor can also prevent neovascularization. A monoclonal antibody for αvβ5 has been shown to inhibit VEGF-induced angiogenesis in rabbit cornea and the chick chorioallantoic membrane model (M. C. Friedlander, et al., *Science,* 1995, 270, 1500-1502). Thus, αvβ5 antagonists are useful for treating and preventing macular degeneration, diabetic retinopathy, cancer and metastatic tumor growth.

Inhibition of αv integrin receptors can also prevent angiogenesis and inflammation by acting as antagonists of other β subunits, such as αvβ6 and αvβ8 (Melpo Christofidou-Solomidou, et al., Expression and Function of Endothelial Cell on Integrin Receptors in Wound-Induced Human Angiogenesis in Human Skin/SCID 25 Mice Chimeras, *American Journal of Pathology,* 1997, 151, 975-83; and, Xiao-Zhu Huang, et al., Inactivation of the Integrin β6 Subunit Gene Reveals a Role of Epithelial Integrins in Regulating Inflammation in the Lungs and Skin, *Journal of Cell Biology,* 1996, 133, 921-28).

An antagonist to the αv integrin can act to inhibit or minimize adhesions that result from either wounding or surgical adhesions. Post-surgical adhesions result as an anomaly of the wound healing process. Cell adhesion and the migration of fibroblasts are major players in this process. Trauma caused by the wounding, a surgical procedure, normal tissue manipulation in surgery, or bleeding during a surgical procedure can act to disrupt the peritoneum and expose the underlying stroma leading to the release of inflammatory mediators and an increase in capillary permeability. Inflammatory cells are subsequently liberated and the formation of a fibrin clot ensues. Adhesions are formed and intensify as fibroblasts and inflammatory cells continue to infiltrate this extracellular matrix rich in fibrin. The extracellular matrix is composed of adhesive proteins which act as ligands for the αv integrin. To inhibit post-surgical adhesion development, application of an αv antagonist could be parenteral, subcutaneous, intravenous, oral, topical or transdermal. The αv integrin antagonist can be administered before, during or after a surgical procedure. When administered during a surgical procedure the antagonists can be administered by aerosol, in a pad, gel, film, sponge, solution, suspension or similar suitable pharmaceutically acceptable carrier to the area in which the surgery is performed.

An aspect of the invention is a composition or medicament comprising a pharmaceutically appropriate carrier and any of the compounds of the present invention. Illustrative of the invention is a composition or medicament made by mixing an instant compound and a pharmaceutically appropriate carrier. Another illustration of the invention is a process for making a composition or medicament comprising mixing any of the compounds described above and a pharmaceutically appropriate carrier. Further illustrative of the present invention are compositions or medicaments comprising one or more compounds of this invention in association with a pharmaceutically appropriate carrier.

As used herein, the term "composition" is intended to encompass a product comprising the specified ingredients in the specified amounts, as well as any product which results, directly or indirectly, from combinations of the specified ingredients in the specified amounts for treating or ameliorating an αv integrin mediated disorder or for use as a medicament.

The compounds of the present invention are αv integrin inhibitors useful for treating or ameliorating an αv integrin mediated disorder. An aspect of the invention includes compounds that are selective inhibitors of an αv integrin receptor, or subtype thereof. In another aspect of the invention, the inhibitor is independently selective to the αvβ3 integrin receptor or the αvβ5 integrin receptor. An aspect of the invention also includes compounds that are inhibitors of a combination of αv integrin receptors, or subtypes thereof. In another aspect of the invention, the compound inhibitor simultaneously antagonizes both the αvβ3 integrin and the αvβ5 integrin receptor subtypes.

An aspect of the present invention includes a method for treating or ameliorating an αv integrin mediated disorder in a subject in need thereof comprising administering to the subject a therapeutically effective amount of a compound of Formula (I) or composition thereof.

The term "therapeutically effective amount" or "effective amount," as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

An aspect of the present invention includes a prophylactic method for preventing an αv integrin mediated disorder in a subject in need thereof comprising administering to the subject a prophylactically effective amount of a compound of Formula (I) or composition thereof.

Another aspect of the present invention includes the preparation of a medicament comprising a therapeutically effective amount of a compound of Formula (I) for use in preventing, treating or ameliorating an αv integrin mediated disorder in a subject in need thereof.

The term "administering" is to be interpreted in accordance with the methods of the present invention whereby an individual compound of the present invention or a composition thereof can be therapeutically administered separately at different times during the course of therapy or concurrently in divided or single combination forms. Prophylactic administration can occur prior to the manifestation of symptoms characteristic of an αv integrin mediated disease or disorder such that the disease or disorder is prevented or, alternatively, delayed in its progression. The instant invention is therefore to be understood as embracing all such regimes of simultaneous or alternating therapeutic or prophylatic treatment.

The term "subject" as used herein, refers to an animal, preferably a mammal, most preferably a human, which has been the object of treatment, observation or experiment and is at risk of (or susceptible to) developing a disease or disorder or having a disease or disorder related to expression of an αv integrin, or subtype thereof.

The term "αv integrin mediated disorder" refers to disorders and diseases associated with pathological unregulated or disregulated cell proliferation resulting from expression of an αv integrin, or subtype thereof.

The term "unregulated" refers to a breakdown in the process of regulating cell proliferation, as in a tumor cell. The term "disregulated" refers to inappropriate cell growth as a result of pathogenesis. The term "subtype" refers to a particular αv integrin receptor selected from those receptors making up the class of αv integrins, such as an αvβ3 integrin receptor or an αvβ5 integrin receptor.

The term "disorders and diseases associated with unregulated or disregulated cell proliferation" refers to disorders wherein cell proliferation by one or more subset of cells in a multicellular organism results in harm (such as discomfort or decreased life expectancy) to the organism. Such disorders can occur in different types of animals and humans and include, and are not limited to, cancers, cancer-associated pathologies, atherosclerosis, transplantation-induced vasculopathies, neointima formation, papilloma, lung fibrosis, pulmonary fibrosis, glomerulonephritis, glomerulosclerosis, congenital multicystic renal dysplasia, kidney fibrosis, diabetic retinopathy, macular degeneration, psoriasis, osteoporosis, bone resorption, inflammatory arthritis, rheumatoid arthritis, restenosis or adhesions.

The term "cancers" refers to, and is not limited to, glioma cancers, lung cancers, breast cancers, colorectal cancers, prostate cancers, gastric cancers, esophageal cancers, leukemias, melanomas, basal cell carcinomas and lymphomas. The term "cancer-associated pathologies" refers to, and is not limited to, unregulated or disregulated cell proliferation, tumor growth, tumor vascularization, angiopathy and angiogenesis. The term "angiogenesis" refers to, and is not limited to, unregulated or disregulated proliferation of new vascular tissue including, but not limited to, endothelial cells, vascular smooth muscle cells, pericytes and fibroblasts. The term "osteoporosis" refers to, and is not limited to, formation or activity of osteoclasts resulting in bone resorption. The term "restenosis" refers to, and is not limited to, in-stent stenosis and vascular graft restenosis.

The term "αv integrin expression" refers to expression of an αv integrin, or subtype thereof, which leads to unregulated or disregulated cell proliferation:
1. by cells which do not normally express an αv integrin, or subtype thereof,
2. by neoplastic cells,
3. in response to stimulation by a growth factor, hypoxia, neoplasia or a disease process,
4. as a result of mutations which lead to constitutive expression of an αv integrin, or subtype thereof.

The expression of an αv integrin, or subtype thereof, includes selective expression of an αv integrin or subtype thereof, selective expression of the αvβ3 integrin or the αvβ5 integrin subtypes, expression of multiple αv integrin subtypes or simultaneous expression of the αvβ3 integrin and the αvβ5 integrin subtypes. Detecting the expression of an αv integrin, or subtype thereof, in inappropriate or abnormal levels is determined by procedures well known in the art.

Another aspect of the present invention includes a method for treating or ameliorating a selective αvβ3 integrin mediated disorder in a subject in need thereof comprising administering to the subject a therapeutically effective amount of a compound of Formula (I) or composition thereof.

Another aspect of the present invention includes a method for treating or ameliorating a selective αvβ5 integrin mediated disorder in a subject in need thereof comprising administering to the subject a therapeutically effective amount of a compound of Formula (I) or composition thereof.

Another aspect of the present invention includes a method for treating or ameliorating a disorder simultaneously mediated by an αvβ3 and αvβ5 integrin in a subject in need thereof comprising administering to the subject a therapeutically effective amount of a compound of Formula (I) or composition thereof.

An aspect of the present invention includes a method for inhibiting αv integrin mediated neoplastic activity comprising administering to a neoplasm or to the microenvironment around the neoplasm an effective amount of a compound of Formula (I) or composition thereof.

The term "neoplastic activity" refers to unregulated or disregulated cell proliferation and the process of angiogenesis or the formation of new vasculature supporting a neoplasm in the endothelial microenvironment around the neoplasm.

The term "neoplasm" refers to tumor cells are cells having unregulated or disregulated proliferation as a result of genetic instability or mutation and an endothelium wherein the endothelial cells have unregulated or disregulated proliferation as a result of a pathogenic condition. Within the scope of the present invention, a neoplasm is not required to express the αv integrin, or subtype thereof, by itself and is not limited to a primary tumor of origin but also to secondary tumors occurring as a result of metastasis of the primary tumor. The term "administering to a neoplasm" refers to administering a compound of Formula (I) or composition thereof to the surface of a neoplasm, to the surface of a neoplastic cell or to the endothelial microenvironment around a neoplasm.

The term "inhibiting αv integrin mediated neoplastic activity" includes attenuating a tumor's growth by limiting its blood supply and, further, preventing the formation of new supportive vasculature by preventing the process of angiogenesis.

An aspect of the present invention includes a method for treating or ameliorating a disease mediated by cells pathologically expressing an αv integrin, or subtype thereof.

The term "disease mediated by cells pathologically expressing an αv integrin" refers to, and is not limited to, a disorders selected from cancers, cancer-associated pathologies, diabetic retinopathy, macular degeneration, osteoporosis, bone resorption, inflammatory arthritis, rheumatoid arthritis or restenosis.

An aspect of the present invention includes a method for sustained neoplasm regression in a subject in need thereof comprising administering to the subject an effective amount of a compound of Formula (I) or composition thereof; wherein the compound or composition thereof is conjugated with and delivers a therapeutic agent to to a neoplasm or to the microenvironment around the neoplasm; and, wherein the therapeutic agent induces apoptosis or attenuates unregulated or disregulated cell proliferation.

The terms "conjugated with" and "delivers a therapeutic agent" refers to a compound of Formula (I) or composition thereof bound to a therapeutic agent by a conjugation means known to those skilled in the art; wherein the compound or composition thereof acts as a targeting agent for antagonizing the αv integrin receptors of a neoplasm or the microenvironment thereof; and, wherein the conjugation means facilitates and selectively delivers the therapeutic agent to the neoplasm or the microenvironment thereof.

The term "therapeutic agent," including but not limited to Technetium[99], refers to imaging agents known to those skilled in the art.

An aspect of the present invention includes a method for use of a compound of Formula (I) or composition thereof advantageously coadministered in one or more tumor or cell anti-proliferation therapies including chemotherapy, radiation therapy, gene therapy or immunotherapy for preventing, treating or ameliorating an αv integrin mediated disorder.

The combination therapy can include:
1. co-administration of a compound of Formula (I) or composition thereof and a chemotherapeutic agent for preventing, treating or ameliorating an αv integrin mediated disorder,
2. sequential administration of a compound of Formula (I) or composition thereof and a chemotherapeutic agent for preventing, treating or ameliorating an αv integrin mediated disorder,
3. administration of a composition containing a compound of Formula (I) and a chemotherapeutic agent for preventing, treating or ameliorating an αv integrin mediated disorder, or,
4. simultaneous administration of a separate composition containing a compound of Formula (I) and a separate composition containing a chemotherapeutic agent for preventing, treating or ameliorating an αv integrin mediated disorder.

For example, the compounds of this invention are useful in combination therapies with at least one other chemotherapeutic agent for the treatment of a number of different cancers and advantageously appear to facilitate the use of a reduced dose of the chemotherapeutic agent that is recommended for a particular cancer or cell proliferation disorder. Therefore, it is contemplated that the compounds of this invention can be used in a treatment regime before the administration of a particular chemotherapeutic agent recommended for the treatment of a particular cancer, during administration of the chemotherapeutic agent or after treatment with a particular chemotherapeutic agent.

The term "chemotherapeutic agents" includes, and is not limited to, anti-angiogenic agents, anti-tumor agents, cytotoxic agents, inhibitors of cell proliferation and the like. The term "treating or ameliorating" includes, and is not limited to, facilitating the eradication of, inhibiting the progression of or promoting stasis of a malignancy. For example, an inhibitor compound of the present invention, acting as an anti-angiogenic agent can be administered in a dosing regimen with at least one other cytotoxic compound, such as a DNA alkylating agent.

Preferred anti-tumor agents are selected from the group consisting of cladribine (2-chloro-2'-deoxy-(beta)-D-adenosine), chlorambucil (4-(bis(2-chlorethyl)amino)benzenebutanoic acid), DTIC-Dome (5-(3,3-dimethyl-1-triazeno)-imidazole-4-carboxamide), platinum chemotherapeutics and nonplatinum chemotherapeutics. Platinum containing anti-tumor agents include, and are not limited to, cisplatin (CDDP) (cis-dichlorodiamineplatinum). Non-platinum containing anti-tumor agents include, and are not limited to, adriamycin (doxorubicin), aminopterin, bleomycin, camptothecin, carminomycin, combretastatin(s), cyclophosphamide, cytosine arabinoside, dactinomycin, daunomycin, epirubicin, etoposide (VP-16), 5-fluorouracil (5FU), herceptin actinomycin-D, methotrexate, mitomycin C, tamoxifen, taxol, taxotere, thiotepa, vinblastine, vincristine, vinorelbine and derivatives and prodrugs thereof. Each anti-tumor agent is administered in a therapeutically effective amount, which varies based on the agent used, the type of malignancy to be treated or ameliorated and other conditions according to methods well known in the art.

As will be understood by those skilled in the art, the appropriate doses of chemotherapeutic agents will be generally around those already employed in clinical therapies wherein the chemotherapeutics are administered alone or in combination with other chemotherapeutics. By way of example only, agents such as cisplatin and other DNA alkylating are used widely to treat cancer. The efficacious dose of cisplatin used in clinical applications is about 20 mg/m$^2$ for 5 days every three weeks for a total of three courses. Cisplatin is not absorbed orally and must therefore be delivered via injection intravenously, subcutaneously, intratumorally or intraperitoneally. Further useful agents include compounds that interfere with DNA replication, mitosis and chromosomal segregation. Such chemotherapeutic agents include adriamycin (doxorubicin), etoposide, verapamil or podophyllotoxin and the like and are widely used in clinical settings for tumor treatment. These compounds are administered through bolus injections intravenously at doses ranging from about 25 to about 75 mg/m² at 21 day intervals (for adriamycin) or from about 35 to about 50 mg/m² (for etoposide) intravenously or at double the intravenous dose orally. Agents that disrupt the synthesis and fidelity of polynucleotide precursors such as 5-fluorouracil (5-FU) are preferentially used to target tumors. Although quite toxic, 5-FU is commonly used via intravenous administration with doses ranging from about 3 to about 15 mg/kg/day.

Another aspect of the present invention includes a method for administering a compound of the present invention in combination with radiation therapy. As used herein, "radiation therapy" refers to a therapy that comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

An aspect of the present invention includes a method for administering a compound of the present invention in combination with a gene therapy or for use of a compound of the present invention as a gene therapy means. The term "gene therapy" refers to a therapy targeting angiogenic endothelial cells or tumor tissue during tumor development. Gene therapy strategies include the restoration of defective cancer-inhibitory genes, cell transduction or transfection with anti-sense DNA (corresponding to genes coding for growth factors and their receptors) and the use of "suicide genes." The term "gene therapy means" refers to the use of a targeting vector comprising a combination of a cationic nanoparticle coupled to an αv-targeting ligand to influence blood vessel biology; whereby genes are selectively delivered to angiogenic blood vessels (as described in Hood, J. D., et al, Tumor Regression by Targeted Gene Delivery to the Neovasculature, *Science*, Jun. 28, 2002, 296, 2404-2407).

Another aspect of the present invention includes a method for treating or ameliorating an αv integrin mediated neoplasm in a subject in need thereof comprising administering to the subject an effective amount of a gene therapy combination product comprising a compound of Formula (I) or composition thereof and a gene therapeutic agent; wherein the product is delivered or "seeded" directly to a neoplasm or the microenvironment thereof by antagonizing the αv integrin receptors of the neoplasm or microenvironment thereof.

The term "delivered or 'seeded' directly to a neoplasm" includes using a compound of Formula (I) or composition thereof as a gene therapy means whereby the compound or composition thereof functions as a targeting agent which directs the conjugate to its intended site of action (i.e., to neoplastic vascular endothelial cells or to tumor cells). Because of the specific interaction of the αv integrin inhibitor as a targeting agent and its corresponding αv integrin receptor site, a compound of this invention can be administered with high local concentrations at or near a targeted αv integrin receptor, or subtype thereof, thus treating the αv integrin mediated disorder more effectively.

Another aspect of the present invention includes a method for administering a compound of the present invention in combination with an immunotherapy. As used herein, "immunotherapy" refers to a therapy targeted to a particular protein involved in tumor development via antibodies specific to such protein. For example, monoclonal antibodies against vascular endothelial growth factor have been used in treating cancers.

An aspect of the present invention includes a method for tumor imaging in a subject in need thereof comprising advantageously coadministering to the subject an effective amount of a compound of Formula (I) or composition thereof; wherein the compound or composition thereof is conjugated with and delivers a non-invasive tumor imaging agent to a tumor or to the microenvironment around the tumor.

The terms "conjugated with" and "delivers a non-invasive tumor imaging agent" refers to a compound of Formula (I) or composition thereof bound to an imaging agent by a conjugation means known to those skilled in the art; wherein the compound or composition thereof acts as a targeting agent for antagonizing the αv integrin receptors of a neoplasm or the microenvironment thereof; and, wherein the conjugation means facilitates and selectively delivers the imaging agent to the neoplasm or the microenvironment thereof (as described in PCT Application WO00/35887, WO00/35492, WO00/35488 or WO99/58162). The term "imaging agent," including but not limited to Technetium[99], refers to imaging agents known to those skilled in the art. The term "conjugation means," including but not limited to appending a compound to a linking group followed by conjugation with an imaging agent chelating group, refers to means known to those skilled in the art.

An aspect of the present invention includes a composition comprising a compound of Formula (I), or pharmaceutically acceptable salt thereof, in association with a pharmaceutically acceptable carrier. Compositions contemplated within this invention can be prepared according to conventional pharmaceutical techniques. A pharmaceutically acceptable carrier may also (but need not necessarily) be used in the composition of the invention.

The term "pharmaceutically acceptable" refers to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

The composition may take a wide variety of forms depending on the form of preparation desired for administration including, but not limited to, intravenous (both bolus and infusion), oral, nasal, transdermal, topical with or without occlusion, and injection intraperitoneally, subcutaneously, intramuscularly, intratumorally or parenterally, all using forms well known to those of ordinary skill in the pharmaceutical arts. The composition may comprise a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation. Compositions suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition may be presented in a form suitable for once-weekly or once-monthly administration; for example, an insoluble salt of the active compound, such as the decanoate salt, may be adapted to provide a depot preparation for intramuscular injection. In preparing the compositions in oral dosage form, one or more of the usual pharmaceutical carriers may be employed, including necessary and inert pharmaceutical excipients, such as water, glycols, oils, alcohols, flavoring agents, preservatives, coloring agents, syrup and the like; in the case of oral liquid preparations, carriers such as starches, sugars, diluents, granulating agents, lubricants, binders, disintegrating agents and the like may be employed.

The dosage unit (tablet, capsule, powder, injection, suppository, measured liquid dosage and the like) containing the pharmaceutical compositions herein will contain an amount of the active ingredient necessary to deliver a therapeutically effective amount as described above. The composition may contain from about 0.001 mg to about 5000 mg of the active compound or prodrug thereof and may be constituted into any form suitable for the mode of administration selected for a subject in need.

An aspect of the present invention contemplates a therapeutically effective amount in a range of from about 0.001 mg to 1000 mg/kg of body weight per day. Another aspect of the present invention includes a range of from about 0.001 to about 500 mg/kg of body weight per day. A further aspect of the present invention includes a range of from about 0.001 to about 300 mg/kg of body weight per day. The compounds may be administered according to a dosage regimen of from about 1 to about 5 times per day and still more preferably 1, 2 or 3 times a day.

For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages to be administered may be readily determined by those skilled in the art and will vary depending factors associated with the particular patient being treated (age, weight, diet and time of administration), the severity of the condition being treated, the compound being employed, the mode of administration and the strength of the preparation. The use of either daily administration or post-periodic dosing may be employed.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.001 to about 5000 mg of the active ingredient of the present invention. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

For oral administration in the form of a tablet or capsule, the active drug component can be optionally combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in which the compound of formula (I) may be incorporated for administration orally or by injection include, aqueous solutions, suitably flavored syrups, aqueous or oil suspensions and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations that generally contain suitable preservatives are employed when intravenous administration is desired.

As is also known in the art, the compounds may alternatively be administered parenterally via injection of a formulation consisting of the active ingredient dissolved in an inert liquid carrier. The injectable formulation can include the active ingredient mixed with an appropriate inert liquid carrier. Acceptable liquid carriers include vegetable oils such as peanut oil, cottonseed oil, sesame oil and the like, as well as organic solvents such as solketal, glycerol and the like. As an alternative, aqueous parenteral formulations may also be used. For example, acceptable aqueous solvents include water, Ringer's solution and an isotonic aqueous saline solution. Further, a sterile non-volatile oil can usually be employed as a solvent or suspending agent in the aqueous formulation. The formulations are prepared by dissolving or suspending the active ingredient in the liquid carrier such that the final formulation contains from 0.005 to 10% by weight of the active ingredient. Other additives including a preservative, an isotonizer, a solubilizer, a stabilizer and a pain-soothing agent may adequately be employed.

Advantageously, compounds of Formula (I) may be administered in a single daily dose, or the total daily dosage may be administered in divided doses of two, three or four times daily. Furthermore, compounds of the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

Because of their ease of administration, tablets and capsules represent an advantageous oral dosage unit form, wherein solid pharmaceutical carriers are employed. If desired, tablets may be sugarcoated or enteric-coated by standard techniques. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The compositions of the present invention also include a composition for slow release of the compound of the invention. The composition includes a slow release carrier (typically, a polymeric carrier) and a compound of the invention. In preparation for slow release, a slow release carrier, typically a polymeric carrier and a compound of the invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the invention. Slow release biodegradable carriers are also well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50-200 nm in diameter and most preferably about 100 nm in diameter).

The present invention also provides methods to prepare the pharmaceutical compositions of this invention. A compound of Formula (I) as the active ingredient is intimately admixed with a pharmaceutical carrier according to conventional pharmaceutical compounding techniques, which carrier may take a wide variety of forms depending on the form of preparation desired for administration. In preparing the compositions in oral dosage form, any of the usual pharmaceutical media may be employed. For solid oral dosage forms, suitable carriers and additives include starches, sugars, diluents, granulating agents, lubricants, binders, disintegrating agents and the like. For liquid oral preparations, suitable carriers and additives include water, glycols, oils, alcohols, flavoring agents, preservatives, coloring agents and the like. Additionally, liquid forms of the active drug component can be combined in suitably flavored suspending or dispersing agents such as the synthetic and natural gums, including for example, tragacanth, acacia, methyl-cellulose and the like. Other dispersing agents that may be employed include glycerin and the like.

The compounds of the present invention can also be administered in the form of liposome delivery systems, such as small unilamellar vesicles, large unilamellar vesicles and multilamellar vesicles. Liposomes containing delivery systems as well known in the art are formed from a variety of phospholipids, such as cholesterol, stearylamine or phosphatidylcholines.

Abbreviations used in the instant specification, particularly the Schemes and Examples, are as follows:

| Boc | tert-butoxycarbonyl |
|---|---|
| BSA | Bovine Serum Albumen |
| Cod | Cyclooctadiene |
| d/hr/min/rt | day(s)/hour(s)/minute(s)/room temperature |
| DBC | 2,6-Dichlorobenzoylchloride |
| DCM | Dichloromethane |
| DIEA | Diisopropylethylamine |
| DMA | Dimethylacetamide |
| DMAP | Dimethylaminopyridine |
| DMF | N,N-Dimethylformamide |
| DMSO | Dimethyl sulfoxide |
| EDC | N-ethyl-N'-dimethylaminopropylcarbodiimide hydrochloride |
| Et$_2$O | Diethyl ether |
| EtOAc | Ethyl acetate |
| EtOH | Ethanol |

-continued

| HATU | O-(7-azabenzotriazol-1-yl)-1,1,3,3-tetramethyluronium Hexafluorophosphate |
|---|---|
| HBTU | O-Benzotriazol-1-yl-N,N,N',N'-tetramethyluronium Hexafluorophosphate |
| HCl | Hydrochloric acid |
| HOBt | 1-Hydroxybenzotriazole |
| HPLC | High Performance Liquid Chromatography |
| LDA | lithium diisopropylamide |
| LiHMDS | lithium hexamethyldisilylamide |
| Me | Methyl |
| MeOH | Methanol |
| MeCN | Acetonitrile |
| NaHMDS | sodium hexamethyldisilylamide |
| NaOH | Sodium hydroxide |
| ND | Not Determined |
| NMM | N-Methylmorpholine |
| PBS | Phosphate Buffer Solution |
| Ph | Phenyl |
| RP-HPLC | Reverse Phase High Performance Liquid Chromatography |
| rt | Room Temperature |
| SDS | Sodium dodecasulfate |
| TEA | Triethylamine |
| TFA | Trifluoroacetic acid |
| THF | Tetrahydrofuran |
| Thi | Thienyl |
| TMS | Tetramethylsilane |
| TFA | Trifluoroacetic acid |
| Tol | Toluene |

General Synthetic Methods

Representative compounds of the present invention can be synthesized in accordance with the general synthetic methods described below and are illustrated more particularly in the schemes that follow. Since the schemes are illustrations whereby intermediate and target compounds of the present invention may be prepared, the invention should not be construed as being limited by the chemical reactions and conditions expressed. Additional representative compounds and stereoisomers, racemic mixtures, diastereomers and enantiomers thereof can be synthesized using the intermediates prepared in accordance with these schemes and other materials, compounds and reagents known to those skilled in the art. All such compounds, stereoisomers, racemic mixtures, diastereomers and enantiomers thereof are intended to be encompassed within the scope of the present invention. The preparation of the various starting materials used in the schemes is well within the skill of persons versed in the art.

Scheme A

Scheme A describes a method for preparing a target compound of Formula (I) (wherein $R_1$ and W are as previously defined within the scope of the invention. Removal of the Boc-protective group from a $R_a$ substituted (wherein $R_a$ is $C_{1-4}$alkyl) Compound A1 was accomplished under acidic conditions (by using an acid such as an acidic mixture of TFA and DCM or an inorganic acid in an appropriate solvent such as dioxane) and resulted in formation of a piperidine Compound A2. Coupling of the piperidine Compound A2 with a carboxylic acid Compound A3 under standard coupling conditions (by using a mixture of coupling agents such as HOBt/EDC, HOBT/HBTU or isobutyl chloroformate in the presence of a suitable base such as NMM or DIEA) afforded the ester Compound A4. Hydrolysis of the ester Compound A4 under acidic or basic conditions yielded a target compound Formula (I). The individual isomers of Formula (I) can be achieved through the chiral separation of intermediate A1-A4, and elaboration of the chiral intermediates to compounds of Formula (I).

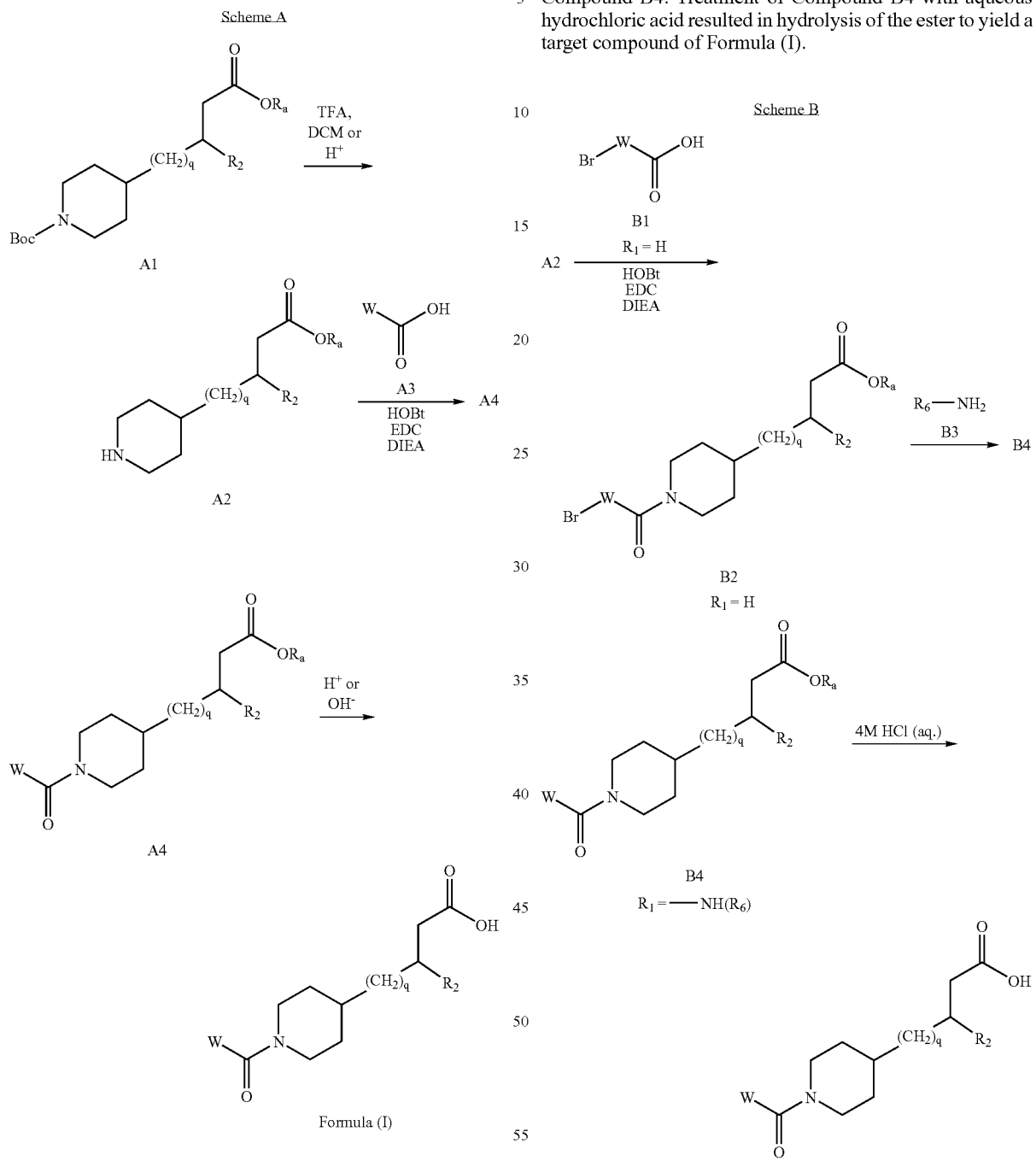

Scheme B

Scheme B describes an alternative method for preparing a target compound of Formula (I) (wherein $R_1$ is —NH($R_6$) and W is —$(CH_2)_{0-4}$alkyl-). Condensation of a Compound A2 with a Compound B1 (wherein $R_1$ is H) possessing a suitable leaving group such as a halogen or a mesylate or tosylate under standard coupling conditions (by using a mixture of coupling agents such as HOBt/EDC, HOBT/HBTU or isobutyl chloroformate in the presence of a suitable base such as NMM or DIEA) resulted in the formation of Compound B2. Reaction of Compound B2 with a substituted amine Compound B3 in the presence of an appropriate base such as LiHMDS, NaHMDS or LDA resulted in the formation of Compound B4. Treatment of Compound B4 with aqueous hydrochloric acid resulted in hydrolysis of the ester to yield a target compound of Formula (I).

Scheme C

Scheme C describes an alternative method whereby a Compound A1 may be prepared. Carboxylic acid Compound C1 was transformed into an amide Compound C2 using N-methyl-O-methylhydroxylamine in the presence of an appropriate activating agent such as HOBt, HBTU, HATU, isobutyl chloroformate or the like. Reaction of the amide Compound C2 with an in situ prepared aryl lithium species, a Grignard reagent or the like resulted in the formation of a ketone Compound C3. The ketone Compound C3 was converted to a mixture of cis and trans isomers of an α,β-unsaturated ester Compound C5 upon reaction with an appropriately substituted phosphorane or phosphonate Compound C4 in the presence of a base such as LiHMDS, NaHMDS, LDA or the like. Conversion of Compound C5 to Compound A1 was accomplished under hydrogenolysis conditions (wherein a hydrogen overpressure of from about 10 to about 50 psi was used) in the presence of an appropriate catalyst such as 5 or 10% palladium on carbon.

under hydrogenolysis conditions using Lindlar's catalyst in pyridine. Condensation of the allylic alcohol Compound D4 with an $R_a$ substituted 3-chloro-3-oxopropionate Compound D5 in the presence of a base such as TEA, DIEA or the like resulted in the formation of a mixed ester Compound D6. Treatment of Compound D6 with chlorotrimethylsilane in the presence of a suitable base such as sodium hydride, potassium hydride, LDA or the like gave rise to an intermediate silyl ketene acetal which rearranged upon heating in a suitable solvent such as THF or $Et_2O$ to a mixed ester Compound D7. Decarboxylation of the ester Compound D7 to form Compound D8 was accomplished upon heating Compound D7 under vacuum. Reduction of the double bond in Compound D8 was accomplished under standard hydrogenation conditions, applying a hydrogen overpressure (of from about 10 to about 50 psi) in the presence of an appropriate catalyst such as 5 or 10% palladium on carbon resulted in formation of a target compound Compound A1 in which $(CH_2)_q$ is $(CH_2)_{2-3}$.

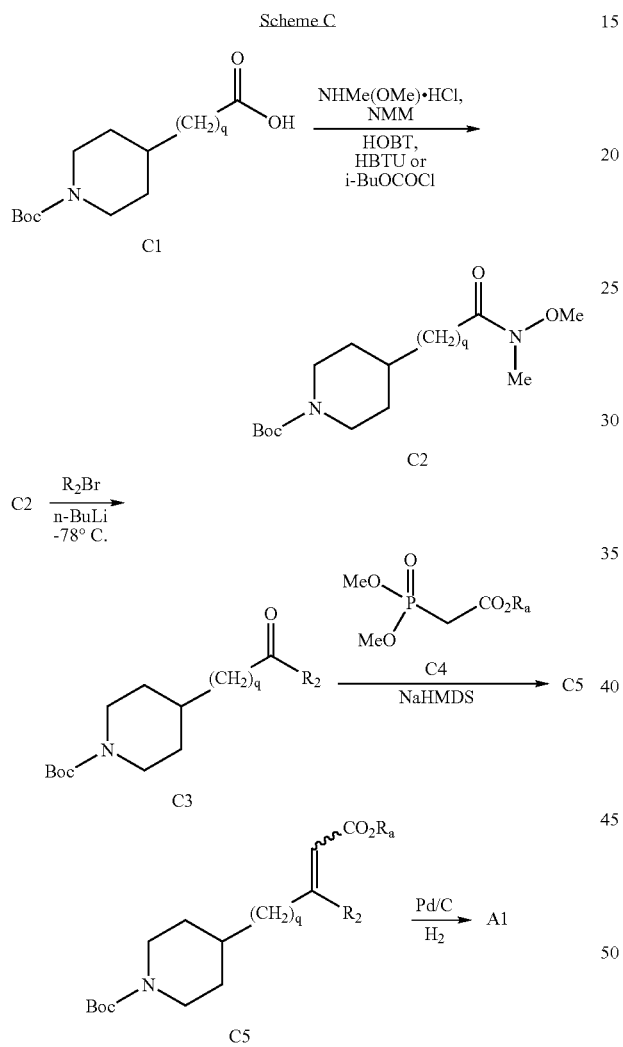

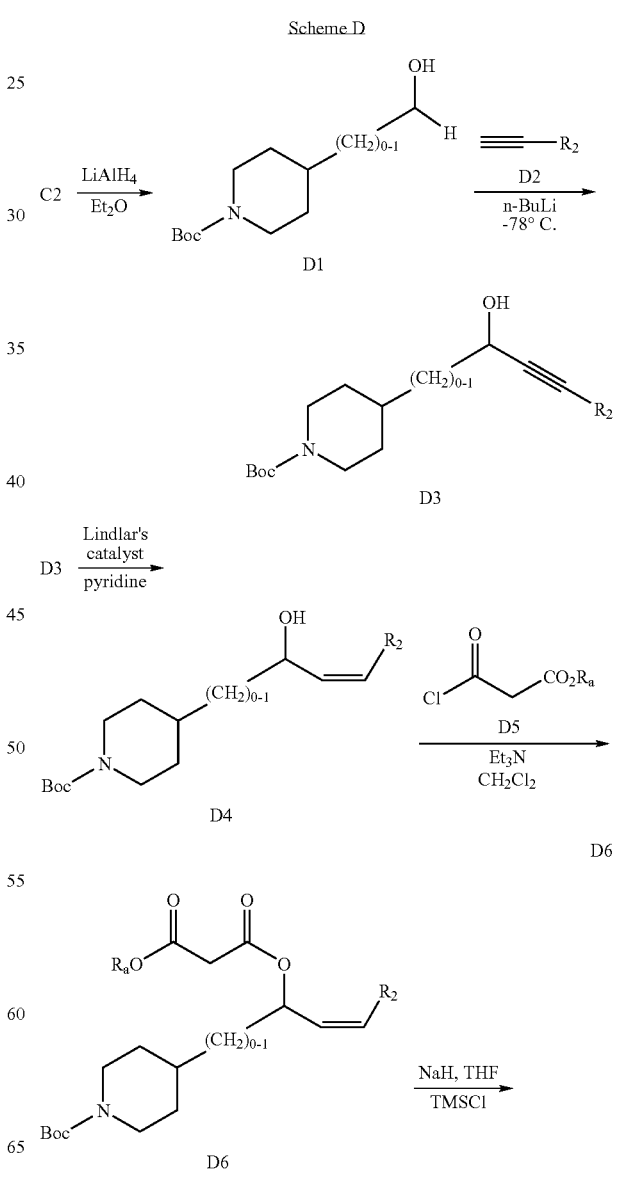

Scheme D

Scheme D describes an alternative method for the synthesis of a Compound A1 in which $(CH_2)_q$ is $(CH_2)_{2-3}$. Reaction of an amide Compound C2 with an appropriate reducing agent such as lithium aluminum hydride or the like resulted in the formation of an aldehyde Compound D1. Condensation of an in situ generated acetylide Compound D2 with the aldehyde Compound D1 at a low temperature resulted in formation of a propargylic alcohol Compound D3. The alkyne Compound D3 was selectively reduced to a cis-olefin Compound D4

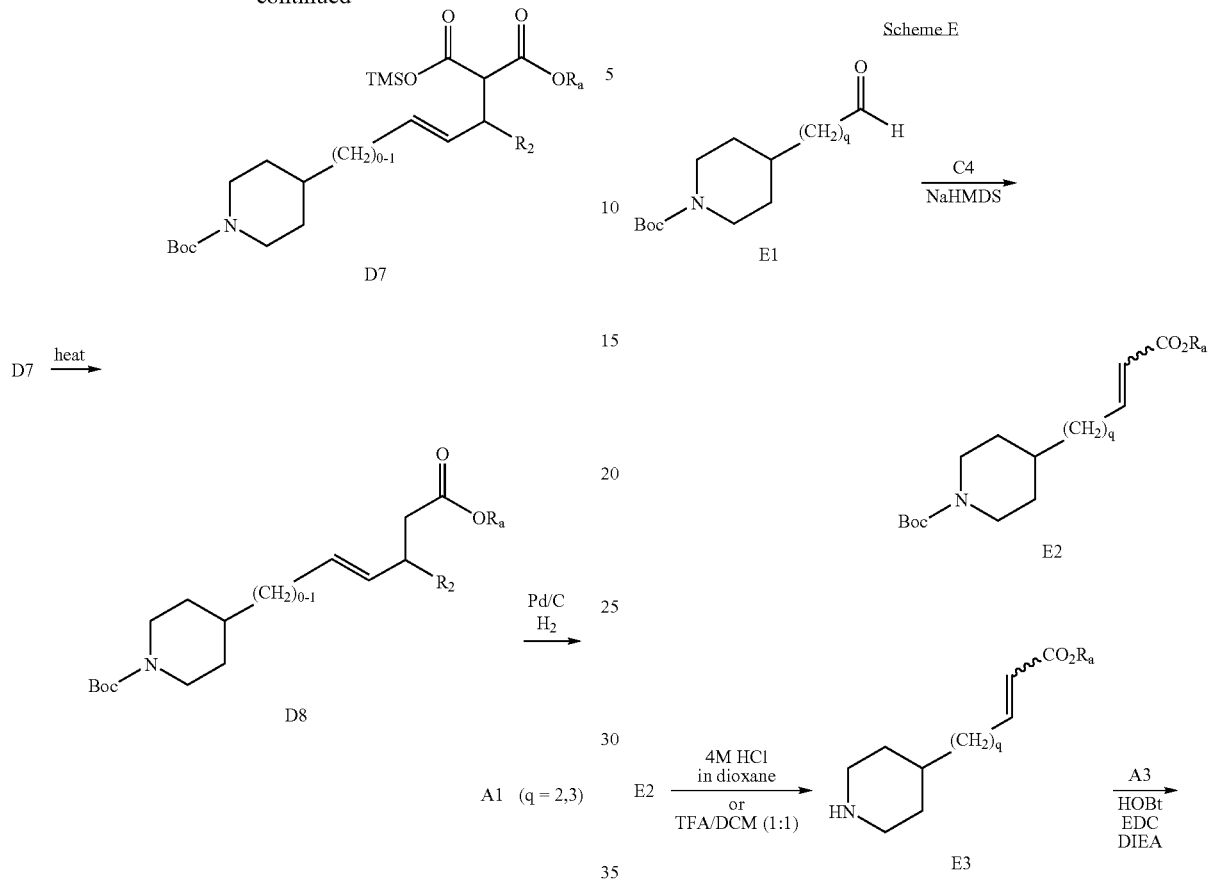

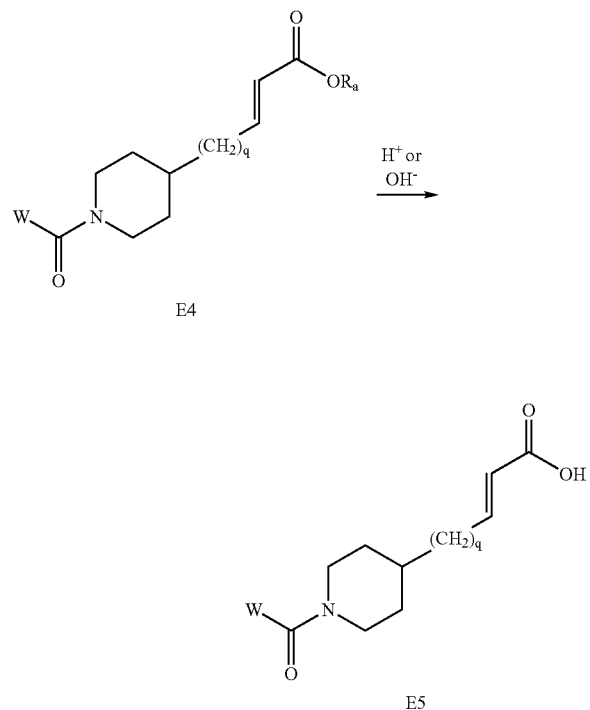

Scheme E

Scheme E describes an alternative method for the synthesis of a target compound of Formula (I.2) (wherein $R_2$ for a compound of Formula (I) is hydrogen, $R_1$ and W are as previously defined. Condensation of an aldehyde Compound E1 using an appropriate carbalkoxymethylene triphenylphosphorane (Wittig reaction) or a trialkyl phosphonoacetate (Horner-Emmons reaction) resulted in the formation of an α,β-unsaturated ester Compound E2. Treatment of Compound E2 under acidic conditions (using an acid such as a 1:1 mixture of TFA in DCM, 4N HCl in dioxane or the like) resulted in the removal of the Boc-protective group, resulting in formation of a substituted piperidine Compound E3. Coupling of the piperidine Compound E3 with a carboxylic acid Compound A3 under standard coupling conditions (using a mixture of coupling agents such as HOBt/EDC, HOBT/HBTU or isobutyl chloroformate in the presence of a suitable base such as NMM or DIEA) resulted in an ester Compound E4. Hydrolysis of the ester Compound E4 under acidic or basic conditions yielded an α,β-unsaturated acid Compound E5. Reduction of the double bond in Compound E5 was accomplished under standard hydrogenation conditions, applying hydrogen overpressure (of from about 10 to about 50 psi) in the presence of an appropriate catalyst such as 5 or 10% palladium on carbon and resulted in the formation of a target compound of Formula (I.2).

-continued

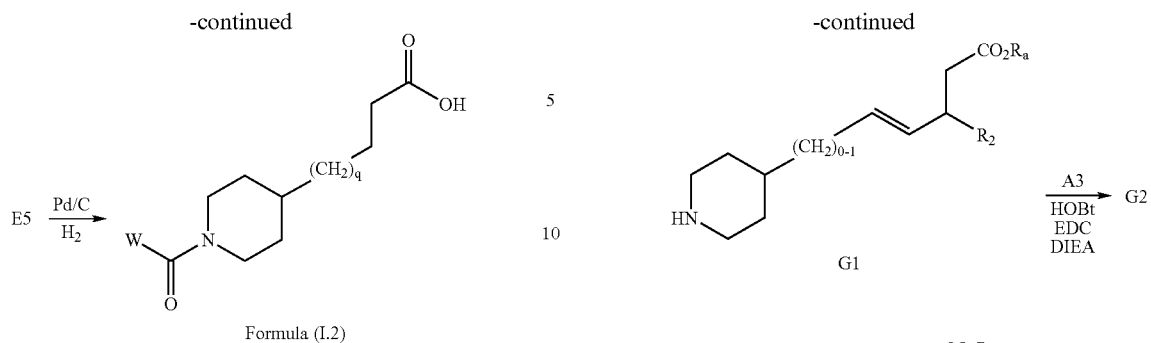

Formula (I.2)

Scheme F

Scheme F describes an alternative method whereby a target Compound A1 may be prepared. A racemic E/Z-mixture of an α,β-unsaturated ester Compound E2 was reacted with an $R_2$ substituted boronic acid Compound F1 in the presence of an appropriate transition metal catalyst such as Rhodium or Indium to yield a target Compound A1.

Scheme F $$R_2\text{---}B(OH)_2$$
$$E2 \xrightarrow[\text{Rh(I) cat.}]{F1} A1$$

Scheme G

Scheme G describes an alternative method for the synthesis of a target compound of Formula (I.3) (wherein $(CH_2)_q$ for a compound of Formula (I) is —$(CH_2)_{2-3}$—, $R_1$ is as previously defined and W is —$(CH_2)_{0-4}$alkyl-). The Boc-protecting group on Compound D8 was removed under acidic conditions (using an acid such as a 1:1 mixture of TFA in DCM, 4N HCl in dioxane or the like) to yield a substituted piperidine Compound G1. Coupling of the piperidine Compound G1 with a carboxylic acid Compound A3 under standard coupling conditions (using a mixture of coupling agents such as HOBt/EDC, HOBT/HBTU or isobutyl chloroformate in the presence of a suitable base such as NMM or DIEA) led to formation of an ester Compound G2. The ester Compound G2 was be converted to Compound G3 upon exposure to strong acidic or basic aqueous conditions (in the presence of a strong acid or base such as concentrated HCl or NaOH). The double bond in Compound G3 was reduced using standard hydrogenation conditions, applying hydrogen overpressure (of from about 10 to about 50 psi) in the presence of an appropriate catalyst such as 5 or 10% palladium on carbon and resulted in the formation of a target compound of Formula (I.3).

Scheme G

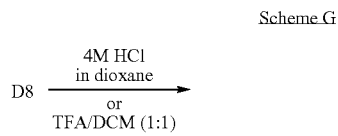

-continued

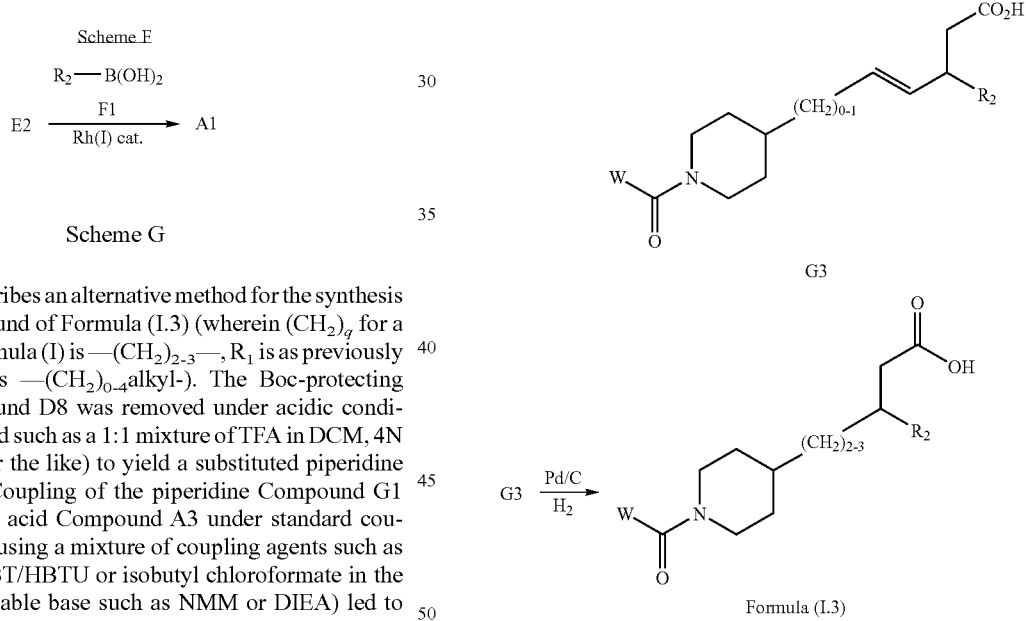

Scheme H

Scheme H describes a method for the synthesis of a target compound of Formula (I.3a) (wherein $R_1$ for a compound of Formula (I.3) is —$NH(R_5)$, W is —$(CH_2)_{0-4}$alkyl- and an $R_5$ heteroaryl substituent is reduced to a partially unsaturated heterocyclyl substituent) by reduction of the double bond in a Compound G3a (wherein $R_1$ in a Compound G3 is —NH($R_5$)) using standard hydrogenation conditions, applying hydrogen overpressure (of from about 10 to about 50 psi) in the presence of an appropriate catalyst such as 5 or 10% palladium on carbon, accompanied by standard reduction of $R_5$ to yield a target compound of Formula (I.3a).

Scheme H

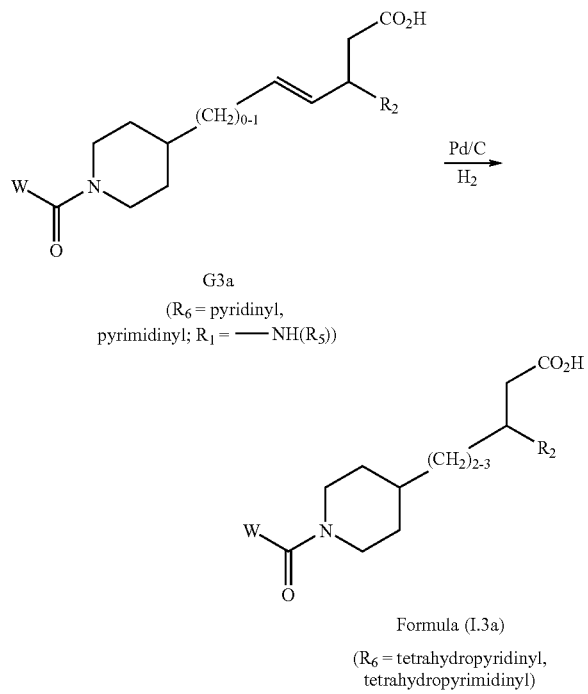

Formula (I.3a)
($R_6$ = tetrahydropyridinyl, tetrahydropyrimidinyl)

Scheme I

Scheme I describes an alternative method for the synthesis of a target Compound B4a (wherein $(CH_2)_q$ for the Compound B4 is not limited to —$(CH_2)_{2-3}$—, $R_6$ is as previously defined, $R_1$ is H, and W is —$(CH_2)_{0-4}$alkyl-). Condensation of a Compound A2 under standard coupling conditions (using a mixture of coupling agents such as HOBt/EDC, HOBT/HBTU or isobutyl chloroformate in the presence of a suitable base such as NMM or DIEA) with a protected amino acid Compound I1 resulted in the formation of a target Compound B4a.

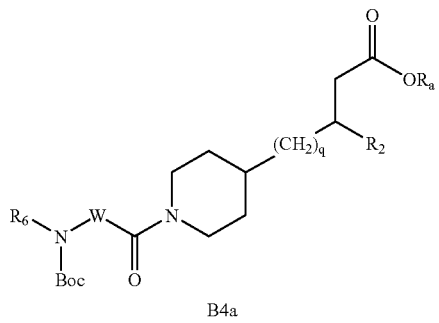

Scheme J

Scheme J describes a method for the synthesis of a target Compound A1 a (wherein $R_2$ in a Compound A1 is a heteroaryl substituent that has been reduced to a partially or fully unsaturated heterocyclyl substituent). The double bond in Compound C5a (wherein $R_2$ in a Compound C5 is a unsaturated heteroaryl substituent) was reduced under standard hydrogenation conditions, applying hydrogen overpressure (of from about 10 to about 50 psi) in the presence of an appropriate catalyst such as 5 or 10% palladium on carbon, accompanied by standard reduction of $R_2$ to yield a target Compound A1a. Compound A1a can be separated into its individual optical isomers by chiral chromatography at this stage. In addition, Compound A1a can be alkylated on the $R_2$ heteroatom using the appropriate alkylating agent such as iodomethane and the appropriate base such as 2,6-di-tert-butylpyridine to yield A1b.

Scheme J

Scheme K

Scheme K describes a method for preparing a target compound of Formula I4. Treatment of a compound of Formula I with an appropriate alcohol in the presence of a coupling agent such as 1,3-dicyclohexylcarbodiimide and an activating agent such as dimethylaminopyridine or the like resulted in the formation of target compound of Formula (I4). Alternatively, a compound of Formula I may be treated with an alkyl halide in the presence of a suitable base such as NMM or DIEA to yield a target compound of Formula I4.

-continued

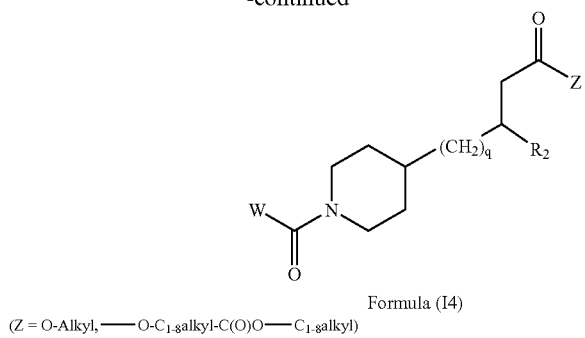

Formula (I4)

(Z = O-Alkyl, —O-C$_{1-8}$alkyl-C(O)O—C$_{1-8}$alkyl)

Scheme L

Scheme L describes a method for the synthesis of a target compound of Formula A1b (wherein R$_2$ in a Compound A1b is a hydroxyaryl, aminoaryl, or thiophenyl substituent that has been deprotected). The double bond in Compound C5b (wherein R$_2$ in a Compound C5 is an O-protected hydroxyaryl, N-protected anilino, or S-protected thioaryl substituent) was reduced under standard hydrogenation conditions, applying hydrogen overpressure (of from about 10 to about 50 psi) in the presence of an appropriate catalyst such as 5% or 10% palladium on carbon, accompanied by removal of the protective group to yield hydroxyaryl or anilino compound A1b. Alternatively, the protective group can be removed via basic or acidic hydrolysis in a subsequent step.

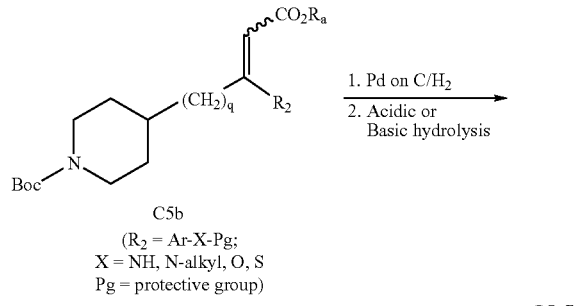

Scheme M

Scheme M describes a method for preparing a target compound of Formula (I5) (wherein R1 and W are as previously defined). The ketone Compound C3 was converted to a mixture of cis and trans isomers of an α,β-unsaturated nitriles Compound M2 upon reaction with an appropriately substituted phosphorane or phosphonate Compound M1 in the presence of a base such as LiHMDS, NaHMDS, LDA or the like. Conversion of Compound M2 to Compound M3 was accomplished under hydrogenolysis conditions (wherein a hydrogen overpressure of about 5 psi was used) in the presence of an appropriate catalyst such as 5 or 10% palladium on carbon. Removal of the Boc-protective group from Compound M3 was accomplished under acidic conditions (by using an acid such as an acidic mixture of TFA and DCM or an inorganic acid in an appropriate solvent such as dioxane) and resulted in formation of a piperidine Compound M4. Coupling of the piperidine Compound M4 with a carboxylic acid Compound A3 under standard coupling conditions (by using a mixture of coupling agents such as HOBt/EDC, HOBT/HBTU or isobutyl chloroformate in the presence of a suitable base such as NMM or DIEA) afforded the nitrile Compound M5. Hydrolysis of the nitrile Compound M5 under acidic conditions yielded a target compound of Formula (I5).

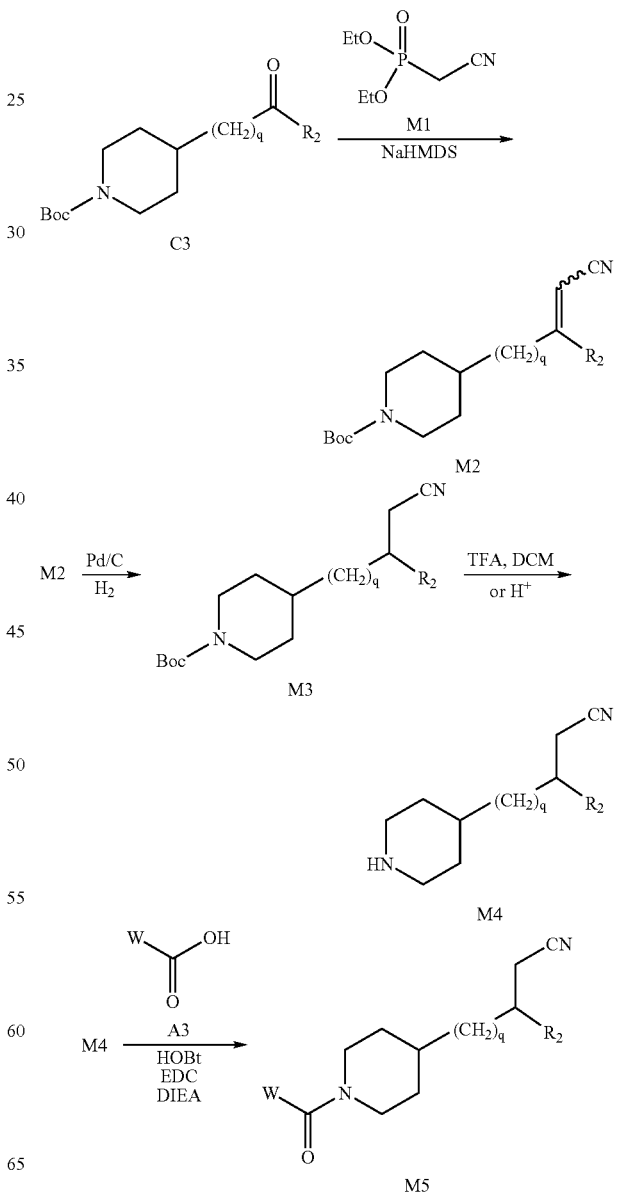

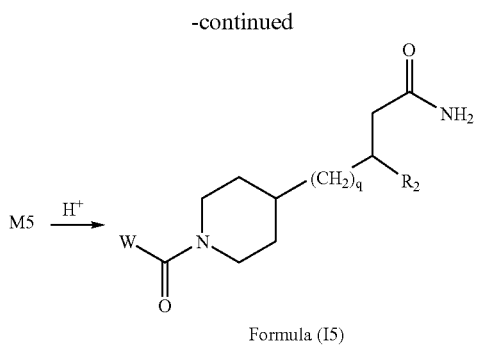

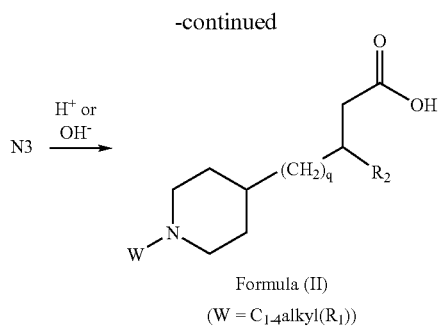

Specific Synthetic Methods

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Microanalyses were performed at Robertson Microlit Laboratories, Inc., Madison, N.J. and are expressed in percentage by weight of each element per total molecular weight. Nuclear magnetic resonance (NMR) spectra for hydrogen atoms were measured in the indicated solvent with (TMS) as the internal standard on a Bruker Avance (300 MHz) spectrometer. The values are expressed in parts per million downfield from TMS. The mass spectra (MS) were determined on a Micromass Platform LC spectrometer as (ESI) m/z (M+H$^+$) using an electrospray technique. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Scheme N

Scheme N describes a method for the synthesis of a target compound of Formula (II) (wherein W is defined as $C_{1-4}$alkyl ($R_1$)). Carboxylic acid Compound A3 was transformed into alcohol Compound N1 using an appropriate reducing agent such as lithium aluminum hydride or the like. Alcohol Compound N1 was transformed into aldehyde Compound N2 using an appropriate oxidizing agent such as pyridinium chlorochromate or the like. Coupling of the aldehyde Compound N2 with a piperidine Compound A2 under standard reductive amination conditions using a reducing agent such as sodium triacetoxyborohydride or the like afforded the ester Compound N3. Hydrolysis of the ester Compound N3 under acidic or basic conditions yielded a target compound Formula (II).

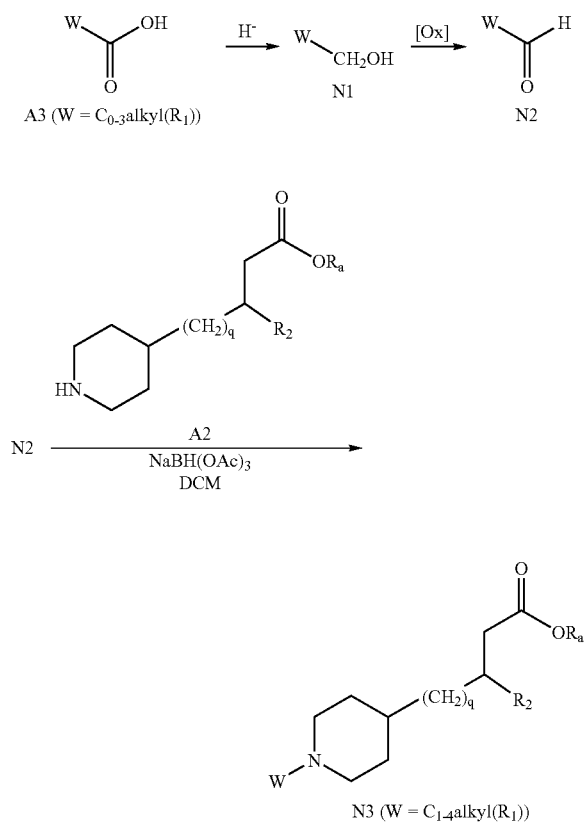

Example 1

1-[[3-[(1,4,5,6-Tetrahydro-2-pyrimidinyl)amino]phenyl]acetyl]-4-piperidinepropanoic acid (Cpd 1)

Methyl iodide (3.21 mL, 51.6 mmol) was added to a solution of 3,4,5,6-tetrahydro-2-pyrimidinethiol Compound 1a (6.00 g, 51.6 mmol) in absolute ethanol (45 mL). The mixture was refluxed for 3 h, concentrated and dried in vacuo to yield Compound 1b as a colorless oil. MS (ES+) m/z 172 (M+41). $^1$H NMR (DMSO-d$_6$, 300 MHz) δ 1.89 (m, 2H), 2.61 (s, 3H), 3.61 (m, 4H), 9.56 (s, 1H).

Boc$_2$O (11.33 g, 51.91 mmol) was added to a solution of Compound 1b (13.4 g, 51.9 mmol) and TEA (7.23 mL, 51.9 mmol) in DCM (70 mL) at 0° C. and the mixture was stirred at rt for 2 d. The organic layer was washed with water (2×75 mL), dried (Na$_2$SO$_4$) and concentrated to give Compound 1c. MS (ES+) m/z 231 (M+H$^+$).

A solution of Compound 1c (0.91 g, 3.95 mmol) and 3-aminophenylacetic acid Compound 1d (0.59 g, 3.95 mmol) in DMA (5 mL) was heated to 80-85° C. for 4 d. The mixture was cooled to rt and diluted with MeCN. The solid was filtered and washed with MeCN and Et$_2$O, then dried in vacuo. Water was added and the pH was adjusted to pH 1-2 by adding conc. HCl dropwise. The resulting solution was lyophilized to give Compound 1e as a light yellow solid. MS (ES+) m/z 234 (M+H$^+$).

Boc$_2$O (19 g, 87 mmol) and TEA (13 mL, 96 mmol) were added to a solution of 4-piperidinemethanol Compound 1f (10 g, 87 mmol), DMAP (catalytic amount), dioxane (90 mL) and water (45 mL) at 5° C. The reaction mixture was stirred overnight at rt and diluted with DCM (100 mL). The organic layer was washed with saturated NH$_4$Cl, dried (Na$_2$SO$_4$) and concentrated to give Compound 1g. MS (ES+) m/z 216 (M+H$^+$).

DMSO (4.28 mL, 60.38 mmol) was added over a 15 min period to a solution of oxalyl chloride (2.63 mL, 30.19 mmol) in DCM (110 mL) at −78° C. After stirring at −78° C. for 30 min, a solution of Compound 1g (5.0 g, 23.2 mmol) in DCM (10 mL) was added dropwise. The resulting mixture was stirred at −78° C. for 2 h. TEA (19.42 mL, 139.3 mmol) was added dropwise and the mixture was warmed to rt and quenched with water. The organic layer was separated, washed sequentially with saturated NH$_4$Cl (75 mL), water (75 mL), saturated NaHCO$_3$ (75 mL) and saturated brine (75 mL), then dried (Na$_2$SO$_4$) and concentrated to give Compound 1h. MS (ES+) m/z 214 (M+H$^+$). $^1$H NMR (DMSO-d$_6$, 300 MHz) δ 1.4 (s, 9H), 1.89 (m, 4H), 2.58 (m, 1H), 3.85 (m, 4H), 9.65 (s, 1H).

A solution of Compound 1h (2.29 g, 10.7 mmol) in DCM (15 mL) was added dropwise to a solution of carbethoxymethylene triphenylphosphorane (4.11 g, 10.7 mmol) in DCM (20 mL) at 0° C. The resulting mixture was warmed to rt and stirred overnight. The mixture was concentrated and the residue was purified by flash chromatography (silica gel, 15-30% ethyl acetate/hexane) to give Compound 1i. MS (ES+) m/z 284 (M+H$^+$). $^1$H NMR (DMSO-d$_6$, 300 MHz) δ 1.2 (t, J=7 Hz, 3H), 1.39 (s, 9H), 1.69 (m, 2H), 2.36 (m, 1H), 2.74 (m, 2H), 3.94 (m, 2H), 4.11 (q, J=7 Hz, 2H), 5.86 (d, J=15 Hz, 2H), 6.82 (dd, J=15, 7 Hz, 2H).

A mixture of Compound 1i (1.6 g, 5.6 mmol), TFA (10 mL) and anisole (1 drop) in DCM (10 mL) was stirred at rt for 1.5 h. The mixture was concentrated and dried in vacuo to give Compound 1j as a TFA salt. MS (ES+) m/z 184 (M+H$^+$).

NMM (0.22 mL, 2.07 mmol), Compound 1e (0.29 g, 1.04 mmol), NMM (0.114 mL, 1.04 mmol), HOBT (0.07 g, 0.51 mmol) and HBTU (0.46 g, 1.24 mmol) were added sequentially to a solution of Compound 1j (0.308 g, 1.04 mmol) in MeCN (20 mL) and DMF (2 mL). The mixture was stirred at 0° C. for 1 h, then at rt overnight, quenched with saturated NH$_4$Cl, concentrated and extracted with EtOAc. The organic layer was dried (Na$_2$SO$_4$), filtered and concentrated in vacuo. The crude product was purified by flash chromatography (silica gel, 10% EtOH/1.5% NH$_4$OH/DCM to 16% EtOH/1.5% NH$_4$OH/DCM) to yield Compound 1k as a colorless solid. MS (ES+) m/z 399 (M+H$^+$).

Compound 1k (0.27 g) was dissolved in ice cold 6N HCl (20 mL) at 0° C. and stirred at rt for 2 d. The mixture was concentrated and MeCN (3×20 mL) was used as an azeotrope. The resulting solid was triturated with Et$_2$O and DCM and purified by RP-HPLC (10-90% MeCN/water, 0.1% TFA) to yield Compound 1l as a TFA salt. MS (ES+) m/z 371 (M+H$^+$). $^1$H NMR (DMSO-d$_6$, 300 MHz) δ 1.07 (m, 2H), 1.65 (m, 4H), 1.7 (m, 2H), 2.41 (m, 1H), 3.05 (m, 2H), 3.72 (s, 2H), 3.91 (m, 2H), 4.37 (m, 2H), 5.74 (d, J=16 Hz, 1H), 6.75 (m, 1H), 7.15 (m, 3H), 7.42 (m, 1H), 8.15 (br s, 1H), 9.76 (s, 1H). Anal. Calcd for C$_{20}$H$_{26}$N$_4$O$_3$·1.57CF$_3$COOH·0.38H$_2$O: C, 49.96; H, 5.14; N, 10.08; F, 16.09; H$_2$O, 1.24. Found: C, 49.62; H, 5.00; N, 9.97; F, 15.98; H$_2$O, 1.25.

10% Palladium on carbon (85 mg) was added to a solution of Compound 1l (0.05 g) in warm EtOH (10 mL) under argon and the mixture was hydrogenated (40 psi) in a Parr apparatus. The mixture was filtered through celite and concentrated at reduced pressure to yield Compound 1 as a sticky solid. MS (ES+) m/z 373 (M+H$^+$).

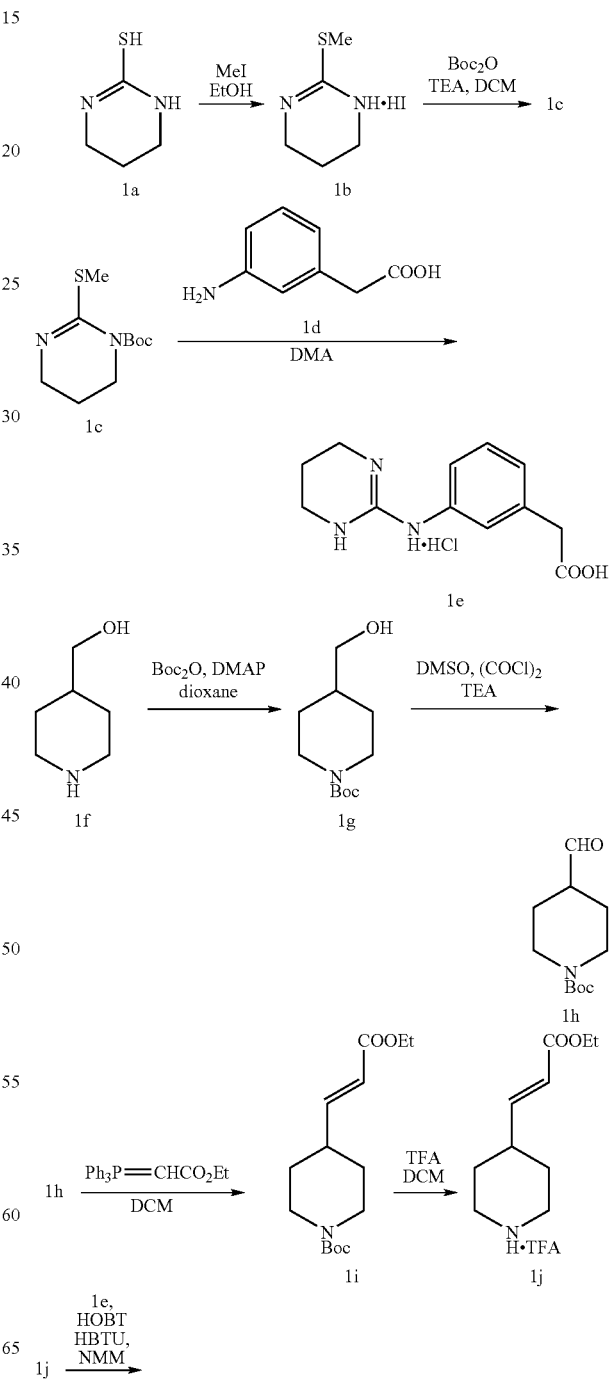

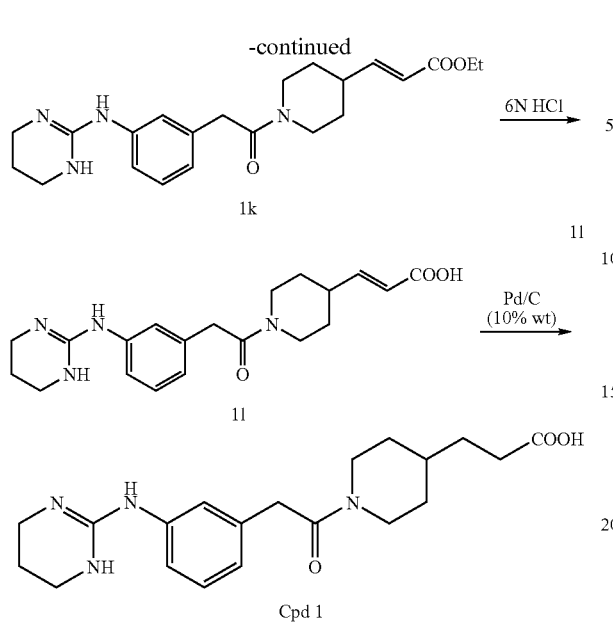

Example 2

1-[1-Oxo-3-[3-[(1,4,5,6-tetrahydro-2-pyrimidinyl)amino]phenyl]propyl]-4-piperidinepropanoic acid (Cpd 2)

Compound 1c (0.84 g, 3.65 mmol) was added to a solution of 3-(3-aminophenyl)propionic acid Compound 2a (0.60 g, 3.65 mmol) in DMA (5 mL). The reaction mixture was stirred at 80-85° C. for 3 d, cooled to rt, diluted with MeCN (30 mL) and filtered. Water was added to the filtrate and the pH was adjusted to 1-2 by adding conc. HCl dropwise. The resulting solution was lyophilized to yield Compound 2b. MS (ES+) m/z 248 (M+H$^+$).

A solution of 4N HCl in dioxane (8 mL) was added dropwise to a solution of Compound 2c (1.0 g, 3.9 mmol) in MeOH (20 mL) at 0° C. The resulting mixture was stirred overnight at rt and concentrated using MeCN (3×20 mL) as an azeotrope. The solid was triturated with Et$_2$O and hexane, dissolved in water and lyophilized to yield Compound 2d as a colorless solid. MS (ES+) m/z 172 (M+H$^+$).

NMM (0.23 mL, 2.11 mmol) was added to a solution of Compound 2d (0.20 g, 0.70 mmol) in MeCN (25 mL) and DMF (2 mL). Compound 2b (0.15 g, 0.70 mmol), NMM (0.15 mL, 1.40 mmol), HOBT (0.05 g, 0.35 mmol) and HBTU (0.32 g, 0.84 mmol) were then added and the mixture was stirred for 1 h at 0° C., followed by overnight at rt. Saturated NH$_4$Cl was added and the reaction mixture was concentrated and extracted with EtOAc (25 mL). The organic layer was dried (Na$_2$SO$_4$), filtered and concentrated in vacuo. The crude mixture was purified by RP-HPLC (10-90% MeCN/water, 0.1% TFA) to yield Compound 2e. MS (ES+) m/z 401 (M+H$^+$).

Compound 2e (0.21 g) was dissolved in 4N HCl (20 mL) at 0° C. and the mixture was stirred overnight at rt. The mixture was concentrated using MeCN (3×25 mL) as an azeotrope and triturated with Et$_2$O to yield Compound 2 as an HCl salt. MS (ES+) m/z 387 (M+H$^+$). $^1$H NMR (DMSO-d$_6$, 300 MHz) δ 0.93 (m, 4H), 1.46 (m, 4H), 1.67 (s, 1H), 1.88 (m, 2H), 2.25 (m, 2H), 2.66 (m, 2H), 2.82 (m, 4H), 3.39 (m, 2H), 3.82 (d, J=13 Hz, 1H), 4.39 (d, J=13 Hz, 1H), 7.15 (m, 3H), 7.39 (m, 1H), 7.97 (br s, 1H), 9.45 (br s, 1H). Anal. Calcd for C$_{21}$H$_{30}$N$_4$O$_3$·1.85 HCl·1.15 H$_2$O: C, 53.14; H, 7.26; N, 11.82; H$_2$O, 4.37. Found: C, 53.19; H, 7.14; N, 11.91; H$_2$O, 4.62.

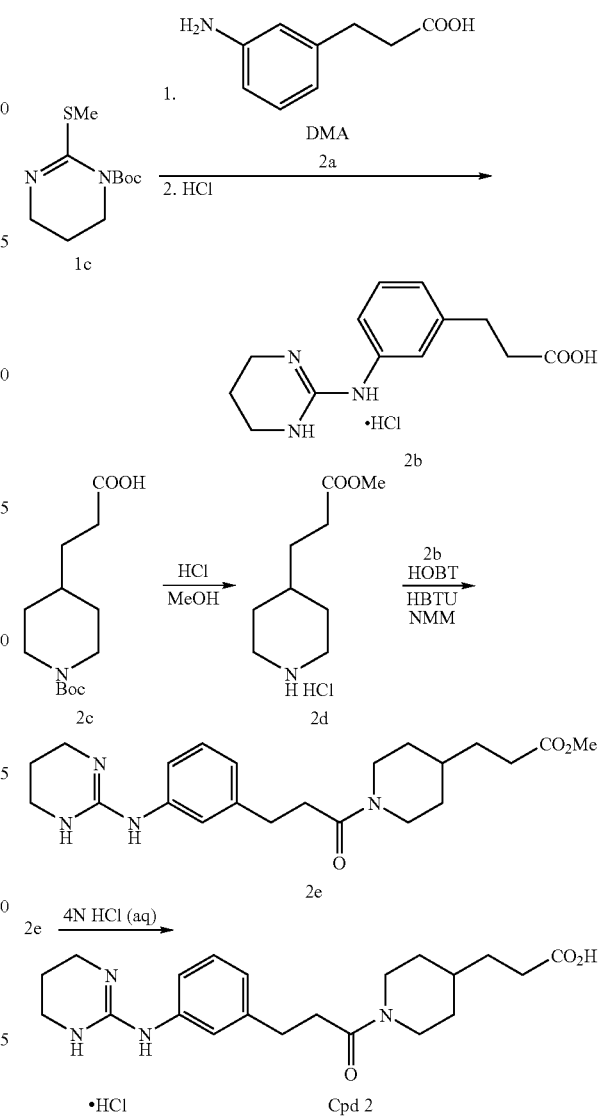

Example 3

β-[1-[[3-[(1,4,5,6-Tetrahydro-5-hydroxy-2-pyrimidinyl)amino]phenyl]acetyl]-4-piperidinyl]-3-quinolinepropanoic acid (Cpd 3)

N,O-Dimethylhydroxylamine hydrochloride (98%, 2.55 g, 26.17 mmol), NMM (14.39 mL, 130.8 mmol), HOBT (1.47 g, 10.90 mmol) and HBTU (9.83 g, 26.16 mmol) were added to a solution of Compound 3a (5.00 g, 21.80 mmol) in MeCN (75 mL). The mixture was stirred for 1 h at 0° C. and overnight at rt, quenched with saturated NH$_4$Cl, concentrated and extracted with EtOAc (3×75 mL). The organic layer was dried (Na$_2$SO$_4$) and concentrated in vacuo. The crude product was purified by flash column chromatography (silica gel, 30-60% ethyl acetate/hexane with a few drops of TEA) to give Compound 3b as a liquid. MS (ES+) m/z 273 (M+H$^+$).

n-BuLi (2.5M in hexane, 7.34 mL, 18.35 mmol) was added dropwise to a stirred solution of 3-bromoquinoline (3.81 g, 18.35 mmol) in anhydrous Et$_2$O (65 mL) at −78° C. over a period of 30 min. The mixture was stirred at −78° C. for 30 min and a solution of Compound 3b (1.0 g, 3.67 mmol) in Et$_2$O (20 mL) was added dropwise over a period of 10 min. The resulting mixture was stirred for 30 min −78° C. and allowed to warm to rt. After stirring for 2 h at rt, the mixture was quenched with a saturated NH$_4$Cl solution and diluted with EtOAc. The organic layer was washed with brine, dried (Na$_2$SO$_4$) and concentrated in vacuo. The residue was purified via chromatography (silica gel, 15-25% ethyl acetate/hexane) to give Compound 3c as a liquid. MS (ES+) m/z 341 (M+H$^+$).

A solution of NaHMDS (1M, 3.17 mL, 3.17 mmol) in THF was added over a period of 15 min to a stirred solution of trimethyl phosphonoacetate (0.51 mL, 3.17 mmol) in THF (15 mL) at 0° C. under argon. After the resulting mixture was stirred for 20 min, a solution of Compound 3c (0.27 g, 0.79 mmol) in THF (3 mL) was added over a period of 15 min. The mixture was stirred at 0° C. for 30 min, refluxed for 2.5 h, cooled to rt, diluted with Et$_2$O (30 mL) and washed with a saturated NaHCO$_3$ solution (2×25 mL) and brine (2×25 mL). The aqueous layer was extracted with Et$_2$O and the combined organic layers were dried (Na$_2$SO$_4$) and concentrated in vacuo. The residue was purified by flash column chromatography (silica gel, 10-30% ethyl acetate/hexane) to give Compound 3d as a mixture of E- and Z-isomers. MS (ES+) m/z 397 (M+H$^+$).

A mixture of the E- and Z-isomers of Compound 3d (0.25 g, 0.63 mmol) and 10% Pd/C (0.12 g) in MeOH (15 mL) was shaken overnight under hydrogen pressure (5 psi) in a Parr apparatus. The mixture was filtered through celite and concentrated under vacuum. The crude product was purified by flash chromatography (70% ethyl acetate in hexane) to yield Compound 3e as an oil. MS (ES+) m/z 399 (M+H$^+$). $^1$H NMR (DMSO-d$_6$, 300 MHz) δ 1.38 (m, 4H), 1.41 (s, 9H), 1.80 (m, 1H), 2.53 (m, 2H), 3.18 (m, 2H), 3.51 (s, 3H), 3.71 (m, 1H), 4.13 (m, 2H), 7.54 (t, J=8 Hz, 1H), 7.69 (t, J=8 Hz, 1H), 7.80 (d, J=8 Hz, 1H), 7.89 (s, 1H), 8.09 (d, J=8 Hz, 1H), 8.75 (s, 1H).

Compound 3e (0.11 g) was dissolved in dioxane (3 mL), one drop of anisole was added and 4N HCl in dioxane (3 mL) was added dropwise. The mixture was stirred at rt for 2 h and concentrated using MeCN as an azeotrope. The resulting solid was triturated with Et$_2$O and hexane and dried to give Compound 3f as a sticky solid. MS (ES+) m/z 299 (M+H$^+$). $^1$H NMR (DMSO-d$_6$, 300 MHz) δ 1.34 (m, 4H), 1.94 (m, 1H), 2.67 (m, 2H), 3.01 (m, 2H), 3.24 (m, 2H), 3.43 (s, 3H), 3.68 (m, 1H), 7.79 (t, J=8 Hz, 1H), 7.94 (t, J=8 Hz, 1H), 8.13 (d, J=8 Hz, 1H), 8.23 (d, J=8 Hz, 1H), 8.48 (m, 1H), 8.70 (m, 1H). Anal. Calcd for C$_{18}$H$_{22}$N$_2$O$_2$·2.2 TFA·0.4H$_2$O: C, 48.36; H, 4.53; N, 5.04; F, 22.54. Found: C, 48.24; H, 4.42; N, 4.99; F, 22.56.

1,3-Diamino-2-hydroxypropane Compound 3i (10.0 g, 111 mmol) was dissolved in ethanol (30 mL) and deionized water (30 mL). Carbon disulfide (6.67 mL, 110.95 mmol) was added dropwise via an addition funnel over a period of 35 min while the temperature was maintained at 25-33° C. to afford a milky white mixture. The resulting mixture was refluxed for 2 h to afford a yellow solution. After cooling the mixture in ice water, concentrated HCl (7 mL) was added dropwise while maintaining the mixture's temperature at 25-26° C. The temperature of the mixture was then raised to 79° C. After stirring for 21 h, the mixture was cooled to 2° C. and filtered via vacuum filtration. A white solid was collected, washed three times with a 1:1 mixture of cold ethanol and water and dried in vacuo at 40° C. to give Compound 3j. MS (ES$^+$) m/z 174 (M$^+$MeCN). $^1$H NMR (DMSO-d$_6$, 300 MHz) δ 2.96 (d, J=15 Hz, 2H), 3.15 (d, J=13 Hz, 2H), 3.33 (m, 1H), 3.89 (m, 1H).

Methyl iodide (2.9 mL, 46 mmol) was added to a stirred solution of Compound 3j (6.1 g, 46 mmol) in absolute ethanol (35 mL) and the mixture was refluxed for 1 h and cooled to rt. After concentration, the residue was triturated with Et$_2$O and dried in vacuo to give Compound 3k as a white solid. MS (ES$^+$) m/z 188 (M+MeCN). $^1$H NMR (DMSO-d$_6$, 300 MHz) δ 2.59 (s, 3H), 3.23 (d, J=13 Hz, 2H), 3.43 (d, J=13 Hz, 2H), 4.16 (m, 1H).

TEA (6.91 mL, 49.61 mmol) was added to a solution of Compound 3k (13.06 g, 49.61 mmol) in DCM (50 mL) and DMA (5 mL). The mixture was cooled in an ice bath and Boc$_2$O (10.82 g, 49.61 mmol) was added at 4° C. The mixture was heated at 41-43° C. for 18 h to afford a light yellow solution. The resulting solution was washed with water (3×75 mL), dried (Na$_2$SO$_4$) and concentrated in vacuo to yield Compound 3l as a solid. MS (ES+) m/z 247(M+H$^+$). $^1$H NMR (DMSO-d$_6$, 300 MHz) δ 1.46 (s, 9H), 1.95 (s, 3H), 2.14 (m, 2H), 2.94 (m, 2H), 3.51 (m, 1H).

3-Aminophenyl acetic acid Compound 1d (2.60 g, 17.25 mmol) was added to a solution of Compound 3l (5.1 g, 21 mmol) in DMA (5 mL). The mixture was heated at 100° C. for 2 d, cooled to rt and diluted with MeCN (75 mL). The resulting precipitate was filtered and washed with MeCN and Et$_2$O, taken up in water and acidified with conc. HCl. After lyophilization, Compound 3m was obtained as a white solid. MS (ES+) m/z 250 (M+H$^+$). $^1$H NMR (DMSO-d$_6$, 300 MHz) δ 3.16 (d, J=13 Hz, 2H), 3.33 (d, J=13 Hz, 2H), 3.59 (s, 2H), 7.12 (m, 3H), 7.35 (m, 1H), 8.14 (s, 1H).

Using the procedure described in Example 2 for converting Compound 2d to Compound 2e, Compound 3m was converted to provide Compound 3n as a solid. MS (ES+) m/z 530 (M+H$^+$). $^1$H NMR (DMSO-d$_6$, 300 MHz) δ 0.92 (m, 4H), 1.33 (m, 2H), 1.90 (m, 1H), 2.88 (m, 4H), 3.17 (m, 3H), 3.33 (m, 2H), 3.43 (s, 3H), 4.06 (m, 2H), 4.32 (m, 1H), 6.98 (m, 3H), 7.27 (m, 1H), 7.48 (m, 1H), 7.66 (m, 1H), 7.79 (m, 1H), 8.01 (m, 3H), 8.25 (br s, 1H), 8.83 (br s, 1H).

Using the procedure described in Example 2 for converting Compound 2e to Compound 2, Compound 3n was converted to provide Compound 3 as a solid. MS (ES+) m/z 516 (M+H$^+$). $^1$H NMR (DMSO-d$_6$, 300 MHz) δ 0.92 (m, 4H), 1.33 (m, 1H), 1.90 (m, 2H), 2.88 (m, 4H), 3.17 (m, 1H), 3.33 (m, 4H), 4.06 (m, 2H), 4.32 (m, 1H), 6.98 (m, 3H), 7.24 (m, 1H), 7.77 (m, 1H), 7.72 (m, 1H), 8.03 (m, 1H), 8.10 (m, 1H), 8.18 (m, 1H), 8.65 (m, 1H), 9.21 (br s, 1H).

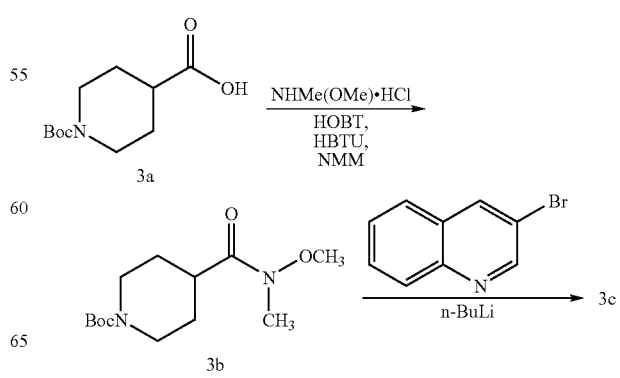

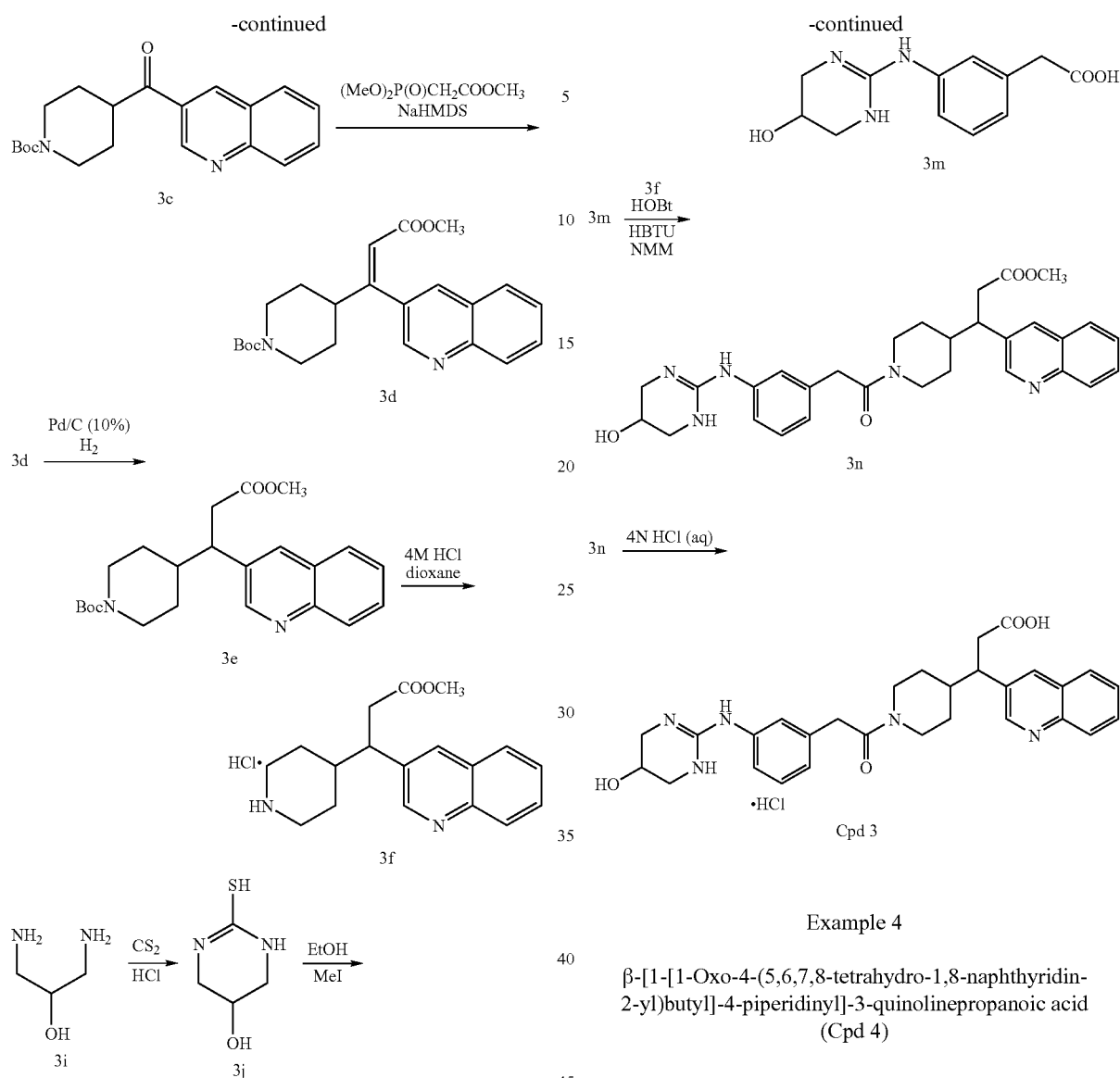

Example 4

β-[1-[1-Oxo-4-(5,6,7,8-tetrahydro-1,8-naphthyridin-2-yl)butyl]-4-piperidinyl]-3-quinolinepropanoic acid (Cpd 4)

Compound 4a was prepared as described in WO 99/31061. Using the procedure described in Example 2 for converting Compound 2d to Compound 2e, Compound 4a was converted and purified by RP-HPLC (10-70% acetonitrile/water, 0.1% TFA) to provide Compound 4b. MS (ES+) m/z 501 (M+H$^+$). $^1$H NMR (DMSO-d$_6$, 300 MHz) δ 1.02 (m, 4H), 1.33 (m, 1H), 2.86 (m, 4H), 2.29 (m, 2H), 2.61 (m, 2H) 2.72 (m, 2H), 2.86 (m, 2H), 2.98 (m, 2H), 3.17 (m, 1H), 3.44 (s, 3H), 3.78 (m, 2H), 4.35 (m, 2H), 6.52 (d, J=7 Hz, 1H), 7.56 (d, J=7 Hz, 1H), 7.78 (m, 2H), 7.99 (m, 2H), 8.41 (s, 1H), 8.91 (s, 1H).

Using the procedure described in Example 2 for converting Compound 2e to Compound 2, Compound 4b was converted to provide Compound 4 as a sticky solid. MS (ES+) m/z 487 (M+H$^+$). $^1$H NMR (DMSO-d$_6$, 300 MHz) δ 0.99 (m, 4H), 1.49 (m, 1H), 2.86 (m, 4H), 2.30 (m, 2H), 2.69 (m, 2H), 2.81 (m, 1H), 2.92 (m, 2H), 3.13 (m, 2H), 3.33 (m, 1H), 3.79 (m, 2H), 4.41 (m, 2H), 6.55 (d, J=7 Hz, 1H), 7.56 (d, J=7 Hz, 1H), 7.86 (m, 1H), 7.98 (m, 2H), 8.72 (m, 2H), 8.83 (s, 1H), 9.15 (s, 1H). Anal. Calcd for C$_{29}$H$_{34}$N$_4$O$_3$·3.5 HCl—H$_2$O: C, 55.09; H, 6.30; N, 8.86; H$_2$O, 3.24. Found: C, 54.83; H, 6.53; N, 9.08; H$_2$O, 3.24.

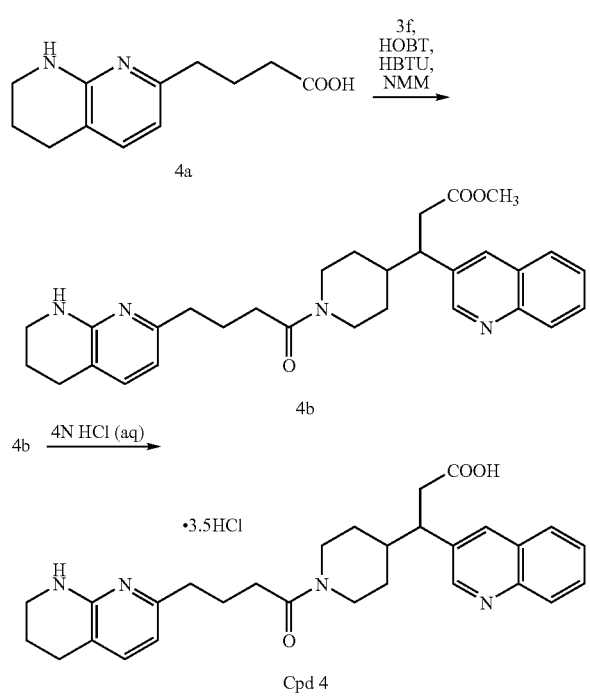

Using the procedure of Example 4 and the appropriate reagents and starting materials known to those skilled in the art, other compounds of the present invention may be prepared including, but not limited to:

| Cpd | Name | MS (m/z) |
|---|---|---|
| 14 | β-(1,3-benzodioxol-5-yl)-1-[1-oxo-3-(5,6,7,8-tetrahydro-1,8-naphthyridin-2-yl)propyl]-4-piperidinepropanoic acid | 466 |
| 15 | β-(1,3-benzodioxol-5-yl)-1-[1-oxo-4-(5,6,7,8-tetrahydro-1,8-naphthyridin-2-yl)butyl]-4-piperidinepropanoic acid | 480 |
| 16 | β-(1,3-benzodioxol-5-yl)-1-[(5,6,7,8-tetrahydro-1,8-naphthyridin-2-yl)acetyl]-4-piperidinepropanoic acid | 452 |
| 17 | 6-methoxy-β-[1-[1-oxo-4-(5,6,7,8-tetrahydro-1,8-naphthyridin-2-yl)butyl]-4-piperidinyl]-3-pyridinepropanoic acid | 467 |
| 82 | 3-(2,3-Dihydro-benzofuran-6-yl)-3-[1-4-(5,6,7,8-tetrahydro-1,8-naphthyridin-2-yl)butyl]-4-piperidinyl]-propanoic acid | | and pharmaceutically acceptable salts thereof.

Example 5

1,2,3,4-Tetrahydro-β-[1-[1-oxo-4-(5,6,7,8-tetrahydro-1,8-naphthyridin-2-yl)butyl]-4-piperidinyl]-3-quinolinepropanoic acid (Cpd 5)

Compound 3d (0.49 g) was combined with 10% Pd/C (0.6 g) in methanol (40 mL) and water (1.5 mL), and hydrogenated at 50 psi of $H_2$ for 3 d. After filtration of catalyst, the evaporated material was purified by flash chromatography (gradient 20-30% ethyl acetate in heptane with a few drops of triethylamine) to provide Compounds 5a (0.23 g, 47%) and 5b (0.16 g, 32%). Cpd 5a: MS (ES+) m/z 403 (M+H$^+$). $^1$H NMR (CDCl$_3$, 300 MHz) δ 1.2-1.7 (m, 4H), 1.45 (s, 9H), 1.9-2.4 (m, 4H), 2.5-3.1 (m, 5H), 3.27 (m, 1H), 3.68 (s, 3H), 3.84 (m, 1H), 4.13 (m, 2H), 6.48 (d, J=8 Hz, 1H), 6.61-6.69 (m, 1H), 6.92-6.99 (m, 2H). Cpd 5b: MS (ES+) m/z 403.5 (M+H$^+$). $^1$H NMR (DMSO-d$_6$, 300 MHz) δ 0.8-1.3 (m, 4H), 1.35 (s, 9H), 1.6-1.8 (m, 4H), 2.6-2.8 (m, 10H), 3.45 (s, 3H), 3.8-4.0 (m, 2H), 7.27 (m, 1H), 8.08 (m, 1H).

Using the procedure described in Example 3 for converting Compound 3e to Compound 3f, Compound 5a was converted to provide Compound 5c as a solid. MS (ES+) m/z 303 (M+H$^+$). $^1$H NMR (DMSO-d$_6$, 300 MHz) δ 1.61 (m, 4H), 1.82 (m, 1H), 2.32 (m, 1H), 2.44 (m, 2H), 2.78 (m, 2H), 3.25 (m, 2H), 3.35 (m, 2H), 3.62 (s, 3H), 3.78 (m, 3H), 7.16 (m, 2H), 8.76 (m, 2H).

Using the procedure described in Example 2 for converting Compound 2d to Compound 2e, Compound 4a was reacted with Compound 5c and purified by RP-HPLC (10-70% acetonitrile/water, 0.1% TFA) to provide Compound 5d. MS (ES+) m/z 505 (M+H$^+$). $^1$H NMR (DMSO-d$_6$, 300 MHz) δ 1.11 (m, 4H), 1.56 (m, 1H), 1.79 (m, 6H), 2.32 (m, 4H), 2.66 (m, 2H), 2.77 (m, 2H), 2.91 (m, 2H), 3.16 (m, 2H), 3.5 (m, 2H), 3.62 (s, 3H), 3.82 (m, 2H), 4.43 (m, 2H), 6.58 (m, 3H), 7.63 (d, J=7 Hz, 1H), 7.93 (m, 2H).

Using the procedure described in Example 2 for converting Compound 2e to Compound 2, Compound 5d was converted to provide Compound 5 as an HCl salt. MS (ES+) m/z 491 (M+H$^+$). $^1$HNMR (DMSO-d$_6$, 300 MHz) δ 1.13 (m, 4H), 1.54 (m, 2H), 1.77 (m, 4H), 2.21 (m, 4H), 2.37 (m, 1H), 2.64 (m, 2H), 2.71 (m, 2H), 2.96 (m, 2H), 3.23 (m, 2H), 3.45 (s, 2H), 3.84 (m, 2H), 4.45 (m, 2H), 6.54 (m, 3H), 6.98 (m, 2H), 7.61 (d, J=8 Hz, 1H), 8.01 (br s, 1H).

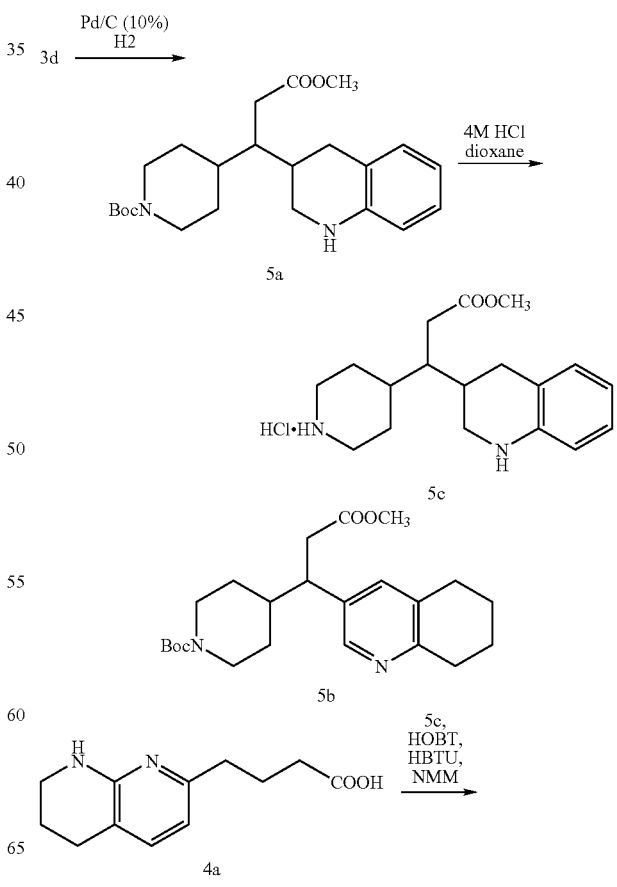

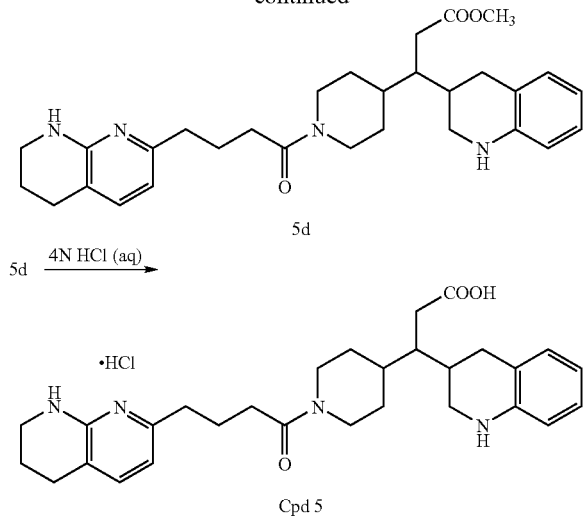

Using the procedure of Example 5 and the appropriate reagents and starting materials known to those skilled in the art, other compounds of the present invention may be prepared including, but not limited to:

| Cpd | Name | MS (m/z) |
|---|---|---|
| 18 | 1,4,5,6-tetrahydro-2-methyl-β-[[1-[1-oxo-3-(5,6,7,8-tetrahydro-1,8-naphthyridin-2-yl)propyl]-4-piperidinyl]methyl]-5-pyrimidinepropanoic acid | 456 |
| 19 | 1,2,3,4-tetrahydro-β-[[1-[1-oxo-3-(5,6,7,8-tetrahydro-1,8-naphthyridin-2-yl)propyl]-4-piperidinyl]methyl]-3-quinolinepropanoic acid | 491 |
| 57 | 5,6,7,8-tetrahydro-β-[[1-[1-oxo-3-(5,6,7,8-tetrahydro-1,8-naphthyridin-2-yl)propyl]-4-piperidinyl]methyl]-3-quinolinepropanoic acid | 491 | and pharmaceutically acceptable salts thereof.

Example 6

β-[2-[1-[3-[(1,4,5,6-Tetrahydro-2-pyrimidinyl)amino]benzoyl]-4-piperidinyl]ethyl]-3-pyridinepropanoic acid (Cpd 6)

Using the procedure described in Example 3 for converting Compound 3a to Compound 3b, N-Boc-piperidin-4-propionic acid Compound 2c was converted to Compound 6a (colorless liquid; purified by flash chromatography (on silica gel, eluted with 30-50% ethyl acetate/hexane with a few drops of TEA). MS (ES+) m/z 301 (M+H⁺). ¹H NMR (DMSO-d₆, 300 MHz) δ 1.14 (m, 4H), 1.45 (s, 9H), 1.62 (m, 1H), 1.68 (m, 2H), 2.44 (t, J=7.5 Hz, 2H), 2.63 (m, 2H), 3.18 (s, 3H), 3.68 (s, 3H), 4.08 (m, 2H).

Using the procedure described in Example 3 for converting Compound 3b to Compound 3c, Compound 6a was converted to Compound 6b (purified by flash chromatography on silica gel, eluted with 30-50% ethyl acetate/hexane with a few drops of TEA). MS (ES+) m/z 319 (M+H⁺).

Using the procedure described in Example 3 for converting Compound 3c to Compound 3d, Compound 6b was converted to Compound 6c (purified by flash chromatography on silica gel, eluted with 30-50% ethyl acetate/hexane with a few drops of TEA). MS (ES+) m/z 375 (M+H⁺).

Using the procedure described in Example 3 for converting Compound 3d to Compound 3e, Compound 6c was converted to Compound 6d (purified by flash chromatography on silica gel, eluted with 15-35% ethyl acetate/hexane with a few drops of TEA). MS (ES+) m/z 377 (M+H⁺). ¹H NMR (DMSO-d₆, 300 MHz) δ 0.91 (m, 4H), 1.12 (m, 2H), 1.29 (m, 1H), 1.41 (s, 9H), 1.53 (m, 3H), 2.63 (m, 2H), 3.98 (m, 2H), 3.35 (s, 3H), 3.48 (m, 1H), 3.88 (m, 2H), 7.34 (m, 1H), 7.68 (m, 1H), 8.43 (m, 2H).

Using the procedure described in Example 3 for converting Compound 3e to Compound 3f, Compound 6d was converted to Compound 6e (white solid). MS (ES+) m/z 277 (M+H⁺). ¹H NMR (DMSO-d₆, 300 MHz) δ 0.91 (m, 2H), 1.19 (m, 4H), 1.44 (m, 1H), 1.71 (m, 2H), 2.71 (m, 2H), 2.82 (m, 2H), 3.08 (m, 2H), 3.21 (m, 1H), 3.49 (s, 3H), 7.51 (m, 1H), 7.94 (m, 1H), 8.53 (m, 2H).

Using the procedure described in Example 1 for converting Compound 1c to Compound 1e, Compound 1c was reacted with 3-aminobenzoic acid Compound 6f to provide Compound 6g as a white amorphous solid. MS (ES+) m/z 220 (M+H⁺). ¹H NMR (DMSO-d₆, 300 MHz) δ 4.13 (m, 2H), 5.42 (t, J=5 Hz, 4H), 6.81 (m, 4H).

Using the procedure described in Example 1 for converting Compound 1j to Compound 1k, Compound 6g was reacted with Compound 6e to produce Compound 6h (purified via RP-HPLC: 5-50% acetonitrile/water, 0.1% TFA). MS (ES+) m/z 478 (M+H⁺).

Using the procedure described in Example 2 for converting Compound 2e to Compound 2, Compound 6h was converted to Compound 6 (purified via RP-HPLC: 5-50% acetonitrile/water, 0.1% TFA). MS (ES+) m/z 464 (M+H⁺). ¹H NMR (DMSO-d₆, 300 MHz) δ 1.11 (m, 2H), 1.19 (m, 2H), 1.49 (m, 4H), 1.68 (m, 1H), 1.72 (m, 4H), 2.72 (m, 4H), 3.15 (m, 1H), 3.65 (m, 2H), 4.38 (m, 2H), 7.12-7.51 (m, 4H), 7.73 (m, 1H), 8.21 (m, 1H), 8.65 (m, 2H).

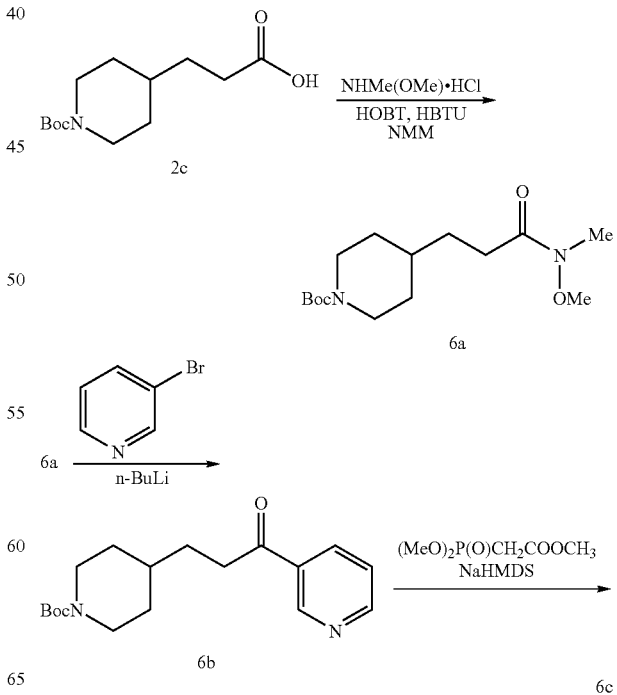

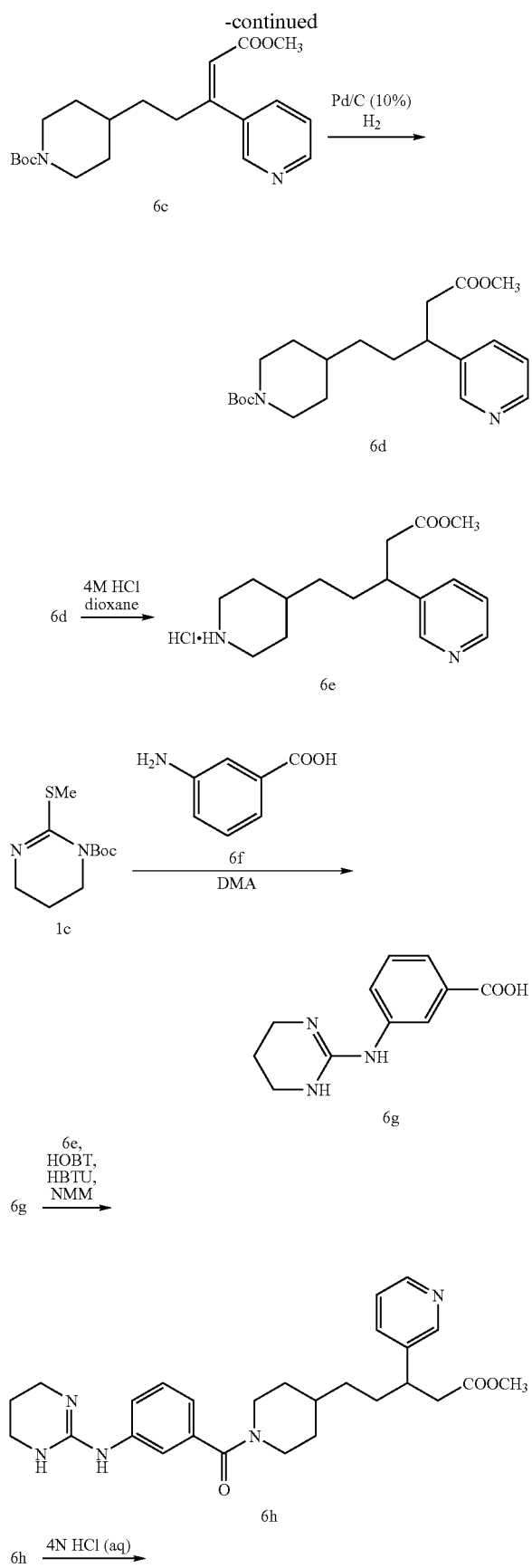

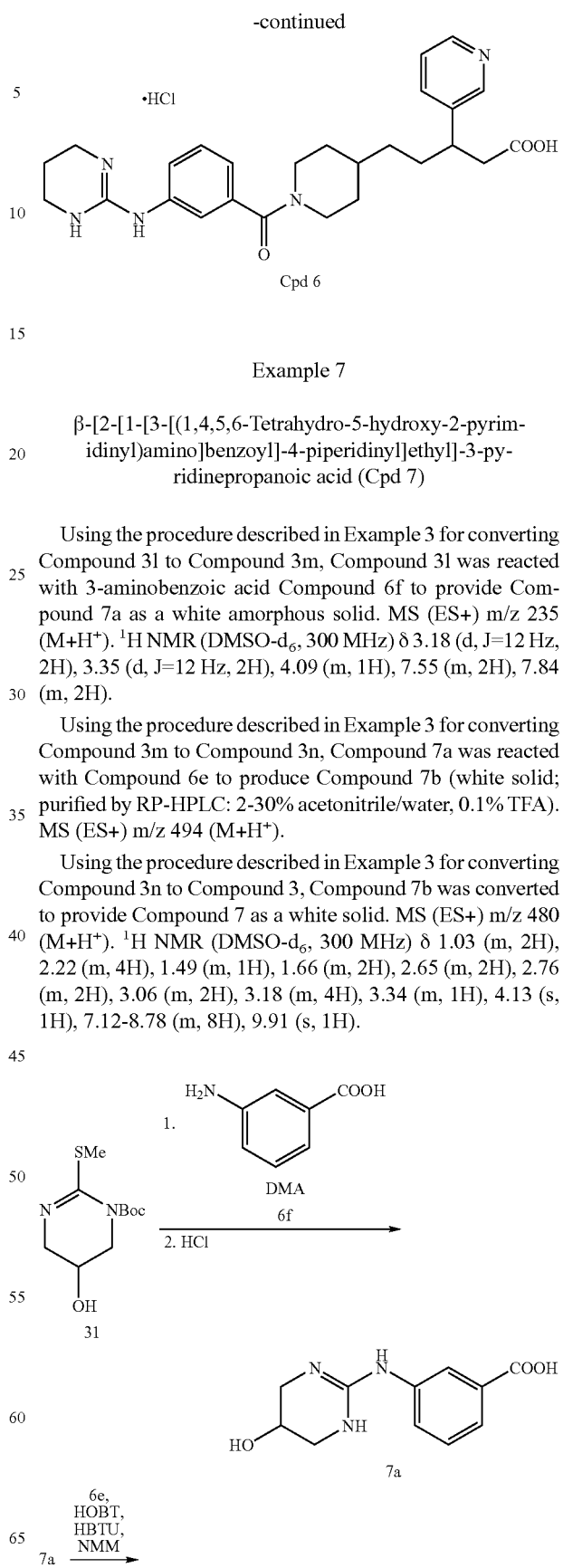

Example 7

β-[2-[1-[3-[(1,4,5,6-Tetrahydro-5-hydroxy-2-pyrimidinyl)amino]benzoyl]-4-piperidinyl]ethyl]-3-pyridinepropanoic acid (Cpd 7)

Using the procedure described in Example 3 for converting Compound 3l to Compound 3m, Compound 3l was reacted with 3-aminobenzoic acid Compound 6f to provide Compound 7a as a white amorphous solid. MS (ES+) m/z 235 (M+H+). $^1$H NMR (DMSO-$d_6$, 300 MHz) δ 3.18 (d, J=12 Hz, 2H), 3.35 (d, J=12 Hz, 2H), 4.09 (m, 1H), 7.55 (m, 2H), 7.84 (m, 2H).

Using the procedure described in Example 3 for converting Compound 3m to Compound 3n, Compound 7a was reacted with Compound 6e to produce Compound 7b (white solid; purified by RP-HPLC: 2-30% acetonitrile/water, 0.1% TFA). MS (ES+) m/z 494 (M+H+).

Using the procedure described in Example 3 for converting Compound 3n to Compound 3, Compound 7b was converted to provide Compound 7 as a white solid. MS (ES+) m/z 480 (M+H+). $^1$H NMR (DMSO-$d_6$, 300 MHz) δ 1.03 (m, 2H), 2.22 (m, 4H), 1.49 (m, 1H), 1.66 (m, 2H), 2.65 (m, 2H), 2.76 (m, 2H), 3.06 (m, 2H), 3.18 (m, 4H), 3.34 (m, 1H), 4.13 (s, 1H), 7.12-8.78 (m, 8H), 9.91 (s, 1H).

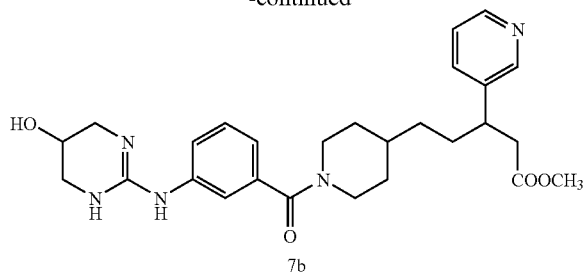

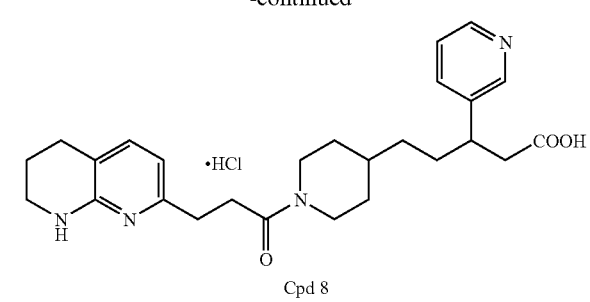

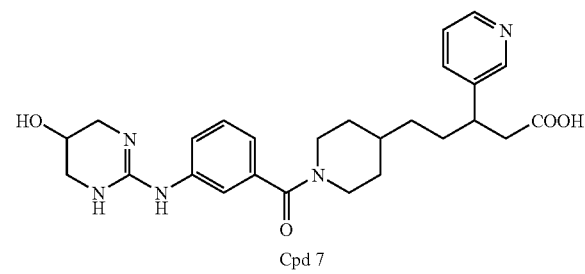

Example 8

β-[2-[1-[1-Oxo-3-(5,6,7,8-tetrahydro-1,8-naphthyridin-2-yl)propyl]-4-piperidinyl]ethyl]-3-pyridinepropanoic acid (Cpd 8)

The acid Compound 8a was derived from the corresponding ethyl ester as described in WO99/31061, the synthesis of which was described in WO 00/72801.

Using the procedure described in Example 5 for converting Compound 4a to Compound 5c, Compound 8a was reacted with Compound 6e to yield Compound 8b (purified by RP-HPLC: 10-90% acetonitrile/water, 0.1% TFA). MS (ES+) m/z 465 (M+H$^+$).

Using the procedure described in Example 5 for converting Compound 5c to Compound 5, Compound 8b was converted to provide Compound 8 as an HCl salt. MS (ES+) m/z 451 (M+H$^+$). $^1$H NMR (DMSO-d$_6$, 300 MHz) δ 1.03 (m, 2H), 1.19 (m, 2H), 1.49 (m, 4H), 1.68 (m, 1H), 1.72 (m, 4H), 2.72 (m, 2H), 2.98 (m, 2H), 3.18 (m, 1H), 3.65 (m, 2H), 4.33 (m, 2H), 7.25 (m, 2H), 7.51 (m, 1H), 7.73 (m, 1H), 8.21 (m, 1H), 8.31 (s, 1H), 8.65 (m, 2H).

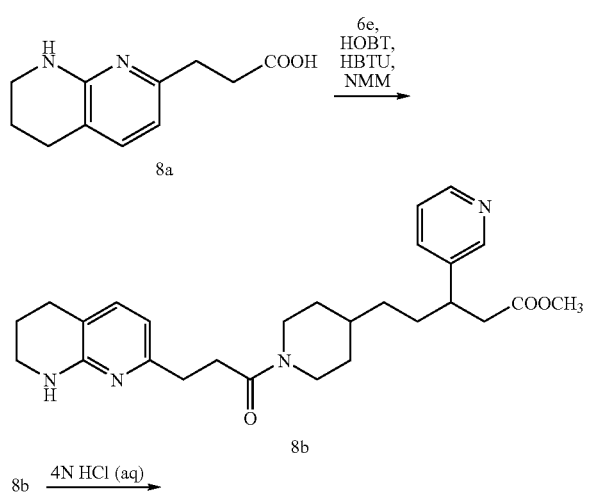

Using the procedure of Example 8 and the appropriate reagents and starting materials known to those skilled in the art, other compounds of the present invention may be prepared including, but not limited to:

| Cpd | Name | MS (m/z) |
|---|---|---|
| 20 | β-(1,3-benzodioxol-5-yl)-1-[1-oxo-3-(5,6,7,8-tetrahydro-1,8-naphthyridin-2-yl)propyl]-4-piperidinepentanoic acid | 494 |
| 21 | 6-methoxy-β-[2-[1-[1-oxo-3-(5,6,7,8-tetrahydro-1,8-naphthyridin-2-yl)propyl]-4-piperidinyl]ethyl]-3-pyridinepropanoic acid | 481 | and pharmaceutically acceptable salts thereof.

Example 9

β-[2-[1-[1-Oxo-4-(2-pyridinylamino)butyl]-4-piperidinyl]ethyl]-3-pyridinepropanoic acid (Cpd 9)

A mixture of Compound 6e (0.14 g, 0.44 mmol) in DCM (10 mL) and NMM (0.09 mL, 0.89 mmol) was stirred for 0.5 h at rt then cooled in an ice bath. 4-Bromobutyrylchloride Compound 9a (0.06 mL, 0.58 mmol) and NMM (0.09 mL, 0.89 mmol) were added and the reaction mixture was stirred for 6 h at 0° C. and overnight at rt. The reaction mixture was washed with saturated NH$_4$Cl solution (5 mL), water (5 mL) and 1N HCl (3×10 mL). The organic layer was dried (Na$_2$SO$_4$) and concentrated in vacuo to yield Compound 9b as a viscous oil. MS (ES+) m/z 345 (M−Br).

DIEA (0.73 mL, 4.23 mmol) was added to a stirred solution of Compound 9b (0.60 g, 1.41 mmol) and 2-aminopyridine Compound 9c (0.39 g, 4.23 mmol) in toluene (10 mL). The mixture was refluxed overnight and concentrated in vacuo. The residue was purified by RP-HPLC (2-30% acetonitrile/water, 0.1% TFA) to give Compound 9d as an oil. MS (ES+) m/z 439 (M+H$^+$).

Using the procedure described in Example 6 for converting Compound 6h to Compound 6, Compound 9d was converted to Compound 9 (purified by RP-HPLC: 2-30% acetonitrile/water, 0.1% TFA). MS (ES+) m/z 425 (M+H$^+$). $^1$H NMR (DMSO-d$_6$, 300 MHz) δ 1.01 (m, 2H), 1.11 (m, 4H), 1.36 (m, 1H), 1.69 (m, 4H), 2.16 (m, 2H), 2.39 (m, 2H), 3.21 (m, 2H), 3.76 (m, 2H), 4.26 (m, 2H), 4.61 (m, 1H), 7.31-8.72 (m, 8H).

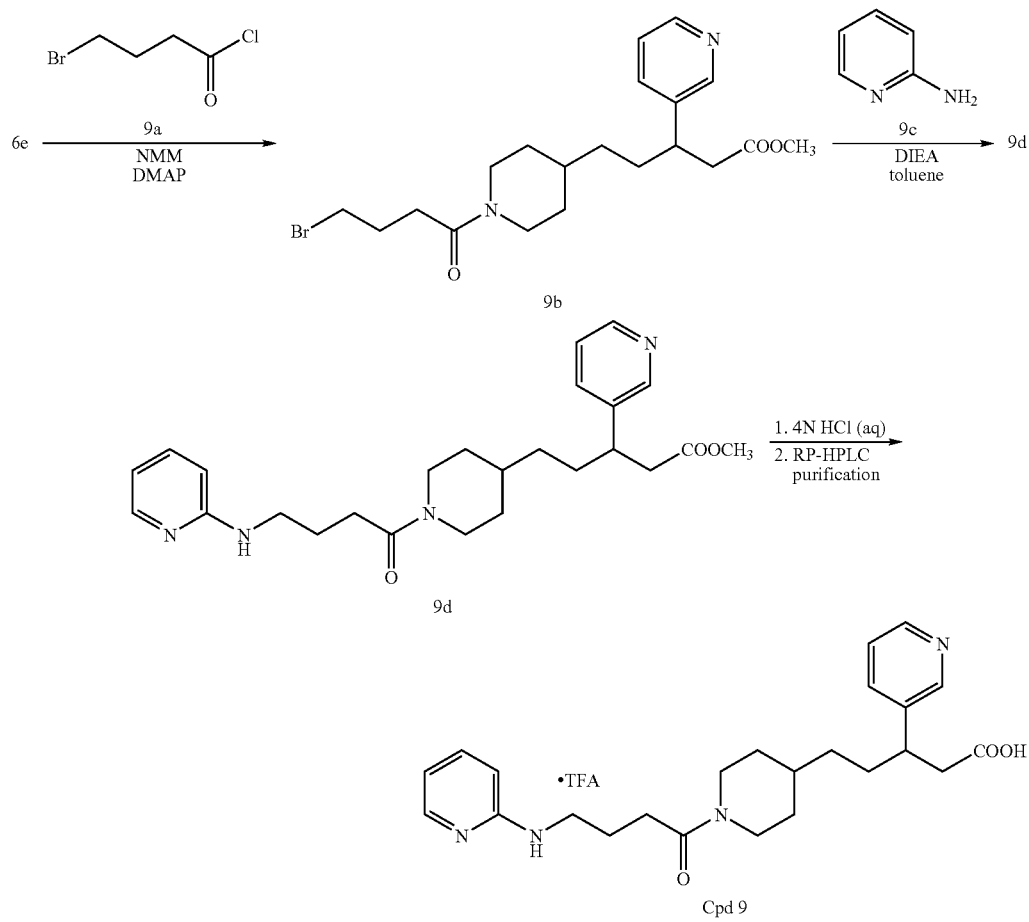

Using the procedure of Example 9 and the appropriate reagents and starting materials known to those skilled in the art, other compounds of the present invention may be prepared including, but not limited to:

| Cpd | Name | MS (m/z) |
|---|---|---|
| 22 | β-[2-[1-[1-oxo-4-(2-pyridinylamino)butyl]-4-piperidinyl]ethyl]-3-quinolinepropanoic acid | 475 |
| 23 | β-(1,3-benzodioxol-5-yl)-1-[1-oxo-4-(2-pyridinylamino)butyl]-4-piperidinepentanoic acid | 468 |
| 24 | β-(1,3-benzodioxol-5-yl)-1-[1-oxo-4-(2-pyridinylamino)butyl]-4-piperidinepropanoic acid | 440 |
| 25 | 6-methoxy-β-[2-[1-[1-oxo-4-(2-pyridinylamino)butyl]-4-piperidinyl]ethyl]-3-pyridinepropanoic acid | 455 | and pharmaceutically acceptable salts thereof.

Example 10

6-Methoxy-β-[2-[1-[3-[(1,4,5,6-tetrahydro-5-hydroxy-2-pyrimidinyl)amino]benzoyl]-4-piperidinyl]ethyl]-3-pyridinepropanoic acid (Cpd 10)

Using the procedure described in Example 6 for converting Compound 6c to Compound 6d, Compound 10a was converted to Compound 10b (colorless liquid; purified by flash chromatography on silica gel, 10-15% ethyl acetate/hexane with a few drops of TEA). MS (ES+) m/z 407 (M+H$^+$) as a racemic mixture that was enantiomerically separated using a chiralcel OJ column eluting with hexane/ethanol (75:25). 1H-NMR (DMSO-d$_6$, 300 MHz) δ 1.04 (m, 4H), 1.19 (m, 2H), 1.47 (s, 9H), 161 (m, 1H), 1.73 (m, 2H), 2.66 (m, 4H), 3.02 (m, 2H), 3.61 (s, 3H), 3.92 (s, 3H), 4.01 (m, 1H), 6.81 (d, J=7 Hz, 1H), 7.38 (d, J=7 Hz, 1H), 8.05 (s, 1H).

Using the procedure described in Example 6 for converting Compound 6d to Compound 6e, Compound 10b was converted to provide Compound 10c as an HCl salt. MS (ES+) m/z 307 (M+H$^+$). $^1$H NMR (DMSO-d$_6$, 300 MHz) δ 0.98 (m, 2H), 1.18 (m, 1H), 1.53 (m, 4H), 1.81 (m, 2H), 2.62 (m, 2H), 2.81 (m, 4H), 3.22 (m, 1H), 3.53 (s, 3H), 3.83 (s, 3H), 6.76 (d, J=9 Hz, 1H), 7.63 (m, 1H), 8.04 (m, 1H). Anal. Calcd for C$_{17}$H$_{26}$N$_2$O$_3$-1.63 CF$_3$COOH-0.2 H$_2$O: C, 49.08; H, 5.70; N, 5.65; H$_2$O, 0.73. Found: C, 49.10; H, 5.66; N, 5.65; H$_2$O, 0.93.

Using the procedure described in Example 7 for converting Compound 7a to Compound 7b, Compound 7a was reacted with Compound 10c to produce Compound 10d. Using the procedure described in Example 3 for converting Compound 3n to Compound 3, Compound 10d was converted to produce Compound 10 as an HCl salt (purified by RP-HPLC: 5-50% acetonitrile/water, 0.1% TFA). MS (ES+) m/z 510 (M+H$^+$). $^1$H NMR (DMSO-d$_6$, 300 MHz) δ 0.99 (m, 2H), 1.14 (m, 1H), 1.53 (m, 6H), 1.67 (m, 2H), 2.58 (m, 2H), 2.94 (m, 1H), 3.15 (d, J=11 Hz, 2H), 3.33 (d, J=12 Hz, 2H), 3.81 (s, 3H), 3.86 (m, 2H), 4.09 (m, 1H), 6.75 (d, J=9 Hz, 1H), 7.12-7.29 (m, 4H), 7.63 (m, 1H), 8.03 (m, 1H).

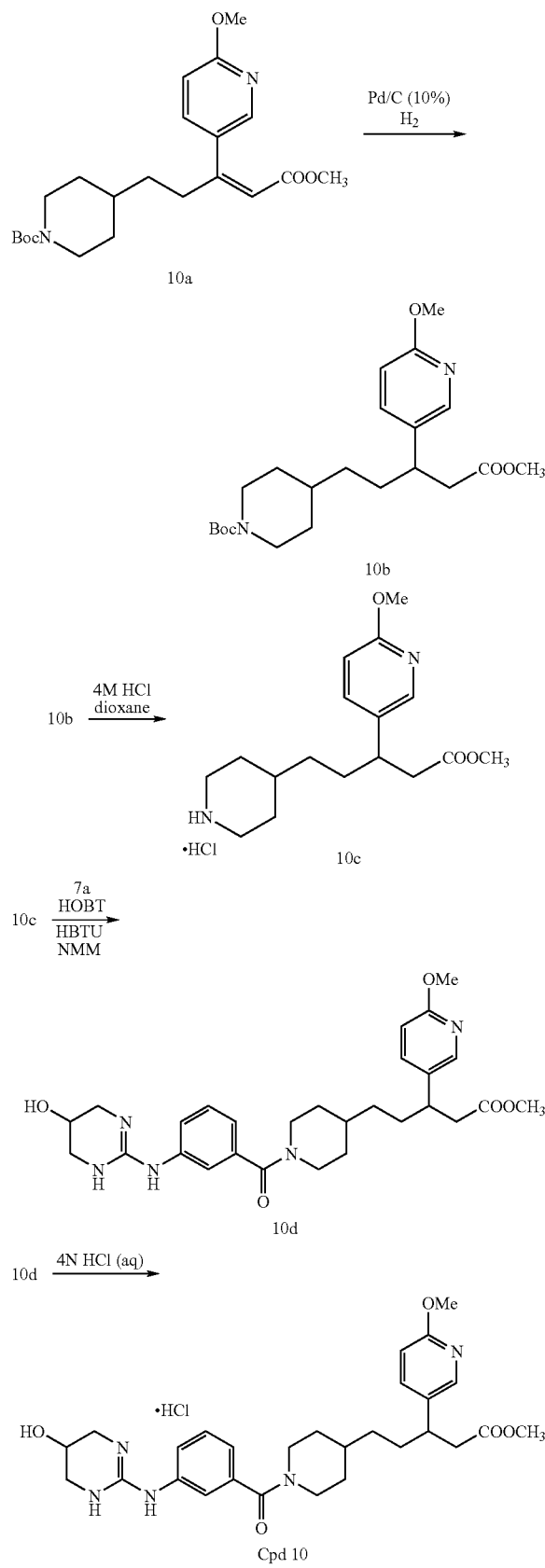

Example 11

Using the procedures described in Examples 6 and 8 for preparing Compound 8, the enantiomers of Compound 21 were produced from the enantiomers of 10b.

The two pure chiral intermediates 10b-1 (isomer 1: faster eluting) and 10b-2 (isomer 2: slower eluting) were obtained by chiral HPLC chromatography (stationary phase: 500 g of Chiralcel OJ; eluent: hexane/ethanol 75/25; wavelength: 220 nm). Compounds 10b-1 and 10b-2 were converted individually to 21a and 21b, respectively, by the same methods used to convert 6d to 8 in Examples 6 and 8.

Using the procedure of Example 11 and the appropriate solvents, columns, reagents and starting materials known to those skilled in the art, other compounds of the present invention may be prepared including, but not limited to:

| Cpd | Name | MS (m/z) |
|---|---|---|
| 28a | 6-methoxy-β-[[1-[1-oxo-3-(5,6,7,8-tetrahydro-1,8-naphthyridin-2-yl)propyl]-4-piperidinyl]methyl]-3-pyridinepropanoic acid | 467 |
| 28b | 6-methoxy-β-[[1-[1-oxo-3-(5,6,7,8-tetrahydro-1,8-naphthyridin-2-yl)propyl]-4-piperidinyl]methyl]-3-pyridinepropanoic acid | 467 |

Example 12

β-(1,3-Benzodioxol-5-yl)-1-[1-oxo-3-(5,6,7,8-tetrahydro-1,8-naphthyridin-2-yl)propyl]-4-piperidinebutanoic acid (Cpd 11)

To a solution of Compound 12a (5 g, 20.55 mmol) and NMM (4.96 mL, 45.11 mmol) in anhydrous THF (50 mL) at −20° C. under nitrogen, isobutyl chloroformate (2.67 mL, 20.58 mmol) was added via syringe. The mixture was stirred for 30 min and N,O-dimethylhydroxylamine (2 g, 20.5 mmol) was added in one portion. The mixture was warmed slowly to rt and stirred for 2 d. After concentration in vacuo, the residue was partitioned between EtOAc and 1N HCl. The organic phase was separated, washed with H$_2$O and saturated NaHCO$_3$, dried (Na$_2$SO$_4$) and concentrated in vacuo to afford Compound 12b as an oil. Compound 12b was used in the next reaction without further purification. Butyllithium (2.5M in hexane, 4.19 mL, 10.48 mmol) was added dropwise to a solution of 4-bromo-1,2-(methylenedioxy)benzene Compound 12c (1.26 mL, 10.48 mmol) in THF (40 mL) at −78° C. The mixture was stirred at −78° C. for 30 min and a solution of Compound 12b (2 g, 6.98 mmol) in THF (10 mL) was added dropwise. After the mixture was stirred at −78° C. for 30 min, the cooling bath was removed. The mixture was stirred an additional 2 h at rt and quenched with a saturated NH$_4$Cl solution. The organic phase was separated, washed with brine, dried (Na$_2$SO$_4$) and concentrated. The residue was purified via RP-HPLC to yield Compound 12d as an oil.

Sodium hexamethyldisilazide (1.0M in THF, 2.07 mL, 2.07 mmol) was added dropwise to a solution of trimethyl phosphonoacetate (0.33 mL, 2.07 mmol) in THF (10 mL) at 0° C. The mixture was stirred at 0° C. for 30 min and a solution of Compound 12d (0.18 g, 0.52 mmol) in THF (5 mL) was added dropwise. The mixture was heated to reflux for 16 h then stirred at rt for additional 24 h, cooled, diluted with Et$_2$O (30 mL) and washed with sat. NaHCO$_3$ and brine. The organic layer was dried (Na$_2$SO$_4$) and concentrated. The residue was purified via RP-HPLC to give Compound 12e. A solution of Compound 12e (0.5 g, 1.24 mmol) in MeOH (20 mL) was hydrogenated at 40 psi of $H_2$ in the presence of 10% palladium on carbon (0.2 g) for 16 h. The catalyst was removed by filtration over celite. The filtrate was concentrated in vacuo to yield Compound 12f as an oil. Compound 12f was used in the next reaction without further purification. TFA (5 mL) was added to a solution of Compound 12f (0.37 g, 0.91 mmol) in DCM (20 mL). The mixture was stirred at rt for 30 min, concentrated in vacuo and the residue was purified via RP-HPLC to give Compound 12g as an oil.

To a solution of Compound 8a (0.28 g, 1.15 mmol) in DMF (40 mL), 1-HOBt (0.135 g, 1.0 mmol), EDC (0.192 g, 1.0 mmol) and DIEA (0.35 mL, 2 mmol) were added under Argon at rt. The mixture was stirred at rt for 45 min. A solution of Compound 12g (0.28 g, 0.067 mmol) and DIEA (0.35 mL, 2 mmol) in DMF (10 mL) was added to the mixture containing Compound 8a. The resulting mixture was stirred overnight at rt. Water (2 mL) was added, followed by DCM (20 mL). The organic layer was separated, dried ($Na_2SO_4$) and concentrated. The resulting crude Compound 12h was used as such in the next reaction. The crude Compound 12h was dissolved in MeOH (20 mL) and 3N aqueous NaOH (6 mL) was added. The mixture was stirred at rt for 5 h and neutralized with 2N HCl. After the solvent was evaporated, the residue was purified via RP-HPLC to yield Compound 11. MS (ES+) m/z 480 (M+H$^+$). 1H-NMR of Compound 11: $^1$HNMR (CDCL$_3$, 300 MHz) δ 1.09 (m, 2H), 1.30 (m, 1H), 1.4-1.7 (m, 3H), 1.86 (m, 1H), 1.94 (m, 2H), 2.47 (m, 1H), 2.58 (d, J=7.5 Hz, 2H), 2.7-3.1 (m, 7H), 3.15 (m, 1H), 3.51 (br s, 2H), 3.99 (dd, J=5.3 Hz, 14.3 Hz, 2H), 4.49 (dd, J=5.3 Hz, 14.3 Hz, 2H), 5.97 (s, 2H), 6.45 (d, J=7.5 Hz, 1H), 6.66 (d, J=7.8 Hz, 1H), 6.69, (s, 1H), 6.75 (d, J=7.8 Hz, 1H), 7.33 (d, J=7.5 Hz, 1H), 9.82 (s, 2H), 15.0 (s, 1H).

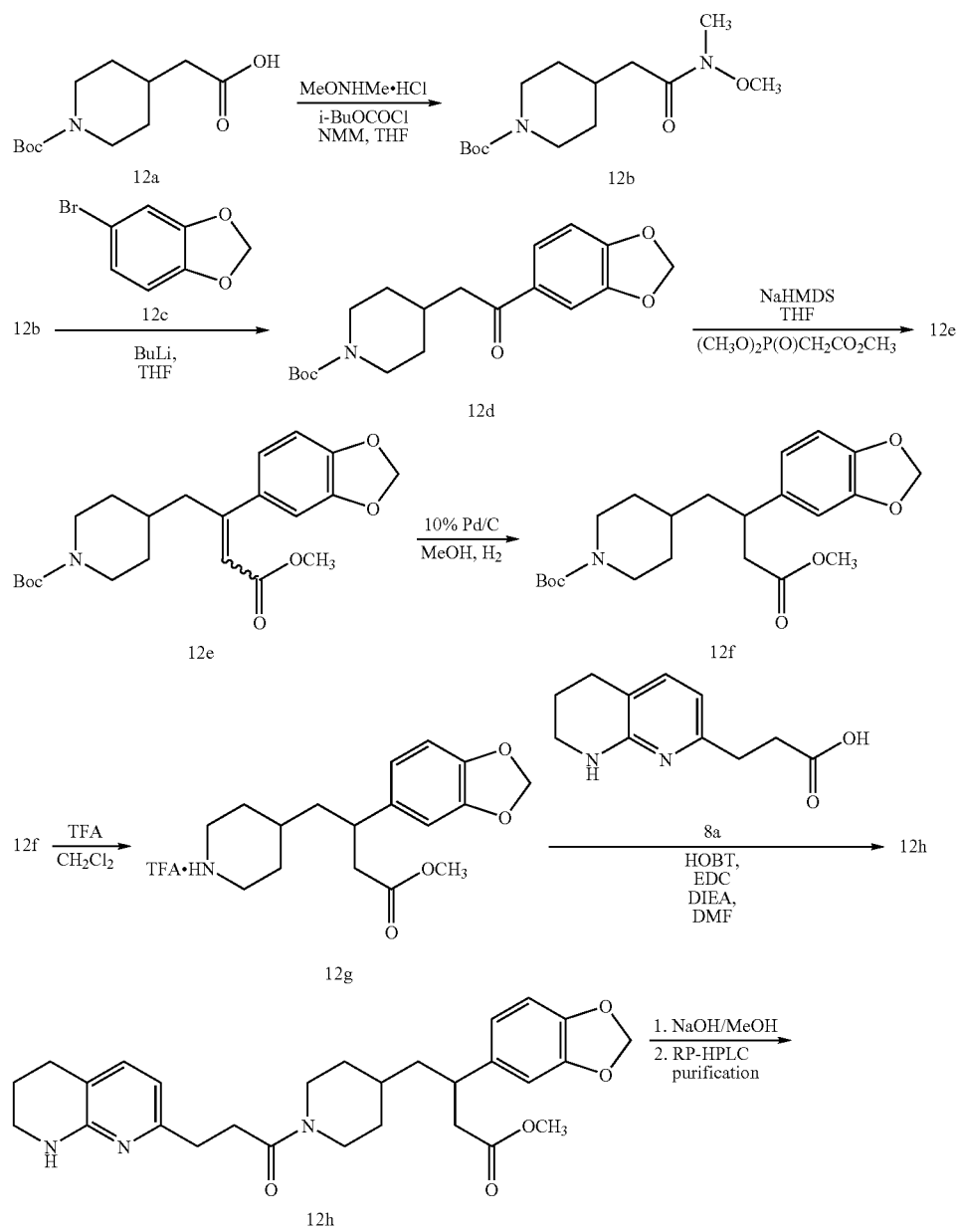

-continued

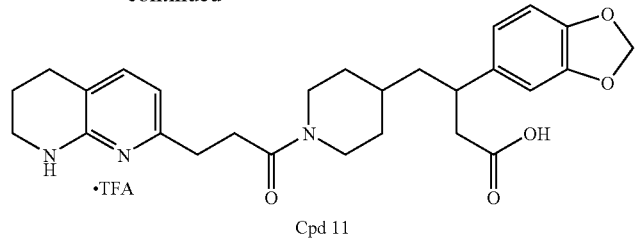

Cpd 11

Using the procedure of Example 12 and the appropriate reagents and starting materials known to those skilled in the art, other compounds of the present invention may be prepared including, but not limited to:

| Cpd | Name | MS (m/z) |
|---|---|---|
| 26 | β-(1,3-benzodioxol-5-yl)-1-[1-oxo-4-(5,6,7,8-tetrahydro-1,8-naphthyridin-2-yl)butyl]-4-piperidinebutanoic acid | 494 |
| 27 | β-(1,3-benzodioxol-5-yl)-1-[3-[(1,4,5,6-tetrahydro-5-hydroxy-2-pyrimidinyl)amino]benzoyl]-4-piperidinebutanoic acid | 509 |
| 28 | 6-methoxy-β-[[1-[1-oxo-3-(5,6,7,8-tetrahydro-1,8-naphthyridin-2-yl)propyl]-4-piperidinyl]methyl]-3-pyridinepropanoic acid | 467 |
| 29 | β-[[1-[1-oxo-4-(5,6,7,8-tetrahydro-1,8-naphthyridin-2-yl)butyl]-4-piperidinyl]methyl]-3-quinolinepropanoic acid | 501 |
| 30 | β-(3-fluorophenyl)-1-[1-oxo-3-(5,6,7,8-tetrahydro-1,8-naphthyridin-2-yl)propyl]-4-piperidinebutanoic acid | 454 |
| 31 | β-(3-fluorophenyl)-1-[1-oxo-4-(5,6,7,8-tetrahydro-1,8-naphthyridin-2-yl)butyl]-4-piperidinebutanoic acid | 468 |
| 32 | β-[[1-[1-oxo-3-(5,6,7,8-tetrahydro-1,8-naphthyridin-2-yl)propyl]-4-piperidinyl]methyl]-3-quinolinepropanoic acid | 487 |
| 33 | β-(4-fluorophenyl)-1-[1-oxo-3-(5,6,7,8-tetrahydro-1,8-naphthyridin-2-yl)propyl]-4-piperidinebutanoic acid | 454 |
| 34 | β-(4-fluorophenyl)-1-[1-oxo-4-(5,6,7,8-tetrahydro-1,8-naphthyridin-2-yl)butyl]-4-piperidinebutanoic acid | 468 |
| 35 | 2-methyl-β-[[1-[1-oxo-3-(5,6,7,8-tetrahydro-1,8-naphthyridin-2-yl)propyl]-4-piperidinyl]methyl]-5-pyrimidinepropanoic acid | 452 |
| 36 | β-(2,3-dihydro-6-benzofuranyl)-1-[1-oxo-3-(5,6,7,8-tetrahydro-1,8-naphthyridin-2-yl)propyl]-4-piperidinebutanoic acid | 478 |
| 37 | β-(3,5-difluorophenyl)-1-[1-oxo-3-(5,6,7,8-tetrahydro-1,8-naphthyridin-2-yl)propyl]-4-piperidinebutanoic acid | 472 |
| 38 | β-(3,5-difluorophenyl)-1-[1-oxo-4-(5,6,7,8-tetrahydro-1,8-naphthyridin-2-yl)butyl]-4-piperidinebutanoic acid | 486 |
| 39 | 1-[1-oxo-3-(5,6,7,8-tetrahydro-1,8-naphthyridin-2-yl)propyl]-β-[3-(trifluoromethyl)phenyl]-4-piperidinebutanoic acid | 504 |
| 40 | 1-[1-oxo-3-(5,6,7,8-tetrahydro-1,8-naphthyridin-2-yl)propyl]-β-[4-(trifluoromethoxy)phenyl]-4-piperidinebutanoic acid | 520 |
| 41 | β-(2-fluoro[1,1'-biphenyl]-4-yl)-1-[1-oxo-3-(5,6,7,8-tetrahydro-1,8-naphthyridin-2-yl)propyl]-4-piperidinebutanoic acid | 530 |
| 42 | β-(3-fluoro-4-methoxyphenyl)-1-[1-oxo-3-(5,6,7,8-tetrahydro-1,8-naphthyridin-2-yl)propyl]-4-piperidinebutanoic acid | 484 |
| 43 | 1-[1-oxo-3-(5,6,7,8-tetrahydro-1,8-naphthyridin-2-yl)propyl]-β-(4-phenoxyphenyl)-4-piperidinebutanoic acid | 528 |
| 44 | β-[[1-[1-oxo-3-(5,6,7,8-tetrahydro-1,8-naphthyridin-2-yl)propyl]-4-piperidinyl]methyl]-4-isoquinolinepropanoic acid | 487 |
| 45 | β-[[1-[1-oxo-3-(5,6,7,8-tetrahydro-1,8-naphthyridin-2-yl)propyl]-4-piperidinyl]methyl]-3-pyridinepropanoic acid | 437 |
| 46 | β-(2,3-dihydro-5-benzofuranyl)-1-[1-oxo-3-(5,6,7,8-tetrahydro-1,8-naphthyridin-2-yl)propyl]-4-piperidinebutanoic acid | 478 |
| 47 | 2,4-dimethoxy-β-[[1-[1-oxo-3-(5,6,7,8-tetrahydro-1,8-naphthyridin-2-yl)propyl]-4-piperidinyl]methyl]-5-pyrimidinepropanoic acid | 498 |
| 48 | 2-methoxy-β-[[1-[1-oxo-3-(5,6,7,8-tetrahydro-1,8-naphthyridin-2-yl)propyl]-4-piperidinyl]methyl]-5-pyrimidinepropanoic acid | 468 |

Example 13

β-[2-[1-[3-[(1,4,5,6-Tetrahydro-2-pyrimidinyl) amino]benzoyl]-4-piperidinyl]ethyl]-3-quinolinepropanoic acid (Cpd 12)

A suspension of lithium aluminum hydride (3.11 g, 0.082 mol) in $Et_2O$ (250 mL) was cooled at -55° C. under Argon. A solution of Compound 3b (18.5 g, 0.068 mol) in $Et_2O$ (75 mL) was added dropwise over a period of 15 min so that the temperature did not exceed -50° C. The cooling bath was removed and the mixture was warmed up to 5° C., cooled again to -35° C. and celite (50 g) was added. The mixture was quenched slowly with bisulphate solution (15.30 g in 43 mL of $H_2O$) while the temperature was kept at -30° C. The resulting mixture was warmed to 0° C., filtered over celite and the solid residue on the filter was washed with EtOAc (750 mL) and $H_2O$ (500 mL). The organic layer was separated, washed with 0.5N HCl (100 mL), saturated $NaHCO_3$ (100 mL) and brine (100 mL). The aqueous layer was extracted with EtOAc (500 mL) and the combined organic layers were dried, filtered and evaporated. The resulting residue was purified by Kugelrohr distillation (120-140° C. at 1.5-2 mm Hg) to yield Compound 13a as a colorless oil.

A mixture of 3-bromoquinoline (10.40 g, 0.05 mol), trimethylsilylacetylene (8.48 mL, 0.06 mol), cuprous iodide (0.5 g) and trans-dichlorobis(triphenylphosphine)palladium (1 g) and TEA (15 mL) was heated at 70° C. in a sealed tube for 1 h. $H_2O$ (150 mL) was added, followed by $Et_2O$ (300 mL). The organic layer was separated and the aqueous layer extracted with $Et_2O$ (200 mL). The combined organic layers were dried ($Na_2SO_4$) and concentrated. The residue was purified by flash column chromatography (eluent: 100% DCM) to give 3-(trimethylsilylethynyl)quinoline as a brown oil. 3-(Trimethylsilylethynyl)quinoline was dissolved in anhydrous MeOH (100 mL) and $K_2CO_3$ (0.69 g, 5 mmol) was added. The mixture was stirred at rt for 1 h and DCM (250 mL) was added. The mixture was filtered over celite. The filtrate was evaporated and the residue was purified by flash column chromatography to give Compound 13b as an off-white solid.

Butyllithium (2.5M in hexane, 9.44 mL, 23.6 mmol) was added dropwise to a solution of Compound 13b (3.62 g, 23.6 mmol) in THF (150 mL) under argon, such that the temperature did not exceed -60° C., then the mixture was cooled to -70° C. The mixture was stirred at -70° C. for 15 min and a solution of Compound 13a in THF (40 mL) was added dropwise while maintaining the temperature between -60 and -70° C. After stirring at -70° C. for 30 min, the mixture was warmed to 0° C. over a period of 20 min and $H_2O$ (1 mL) was added. The resulting mixture was dried over $K_2CO_3$, filtered and evaporated. The residue was purified by flash column chromatography (eluent gradient: DCM/MeOH: 100:0 to 95:5) to yield Compound 13c as an oil. A mixture of Compound 13c (6.05 g) in pyridine (100 mL) was hydrogenated in the presence of Lindlar's catalyst (1 g) at 1 psi of hydrogen for 7 h. The catalyst was removed by filtration over celite and the solvent was evaporated. The residue was purified by flash column chromatography (eluent gradient: hexane/EtOAc: 9:1 to 1:1) to yield Compound 13d as a solid.

A solution of methyl 3-chloro-3-oxopropionate (1.24 mL, 11.53 mmol) in DCM (20 mL) was added dropwise over a period of 30 min to a solution of Compound 13d (4.25 g, 11.53 mmol) and TEA (1.81 mL, 13 mmol) in DCM (80 mL) at 0° C. under argon. The mixture was stirred overnight at rt. Aqueous $NH_4Cl$ solution (50 mL) and DCM (150 mL) were added. The organic layer was separated and washed with sat. $NaHCO_3$ (100 mL) and brine (100 mL), dried ($Na_2SO_4$), filtered and evaporated. The residue was purified by flash column chromatography (eluent gradient: hexane/EtOAc: 4:1 to 1:1) to yield Compound 13e as an oil.

A solution of Compound 13e (4.45 g, 9.5 mmol) in THF (20 mL) was added dropwise to a flask containing sodium hydride (60% in mineral oil, 0.57 g, 14.25 mmol, triple washed with hexane (3×25 mL)) at 60° C. under argon. The mixture was heated to 60° C. for 15 min. Chlorotrimethylsilane (2.41 g, 19 mmol) was added via syringe and the mixture was heated for 4 h at 60° C. $H_2O$ (0.5 mL) was added and the mixture was stirred overnight at rt. The reaction mixture was evaporated, DCM (250 mL) was added and the mixture was dried ($Na_2SO_4$). After filtration and evaporation, the residue was heated at 130° C. for 2 h under vacuum. Purification by flash column chromatography (eluent: 1% MeOH in DCM) gave Compound 13f as a yellow oil.

A solution of Compound 13f (0.375 g, 0.88 mmol) in MeOH (50 mL) was hydrogenated in the presence of 10% palladium on carbon (120 mg) at 1 psi of hydrogen for 2 h. The catalyst was removed by filtration over celite and the solvent was evaporated to give a crude Compound 13g, which was used as such for the next reaction. TFA (10 mL) was added to a solution of Compound 13g (0.35 g, 0.82 mmol) in DCM (10 mL). The mixture was stirred at rt for 1 h and concentrated under vacuum to give crude Compound 13h, which was used as such for the next reaction.

Isobutyl chloroformate (0.118 mL, 0.90 mmol) was added to a solution of Compound 6g (230 mg, 0.90 mmol) and NMM (0.385 mL, 3.5 mmol) in DMF (8 mL) under argon at 0° C. The mixture was stirred at 0° C. for 5 min and a solution of Compound 13h (0.455 g, 0.82 mmol) in DMF (7 mL) was added dropwise. After the addition was complete, the cooling bath was removed. The mixture was stirred at rt overnight. $H_2O$ (0.5 mL) was added and the mixture was concentrated under high vacuum at 80° C. The residue was purified by RP-HPLC to yield Compound 13i as a white powder.

1N aqueous NaOH (10 mL) was added to a solution of Compound 13i (0.15 g, 0.2 mmol) in 1,4-dioxane (10 mL). The reaction mixture was stirred for 20 h at rt and neutralized with 1N HCl (10 mL). Purification by RP-HPLC yielded Compound 12 as a white powder after lyophilization. MS (ES+) m/z 514 (M+H$^+$). 1H-NMR of Compound 12: $^1$HNMR (DMSO-d$_6$, 300 MHz) δ 0.97-1.86 (m, 18H), 2.66 (m, 2H), 2.90 (m, 1H), 3.55 (m, 1H), 7.14 (s, 1H), 7.18 (d, J=8.5 Hz, 1H), 7.24 (d, J=8.5 Hz, 1H), 7.44 (t, J=7.6 Hz, 1H), 7.65 (t, J=7.6 Hz, 1H), 7.78 (t, J=7.6 Hz, 1H), 8.01 (t, J=8.5 Hz, 2H), 8.19 (s, 1H), 8.35 (s, 1H), 8.91 (s, 1H).

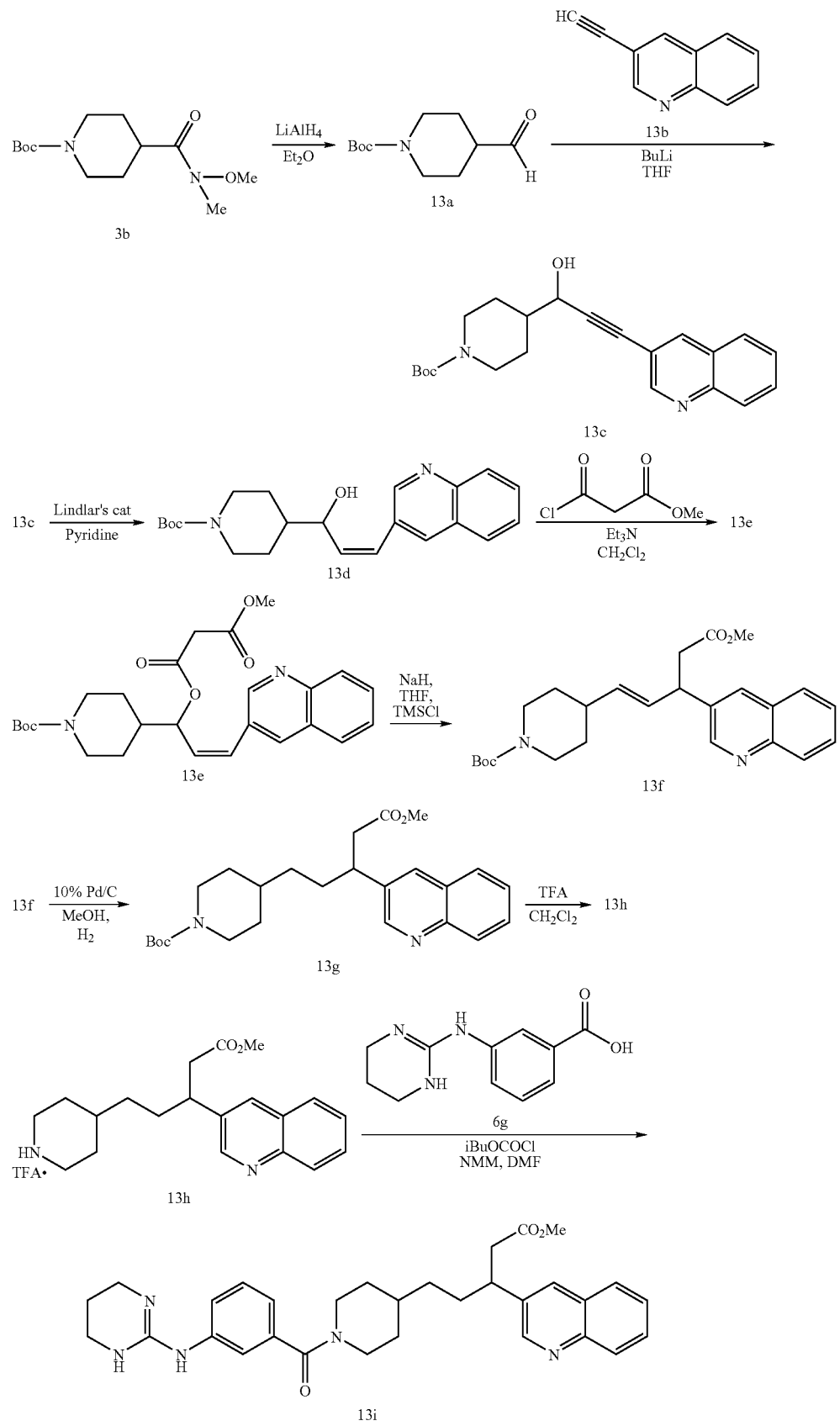

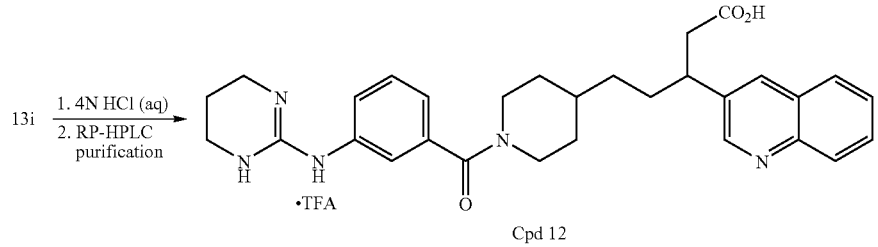

Cpd 12

Using the procedure of Example 13 and the appropriate reagents and starting materials known to those skilled in the art, other compounds of the present invention may be prepared including, but not limited to:

| Cpd | Name | MS (m/z) |
|---|---|---|
| 49 | β-[2-[1-[3-[(1,4,5,6-tetrahydro-5-hydroxy-2-pyrimidinyl)amino]benzoyl]-4-piperidinyl]ethyl]-3-quinolinepropanoic acid | 530 |
| 50 | β-[2-[1-[3-[(3,4,5,6-tetrahydro-2-pyridinyl)amino]benzoyl]-4-piperidinyl]ethyl]-3-quinolinepropanoic acid | 513 |
| 51 | β-[2-[1-[1-oxo-3-(5,6,7,8-tetrahydro-1,8-naphthyridin-2-yl)propyl]-4-piperidinyl]ethyl]-3-quinolinepropanoic acid | 501 |
| 52 | β-[2-[1-[1-oxo-3-(5,6,7,8-tetrahydro-1,8-naphthyridin-2-yl)propyl]-4-piperidinyl]ethyl]-3-quinolinepropanoic acid | 507 |
| 53 | β-(1,3-benzodioxol-5-yl)-1-[3-[(3,4,5,6-tetrahydro-2-pyridinyl)amino]benzoyl]-4-piperidinepentanoic acid | 506 |
| 54 | β-(1,3-benzodioxol-5-yl)-1-[3-[(1,4,5,6-tetrahydro-5-hydroxy-2-pyrimidinyl)amino]benzoyl]-4-piperidinepentanoic acid | 523 |
| 55 | β-(1,3-benzodioxol-5-yl)-1-[(5,6,7,8-tetrahydro-1,8-naphthyridin-2-yl)acetyl]-4-piperidinepentanoic acid | 480 |

Example 14

1-[1-oxo-3-(5,6,7,8-tetrahydro-1,8-naphthyridin-2-yl)propyl]-β-phenyl-4-piperidinebutanoic acid (Cpd 13)

Di-tert-butyl dicarbonate (41.25 g, 189 mmol) was added in one portion to a solution of 4-(2-hydroxyethyl)piperidine Compound 14a (24.42 g, 189 mmol) in DMF (200 mL) at 0° C. After 1 hour, the cooling bath was removed and the reaction mixture was allowed to stir for 20 h at RT. The reaction mixture was treated with Et$_2$O (200 mL) and H$_2$O (500 mL). The organic layer was separated, washed with sat NH$_4$Cl (200 mL) and brine (200 mL) and dried MgSO$_4$). After filtration and evaporation, Compound 14b was obtained as a transparent oil and used as such without further purification.

A solution of DMSO (14 g, 179 mmol) in DCM (80 mL) was added dropwise over a period of 1.5 h to a 2M solution of oxalyl chloride (62.8 mL, 125.6 mmol) in dry DCM (200 mL) at −78° C., such that the temperature did not exceed −60° C. A solution of Compound 14a in DCM (30 mL) was added dropwise at −78° C. over a 50 min period. After stirring 30 min at −78° C., the cooling bath was removed and the temperature of the reaction mixture was allowed to rise to −30° C. over a 30 min period. TEA (25.41 g, 251 mmol) was added and the reaction mixture was allowed to stir for 1 h at rt. The solid precipitate that had formed was removed by filtration and the filtrate was washed with 0.3N HCl (2×100 mL) and brine (200 mL). The organic phase was dried (Na$_2$SO$_4$), evaporated and the residue was purified via flash column chromatography (eluent gradient: hexane/EtOAc 100/0 to 70/30) to yield Compound 14c.

A 1M solution of LiHMDS (73 mL, 73 mmol) was added via syringe to a solution of trimethyl phosphonoacetate (13.29 g, 73 mmol) in THF (200 mL) at −78° C. under argon. The reaction mixture was then stirred for 20 min at −78° C. and a solution of Compound 14c (8.3 g, 36.5 mmol) in THF (50 mL) was added over a 30 min period. After stirring for 15 min at −78° C., the cooling bath was removed and the reaction mixture was heated to reflux for 2. The reaction mixture was allowed to cool to room temperature and a saturated NH$_4$Cl solution (40 mL) was added. Et$_2$O (200 mL) was added, the organic layer was separated and washed with brine (140 mL) and dried (Na$_2$SO$_4$). After filtration and evaporation, the residue was purified via flash column chromatography (eluent gradient: hexane/EtOAc: 100/0 to 85/15), yielding a mixture of E- and Z-isomers of Compound 14d.

Compound 14d, phenyl boronic acid (1.55 g, 12.32 mmol), [RhCl(Cod)]2 (0.1 g, 0.227 mmol) and Cod (0.557 g, 5.15 mmol) were combined in H$_2$O (15 mL) and heated to 100° C. for 3 h under a nitrogen atmosphere. Phenylboronic acid (1.0 g, 8.2 mmol) was added again and the reaction mixture was heated to 100° C. for another 6 h. The reaction mixture was allowed to cool to rt, Et$_2$O (100 mL) was added and the organic layer was separated. The aqueous layer was washed with Et$_2$O (2×100 mL) and the combined organic layers were dried (Na$_2$SO$_4$), filtered and evaporated. The residue was purified via flash column chromatography, yielding Compound 14e.

TFA (6 mL) was added to a solution of Compound 14e (1.48 g, 4.09 mmol) in DCM (14 mL). The mixture was stirred at rt for 20 min, concentrated under vacuum and purified via RP-HPLC to yield Compound 14f as a trifluoroacetate salt.

HOBt (0.333 g, 2.46 mmol), EDC (0.47 g, 2.46 mmol) and NMM (0.68 g, 5.28 mmol) were added to a solution of Compound 8a (0.64 g, 2.64 mmol) in DMF (30 mL) under argon. The mixture was stirred at rt for 1 h, then a solution of Compound 14f (0.66 g, 1.76 mmol) and NMM (0.68 g, 5.28 mmol) in DMF (10 mL) was added. The resulting mixture was stirred overnight at rt. Water (2 mL) was added, followed by DCM (20 mL). The organic layer was separated, dried (Na$_2$SO$_4$) and concentrated. The resulting crude Compound 14g was used as such in the next reaction. To a solution of Compound 14g in dioxane (2 mL) and H$_2$O (1 mL) was added NaOH (0.78 g, 19.5 mmol). The mixture was stirred at rt for 5 h and neutralized with 2N HCl. After the solvent was evaporated, the residue was purified by RP-HPLC to give Compound 13 after lyophilization.

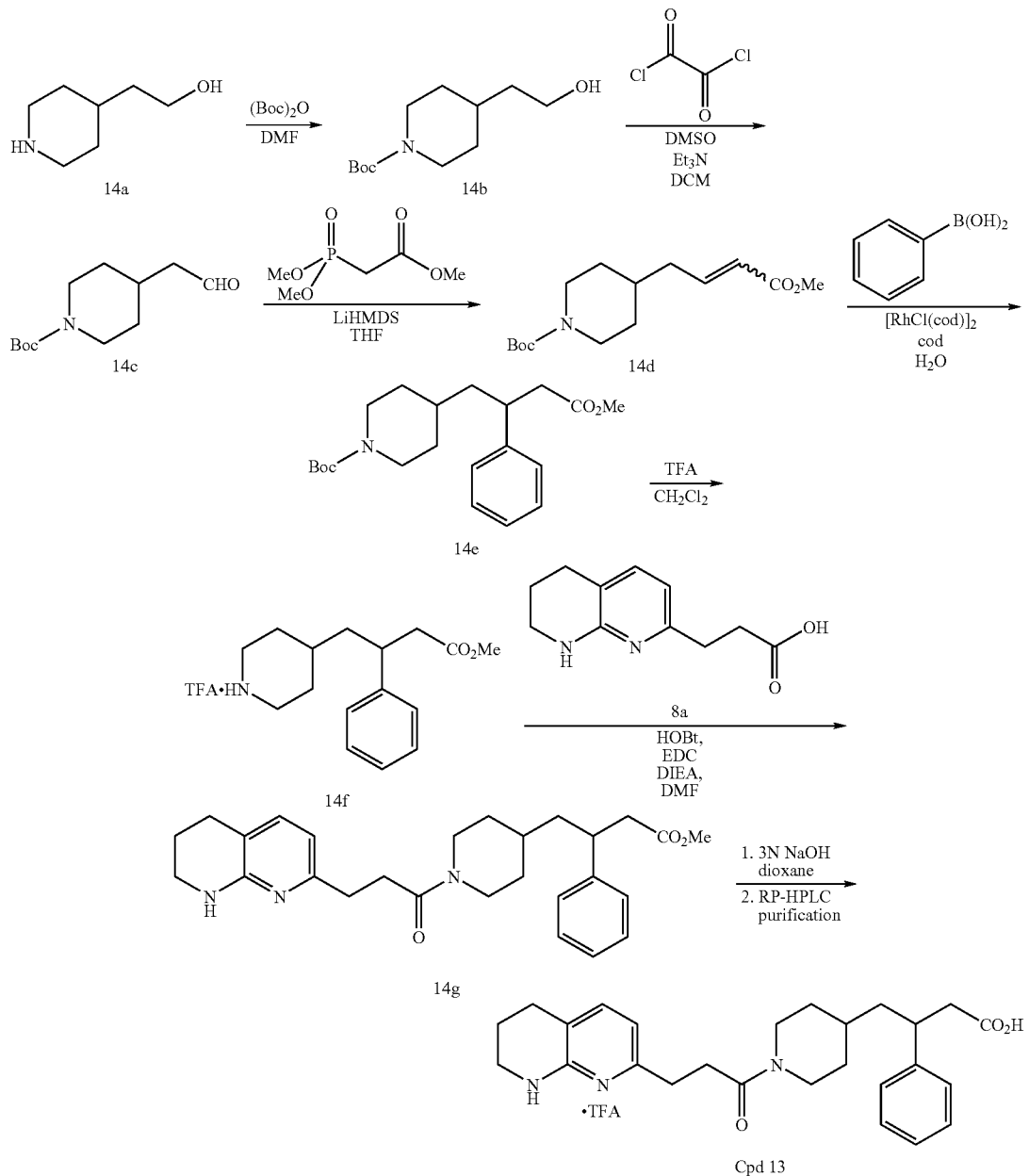

Using the procedure of Example 14 and the appropriate reagents and starting materials known to those skilled in the art, other compounds of the present invention may be prepared including, but not limited to:

| Cpd | Name | MS (m/z) |
|---|---|---|
| 56 | β-(2-naphthalenyl)-1-[1-oxo-3-(5,6,7,8-tetrahydro-1,8-naphthyridin-2-yl)propyl]-4-piperidinebutanoic acid | 486 | and pharmaceutically acceptable salts thereof.

Example 15

Isomers 1, 2, 3, and 4 of 1,2,3,4-tetrahydro-β-[[1-[1-oxo-3-(5,6,7,8-tetrahydro-1,8-naphthyridin-2-yl)propyl]-4-piperidinyl]methyl]-3-quinolinepropanoic acid (Cpd 19-1, 19-2, 19-3, 19-4)

To a stirred solution of the Weinreb amide 12b (3.00 g, 10.48 mmol) and 3-bromoquinoline Compound 15a (10.9 g, 52.38 mmol) in THF (120 mL) were added dropwise n-BuLi (2.5 M solution in hexane; 21.0 mL, 52.38 mmol) over a period of 20 min at −78° C. The reaction mixture was kept below −74° C. during the addition. After the addition, the mixture was stirred for 30 min at −78° C., and then the cooling bath was removed. The reaction mixture was allowed to warm up to rt over a period of 1 h. The reaction mixture was quenched by the addition of saturated NH₄Cl in water (50 mL), and it was extracted with EtOAc (100 mL). The organic layer was washed with brine (10 mL), and dried over MgSO₄, filtered and concentrated under reduced pressure. The residue was purified by flash column chromatography (30% EtOAc/hexane) to give the ketone Compound 15b as an amber foam. MS (ES+) m/z 355.4 (M+H⁺). ¹H-NMR (CDCl₃, 300 MHz) δ 1.26 (m, 2H), 1.46 (s, 9H), 1.78 (m, 2H), 2.22 (m, 1H), 2.77 (m, 2H), 3.02 (d, J=7 Hz, 2H), 4.08-4.18 (m, 2H), 7.64 (t, J=7 Hz, 1H), 7.85 (t, J=8 Hz, 1H), 7.96 (d, J=8 Hz, 1H), 8.17 (d, J=8 Hz, 1H), 8.70 (br s, 1H), 9.42 (br s, 1H).

To a THF (166 mL) solution of trimethyl phosphonoacetate (11.65 mL, 80.58 mmol) was added dropwise NaHMDS (1.0M in THF; 67.2 mL, 67.15 mmol) over a period of 10 min at −78° C. The resulting partially solidified mixture was stirred at -50° C. for 20 min. To the resulting thick solidified mixture, a THF (119 mL) solution of the ketone Compound 15b (4.76 g, 13.43 mmol) was added at -50° C. over a period of 5 min. After the addition, the cooling bath was changed to a water bath and it was stirred for 15 min. The reaction mixture was then refluxed for 2.5 h. The reaction was monitored by HPLC. After cooling to rt, the mixture was diluted with EtOAc (400 mL) and it was washed with saturated NaHCO₃ (50 mL×2), and brine (50 mL). The organic layer was dried over MgSO₄, filtered, and concentrated under reduced pressure. The residue was purified by flash column chromatography (100 g, 6.5×5 cm, 20% to 30% EtOAc/hexane) to give the olefin Compound 15c as an amber-red syrup, mixture of E,Z-isomers. MS (ES+) m/z 411.3 (M+H⁺).

A MeOH (150 mL) solution of the olefin Compound 15c (2.76 g, 6.72 mmol) was added to 10% Pd/C (5.52 g as is, 50% water wet). The solution was vacuum/N₂ degassed and then pressurized to 60 psi H₂ pressure. The reaction was agitated at rt for 22 h. The reaction mixture was filtered and the filtrates were concentrated under reduced pressure. The residue was purified by flash column chromatography (70 g, 3×25 cm column, eluting with 30% EtOAc/hexane) to afford the hydroquinoline Compound 15d as a light yellow gum) and Compound 15e as a minor product.

Alternatively, toluene can be used as the solvent. A solution of Compound 15c (17.14 g, mmol), was combined with 10% Pd/C (8.6 g) in toluene (210 mL) with TEA (2.1 mL). The reaction mixture was shaken on a Parr apparatus at 50° C. and 50 psi for about 28 h. It was stopped when the hydrogen uptake slowed. After chromatography Compound 15d was isolated. MS (ES+) m/z 417.1 (M+H⁺). ¹HNMR (CDCl₃, 300 MHz) δ 1.0-1.6 (m, 6H), 1.45 (s, 9H), 2.0-2.7 (m, 8H), 3.00 (m, 1H), 3.26 (m, 1H), 3.67 (s, 3H), 3.83 (m, 1H), 4.11 (m, 2H), 6.49 (d, J=8 Hz, 1H), 6.62 (t, J=7 Hz, 1H), 6.97 (m, 2H).

The individual enantiomers of Compound 19 were prepared by separating the isomers of 15d and taking them to final product Compounds 19-1, 19-2, 19-3, and 19-4, by the same method that Compound 5a was converted to Compound 5 in Example 5, but using the tetrahydronaphthyridine Compound 8a instead of 4a.

The four isomers of Compound 15d were separated by sequential chiral chromatography. The UV triggered preparative HPLC work was accomplished using a Dynamic Axial Compression type Prochrom LC50 column, which was filled with 500 grams of stationary phase. A Prep LC 4000 (Waters) quaternary gradient low pressure mixing pump, a K-2500 UV detector (KNAUER), a 233 XL auto injector (Gilson), a 402 Syringe pump (Gilson), a 202 fraction collector (Gilson), an rh.7030L fraction collector valve (Gilson), and Unipoint control software (Gilson) were utilized. Isomers (numbered based on elution order: isomer 1 first eluting) 15d-1 and 15d-2 were separated from isomers 15d-3 and 15d-4 using a Chiralpak® OD column: Cellulose tris-(3,5-dimethylphenylcarbamate) coated on a 20 µm silica-gel, 5 cm ID; 41 cm length; using methanol as eluent: 100 vol % at 80 mL/min. and a wavelength 220 nM. This resulted in 15d-1 and 15d-2 as a mixture and 15d-3 and 15d-4 as a mixture. The isomers 15d-1 and 15d-2 were separated on a chiral column: Chiralpak® AD: Amylose tris-(3,5-dimethylphenylcarbamate) coated on a 20 µm silica-gel, 5 cm ID, 41 cm length; using ethanol as eluent: 100 vol % at 80 mL/min.; wavelength 220 nM. This results in two pure isomers 15d-1 and 15d-2, which were individually converted to 19-1 and 19-2, respectively, by the methods described in Example 5 with the appropriate reagents and starting materials.

The isomers 15d-3 and 15d-4 were separated on a chiral column: Chiralpak® AD, Amylose tris-(3,5-dimethylphenylcarbamate) coated on a 20 µm silica-gel, 500 gr; 5 cm ID; 41 cm length and as eluent using ethanol: 100 vol % at 80 mL/min.; wavelength 220 nM. This resulted in two pure isomers 15d-3 and 15d-4, which were individually converted to 19-3 and 19-4, respectively, by the methods described in Example 5 with the appropriate reagents and starting materials.

Cpds 19-1, 19-2, 19-3, 19-4: ¹H-NMR (DMSO-d₆, 300 MHz) δ 0.86-2.95 (m, 24H), 3.22 (br d, 1H), 3.41 (br s, 2H), 3.82 (br d, 1H), 4.37 (br d, 1H), 6.65 (m, 3H), 6.95 (m, 2H), 7.61 (d, J=7 Hz, 1H), 7.95 (br s, 1H).

| Compound No. | Optical Rotation of 15d (in MeOH) | Compound No. | Optical Rotation of 19 (in MeOH) |
|---|---|---|---|
| 15d-1 | +30° | 19-1 | +15.85° |
| 15d-2 | +62.03° | 19-2 | +24.15° |
| 15d-3 | −64.57° | 19-3 | −24.78° |
| 15d-4 | −30.99° | 19-4 | −14.57° |

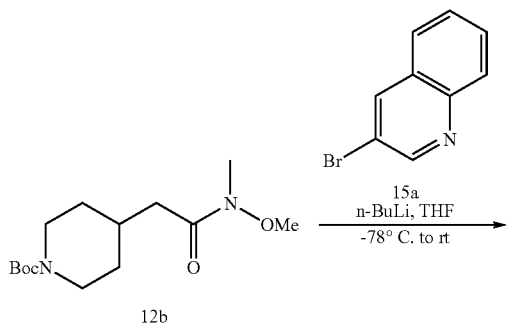

-continued

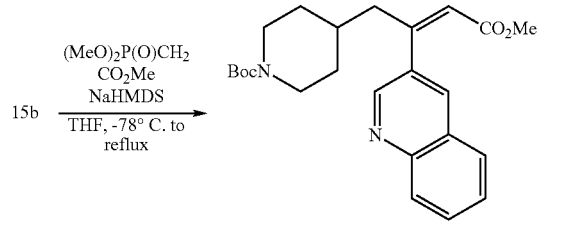

15c

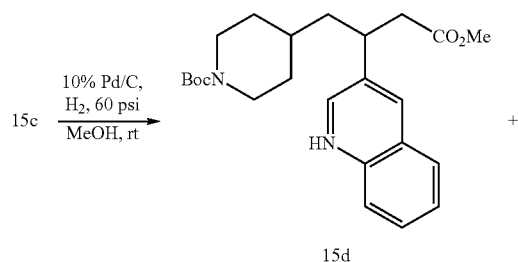

15d

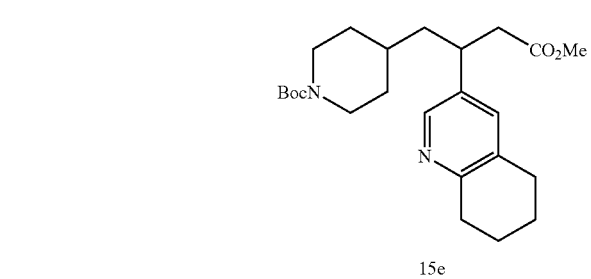

15e

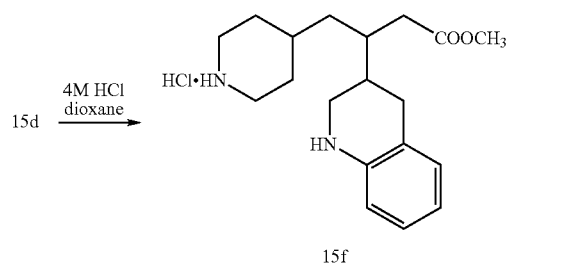

15f

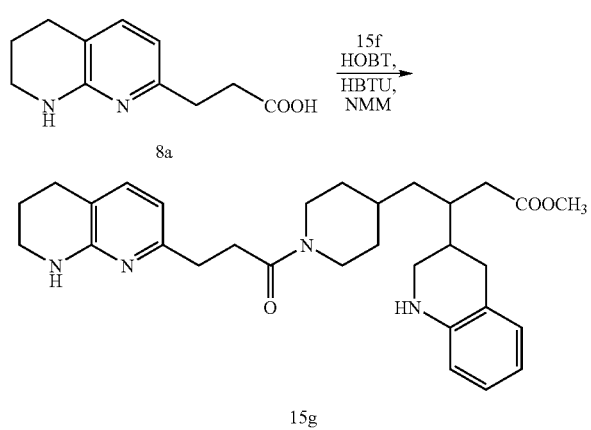

15g

-continued

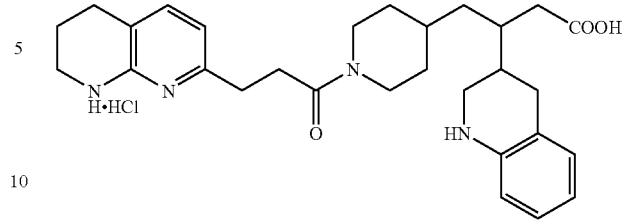

Cpds 19-1, 19-2, 19-3, 19-4

Using the procedures of Example 19 and the appropriate solvents and starting materials known to those skilled in the art, other individual isomers of the compounds of the present invention may be prepared including, but not limited to:

| Cpd | Name | MS (m/z) |
|---|---|---|
| 5-1, 5-2, 5-3, 5-4 | 1,2,3,4-Tetrahydro-β-[1-[1-oxo-4-(5,6,7,8-tetrahydro-1,8-naphthyridin-2-yl)butyl]-4-piperidinyl]-3-quinolinepropanoic acid | 491 |
| 58a | 5,6,7,8-Tetrahydro-β-[1-[1-oxo-4-(5,6,7,8-tetrahydro-1,8-naphthyridin-2-yl)butyl]-4-piperidinyl]-3-quinolinepropanoic acid | 491 |
| 58b | 5,6,7,8-Tetrahydro-β-[1-[1-oxo-4-(5,6,7,8-tetrahydro-1,8-naphthyridin-2-yl)butyl]-4-piperidinyl]-3-quinolinepropanoic acid | 491 | and pharmaceutically acceptable salts thereof.

| Compound No. | Optical Rotation of 5a (in MeOH) | Compound No. | Optical Rotation of 5 (in MeOH) |
|---|---|---|---|
| 5a-3 | −62° | 5-3 | −26.41° |
| 5a-4 | −46° | 5-4 | −19.57° |

Example 16

N-Methyl-1,2,3,4-tetrahydro-β-[[1-[1-oxo-3-(5,6,7,8-tetrahydro-1,8-naphthyridin-2-yl)propyl]-4-piperidinyl]methyl]-3-quinolinepropanoic acid (Cpd 67)

Compound 67 was prepared by the same method used to convert Compound 15d to Compound 19 as described in Example 15, except in this case the intermediate Compound 15d was alkylated prior to the Boc deprotection step. The alkylated product Compound 16a was converted to Compound 67 in the same manner Compound 15d was converted to Compound 19. Compound 15d (280 mg, 0.67 mmol) was dissolved in anhydrous DMF (10 mL) and treated with 2,6-di-tert-butylpyridine (0.181 mL, 0.81 mmol) and iodomethane (0.050 mL, 0.81 mmol) and left at rt for 20 h. The crude reaction mixture was evaporated and then purified by flash chromatography (20% EtOAc in hexane, few drops of triethyl amine) to yield 16a (90 mg, 31%) as a glassy solid. MS (ES+) m/z 431 (M+H$^+$). $^1$H NMR (DMSO-d$_6$, 300 MHz) δ 1.0-1.7 (m, 7H), 1.45 (s, 9H), 2.0-2.7 (m, 8H), 2.88 (s, 3H), 3.01 (m, 1H), 3.09 (m, 1H), 3.67 (s, 3H), 4.01 (m, 2H), 6.4-6.6 (m, 2H), 6.96 (d, J=7 Hz, 1H), 7.08 (t, J=8 Hz, 1H).

| Cpd | Name | MS (m/z) |
|---|---|---|
| 67 | N-Methyl-1,2,3,4-tetrahydro-β-[[1-[1-oxo-3-(5,6,7,8-tetrahydro-1,8-naphthyridin-2-yl)propyl]-4-piperidinyl]methyl]-3-quinolinepropanoic acid | 505 |

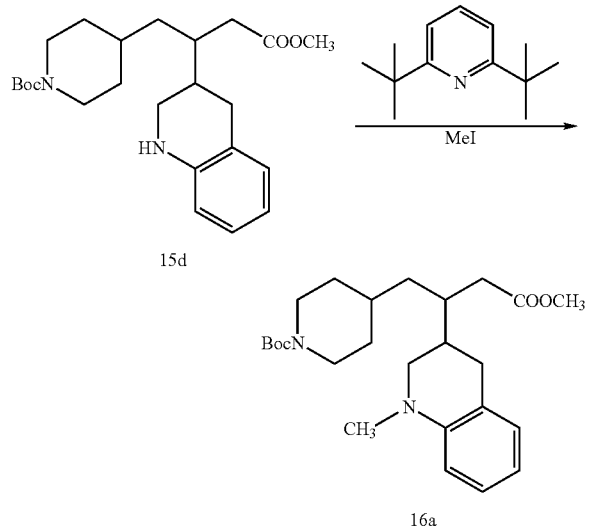

Example 17

4-[1-(3-5,6,7,8-Tetrahydro-[1,8]naphthyridin-2-yl-propionyl)-piperidin-4-yl]-butyric acid tert-butyl ester (Cpd 70)

Using the procedure described in Example 3 for converting Compound 3d to Compound 3e, Compound 14d was converted to Compound 17a. MS (ES+) m/z 286 (M+H$^+$).

Using the procedure described in Example 3 for converting Compound 3e to Compound 3f, Compound 17a was converted to Compound 17b. MS (ES+) m/z 186 (M+H$^+$).

Using the procedure described in Example 14 for converting Compound 14f to Compound 14g, Compound 17b was reacted with Compound 8a to yield Compound 17c. MS (ES+) m/z 374.2 (M+H$^+$).

3N NaOH (3.21 mL, 9.63 mmol) was added to a solution of Compound 17c (1.8 g, 4.82 mmol) in MeOH (9 mL). The resulting mixture was stirred for 4.5 h at rt. 2N HCl (4.82 mL, 9.64 mmol) was added, and the mixture was concentrated under reduced pressure. DCM was added to the residue, and the solid was removed via filtration. The filtrate was evaporated to yield Compound 17d. MS (ES+) m/z 360.3 (M+H$^+$).

t-Butanol (0.476 mL, 4.98 mmol), 1,3-dicyclohexylcarbodiimide (1M in DCM; 1 mL, 1 mmol), and DMAP (1M in DCM; 0.11 mL, 0.11 mmol) were added to a solution of Compound 17d (0.3 g, 0.83 mmol) in DCM (2 mL). The resulting mixture was stirred overnight at rt. The mixture was filtered and concentrated at reduced pressure and the residue was purified by RP-HPLC (10-90% MeCN/water, 0.1% TFA) to yield C Compound 70. MS (ES+) m/z 388.4 (M+H$^+$). $^1$H NMR (CDCl$_3$, 300 MHz) δ 0.98-1.86 (m, 9H), 1.42 (s, 9H), 1.93 (m, 2H), 2.20 (t, J=7.5 Hz, 2H), 2.58 (t, J=7.5 Hz, 1H), 2.68-3.10 (m, 7H), 3.50 (t, J=5.4 Hz, 2H), 4.05 (d, J=12.3 Hz, 1H), 4.54 (d, J=12.3 Hz, 1H), 6.49 (d, J=6.9 Hz, 1H), 7.33 (d, J=6.9 Hz, 1H).

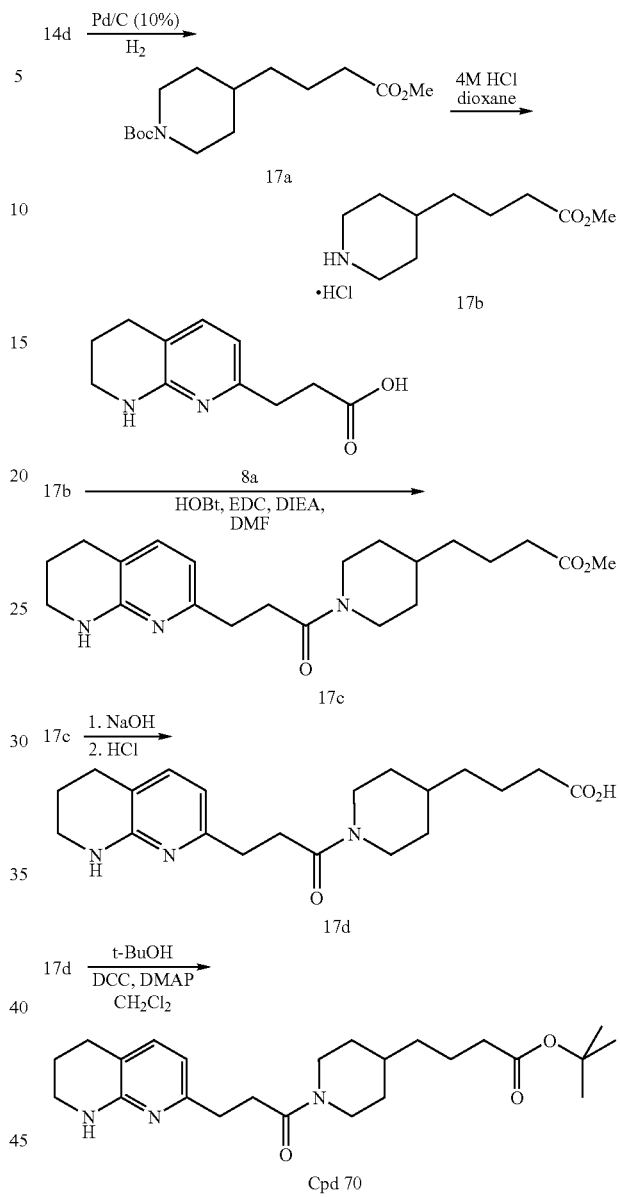

Using the procedure of Example 17 and the appropriate reagents and starting materials known to those skilled in the art, other compounds of the present invention may be prepared including, but not limited to:

| Cpd | Name | MS (m/z) |
|---|---|---|
| 68 | 4-[1-(3-5,6,7,8-Tetrahydro-[1,8]naphthyridin-2-yl-propionyl)-piperidin-4-yl]-butyric acid ethyl ester | 388.4 |
| 69 | 4-[1-(3-5,6,7,8-Tetrahydro-[1,8]naphthyridin-2-yl-propionyl)-piperidin-4-yl]-butyric acid isopropyl ester | 402.3 |
| 71 | 4-[1-(3-5,6,7,8-Tetrahydro-[1,8]naphthyridin-2-yl-propionyl)-piperidin-4-yl]-butyric acid octyl ester | 472.5 |
| 72 | 4-[1-(3-5,6,7,8-Tetrahydro-[1,8]naphthyridin-2-yl-propionyl)-piperidin-4-yl]-butyric acid isobutyl ester | 416.4 |
| 73 | 4-[1-(3-5,6,7,8-Tetrahydro-[1,8]naphthyridin-2-yl-propionyl)-piperidin-4-yl]-butyric acid methyl ester | 374.2 |

Example 18

4-[1-(3-5,6,7,8-Tetrahydro-[1,8]naphthyridin-2-yl-propionyl)-piperidin-4-yl]-butyric acid 2,2-dimethyl-propionyloxymethyl ester (Cpd 74)

3N NaOH (3.21 mL, 9.63 mmol) was added to a solution of Compound 17c (1.8 g, 4.82 mmol) in MeOH (10 mL). The resulting mixture was stirred for 4 h at rt and concentrated at reduced pressure to yield 18a. MS (ES+) m/z 360.3 (M+H+).

Chloromethyl pivalate (0.21 mL, 1.46 mmol) and 25% aqueous NaI (0.13 mL) were added to a suspension of Compound 18a (0.5 g, 1.3 mmol) in acetone (10 mL) and the resulting mixture was heated to reflux for 5 h. The solvent was removed at reduced pressure and the residue was purified by RP-HPLC (10-90% MeCN/water, 0.1% TFA) to yield Compound 74. MS (ES+) m/z 474.3 (M+H+). $^1$H NMR (CDCl$_3$, 300 MHz) δ 1.05 (m, 2H), 1.20 (s, 9H), 1.27 (m, 2H), 1.50 (m, 1H), 1.67 (m, 2H), 1.77 (m, 2H), 1.95 (m, 2H), 2.37 (t, J=7.8 Hz, 2H), 2.57 (t, J=13.2 Hz, 1H), 2.75 (t, J=7.5 Hz, 2H), 2.82 (m, 2H), 2.95-3.10 (m, 3H), 3.51 (t, J=6 Hz, 2H), 4.05 (d, J=13.2 Hz, 1H), 4.56 (d, J=13.2 Hz, 1H), 5.76 (s, 2H), 6.50 (d, J=7.5 Hz, 1H), 7.33 (d, J=7.5 Hz, 1H).

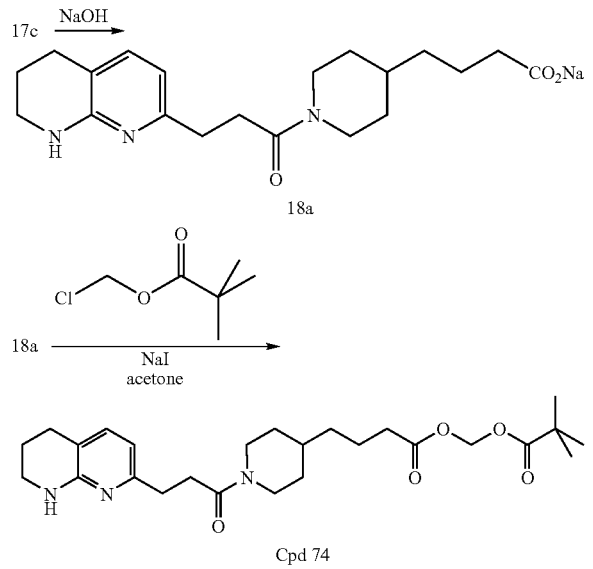

Example 19

3-(2,3-Dihydro-benzofuran-6-yl)-4-[1-(3-5,6,7,8-tetrahydro-[1,8]naphthyridin-2-yl-propionyl)-piperidin-4-yl]-butyric acid (Cpd 36a)

Using the procedure described in Example 12 for converting Compound 12b to Compound 12d, Compound 12b was converted to Compound 19b upon reaction with n-BuLi and 6-bromo-2,3-dihydrobenzofuran 19a (Compound 19a was obtained in three steps from 1,4-dibromo-2-fluorobenzene as described in Organic Letters (2001), 3(21), 3357-3360). MS (ES+) m/z 368.4 (M+Na+).

Using the procedure described in Example 12 for converting Compound 12d to Compound 12e, Compound 19b was converted to Compound 19c. MS (ES+) m/z 424.4 (M+Na+).

Using the procedure described in Example 12 for converting Compound 12e to Compound 12f, Compound 19c was converted to Compound 19d. MS (ES+) m/z 426.5 (M+Na+).

Racemic Compound 19d was separated into the two enantiomerically pure Compounds 19e and 19f on a chiral column using methanol as eluent (Stationary phase: Chiralpak AD 20 µm (Daicel); eluent: methanol; column diameter: 50 mm; detector: 0.5 mm Knauer superpreparative cell; wavelength: 225 nm). Compound 19f (second eluting isomer): [α]$^{20}_D$-24.3 (c 0.717, MeOH). Compound 19e (first eluting isomer): [α]$^{20}_D$+24.8 (c 0.775, MeOH).

Using the procedure described in Example 12 for converting Compound 12f to Compound 12g, Compound 19f was converted to Compound 19g. MS (ES+) m/z 304.4 (M+H+).

Using the procedure described in Example 12 for converting Compound 12g to Compound 12h, Compound 19g was converted to Compound 19h. MS (ES+) m/z 492 (M+H+).

The crude Compound 19h was dissolved in MeOH (20 mL) and 3N aqueous NaOH (6 mL) was added. The mixture was stirred at rt for 5 h and neutralized with 2N HCl. After the solvent was evaporated, the residue was purified via RP-HPLC to yield Compound 36a. MS (ES+) m/z 478.8 (M+H+). $^1$HNMR (CDCl$_3$, 300 MHz) δ 1.09 (1.07 (m, 2H), 1.27 (m, 1H), 1.40-1.86 (m, 3H), 1.73-2.0 (m, 3H), 2.42 (t, J=12.5 Hz, J=4.4 Hz, 1H), 2.55 (d, J=7.3 Hz, 2H), 2.67-3.24 (m, 10H), 3.5 (br s, 2H), 3.93 (dd, J=19.8 Hz, J=16.2 Hz, 1H), 4.43 (dd, J=16.2 Hz, J=14.7 Hz, 1H), 4.57 (t, J=7.5 Hz, 1H), 6.62 (s, 1H), 6.67 (d, J=8.1 Hz, 1H), 7.10 (d, J=8.1 Hz, 1H), 7.33 (d, J=7.5 Hz, 1H), 8.41 (br s, 1H). Anal. Calcd for C$_{28}$H$_{35}$N$_3$O$_4$-1.05 HCl-0.6 H$_2$O: C, 63.86; H, 7.13; N, 7.98; Cl, 7.07; H$_2$O, 2.06. Found: C, 63.67; H, 7.32; N, 8.12; Cl, 6.94; H$_2$O, 1.91. [α]$^{20}_D$-31.1 (c 0.675, MeOH).

Enantiomer 36b was obtained from the fast moving enantiomer Compound 19e using procedures described for converting 19f to Compound 36a.

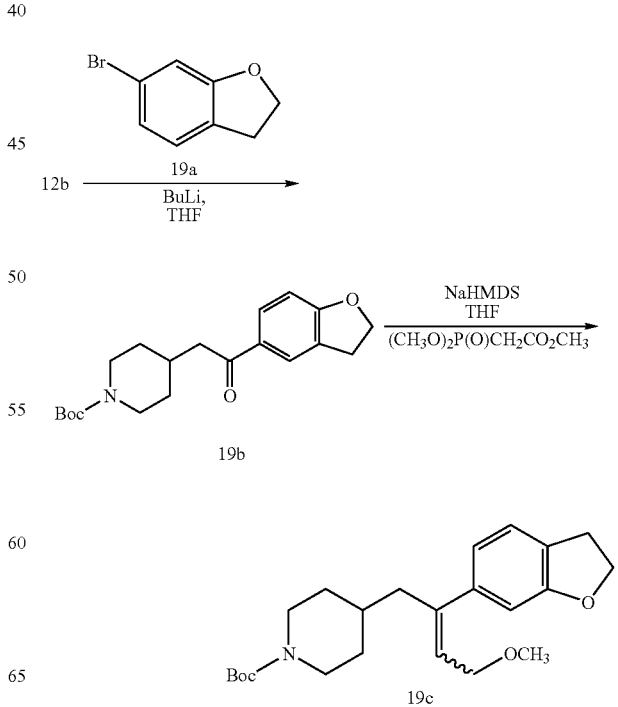

-continued

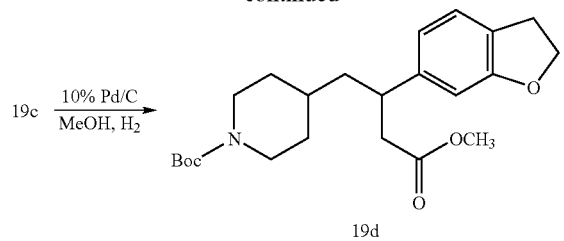
19d

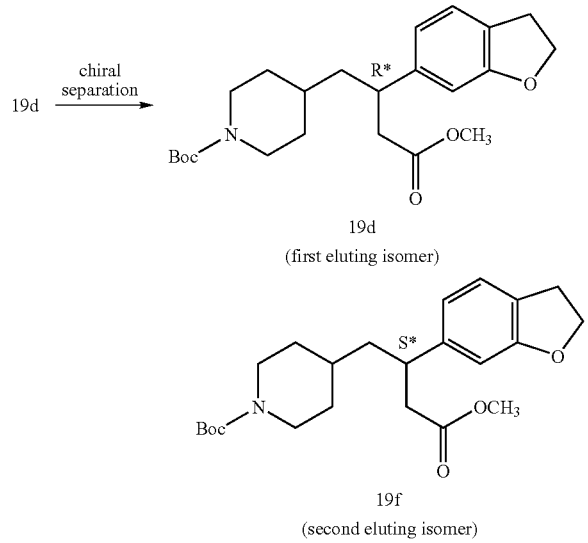
19d
(first eluting isomer)

19f
(second eluting isomer)

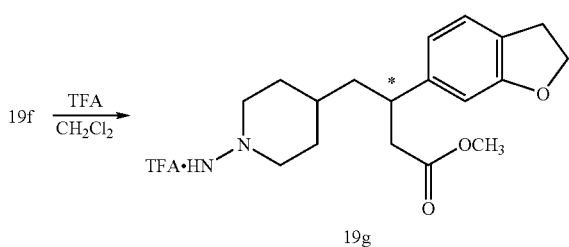
19g

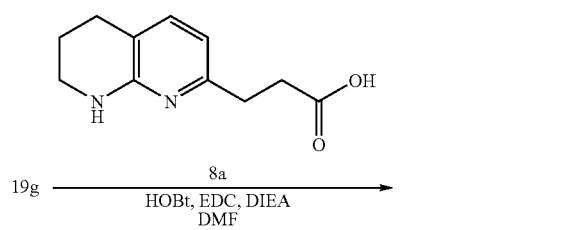
8a

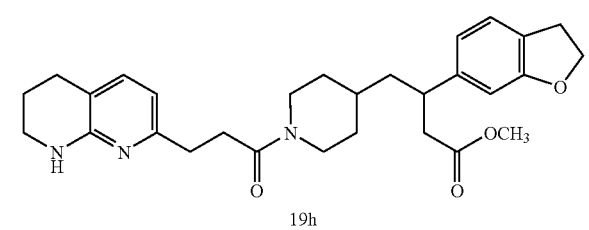
19h

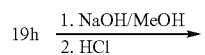

-continued

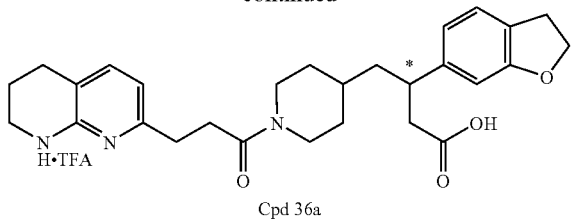
Cpd 36a

Example 20

3-(4-Hydroxy-3-methoxy-phenyl)-4-[1-(3-5,6,7,8-tetrahydro-[1,8]naphthyridin-2-yl-propionyl)-piperidin-4-yl]-butyric acid (Cpd 76)

To a solution of bromo-methoxyphenol Compound 20a (10 g, 49.2 mmol) and N,N-diethyl-N-diisopropylamine (0.7 g, 54.2 mmol) in dry DCM (100 mL) was added 2-(trimethylsilyl)ethoxymethyl chloride (9.03 g, 54.2 mmol). The resulting mixture was stirred for 2 h at rt, and water and brine were added. The organic layer was separated and dried over $Na_2SO_4$. The solvent was removed under reduced pressure and the residue was purified via flash column chromatography (silica gel; eluent: hexane:EtOAc; 9:1) to yield Compound 20b. MS (ES+) m/z 396/398 (M+H$^+$).

Using the procedure described in Example 12 for converting Compound 12b to Compound 12d, Compound 12b was converted to Compound 20c. MS (ES+) m/z 502.2 (M+Na$^+$).

Using the procedure described in Example 12 for converting Compound 12d to Compound 12e, Compound 20c was converted to Compound 20d. MS (ES+) m/z 558.2 (M+Na$^+$).

Using the procedure described in Example 12 for converting Compound 12e to Compound 12f, Compound 20d was converted to Compound 20e. MS (ES+) m/z 408.3 (M+H$^+$).

Using the procedure described in Example 12 for converting Compound 12f to Compound 12g, Compound 20e was converted to Compound 20f. MS (ES+) m/z 308.1 (M+H$^+$).

Using the procedure described in Example 12 for converting Compound 12g to Compound 12h, Compound 20f was converted to Compound 20g. MS (ES+) m/z 496.8 (M+H$^+$).

Using the procedure described in Example 12 for converting Compound 12h to Compound 11, Compound 20g was converted to Compound 76. MS (ES+) m/z 482.4 (M+H$^+$). $^1$HNMR (DMSO-d$_6$, 300 MHz) δ 0.93 (m, 2H), 1.25 (m, 1H), 1.5 (m, 3H), 1.8 (m, 3H), 2.47 (m, 6H), 2.72 (m, 3H), 2.83 (d, J=7.3 Hz, 2H), 2.99 (m, 1H), 3.40 (br s, 2H), 3.74 (s, 3H), 3.77 (dd, J=14.7 Hz, J=14.3 Hz, 1H), 4.28 (dd, J=14.7 Hz, J=14.3 Hz, 1H), 6.60 (d, J=8.1 Hz, 1H), 6.63 (d, J=7.2 Hz, 1H), 6.66 d, J=8.1 Hz, 1H), 6.77 (br s, 1H), 7.59 (d, J=7.2 Hz, 1H), 8.04 (br s, 1H).

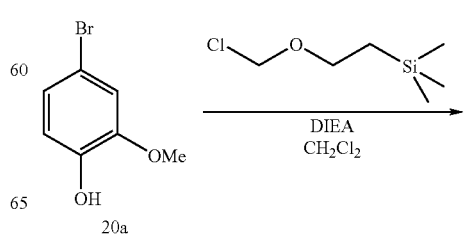
20a

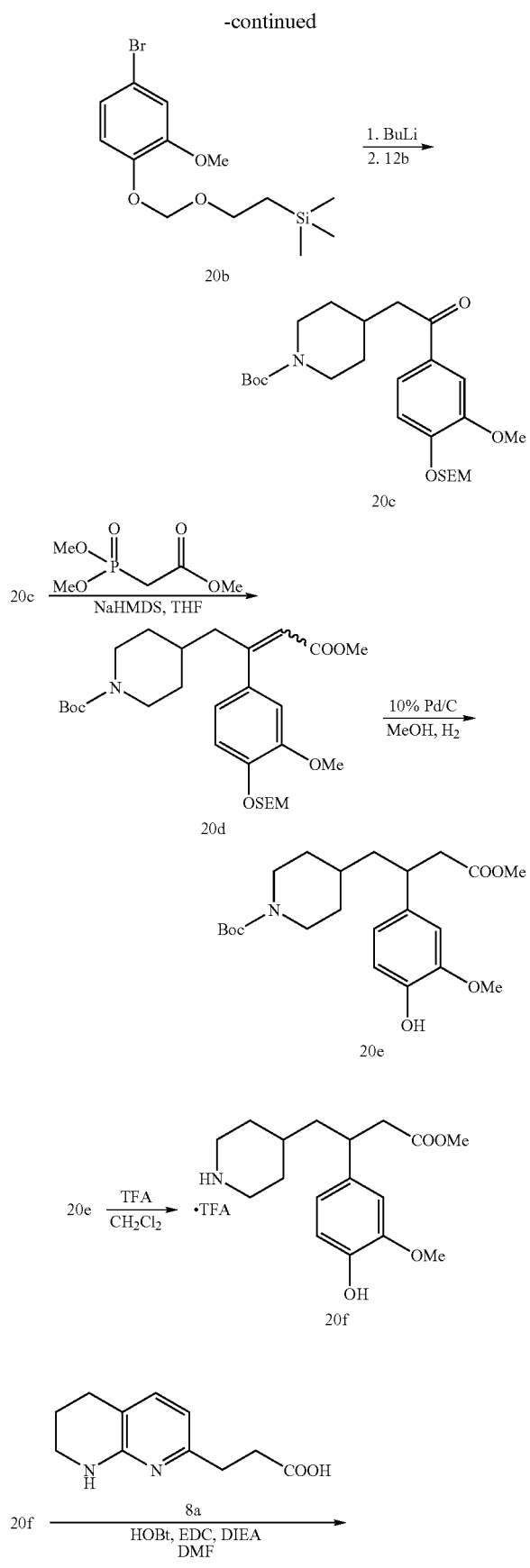

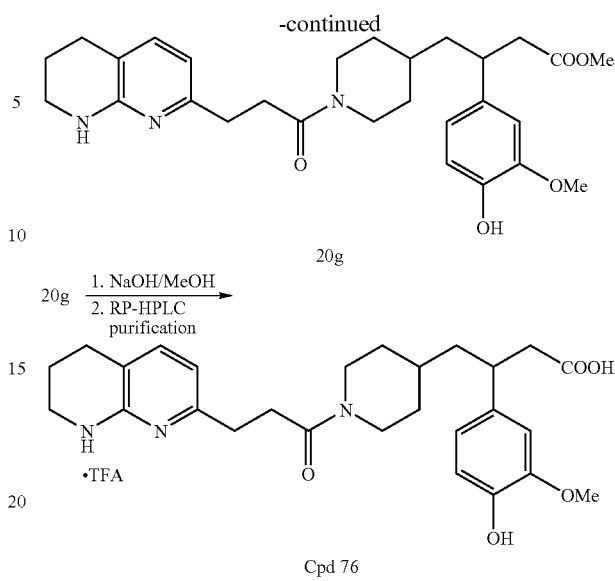

Derivatives in which the hydroxyl substituent of Compound 76 is alkylated or acylated can be made using general methods, starting materials, and reagents known to one skilled in the art.

Example 21

3-(3-Methylamino-phenyl)-4-[1-(3-5,6,7,8-tetrahydro-[1,8]naphthyridin-2-yl-propionyl)-piperidin-4-yl]-butyric acid (Cpd 79)

A solution of 3-bromoaniline Compound 21a (2 mL, 18.4 mmol), di-tert-butyl dicarbonate (4.05 g, 18.6 mmol) in THF (20 mL) was heated to reflux for 30 h under $N_2$. The mixture was evaporated under reduced pressure, and the residue was dissolved in EtOAc. The solution was washed with saturated $NaHCO_3$ solution and brine. The organic layer was dried over $MgSO_4$, filtered, and evaporated, to yield Compound 21b. MS (ES+) m/z 256.8/258.8 (M−$CH_3$).

Sodium hydride (60% in oil; 0.78 g, 19.5 mmol) was added in small portions to a solution of Compound 21b (4.18 g, 15.4 mmol) and methyl iodide (1.21 mL, 19.5 mmol) in DMF (50 mL) at 0° C. The resulting mixture was allowed to warm to rt and stirred for 1 h. The mixture was poured in ice-water and extracted with EtOAc. The organic layer was separated, dried over $MgSO_4$, filtered, and evaporated under reduced pressure to yield Compound 21c. MS (ES+) m/z 270.9/272.9 (M−$CH_3$).

Using the procedure described in Example 12 for converting Compound 12b to Compound 12d, Compound 21c was converted to Compound 21d. MS (ES+) m/z 455.0 (M+$Na^+$).

Using the procedure described in Example 12 for converting Compound 12d to Compound 12e, Compound 21d was converted to Compound 21e. MS (ES+) m/z 510.9 (M+$Na^+$).

Using the procedure described in Example 12 for converting Compound 12e to Compound 12f, Compound 21e was converted to Compound 21f. MS (ES+) m/z 512.8 (M+$Na^+$).

Using the procedure described in Example 12 for converting Compound 12f to Compound 12g, Compound 21f was converted to Compound 21g. MS (ES+) m/z 291.0 (M+$H^+$).

Using the procedure described in Example 12 for converting Compound 12g to Compound 12h, Compound 21g was converted to Compound 21h. MS (ES+) m/z 479.0 (M+$H^+$).

Using the procedure described in Example 12 for converting Compound 12h to Compound 11, Compound 21h was converted to Compound 79. MS (ES+) m/z 465.0 (M+H$^+$). $^1$HNMR (DMSO-d$_6$, 300 MHz) δ 0.99 (m, 2H), 1.21 (m, 1H), 1.4-1.65 (m, 3H), 1.72 (m, 1H), 1.86 (m, 2H), 2.3-3.0 (m, 13H), 3.17 (m, 1H), 3.42 (m, 2H), 3.87 (dd, J=17.7 Hz, J=15.2 Hz, 1H), 4.40 (dd, J=15.2 Hz, J=11.6 Hz, 1H), 6.41 (d, J=7.5 Hz, 1H), 7.1-7.4 (m, 5H).

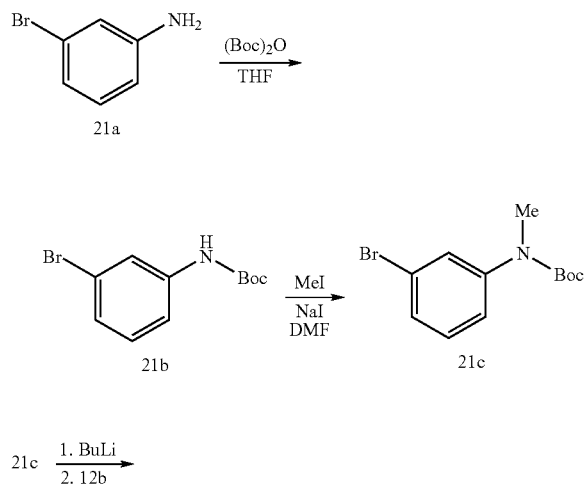

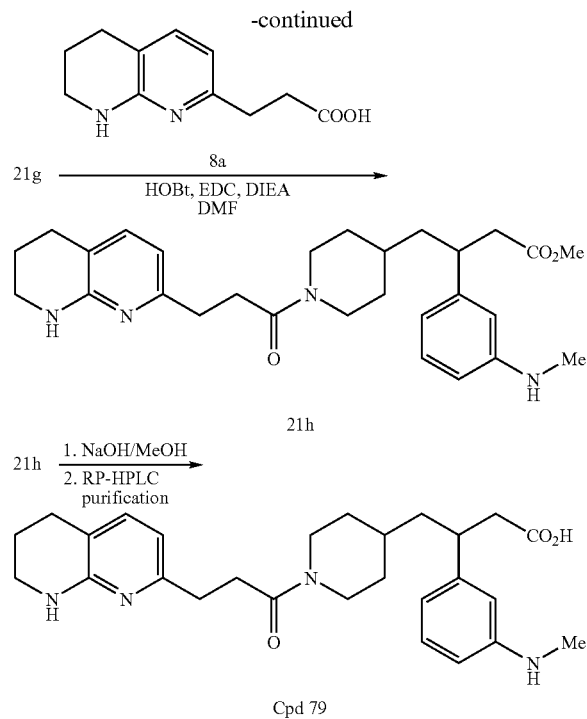

Using the procedure of Example 21 and the appropriate reagents and starting materials known to those skilled in the art, other compounds of the present invention may be prepared including, but not limited to:

| Cpd | Name | MS (m/z) |
| --- | --- | --- |
| 78 | 3-(3-Ethylamino-phenyl)-4-[1-(3-5,6,7,8-tetrahydro-[1,8]naphthyridin-2-yl-propionyl)-piperidin-4-yl]-butyric acid | 479.0 |

Example 22

3-Naphthalen-2-yl-4-[1-(3-5,6,7,8-tetrahydro-[1,8]naphthyridin-2-yl-propionyl)-piperidin-4-yl]-butyric acid (Cpd 56a)

Using the procedure described in Example 19 for converting Compound 12b to Compound 19b, Compound 12b was converted to Compound 22a upon reaction with 2-bromonaphthalene. MS (ES+) m/z 376 (M+Na$^+$).

Using the procedure described in Example 19 for converting Compound 19b to Compound 19c, Compound 22a was converted to Compound 22b. MS (ES+) m/z 432.1 (M+Na$^+$).

Using the procedure described in Example 19 for converting Compound 19c to Compound 19d, Compound 22b was converted to Compound 22c. MS (ES+) m/z 434.1 (M+Na$^+$).

Racemic Compound 22c was separated into the two enantiomerically pure Compounds 22d and 22e on a chiral column using ethanol as eluent (Stationary phase: Chiralpak AD 20 μm (Daicel); column diameter: 50 mm; detector: 0.5 mm Knauer superpreparative cell; wavelength: 225 nm). 22d (first eluting isomer): [α]$^{20}_D$+0.177 (c 0.75, MeOH). 22e (second eluting isomer): [α]$^{20}_D$−0.167 (c 0.683, MeOH).

Using the procedure described in Example 19 for converting Compound 19f to Compound 19g, Compound 22e was converted to Compound 22f. MS (ES+) m/z 312.0 (M+H$^+$).

Using the procedure described in Example 19 for converting Compound 19g to Compound 19h, Compound 22f was reacted with Compound 8a to yield Compound 22g. MS (ES+) m/z 500.0 (M+H$^+$).

Using the procedure described in Example 19 for converting Compound 19h to Compound 36a, Compound 22g was converted to Compound 56a. MS (ES+) m/z 486.0 (M+H$^+$). $^1$HNMR (CDCl$_3$, 300 MHz) δ 0.95-1.35 (m, 3H), 1.44-2.0 (m, 6H), 2.35 (t, J=12.7 Hz, 1H), 2.55-3.1 (m, 9H), 3.40 (m, 3H), 3.89 (m, 1H), 4.42 (m, 1H), 6.45 (d, J=7.4 Hz, 1H), 7.24 (d, J=7.4 Hz, 1H), 7.35 (d, J=8.1 Hz, 1H), 7.45 (m, 2H), 7.65 (s, 1H), 6.45 (d, J=7.4 Hz, 1H), 7.7-7.85 (m, 3H). Anal. Calcd for C$_{30}$H$_{35}$N$_3$O$_3$-1.1 HCl-0.75 H$_2$O: C, 66.83; H, 7.03; N, 7.80; Cl, 7.24; H$_2$O, 2.51. Found: C, 66.53; H, 7.26; N, 8.15; Cl, 7.27; H$_2$O, 2.39. [α]$^{20}_D$-0.193 (c 0.717, MeOH).

Enantiomer 56b was obtained from the fast moving enantiomer 22d using procedures described for converting 22e to Compound 56a.

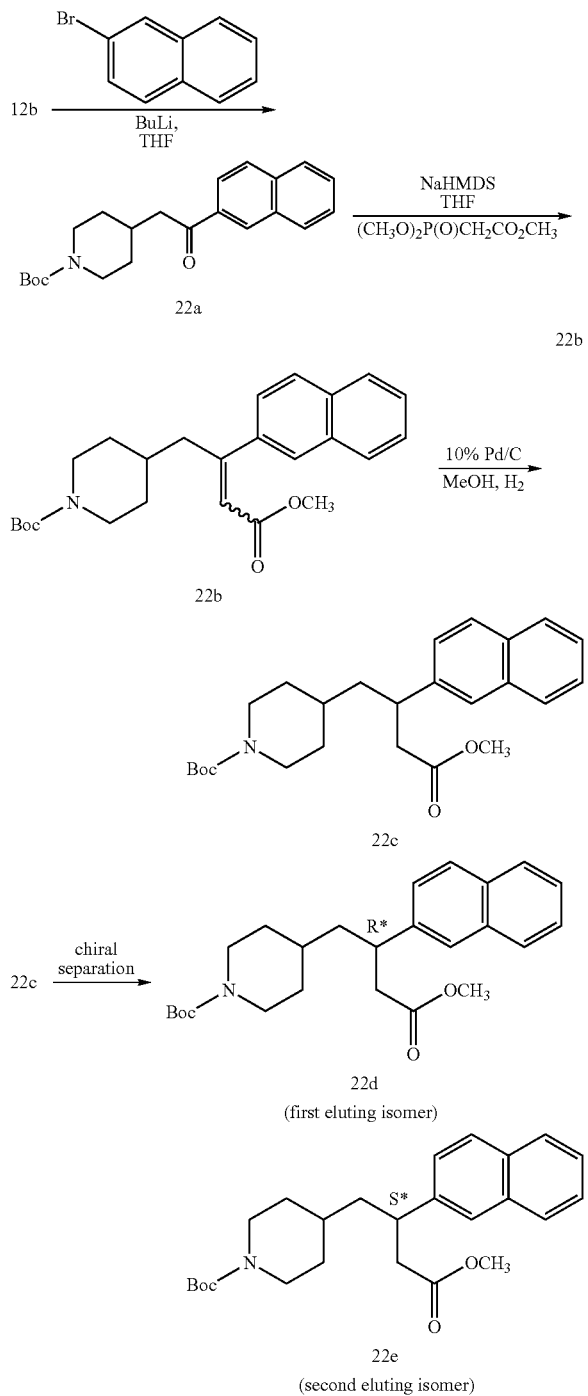

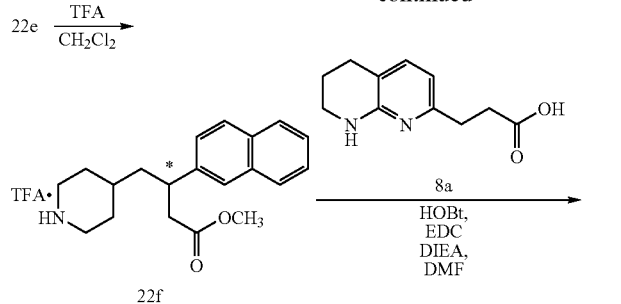

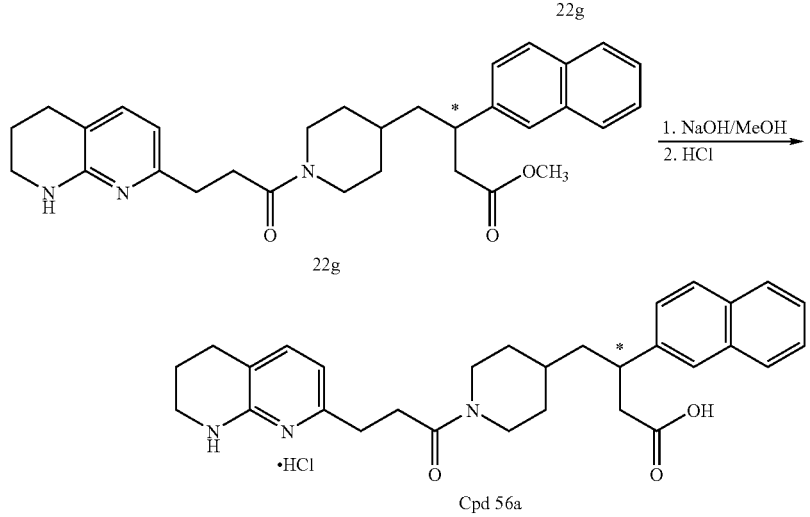

Example 23

3-(3-Fluoro-phenyl)-4-[1-(3-5,6,7,8-tetrahydro-[1,8] naphthyridin-2-yl-propionyl)-piperidin-4-yl]-butyramide (Cpd 64)

Using the procedure described in Example 12 for converting Compound 12b to Compound 12d, Compound 12b was converted to Compound 23a upon reaction with 1-bromo-3-fluorobenzene. MS (ES+) m/z 344 (M+Na+).

Using the procedure described in Example 12 for converting Compound 12d to Compound 12e, Compound 23a was converted to Compound 23b upon reaction with Diethyl cyanomethylphosphonate. MS (ES+) m/z 367.4 (M+Na+).

A solution of Compound 23b (2.06 g, 5.98 mmol) in EtOH (50 mL) was hydrogenated at 5 psi in the presence of 10% palladium on carbon (200 mg) for 40 h. The catalyst was removed by filtration over celite. The filtrate was concentrated in vacuo to yield Compound 23c. MS (ES+) m/z 369.5 (M+Na+).

Using the procedure described in Example 12 for converting Compound 12f to Compound 12g, Compound 23c was converted to Compound 23d. MS (ES+) m/z 247 (M+H+).

Using the procedure described in Example 12 for converting Compound 12g to Compound 12h, Compound 23d was reacted with Compound 8a to yield Compound 23e. MS (ES+) m/z 435 (M+H+).

A mixture of Compound 23e (150 mg, 0.345 mmol) and 12N HCl (10 mL) was heated to 40° C. for 3 h. The mixture was evaporated to dryness and further dried by lyophilization to yield Compound 64. MS (ES+) m/z 453.5 (M+Na+).

$^1$HNMR (DMSO-d$_6$, 300 MHz) δ 0.8-1.1 (m, 2H), 1.25 (m, 1H), 1.4-1.65 (m, 3H), 1.7-1.9 (m, 4H), 2.25-2.5 (m, 4H), 2.7-2.9 (m, 8H), 3.21 (m, 1H), 3.82 (t, J=13.6 Hz, 1H), 4.31 (t, J=13.6 Hz, 1H), 6.66 (d, J=7.3 Hz, 1H), 6.71 (br s, 1H), 6.95-7.15 (m, 3H), 7.25 (br s, 1H), 7.36 (dd, J=15.1 Hz, J=7.3 Hz, 1H), 7.63 (d, J=7.3 Hz, 1H), 7.98 (br s, 1H), 13.77 (br s, 1H).

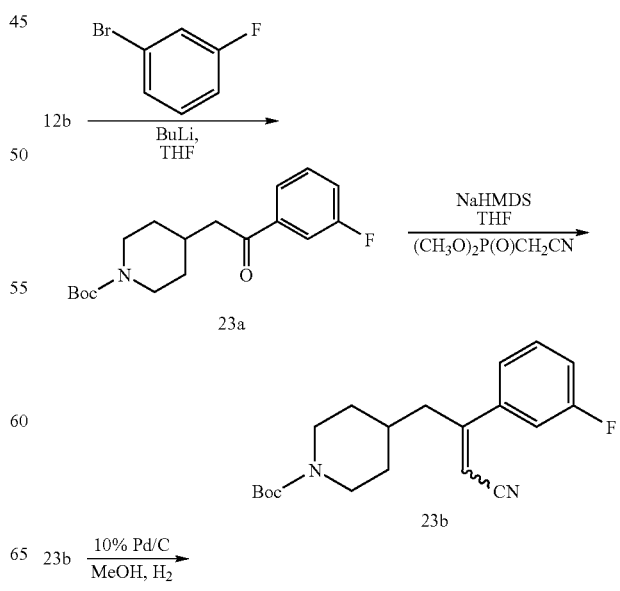

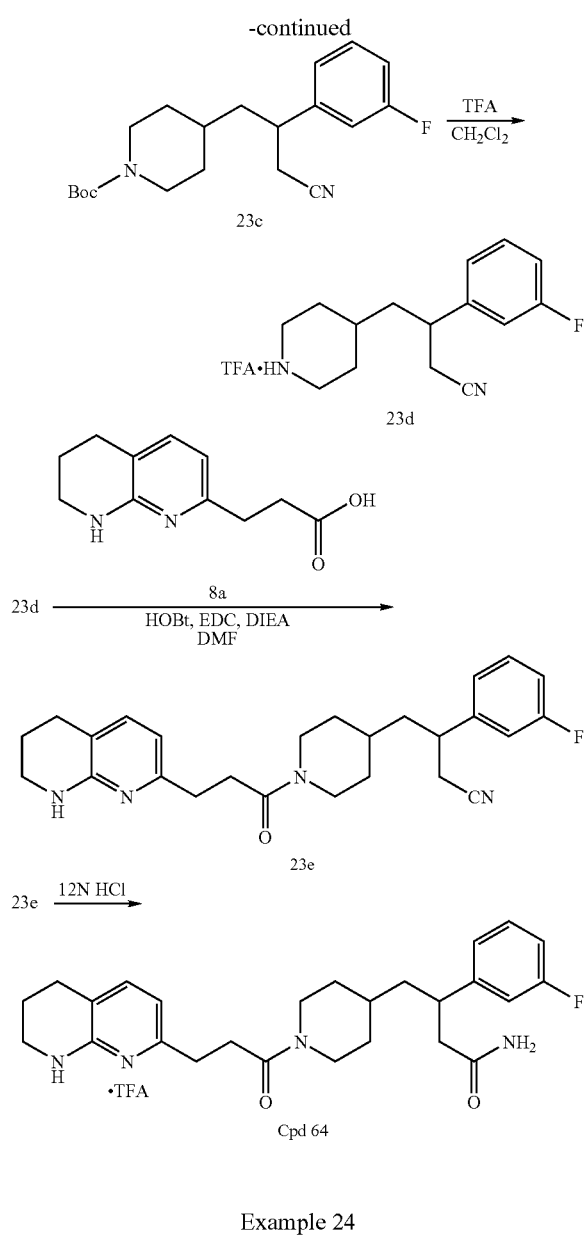

Example 24

3-(3-Fluoro-phenyl)-4-[1-(3-5,6,7,8-tetrahydro-[1,8]naphthyridin-2-yl-propyl]-piperidin-4-yl]-butyric acid (Cpd 81)

Lithium aluminum hydride (1.0M in THF; 16.5 mL, 16.5 mmol) was added slowly to a suspension of Compound 8a (2.0 g, 8.2 mmol) in dry THF (60 mL) at 0° C. The cooling bath was removed, and the mixture was stirred for 24 hr at rt. The mixture was quenched with water and celite was added. The mixture was extracted with Et$_2$O and EtOAc. The organic phase was dried over Na$_2$SO$_4$, filtered, and concentrated under reduced pressure, yielding Compound 24a. MS (ES+) m/z 193.2 (M+H$^+$).

Compound 24a (0.5 g, 2.6 mmol) was added to a suspension of pyridinium chlorochromate (0.67 g, 3.12 mmol) in DCM (5 mL). The mixture was stirred overnight at rt. Diethyl ether was added, and the mixture was filtered. The filtrate was dried over Na$_2$SO$_4$. After removal of the drying agent via filtration, the solvent was removed under reduced pressure, yielding a mixture of 24a and 24b that was used as such for the next reaction. Compound 24b: MS (ES+) m/z 191.1 (M+H$^+$).

Sodium triacetoxyborohydride (25.6 mg, 0.074 mmol) was added to a mixture of 24a and 24b (0.01 g, 0.05 mmol) and piperidine Compound 24c (0.015 g, 0.05 mmol; obtained using the procedure described in Example 12 for converting Compound 12a to Compound 12g, and wherein bromo-3-fluorobenzene was substituted for the 4-bromo-1,2-(methyl-enedioxy)benzene (Compound 12c) and was reacted to form a 3-fluorophenyl compound analogous to compound 12f) in DCM (0.2 mL) and the mixture was stirred for 4 hr at rt. Diethyl ether was added, and the organic layer was separated and dried over Na$_2$SO$_4$. The drying agent was removed by filtration, and the solvent was removed under reduced pressure. The residue was purified via column chromatography (eluent gradient: DCM:MeOH:NH$_4$OH; 100:0:0 to 90:9:1) to yield Compound 24d. MS (ES+) m/z 454.4 (M+H$^+$).

Using the procedure described in Example 12 for converting Compound 12h to Compound 11, Compound 24d was converted to Compound 81. MS (ES+) m/z 440.5 (M+H$^+$).

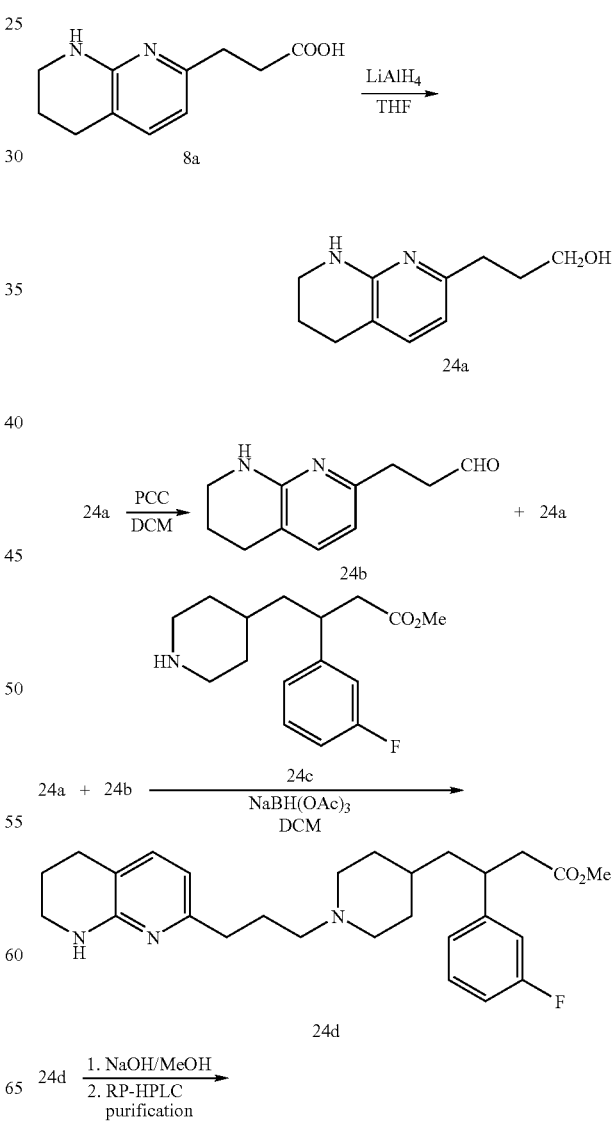

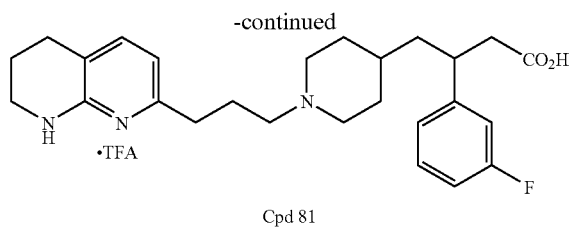

Cpd 81

Example 25

β-(3-fluorophenyl)-1-[1-oxo-3-(5,6,7,8-tetrahydro-1,8-naphthyridin-2-yl)propyl]-4-piperidinebutanoic acid (Cpd 30a and 30b)

Compound 30 was synthesized following the process set forth in Example 12 wherein bromo-3-fluorobenzene was substituted for the 4-bromo-1,2-(methylenedioxy)benzene (Compound 12c) and was reacted to form a 3-fluorophenyl compound analogous to compound 12f.

Additional Compound 30 was resolved into two isomers (Cpd 30a and Cpd 30b) by generally following the procedure set in Example 19, wherein the stationary phase was Chiralcel OD; eluent: hexane/EtOH: 95/5; wavelength: 220 nm. The isomer of most interest was the second eluting isomer. The separated isomers were converted into Compounds 30a and 30b by completion of the synthesis from Compound 12f on as set forth in Example 12 to yield Compounds 30a and 30b.

Prospective Example 26

3-(2,3-Dihydro-benzofuran-6-yl)-4-[1-(3-5,6,7,8-tetrahydro-[1,8]naphthyridin-2-yl-butyl)-piperidin-4-yl]-propanoic acid (Cpd 80)

Using the procedure described in Example 3 for converting Compound 3b to Compound 3c, Compound 3b may be converted to provide Compound 26a when reacted with 6-bromo-2,3-dihydrobenzofuran.

Using the procedure described in Example 3 for converting Compound 3c to Compound 3d, Compound 26a may be converted to provide Compound 26b.

Using the procedure described in Example 3 for converting Compound 3d to Compound 3e, Compound 26b may be converted to provide Compound 26c.

Using the procedure described in Example 3 for converting Compound 3e to Compound 3f, Compound 26c may be converted to provide Compound 26d.

Using the procedure described in Example 3 for converting Compound 3f to Compound 3g, Compound 26d may be converted to provide Compound 26e.

Using the procedure described in Example 4 for converting Compound 4a to Compound 4b, Compound 26e may be converted to provide Compound 26f.

Using the procedure described in Example 4 for converting Compound 4b to Compound 4, Compound 26f may be converted to provide Compound 80.

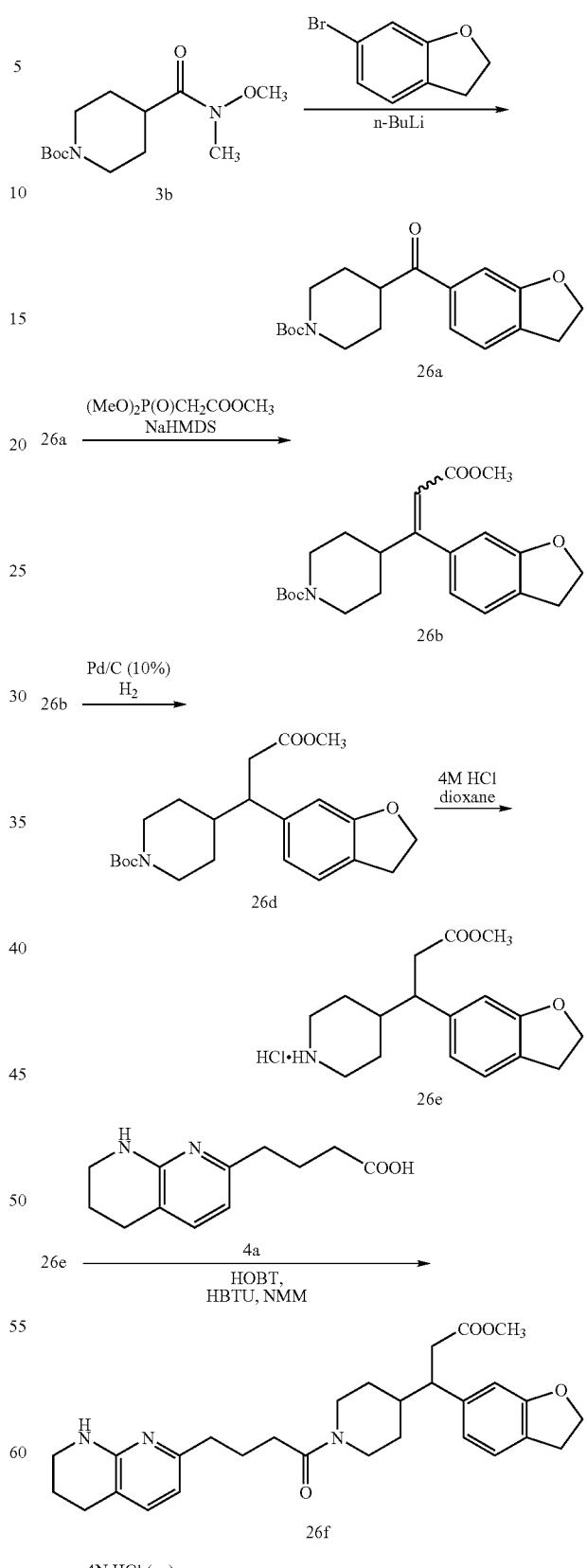

-continued

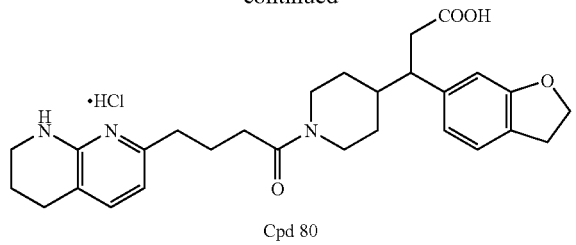

Cpd 80

BIOLOGICAL EXPERIMENTAL EXAMPLES

As demonstrated by biological studies described hereinafter, as shown in Table I, the compounds of the present invention are αvβ3 and αvβ5 integrin receptor antagonists useful in treating an integrin mediated disorder.

Example 1

In Vitro Solid Phase Purified αvβ3 Binding Assay

The vitronectin/αvβ3 binding assay methods were derived from Mehta et al. (*Biochem J,* 1998, 330, 861). Human αvβ3 (Chemicon International Inc., Temecula, Calif.), at a concentration of 1 μg/ml dissolved in Tris buffer (20 mM Tris, 1 mM $CaCl_2$, 1 mM $MgCl_2$, 10 μM $MnCl_2$, 150 mM NaCl), was immobilized on Immulon 96 well plates (Dynex Technologies, Chantilly, Va.) overnight at 4° C. Plates were washed and treated with blocking buffer (3% BSA in Tris buffer) for 2 h at 37° C. Plates were then rinsed 2 times with assay buffer comprised of Tris buffer. Synthesized compounds were added to wells in duplicate immediately prior to the addition of 2 nM vitronectin (Sigma, St. Louis, Mo.). Following a 3 hour incubation at 37° C., plates were washed 5 times in assay buffer. An anti-human vitronectin IgG rabbit polyclonal antibody (Calbiochem, San Diego, Calif.) was added (1:2000) and plates were incubated for 1 hour at room temperature. VectaStain ABC peroxidase kit reagents (Vector Laboratories, Burlingame, Calif.) employing a biotin labeled anti-rabbit IgG, were utilized for detection of bound antibody. Plates were read at 490 nm on a Molecular Devices (Sunnyvale, Calif.) microplate reader. Table 1 shows the results of the in vitro solid phase purified αvβ3 binding assay for representative compounds of the present invention.

Example 2

In Vitro Solid Phase Purified GP IIb/IIIa Binding Assay

A 96 well Immulon-2 microtiter plate (Dynatech-Immulon) was coated with 50 μL/well of RGD-affinity purified GP IIb/IIIa (effective range 0.5-10 μg/mL) in 10 mM HEPES, 150 mM NaCl, 1 mM $MgCl_2$ at pH 7.4. The plate was covered and incubated overnight at 4° C. The GP IIb/IIIa solution was discarded and 150 μL of 5% BSA was added and incubated at RT for 1-3 h. The plate was washed extensively with modified Tyrodes buffer. Biotinylated fibrinogen (25 μL/well) at 2× final concentration was added to the wells that contain the test compounds (25 μL/well). The plate was covered and incubated at RT for 2-4 h. Twenty minutes prior to incubation completion, one drop of Reagent A (VectaStain ABC Horseradish Peroxidase kit, Vector Laboratories, Inc.) and one drop Reagent B were added with mixing to 5 mL modified Tyrodes buffer mix and let stand. The ligand solution was discarded and the plate washed (5×200 μL/well) with modified Tyrodes buffer. Vecta Stain HRP-Biotin-Avidin reagent (50 μL/well, as prepared above) was added and incubated at RT for 15 min. The Vecta Stain solution was discarded and the wells washed (5×200 μL/well) with modified Tyrodes buffer. Developing buffer (10 mL of 50 mM citrate/phosphate buffer @ pH 5.3, 6 mg o-phenylenediamine, 6 μL 30% $H_2O_2$; 50 μL/well) was added and incubated at RT for 3-5 min and then 2 $\underline{N}$ $H_2SO_4$ (50 μL/well) was added. The absorbance was read at 490 nM. Table 1 shows the results of the in-vitro solid phase purified GP IIb/IIIa binding assay for representative compounds of the present invention.

Example 3

In Vitro Solid Phase Purified αcβ5 Binding Assay

The vitronectin/$α_Vβ_5$ binding assay method was performed in the same manner as the vitronectin/$α_Vβ_3$ binding assay of Example 2, with the difference that 1 μg/mL of human purified $α_Vβ_5$ (Chemicon International, Inc.) was immobilized onto Immulon 96 well plates (Dynex Technologies) instead of $α_Vβ_3$. All other aspects of the assay including buffers, reagents and incubation times remain unchanged.

TABLE 1

| Cpd | $α_vβ_3 IC_{50}$ (uM) | | $α_vβ_5 IC_{50}$ (uM) | | $α_{IIb}β_3 IC_{50}$ (uM) | |
|---|---|---|---|---|---|---|
| 1 | 0.0560 ± 0.007 | N = 2 | >5 | ND | 4.33 ± 0.15 | N = 2 |
| 2 | 5.4000 ± | N = 1 | | | 4.78 ± 1.013 | N = 2 |
| 3 | 0.0036 ± 0.0004 | N = 5 | 2.5 | | 0.21 | N = 1 |
| 4 | 0.0005 ± 0.0001 | N = 3 | 0.0355 ± 0.0089 | N = 4 | 0.87 ± 0.19 | N = 2 |
| 5 | 0.0037 ± 0.0014 | N = 3 | 0.2607 ± 0.0569 | N = 3 | 14.84 ± 0.68 | N = 2 |
| 5-3 | 0.1613 | N = 1 | >5 | N = 1 | ND | |
| 5-4 | 0.0054 ± 0.0002 | N = 3 | 0.1616 ± 0.0627 | N = 3 | 9.82 | N = 1 |
| 6 | 0.0076 ± 0.0021 | N = 2 | 0.54 | N = 1 | 1.62 ± 0.05 | N = 2 |
| 7 | 0.0082 ± 0.0014 | N = 2 | 0.0395 ± 0.0085 | N = 2 | 1.67 ± 0.74 | N = 2 |
| 8 | 0.0179 ± 0.0034 | N = 4 | 0.253 | N = 1 | 1.36 ± 0.43 | N = 2 |
| 9 | >1 | N = 1 | ND | | 8.51 ± 2.36 | N = 2 |
| 10 | 0.0024 ± 0.0013 | N = 2 | 0.0335 ± 0.0075 | N = 2 | 1.67 | N = 1 |
| 11 | 0.0011 ± 0.0002 | N = 3 | 0.0023 ± 0.0009 | N = 3 | 2.52 ± 0.30 | N = 2 |
| 12 | 0.0042 ± 0.0014 | N = 3 | 0.078 ± 0.017 | N = 2 | 0.136 ± 0.003 | N = 2 |
| 13 | 0.0032 ± 0.0006 | N = 2 | 0.036 ± 0.0133 | N = 2 | 11.09 ± 3.40 | N = 2 |
| 14 | 0.0361 ± 0.0001 | N = 2 | 0.108 ± 0.034 | N = 1 | 5.04 | N = 1 |
| 15 | 0.0019 ± 0.0002 | N = 4 | 0.0334 ± 0.0063 | N = 4 | 4.03 ± 0.43 | N = 2 |
| 16 | 0.2810 | N = 1 | 0.775 | N = 1 | 25.38 | N = 1 |
| 17 | 0.0008 ± 0.0001 | N = 4 | 0.0313 ± 0.0060 | N = 4 | 6.60 ± 1.42 | N = 2 |

TABLE 1-continued

| Cpd | $\alpha_v\beta_3$ IC$_{50}$ (uM) | | $\alpha_v\beta_5$ IC$_{50}$ (uM) | | $\alpha_{IIb}\beta_3$ IC$_{50}$ (uM) | |
|---|---|---|---|---|---|---|
| 18 | >5 | N = 1 | >5 | N = 1 | >50 | N = 1 |
| 19 | 0.0025 ± 0.0004 | N = 3 | 0.0171 ± 0.0025 | N = 3 | 13.77 ± 9.69 | N = 2 |
| 19-1 | 0.0367 | N = 1 | 1.12 | N = 1 | >50 | N = 1 |
| 19-2 | 0.0013 ± 0.0001 | N = 2 | 0.0092 ± 0.0004 | N = 2 | 12.9 | N = 1 |
| 19-3 | 0.0447 ± 0.0204 | N = 2 | 1.17 ± 0.02 | N = 2 | ND | |
| 19-4 | 0.0013 ± 0.0007 | N = 3 | 0.0075 ± 0.0018 | N = 3 | 4.86 | N = 1 |
| 20 | 0.1417 ± 0.027 | N = 3 | 0.995 | N = 1 | 1.80 | N = 1 |
| 21 | 0.0280 ± 0.0031 | N = 3 | 0.78 | N = 1 | 1.80 ± 0.63 | N = 2 |
| 21b | 0.405 | N = 1 | 0.28 | N = 1 | 1.97 | N = 1 |
| 21a | 0.0213 ± 0.0019 | N = 3 | 0.8413 ± 0.4054 | N = 3 | 5.31 | N = 1 |
| 22 | 0.0046 ± 0.0008 | N = 3 | 0.195 | N = 1 | 0.43 ± 0.07 | N = 2 |
| 23 | 0.2980 ± 0.1460 | N = 2 | 2.010 | N = 1 | 4.93 | N = 1 |
| 24 | 0.3070 | N = 1 | 0.387 | N = 1 | 19.30 | N = 1 |
| 25 | 0.0456 ± 0.0066 | N = 2 | 0.773 ± 0.118 | N = 2 | 8.67 ± 1.72 | N = 2 |
| 26 | 0.0277 ± 0.0053 | N = 2 | 0.5 | N = 1 | 5.92 | N = 1 |
| 27 | 0.0480 | N = 1 | 0.81 | N = 1 | 1.62 ± 0.56 | N = 2 |
| 28 | 0.0007 ± 0.0002 | N = 3 | 0.0027 ± 0.0008 | N = 4 | 6.10 ± 2.44 | N = 2 |
| 28a | 0.0003 ± 0.0002 | N = 3 | 0.0042 ± 0.0018 | N = 3 | 1.83 ± 0.57 | N = 2 |
| 28b | 0.0208 ± 0.0053 | N = 2 | 0.1262 ± 0.0448 | N = 2 | 24.26 | N = 1 |
| 29 | 0.0022 ± 0.0008 | N = 3 | 0.119 ± 0.0150 | N = 3 | 1.74 ± 0.89 | N = 2 |
| 30 | 0.0010 ± 0.0002 | N = 3 | 0.0028 ± 0.0001 | N = 3 | 14.39 ± 5.98 | N = 2 |
| 30a | 0.0004 ± 0.0002 | N = 3 | 0.0019 ± 0.0004 | N = 2 | 2.93 ± 1.86 | N = 2 |
| 30b | 0.0317 ± 0.0147 | N = 2 | 0.0482 ± 0.0028 | N = 2 | >50 | N = 1 |
| 31 | 0.0330 | N = 1 | 0.3 | N = 1 | 21.57 ± 4.87 | N = 2 |
| 32 | 0.0008 ± 0.0002 | N = 3 | 0.0022 ± 0.0007 | N = 3 | 1.055 ± 0.56 | N = 2 |
| 33 | 0.0013 ± 0.0004 | N = 3 | 0.0226 ± 0.0052 | N = 3 | >50 | N = 1 |
| 34 | 0.1476 ± 0.1004 | N = 2 | 1.041 ± 0.109 | N = 2 | >50 | N = 1 |
| 35 | 0.0007 ± 0.0004 | N = 2 | 0.0007 ± 0.0002 | N = 3 | 0.965 ± 0.07 | N = 2 |
| 36 | 0.0008 ± 0.00006 | N = 4 | 0.0007 ± 0.0002 | N = 3 | 3.11 ± 0.04 | N = 2 |
| 36a | 0.0004 | N = 3 | 0.0009 ± 0.0006 | N = 2 | 0.79 ± 0.05 | N = 3 |
| 36b | 0.084 | N = 1 | 0.129 | N = 2 | >50 | N = 1 |
| 37 | 0.0158 ± 0.0043 | N = 2 | 0.0897 ± 0.0116 | N = 3 | >50 | N = 1 |
| 38 | 0.4840 | N = 1 | 2.11 | N = 1 | >50 | N = 1 |
| 39 | 0.0066 ± 0.0018 | N = 2 | 0.0287 ± 0.0133 | N = 2 | >50 | N = 1 |
| 40 | 0.0052 ± 0.0002 | N = 2 | 0.308 ± 0.0630 | N = 2 | 23.95 ± 9.89 | N = 2 |
| 41 | 0.0018 ± 0.0010 | N = 2 | 0.8725 ± 0.1575 | N = 2 | 19.3 ± 2.60 | N = 2 |
| 42 | 0.0007 ± 0.0003 | N = 3 | 0.0189 ± 0.0046 | N = 3 | 5 ± 0.74 | N = 2 |
| 43 | 0.0079 ± 0.0007 | N = 2 | 0.2225 ± 0.0885 | N = 2 | 28.82 ± 15.8 | N = 2 |
| 44 | 0.0022 ± 0.0009 | N = 3 | 0.002 ± 0.0006 | N = 3 | 5.44 ± 1.1 | N = 2 |
| 45 | 0.0008 ± 0.0001 | N = 3 | 0.0017 ± 0.0003 | N = 3 | 6.61 ± 2.85 | N = 2 |
| 46 | 0.0035 ± 0.0006 | N = 2 | 0.0659 ± 0.0171 | N = 2 | 13.64 ± 1.33 | N = 2 |
| 47 | 0.0014 ± 0.0007 | N = 3 | 0.0046 ± 0.0017 | N = 3 | 1.47 ± 0.37 | N = 2 |
| 48 | 0.0010 ± 0.0005 | N = 3 | 0.0033 ± 0.0014 | N = 3 | 1.21 ± 0.20 | N = 2 |
| 49 | 0.0018 ± 0.0005 | N = 3 | 0.0895 ± 0.0255 | N = 2 | 0.16 ± 0.02 | N = 3 |
| 50 | 0.0156 ± 0.0044 | N = 4 | 0.676 | N = 1 | 0.19 ± 0.04 | N = 2 |
| 51 | 0.0030 ± 0.0006 | N = 4 | 0.169 ± 0.019 | N = 2 | 0.48 ± 0.01 | N = 2 |
| 52 | 0.0064 ± 0.0014 | N = 4 | >50 | N = 1 | 0.57 ± 0.04 | N = 2 |
| 53 | 0.0298 ± 0.0137 | N = 5 | 0.1375 ± 0.0415 | N = 2 | 0.94 ± 0.05 | N = 2 |
| 54 | 0.0017 ± 0.0005 | N = 3 | 0.0347 ± 0.0117 | N = 3 | 0.24 | N = 1 |
| 55 | 0.0950 | N = 1 | 0.737 | N = 1 | 15.59 | N = 1 |
| 56 | 0.0019 ± 0.0006 | N = 3 | 0.0245 ± 0.0065 | N = 2 | 39.12 ± 0.785 | N = 2 |
| 56a | 0.0005 ± 0.0002 | N = 3 | 0.0265 ± 0.0034 | N = 3 | 14.66 | N = 1 |
| 56b | 0.3263 ± 0.0894 | N = 3 | 0.8096 ± 0.1045 | N = 3 | ND | |
| 57 | 0.0016 ± 0.0007 | N = 3 | 0.0109 ± 0.0042 | N = 3 | 3.04 ± 0.55 | N = 2 |
| 58a | 0.0004 ± 0.0003 | N = 3 | 0.0323 ± 0.0082 | N = 3 | 1.44 ± 0.39 | N = 2 |
| 58b | 0.083 ± 0.020 | N = 2 | 0.5760 ± 0.1490 | N = 2 | 35.5 | N = 1 |
| 59 | 0.0026 ± 0.0014 | N = 2 | 0.0096 ± 0.0038 | N = 2 | 7.805 ± 4.67 | N = 2 |
| 60 | 0.0010 ± 0.0008 | N = 2 | 0.0309 ± 0.0006 | N = 2 | 4.53 ± 2.47 | N = 2 |
| 61 | 0.0045 ± 0.0007 | N = 3 | 0.0253 ± 0.0073 | N = 3 | 37.45 ± 31.58 | N = 2 |
| 62 | 0.0900 ± 0.0020 | N = 2 | 0.1700 ± 0.0810 | N = 2 | >50 | N = 2 |
| 63 | 0.0018 ± 0.0008 | N = 3 | 0.0070 ± 0.0008 | N = 3 | 10.23 ± 6.41 | N = 2 |
| 64 | 0.0615 ± 0.0055 | N = 2 | 0.1473 ± 0.0847 | N = 2 | >50 | N = 1 |
| 65 | 0.0008 | N = 2 | 0.0346 ± 0.0002 | N = 2 | 3.84 | N = 1 |
| 66 | 0.0012 ± 0.0001 | N = 3 | 0.0103 ± 0.0014 | N = 3 | 28.27 | N = 1 |
| 67 | 0.048 ± 0.0030 | N = 2 | 0.176 ± 0.0350 | N = 2 | 7.82 | N = 1 |
| 68 | 0.413 | N = 1 | >1 | N = 1 | 35.6 | N = 1 |
| 69 | >0.5 | N = 1 | >1 | N = 1 | >50 | N = 1 |
| 70 | >0.5 | N = 1 | >1 | N = 1 | >50 | N = 1 |
| 71 | >0.5 | N = 1 | >1 | N = 1 | >50 | N = 1 |
| 72 | >0.5 | N = 1 | >1 | N = 1 | >50 | N = 1 |
| 73 | >0.5 | N = 1 | >1 | N = 1 | >50 | N = 1 |
| 74 | 0.193 | N = 1 | >1 | N = 1 | >50 | N = 1 |
| 75 | 0.0053 ± 0.0010 | N = 2 | 0.0419 ± 0.0052 | N = 3 | >50 | N = 1 |
| 76 | 0.0018 ± 0.0003 | N = 2 | 0.0397 ± 0.0121 | N = 2 | 5.38 | N = 1 |
| 76a | 0.0011 ± 0.0002 | N = 2 | 0.0169 ± 0.0021 | N = 2 | 10.38 | N = 1 |
| 77 | 0.138 | N = 1 | 0.789 ± 0.065 | N = 2 | ND | |
| 78 | 0.0057 ± 0.0001 | N = 2 | 0.0260 ± 0.0030 | N = 2 | 24.72 | N = 1 |

TABLE 1-continued

| Cpd | $\alpha_v\beta_3 IC_{50}$ (uM) | | $\alpha_v\beta_5 IC_{50}$ (uM) | | $\alpha_{IIb}\beta_3 IC_{50}$ (uM) | |
|---|---|---|---|---|---|---|
| 79 | 0.0035 ± 0.0015 | N = 3 | 0.025 ± 0.0060 | N = 2 | 40.23 | N = 1 |
| 81 | 0.0067 ± 0.0002 | N = 3 | 0.0101 ± 0.0017 | N = 3 | 22.73 | N = 1 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I) or Formula (II):

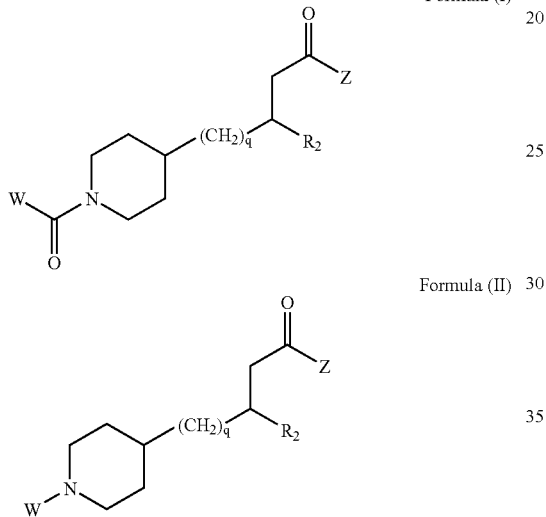

wherein
W is $C_{0-6}$alkyl($R_1$),
$R_1$ is 5,6,7,8-tetrahydro-1,8-naphthyridin-2-yl
$R_7$ is one to two substituents independently selected from the group consisting of hydrogen, —$C_{1-8}$alkoxy($R_9$), —$NH_2$, —NH—$C_{1-8}$alkyl($R_9$), —N($C_{1-8}$alkyl($R_9$))$_2$, —C(=O)H, —C(=O)—$C_{1-8}$alkyl($R_9$), —C(=O)—$NH_2$, —C(=O)—NH—$C_{1-8}$alkyl($R_9$), —C(=O)—N($C_{1-8}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —$CO_2$H, —$CO_2$—$C_{1-8}$alkyl($R_9$), —$CO_2$-aryl($R_{10}$), —C(=NH)—$NH_2$, —SH, —S—$C_{1-8}$alkyl($R_9$), —S—$C_{1-8}$alkyl-S—$C_{1-8}$alkyl($R_9$), —S—$C_{1-8}$alkyl-$C_{1-8}$alkoxy($R_9$), —S—$C_{1-8}$alkyl-NH—$C_{1-8}$alkyl($R_9$), —$SO_2$—$C_{1-8}$alkyl($R_9$), —$SO_2$—$NH_2$, —$SO_2$—NH—$C_{1-8}$alkyl($R_9$), —$SO_2$—N($C_{1-8}$alkyl($R_9$))$_2$, —$SO_2$-aryl($R_{10}$), cyano, (halo)$_{1-3}$, hydroxy, nitro, oxo, -cycloalkyl($R_{10}$), -heterocyclyl($R_{10}$), -aryl($R_{10}$) and -heteroaryl($R_{10}$);

$R_8$ is one to four substituents independently selected from the group consisting of hydrogen, —$C_{1-8}$alkyl($R_9$), —C(=O)H, —C(=O)—$C_{1-8}$alkyl($R_9$), —C(=O)—$NH_2$, —C(=O)—NH—$C_{1-8}$alkyl($R_9$), —C(=O)—N($C_{1-8}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —$CO_2$H, —$CO_2$—$C_{1-8}$alkyl($R_9$), —$CO_2$-aryl($R_{10}$), —C(=NH)—$NH_2$, —$SO_2$—$C_{1-8}$alkyl($R_9$), —$SO_2$—$NH_2$, —$SO_2$—NH—$C_{1-8}$alkyl($R_9$), —$SO_2$—N($C_{1-8}$alkyl($R_9$))$_2$, —$SO_2$-aryl($R_{10}$), -cycloalkyl($R_{10}$) and -aryl($R_{10}$) when attached to a nitrogen atom; and, wherein $R_8$ is one to four substituents independently selected from the group consisting of hydrogen, —$C_{1-8}$alkyl($R_9$), —$C_{1-8}$alkoxy($R_9$), —O-cycloalkyl($R_{10}$), —O-aryl($R_{10}$), —C(=O)H, —C(=O)—$C_{1-8}$alkyl($R_9$), —C(=O)—$NH_2$, —C(=O)—NH—$C_{1-8}$alkyl($R_9$), —C(=O)—N($C_{1-8}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —$CO_2$H, —$CO_2$—$C_{1-8}$alkyl($R_9$), —$CO_2$-aryl($R_{10}$), —C(=NH)—$NH_2$, —$SO_2$—$C_{1-8}$alkyl($R_9$), —$SO_2$—$NH_2$, —$SO_2$—NH—$C_{1-8}$alkyl($R_9$), —$SO_2$—N($C_{1-8}$alkyl($R_9$))$_2$, —$SO_2$-aryl($R_{10}$), —SH, —S—$C_{1-8}$alkyl($R_9$), —S—$C_{1-8}$alkyl-S—$C_{1-8}$alkyl($R_9$), —S—$C_{1-8}$alkyl-$C_{1-8}$alkoxy($R_9$), —S—$C_{1-8}$alkyl-NH—$C_{1-8}$alkyl($R_9$), —$NH_2$, —NH—$C_{1-8}$alkyl($R_9$), —N($C_{1-8}$alkyl($R_9$))$_2$, cyano, halo, hydroxy, nitro, oxo, -cycloalkyl($R_{10}$), -heterocyclyl($R_{10}$), -aryl($R_{10}$) and -heteroaryl($R_{10}$) when attached to a carbon atom;

$R_9$ is selected from the group consisting of hydrogen, —$C_{1-8}$alkoxy, —$NH_2$, —NH—$C_{1-8}$alkyl, —N($C_{1-8}$alkyl)$_2$, —C(=O)H, —C(=O)—$NH_2$, —C(=O)—NH—$C_{1-8}$alkyl, —C(=O)—N($C_{1-8}$alkyl)$_2$, —$CO_2$H, —$CO_2$—$C_{1-8}$alkyl, —$SO_2$—$C_{1-8}$alkyl, —$SO_2$—$NH_2$, —$SO_2$—NH—$C_{1-8}$alkyl, —$SO_2$—N($C_{1-8}$alkyl)$_2$, cyano, (halo)$_{1-3}$, hydroxy, nitro and oxo;

$R_{10}$ is one to four substituents independently selected from the group consisting of hydrogen, —$C_{1-8}$alkyl, —C(=O)H, —C(=O)—$C_{1-8}$alkyl, —C(=O)—$NH_2$, —C(=O)—NH—$C_{1-8}$alkyl, —C(=O)—N($C_{1-8}$alkyl)$_2$, —$CO_2$H, —$CO_2$—$C_{1-8}$alkyl, —$SO_2$—$C_{1-8}$alkyl, —$SO_2$—$NH_2$, —$SO_2$—NH—$C_{1-8}$alkyl and —$SO_2$—N($C_{1-8}$alkyl)$_2$ when attached to a nitrogen atom; and, wherein $R_{10}$ is one to four substituents independently selected from the group consisting of hydrogen, —$C_{1-8}$alkyl, —$C_{1-8}$alkoxy, —C(=O)H, —C(=O)—$C_{1-8}$alkyl, —C(=O)—$NH_2$, —C(=O)—NH—$C_{1-8}$alkyl, —C(=O)—N($C_{1-8}$alkyl)$_2$, —$CO_2$H, —$CO_2$—$C_{1-8}$alkyl, —$SO_2$—$C_{1-8}$alkyl, —$SO_2$—$NH_2$, —$SO_2$—NH—$C_{1-8}$alkyl, —$SO_2$—N($C_{1-8}$alkyl)$_2$, —$NH_2$, —NH—$C_{1-8}$alkyl, —N($C_{1-8}$alkyl)$_2$, cyano, halo, hydroxy, nitro and oxo when attached to a carbon atom;

$R_2$ is selected from the group consisting of hydrogen, —$C_{1-8}$alkyl($R_7$), —$C_{2-8}$alkenyl($R_7$), —$C_{2-8}$alkynyl($R_7$), -cycloalkyl($R_8$), -heterocyclyl($R_8$), -aryl($R_8$) and -heteroaryl($R_8$);

q is selected from the group consisting of 0, 1, 2 or 3;

Z is selected from the group consisting of hydroxy, —$NH_2$, —NH—$C_{1-8}$alkyl, —N($C_{1-8}$alkyl)$_2$, —O—$C_{1-8}$alkyl, —O—$C_{1-8}$alkyl-OH, —O—$C_{1-8}$alkyl-$C_{1-8}$alkoxy, —O—$C_{1-8}$alkylcarbonyl$C_{1-8}$alkyl, —O—$C_{1-8}$alkyl-$CO_2$H, —O—$C_{1-8}$alkyl-C(O)O—$C_{1-8}$alkyl, —O—

$C_{1-8}$alkyl-O—C(O)$C_{1-8}$alkyl, —O—$C_{1-8}$alkyl-NH$_2$, —O—$C_{1-8}$alkyl-NH—$C_{1-8}$alkyl, —O—$C_{1-8}$alkyl-N($C_{1-8}$alkyl)$_2$, —O—$C_{1-8}$alkylamide, —O—$C_{1-8}$alkyl-C(O)—NH—$C_{1-8}$alkyl, —O—$C_{1-8}$alkyl-C(O)—N($C_{1-8}$alkyl)$_2$ and —NHC(O)$C_{1-8}$alkyl;
and pharmaceutically acceptable salts, racemic mixtures and enantiomers thereof.

2. The compound of claim 1 wherein $R_7$ is one to two substituents independently selected from the group consisting of hydrogen, —$C_{1-4}$alkoxy($R_9$), —NH$_2$, —NH—$C_{1-4}$alkyl($R_9$), —N($C_{1-4}$alkyl($R_9$))$_2$, —C(=O)H, —C(=O)—$C_{1-4}$alkyl($R_9$), —C(=O)—NH$_2$, —C(=O)—NH—$C_{1-4}$alkyl($R_9$), —C(=O)—N($C_{1-4}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —CO$_2$H, —CO$_2$—$C_{1-4}$alkyl($R_9$), —CO$_2$-aryl($R_{10}$), —C(NH)—NH$_2$, —SH, —S—$C_{1-4}$alkyl($R_9$), —S—$C_{1-4}$alkyl-S—$C_{1-4}$alkyl($R_9$), —S—$C_{1-4}$alkyl-$C_{1-4}$alkoxy($R_9$), —S—$C_{1-4}$alkyl-NH—$C_{1-4}$alkyl($R_9$), —SO$_2$—$C_{1-4}$alkyl($R_9$), —SO$_2$—NH$_2$, —SO$_2$—NH—$C_{1-4}$alkyl($R_9$), —SO$_2$—N($C_{1-4}$alkyl($R_9$))$_2$, —SO$_2$-aryl($R_{10}$), cyano, (halo)$_{1-3}$, hydroxy, nitro, oxo, -cycloalkyl($R_{10}$), -heterocyclyl($R_{10}$), -aryl($R_{10}$) and -heteroaryl($R_{10}$).

3. The compound of claim 1 wherein $R_7$ is one to two substituents independently selected from the group consisting of hydrogen, —$C_{1-4}$alkoxy($R_9$), —NH$_2$, —NH—$C_{1-4}$alkyl($R_9$), —N($C_{1-4}$alkyl($R_9$))$_2$, (halo)$_{1-3}$, hydroxy and oxo.

4. The compound of claim 1 wherein $R_7$ is hydrogen.

5. The compound of claim 1 wherein $R_8$ is one to four substituents independently selected from the group consisting of hydrogen, —$C_{1-4}$alkyl($R_9$), —C(=O)H, —C(=O)—$C_{1-4}$alkyl($R_9$), —C(O)—NH$_2$, —C(=O)—NH—$C_{1-4}$alkyl($R_9$), —C(=O)—N($C_{1-4}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —CO$_2$H, —CO$_2$—$C_{1-4}$alkyl($R_9$), —CO$_2$-aryl($R_{10}$), —C(NH)—NH$_2$, —SO$_2$—$C_{1-4}$alkyl($R_9$), —SO$_2$—NH$_2$, —SO$_2$—NH—$C_{1-4}$alkyl($R_9$), —SO$_2$—N($C_{1-4}$alkyl($R_9$))$_2$, —SO$_2$-aryl($R_{10}$), -cycloalkyl($R_{10}$) and -aryl($R_{10}$) when attached to a nitrogen atom; and, wherein $R_8$ is one to four substituents independently selected from the group consisting of hydrogen, —$C_{1-4}$alkyl($R_9$), —$C_{1-4}$alkoxy($R_9$), —O-cycloalkyl($R_{10}$), —O-aryl($R_{10}$), —C(=O)H, —C(=O)—$C_{1-4}$alkyl($R_9$), —C(=O)—NH$_2$, —C(=O)—NH—$C_{1-4}$alkyl($R_9$), —C(=O)—N($C_{1-4}$alkyl-$R_{11}$)$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —CO$_2$H, —CO$_2$—$C_{1-4}$alkyl($R_9$), —CO$_2$-aryl($R_{10}$), —C(NH)—NH$_2$, —SO$_2$—$C_{1-4}$alkyl($R_9$), —SO$_2$—NH$_2$, —SO$_2$—NH—$C_{1-4}$alkyl($R_9$), —SO$_2$—N($C_{1-4}$alkyl($R_9$))$_2$, —SO$_2$-aryl($R_{10}$), —SH, —S—$C_{1-4}$alkyl($R_9$), —S—$C_{1-4}$alkyl-S—$C_{1-4}$alkyl($R_9$), —S—$C_{1-4}$alkyl-$C_{1-4}$alkoxy($R_9$), —S—$C_{1-4}$alkyl-NH—$C_{1-4}$alkyl($R_9$), —NH$_2$, —NH—$C_{1-4}$alkyl($R_9$), —N($C_{1-4}$alkyl($R_9$))$_2$, cyano, halo, hydroxy, nitro, oxo, -cycloalkyl($R_{10}$), -heterocyclyl($R_{10}$), -aryl($R_{10}$) and -heteroaryl($R_{10}$) when attached to a carbon atom.

6. The compound of claim 1 wherein $R_8$ is one to four substituents independently selected from the group consisting of hydrogen, —$C_{1-4}$alkyl($R_9$), —C(=O)H, —C(=O)—NH$_2$, —C(=O)—NH—$C_{1-4}$alkyl($R_9$), —C(=O)—N($C_{1-4}$alkyl($R_9$))$_2$, —CO$_2$H, —CO$_2$—$C_{1-4}$alkyl($R_9$) and —SO$_2$—NH$_2$ when attached to a nitrogen atom; and, wherein $R_8$ is one to four substituents independently selected from the group consisting of hydrogen, —$C_{1-4}$alkyl($R_9$), —$C_{1-4}$alkoxy($R_9$), —O-aryl($R_{10}$), —C(=O)H, —C(=O)—NH$_2$, —C(=O)—NH—$C_{1-4}$alkyl($R_9$), —C(=O)—N($C_{1-4}$alkyl($R_9$))$_2$, —CO$_2$H, —CO$_2$—$C_{1-4}$alkyl($R_9$), —SO$_2$—NH$_2$, —NH$_2$, —NH—$C_{1-4}$alkyl($R_9$), —N($C_{1-4}$alkyl($R_9$))$_2$, cyano, halo, hydroxy, nitro and oxo when attached to a carbon atom.

7. The compound of claim 1 wherein $R_8$ is one to four substituents independently selected from the group consisting of hydrogen and —$C_{1-4}$alkyl($R_9$) when attached to a nitrogen atom; and, wherein $R_8$ is one to four substituents independently selected from the group consisting of hydrogen, —$C_{1-4}$alkyl($R_9$), —$C_{1-4}$alkoxy($R_9$), —O-aryl($R_{10}$), —NH$_2$, —NH—$C_{1-4}$alkyl($R_9$), —N($C_{1-4}$alkyl($R_9$))$_2$, halo, hydroxy and oxo when attached to a carbon atom.

8. The compound of claim 1 wherein $R_8$ is one to four substituents independently selected from the group consisting of hydrogen and —$C_{1-4}$alkyl($R_9$) when attached to a nitrogen atom; and, wherein $R_8$ is one to four substituents independently selected from the group consisting of hydrogen, —$C_{1-4}$alkyl($R_9$), —$C_{1-4}$alkoxy($R_9$), —O-aryl($R_{10}$) and hydroxy when attached to a carbon atom.

9. The compound of claim 1 wherein $R_9$ is selected from the group consisting of hydrogen, —$C_{1-4}$alkoxy, —NH$_2$, —NH—$C_{1-4}$alkyl, —N($C_{1-4}$alkyl)$_2$, —C(=O)H, —C(=O)—NH$_2$, —C(=O)—NH—$C_{1-4}$alkyl, —C(=O)—N($C_{1-4}$alkyl)$_2$, —CO$_2$H, —CO$_2$—$C_{1-4}$alkyl, —SO$_2$—$C_{1-4}$alkyl, —SO$_2$—NH$_2$, —SO$_2$—NH—$C_{1-4}$alkyl, —SO$_2$—N($C_{1-4}$alkyl)$_2$, cyano, (halo)$_{1-3}$, hydroxy, nitro and oxo.

10. The compound of claim 1 wherein $R_9$ is selected from the group consisting of hydrogen, —$C_{1-4}$alkoxy, —NH$_2$, —NH—$C_{1-4}$alkyl, —N($C_{1-4}$alkyl)$_2$, —C(=O)H, —CO$_2$H, —C(=O)—$C_{1-4}$alkoxy, (halo)$_{1-3}$, hydroxy and oxo.

11. The compound of claim 1 wherein $R_9$ is selected from the group consisting of hydrogen, —$C_{1-4}$alkoxy, —NH$_2$, —NH—$C_{1-4}$alkyl, —N($C_{1-4}$alkyl)$_2$, (halo)$_{1-3}$ and hydroxy.

12. The compound of claim 1 wherein $R_{10}$ is one to four substituents independently selected from the group consisting of hydrogen, —$C_{1-4}$alkyl, —C(=O)H, —C(=O)—$C_{1-4}$alkyl, —C(=O)—NH$_2$, —C(=O)—NH—$C_{1-4}$alkyl, —C(=O)—N($C_{1-4}$alkyl)$_2$, —CO$_2$H, —CO$_2$—$C_{1-4}$alkyl, —SO$_2$—$C_{1-4}$alkyl, —SO$_2$—NH$_2$, —SO$_2$—NH—$C_{1-4}$alkyl and —SO$_2$—N($C_{1-4}$alkyl)$_2$ when attached to a nitrogen atom; and, wherein $R_{10}$ is one to four substituents independently selected from the group consisting of hydrogen, —$C_{1-4}$alkyl, —$C_{1-4}$alkoxy, —C(=O)H, —C(=O)—$C_{1-4}$alkyl, —C(=O)—NH$_2$, —C(=O)—NH—$C_{1-4}$alkyl, —C(=O)—N($C_{1-4}$alkyl)$_2$, —CO$_2$H, —CO$_2$—$C_{1-4}$alkyl, —SO$_2$—$C_{1-4}$alkyl, —SO$_2$—NH$_2$, —SO$_2$—NH—$C_{1-4}$alkyl, —SO$_2$—N($C_{1-4}$alkyl)$_2$, —NH$_2$, —NH—$C_{1-4}$alkyl, —N($C_{1-4}$alkyl)$_2$, cyano, halo, hydroxy, nitro and oxo when attached to a carbon atom.

13. The compound of claim 1 wherein $(R_{10})_{1-4}$ is selected from the group consisting of hydrogen, —$C_{1-4}$alkyl, —$C_{1-4}$alkoxy, —C(=O)H, —C(=O)—$C_{1-4}$alkyl, —CO$_2$H, —CO$_2$—$C_{1-4}$alkyl, —NH$_2$, —NH—$C_{1-4}$alkyl, —N($C_{1-4}$alkyl)$_2$, halo, hydroxy, nitro and oxo when attached to a carbon atom.

14. The compound of claim 1 wherein $R_{10}$ is hydrogen.

15. The compound of claim 1 wherein $R_2$ is selected from the group consisting of hydrogen, —$C_{1-4}$alkyl($R_7$), —$C_{2-4}$alkenyl($R_7$), —$C_{2-4}$alkynyl($R_7$), -cycloalkyl($R_8$), -heterocyclyl($R_8$), -aryl($R_8$) and -heteroaryl($R_8$).

16. The compound of claim 1 wherein $R_2$ is selected from the group consisting of hydrogen, -cycloalkyl($R_8$), -heterocyclyl($R_8$), -aryl($R_8$) and -heteroaryl($R_8$).

17. The compound of claim 1 wherein $R_2$ is selected from the group consisting of hydrogen, -cycloalkyl($R_8$), -heterocyclyl($R_8$), -phenyl($R_8$), -naphthalenyl($R_8$) and -heteroaryl($R_8$).

18. The compound of claim 1 wherein $R_2$ is selected from the group consisting of hydrogen, -tetrahydropyrimidinyl ($R_8$), -1,3-benzodioxolyl($R_8$), -dihydrobenzofuranyl($R_8$), -tetrahydroquinolinyl($R_8$), -phenyl($R_8$), -naphthalenyl($R_8$), -pyridinyl($R_8$), -pyrimidinyl($R_8$) and -quinolinyl($R_8$).

19. The compound of claim 1 wherein q is 1, 2 or 3.

20. The compound of claim 1 wherein Z is selected from the group consisting of hydroxy, —$NH_2$, —NH—$C_{1-8}$alkyl, —N($C_{1-8}$alkyl)$_2$, —O—$C_{1-8}$alkyl, —O—$C_{1-8}$alkyl-OH, —O—$C_{1-8}$alkyl$C_{1-4}$alkoxy, —O—$C_{1-8}$alkylcarbonyl $C_{1-4}$alkyl, —O—$C_{1-8}$alkyl-$CO_2H$, —O—$C_{1-8}$alkyl-C(O) O—$C_{1-6}$alkyl, $C_{1-8}$alkyl-OC(O)—$C_{1-6}$alkyl, —O—$C_{1-8}$alkyl-$NH_2$, —O—$C_{1-8}$alkyl-NH—$C_{1-8}$alkyl, —O—$C_{1-8}$alkyl-N($C_{1-8}$alkyl)$_2$, O—$C_{1-8}$alkylamide, $C_{1-8}$alkyl-C(O)—NH—$C_{1-8}$alkyl, —O—$C_{1-8}$alkyl-C(O)—N($C_{1-8}$alkyl)$_2$ and —NHC(O)$C_{1-8}$alkyl.

21. A compound of Formula (I):

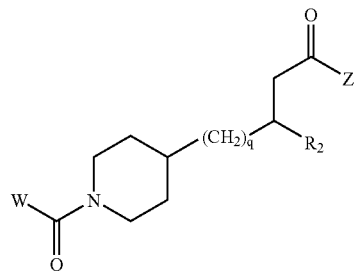

Formula (I)

wherein W, $R_1$, $R_2$, q and Z are selected from:

| W | $R_1$ | $R_2$ | q | Z |
|---|---|---|---|---|
| —(CH$_2$)$_3$—$R_1$ | 5,6,7,8-tetrahydro-[1,8]naphthyridin-2-yl | quinolin-3-yl | 0 | OH |
| —(CH$_2$)$_3$—$R_1$ | 5,6,7,8-tetrahydro-[1,8]naphthyridin-2-yl | 1,2,3,4-tetrahydro-quinolin-3-yl | 0 | OH |
| —(CH$_2$)$_2$—$R_1$ | 5,6,7,8-tetrahydro-[1,8]naphthyridin-2-yl | pyridin-3-yl | 2 | OH |
| —(CH$_2$)$_2$—$R_1$ | 5,6,7,8-tetrahydro-[1,8]naphthyridin-2-yl | 1,3-benzodioxol-5-yl | 1 | OH |
| —(CH$_2$)$_2$—$R_1$ | 5,6,7,8-tetrahydro-[1,8]naphthyridin-2-yl | phenyl | 1 | OH |
| —(CH$_2$)$_2$—$R_1$ | 5,6,7,8-tetrahydro-[1,8]naphthyridin-2-yl | 1,3-benzodioxol-5-yl | 0 | OH |
| —(CH$_2$)$_3$—$R_1$ | 5,6,7,8-tetrahydro-[1,8]naphthyridin-2-yl | 1,3-benzodioxol-5-yl | 0 | OH |
| —CH$_2$—$R_1$ | 5,6,7,8-tetrahydro-[1,8]naphthyridin-2-yl | 1,3-benzodioxol-5-yl | 0 | OH |
| —(CH$_2$)$_3$—$R_1$ | 5,6,7,8-tetrahydro-[1,8]naphthyridin-2-yl | (6-OCH$_3$)-pyridin-3-yl | 0 | OH |
| —(CH$_2$)$_2$—$R_1$ | 5,6,7,8-tetrahydro-[1,8]naphthyridin-2-yl | 1,4,5,6-tetrahydro-2-Me-pyrimidin-5-yl | 1 | OH |
| —(CH$_2$)$_2$—$R_1$ | 5,6,7,8-tetrahydro-[1,8]naphthyridin-2-yl | 1,2,3,4-tetrahydro-quinolin-3-yl | 1 | OH |
| —(CH$_2$)$_2$—$R_1$ | 5,6,7,8-tetrahydro-[1,8]naphthyridin-2-yl | 1,3-benzodioxol-5-yl | 2 | OH |
| —(CH$_2$)$_2$—$R_1$ | 5,6,7,8-tetrahydro-[1,8]naphthyridin-2-yl | (6-OCH$_3$)-pyridin-3-yl | 2 | OH |
| —(CH$_2$)$_3$—$R_1$ | 5,6,7,8-tetrahydro-[1,8]naphthyridin-2-yl | 1,3-benzodioxol-5-yl | 1 | OH |
| —(CH$_2$)$_2$—$R_1$ | 5,6,7,8-tetrahydro-[1,8]naphthyridin-2-yl | (6-OCH$_3$)-pyridin-3-yl | 1 | OH |
| —(CH$_2$)$_3$—$R_1$ | 5,6,7,8-tetrahydro-[1,8]naphthyridin-2-yl | quinolin-3-yl | 1 | OH |
| —(CH$_2$)$_2$—$R_1$ | 5,6,7,8-tetrahydro-[1,8]naphthyridin-2-yl | (3-F)phenyl | 1 | OH |
| —(CH$_2$)$_3$—$R_1$ | 5,6,7,8-tetrahydro-[1,8]naphthyridin-2-yl | (3-F)phenyl | 1 | OH |

-continued

| W | R₁ | R₂ | q | Z |
|---|---|---|---|---|
| —(CH₂)₂—R₁ | 5,6,7,8-tetrahydro-[1,8]naphthyridin-2-yl | quinolin-3-yl | 1 | OH |
| —(CH₂)₂—R₁ | 5,6,7,8-tetrahydro-[1,8]naphthyridin-2-yl | (4-F)phenyl | 1 | OH |
| —(CH₂)₃—R₁ | 5,6,7,8-tetrahydro-[1,8]naphthyridin-2-yl | (4-F)phenyl | 1 | OH |
| —(CH₂)₂—R₁ | 5,6,7,8-tetrahydro-[1,8]naphthyridin-2-yl | (2-CH₃)pyrimidin-5-yl | 1 | OH |
| —(CH₂)₂—R₁ | 5,6,7,8-tetrahydro-[1,8]naphthyridin-2-yl | 2,3-dihydro-benzofuran-6-yl | 1 | OH |
| —(CH₂)₂—R₁ | 5,6,7,8-tetrahydro-[1,8]naphthyridin-2-yl | (3,5-difluoro)-phenyl | 1 | OH |
| —(CH₂)₃—R₁ | 5,6,7,8-tetrahydro-[1,8]naphthyridin-2-yl | (3,5-difluoro)-phenyl | 1 | OH |
| —(CH₂)₂—R₁ | 5,6,7,8-tetrahydro-[1,8]naphthyridin-2-yl | (3-CF₃)-phenyl | 1 | OH |
| —(CH₂)₂—R₁ | 5,6,7,8-tetrahydro-[1,8]naphthyridin-2-yl | (4-OCF₃)-phenyl | 1 | OH |
| —(CH₂)₂—R₁ | 5,6,7,8-tetrahydro-[1,8]naphthyridin-2-yl | (3-F-4-Ph)-phenyl | 1 | OH |
| —(CH₂)₂—R₁ | 5,6,7,8-tetrahydro-[1,8]naphthyridin-2-yl | (3-F-4-OCH₃)-phenyl | 1 | OH |
| —(CH₂)₂—R₁ | 5,6,7,8-tetrahydro-[1,8]naphthyridin-2-yl | (4-OPh)-phenyl | 1 | OH |
| —(CH₂)₂—R₁ | 5,6,7,8-tetrahydro-[1,8]naphthyridin-2-yl | isoquinolin-4-yl | 1 | OH |
| —(CH₂)₂—R₁ | 5,6,7,8-tetrahydro-[1,8]naphthyridin-2-yl | pyridin-3-yl | 1 | OH |
| —(CH₂)₂—R₁ | 5,6,7,8-tetrahydro-[1,8]naphthyridin-2-yl | dihydrobenzofuran-5-yl | 1 | OH |
| —(CH₂)₂—R₁ | 5,6,7,8-tetrahydro-[1,8]naphthyridin-2-yl | (2,4-OCH₃)-pyrimidin-5-yl | 1 | OH |
| —(CH₂)₂—R₁ | 5,6,7,8-tetrahydro-[1,8]naphthyridin-2-yl | (2-OCH₃)-pyrimidin-5-yl | 1 | OH |
| —(CH₂)₂—R₁ | 5,6,7,8-tetrahydro-[1,8]naphthyridin-2-yl | quinolin-3-yl | 2 | OH |
| —CH₂—R₁ | 5,6,7,8-tetrahydro-[1,8]naphthyridin-2-yl | 1,3-benzodioxol-5-yl | 2 | OH |
| —(CH₂)₂—R₁ | 5,6,7,8-tetrahydro-[1,8]naphthyridin-2-yl | naphthalene-2-yl | 1 | OH |
| —(CH₂)₂—R₁ | 5,6,7,8-tetrahydro-[1,8]naphthyridin-2-yl | 5,6,7,8-tetrahydro-quinolin-3-yl | 1 | OH |
| —(CH₂)₃—R₁ | 5,6,7,8-tetrahydro-[1,8]naphthyridin-2-yl | 5,6,7,8-tetrahydro-quinolin-3-yl | 0 | OH |
| —(CH₂)₂—R | 5,6,7,8-tetrahydro-[1,8]naphthyridin-2-yl | (3-OCH₃)phenyl | 1 | OH |
| —(CH₂)₂—R₁ | 5,6,7,8-tetrahydro-[1,8]naphthyridin-2-yl | (4-OCH₃)phenyl | 1 | OH |
| —(CH₂)₂—R₁ | 5,6,7,8-tetrahydro-[1,8]naphthyridin-2-yl | H | 1 | OH |

-continued

| W | R₁ | R₂ | q | Z |
|---|----|----|---|---|
| —(CH₂)₂—R₁ | 5,6,7,8-tetrahydro-[1,8]naphthyridin-2-yl | tetrahydrofuran-3-yl | 1 | OH |
| —(CH₂)₂—R₁ | 5,6,7,8-tetrahydro-[1,8]naphthyridin-2-yl | thiophen-2-yl | 1 | OH |
| —(CH₂)₂—R₁ | 5,6,7,8-tetrahydro-[1,8]naphthyridin-2-yl | (3-F)phenyl | 1 | NH₂ |
| —(CH₂)₂—R₁ | 5,6,7,8-tetrahydro-[1,8]naphthyridin-2-yl | 2,3-dihydro-benzo[1,4]-dioxin-6-yl | 1 | OH |
| —(CH₂)₂—R₁ | 5,6,7,8-tetrahydro-[1,8]naphthyridin-2-yl | (3-SCH₃)phenyl | 1 | OH |
| —(CH₂)₂—R₁ | 5,6,7,8-tetrahydro-[1,8]naphthyridin-2-yl | N-methyl-1,2,3,4-tetrahydro-quinolin-3-yl | 1 | OH |
| —(CH₂)₂—R₁ | 5,6,7,8-tetrahydro-[1,8]naphthyridin-2-yl | H | 1 | —O-ethyl |
| —(CH₂)₂—R₁ | 5,6,7,8-tetrahydro-[1,8]naphthyridin-2-yl | H | 1 | —O-2-propyl |
| —(CH₂)₂—R₁ | 5,6,7,8-tetrahydro-[1,8]naphthyridin-2-yl | H | 1 | —O-t-butyl |
| —(CH₂)₂—R₁ | 5,6,7,8-tetrahydro-[1,8]naphthyridin-2-yl | H | 1 | —O-n-octyl |
| —(CH₂)₂—R₁ | 5,6,7,8-tetrahydro-[1,8]naphthyridin-2-yl | H | 1 | —O-s-butyl |
| —(CH₂)₂—R₁ | 5,6,7,8-tetrahydro-[1,8]naphthyridin-2-yl | H | 1 | —O-methyl |
| —(CH₂)₂—R₁ | 5,6,7,8-tetrahydro-[1,8]naphthyridin-2-yl | H | 1 | —O—CH₂—OC(O)-t-butyl |
| —(CH₂)₂—R₁ | 5,6,7,8-tetrahydro-[1,8]naphthyridin-2-yl | (3-(NMe₂)phenyl | 1 | OH |
| —(CH₂)₂—R₁ | 5,6,7,8-tetrahydro-[1,8]naphthyridin-2-yl | (3-OMe-4-OH)phenyl | 1 | OH |
| —(CH₂)₂—R₁ | 5,6,7,8-tetrahydro-[1,8]naphthyridin-2-yl | (3-NHEt)phenyl | 1 | OH |
| —(CH₂)₂—R₁ | 5,6,7,8-tetrahydro-[1,8]naphthyridin-2-yl | (3-NHMe)phenyl | 1 | OH |
| —(CH₂)₃—R₁ | 5,6,7,8-tetrahydro-[1,8]naphthyridin-2-yl | dihydrobenzofuran-6-yl | 0 | OH | and pharmaceutically acceptable salts, racemic mixtures and enantiomers thereof.

22. A compound of claim 1 wherein the compound is selected from the group consisting of:

a compound of Formula (I) wherein W is —(CH₂)₃—R₁; R₁ is -5,6,7,8-tetrahydro-1,8-naphthyridin-2-yl; R₂ is -3-quinolinyl, q is 0 and Z is OH;

a compound of Formula (I) wherein W is —(CH₂)₃—R₁; R₁ is -5,6,7,8-tetrahydro-1,8-naphthyridin-2-yl; R₂ is -1,2,3,4-tetrahydro-3-quinolinyl, q is 0 and Z is OH;

a compound of Formula (I) wherein W is —(CH₂)₂—R₁; R₁ is -5,6,7,8-tetrahydro-1,8-naphthyridin-2-yl; R₂ is -3-pyridinyl, q is 2 and Z is OH;

a compound of Formula (I) wherein W is —(CH₂)₂—R₁; R₁ is -5,6,7,8-tetrahydro-1,8-naphthyridin-2-yl; R₂ is -1,3-benzodioxol-5-yl, q is 1 and Z is OH;

a compound of Formula (I) wherein W is —(CH₂)₂—R₁; R₁ is -5,6,7,8-tetrahydro-1,8-naphthyridin-2-yl; R₂ is -Ph, q is 1 and Z is OH;

a compound of Formula (I) wherein W is —(CH₂)₂—R₁; R₁ is -5,6,7,8-tetrahydro-1,8-naphthyridin-2-yl; R₂ is -1,3-benzodioxol-5-yl, q is 0 and Z is OH;

a compound of Formula (I) wherein W is —(CH₂)₃—R₁; R₁ is -5,6,7,8-tetrahydro-1,8-naphthyridin-2-yl; R₂ is -1,3-benzodioxol-5-yl, q is 0 and Z is OH;

a compound of Formula (I) wherein W is —CH₂—R₁; R₁ is -5,6,7,8-tetrahydro-1,8-naphthyridin-2-yl; R₂ is -1,3-benzodioxol-5-yl, q is 0 and Z is OH;

a compound of Formula (I) wherein W is —(CH₂)₃—R₁; R₁ is -5,6,7,8-tetrahydro-1,8-naphthyridin-2-yl; R₂ is -(6-MeO)pyridin-3-yl, q is 0, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is –1,4,5,6-tetrahydro-2-Me-pyrimidin-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -1,2,3,4-tetrahydro-3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -1,3-benzodioxol-5-yl, q is 2 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(6-MeO)pyridin-3-yl, q is 2 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -1,3-benzodioxol-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(6-MeO)pyridin-3-yl, q is 1 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-F)Ph, q is 1 and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -(3-F)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(4-F)Ph, q is 1, and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -(4-F)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(2-Me)pyrimidin-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -2,3-dihydro-benzofuran-6-yl, q is 1, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3,5-F$_2$)Ph, q is 1, and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -(3,5-F$_2$)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-CF$_3$)Ph, q is 1, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(4-OCF$_3$)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-F-4-Ph)Ph, q is 1, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-F-4-OMe)Ph, q is 1, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(4-OPh)Ph, q is 1, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -4-isoquinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-pyridinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -5-dihydrobenzofuranyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -2,4-(OMe)-2-pyrimid-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(2-OMe)pyrimidin-5-yl, q is 1, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-quinolinyl, q is 2, and Z is OH;

a compound of Formula (I) wherein W is —CH$_2$—R$_1$; R$_1$ is -5,6,7,8-tetrahydro-1,8-naphthyridin-2-yl; R$_2$ is -1,3-benzodioxol-5-yl, q is 2, and Z is OH; and, a compound of Formula (I) wherein W is —(CH$_2$)$_2$—R$_1$; R$_1$ is -5,6,7,8-tetrahydro-1,8-naphthyridin-2-yl; R$_2$ is -2-naphthalenyl, q is 1 and Z is OH.

23. A compound of claim 22 wherein the compound is selected from the group consisting of:

a compound of Formula (I) wherein W is —(CH$_2$)$_3$—R$_1$; R$_1$ is -5,6,7,8-tetrahydro-1,8-naphthyridin-2-yl; R$_2$ is -1,2,3,4-tetrahydro-3-quinolinyl, q is 0, and Z is OH;

a compound of Formula (I) wherein W is —(CH$_2$)$_3$—R$_1$; R$_1$ is -5,6,7,8-tetrahydro-1,8-naphthyridin-2-yl; R$_2$ is -1,3-benzodioxol-5-yl, q is 0, and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -1,2,3,4-tetrahydro-3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(6-MeO)pyridin-3-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(3-F)Ph, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-quinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -(2-Me)pyrimidin-5-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -2,3-dihydro-benzofuran-6-yl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -4-isoquinolinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -3-pyridinyl, q is 1 and Z is OH;

a compound of Formula (I) wherein W is —(CH$_2$)$_2$—R$_1$; R$_1$ is -5,6,7,8-tetrahydro-1,8-naphthyridin-2-yl; R$_2$ is -2,4-(OMe)-2-pyrimid-5-yl, q is 1, and Z is OH; and, a compound of Formula (I) wherein W is —(CH$_2$)$_2$—R$_1$; R$_1$ is -5,6,7,8-tetrahydro-1,8-naphthyridin-2-yl; R$_2$ is -(2-OMe)pyrimidin-5-yl, q is 1, and Z is OH.

24. The compound of claim 1 wherein W is —(CH$_2$)$_3$—R$_1$; R$_1$ is -5,6,7,8-tetrahydro-1,8-naphthyridin-2-yl; R$_2$ is -1,2,3,4-tetrahydro-3-quinolinyl, q is 0 and Z is OH.

25. The compound of claim 1 wherein W is —(CH$_2$)$_3$—R$_1$; R$_1$ is -5,6,7,8-tetrahydro-1,8-naphthyridin-2-yl; R$_2$ is -1,3-benzodioxol-5-yl, q is 0 and Z is OH.

26. The compound of claim 1 wherein W is —(CH$_2$)$_2$—R$_1$; R$_1$ is -5,6,7,8-tetrahydro-1,8-naphthyridin-2-yl; R$_2$ is -1,2,3,4-tetrahydro-3-quinolinyl, q is 1 and Z is OH.

27. The compound of claim 1 wherein W is —(CH$_2$)$_2$—R$_1$; R$_1$ is -5,6,7,8-tetrahydro-1,8-naphthyridin-2-yl; R$_2$ is -(6-MeO)pyridin-3-yl, q is 1 and Z is OH.

28. The compound of claim 1 wherein W is —(CH$_2$)$_2$—R$_1$; R$_1$ is -5,6,7,8-tetrahydro-1,8-naphthyridin-2-yl; R$_2$ is -(3-F)Ph, q is 1 and Z is OH.

29. The compound of claim 1 wherein W is —(CH$_2$)$_2$—R$_1$; R$_1$ is -5,6,7,8-tetrahydro-1,8-naphthyridin-2-yl; R$_2$ is -3-quinolinyl, q is 1 and Z is OH.

30. The compound of claim 1 wherein W is —(CH$_2$)$_2$—R$_1$; R$_1$ is -5,6,7,8-tetrahydro-1,8-naphthyridin-2-yl; R$_2$ is -(2-Me)pyrimidin-5-yl, q is 1 and Z is OH.

31. The compound of claim 1 wherein W is —(CH$_2$)$_2$—R$_1$; R$_1$ is -5,6,7,8-tetrahydro-1,8-naphthyridin-2-yl; R$_2$ is -2,3-dihydro-benzofuran-6-yl, q is 1 and Z is OH.

32. The compound of claim 1 wherein W is —(CH$_2$)$_2$—R$_1$; R$_1$ is -5,6,7,8-tetrahydro-1,8-naphthyridin-2-yl; R$_2$ is -4-isoquinolinyl, q is 1 and Z is OH.

33. The compound of claim 1 wherein W is —(CH$_2$)$_2$—R$_1$; R$_1$ is -5,6,7,8-tetrahydro-1,8-naphthyridin-2-yl; R$_2$ is -3-pyridinyl, q is 1, and Z is OH.

34. The compound of claim 1 wherein W is —(CH$_2$)$_2$—R$_1$; R$_1$ is -5,6,7,8-tetrahydro-1,8-naphthyridin-2-yl; R$_2$ is -2,4-(OMe)$_2$-pyrimid-5-yl, q is 1 and Z is OH.

35. The compound of claim 1 wherein W is —(CH$_2$)$_2$—R$_1$; R$_1$ is -5,6,7,8-tetrahydro-1,8-naphthyridin-2-yl; R$_2$ is -(2-OMe)pyrimidin-5-yl, q is 1 and Z is OH.

36. The compound of claim 1 wherein W is —(CH$_2$)$_3$—R$_1$; R$_1$ is -5,6,7,8-tetrahydro-1,8-naphthyridin-2-yl; R$_2$ is 2,3-dihydro-benzofuran-6-yl, q is 0 and Z is OH.

37. The compound of claim 1 wherein W is —(CH$_2$)$_3$—R$_1$; R$_1$ is -5,6,7,8-tetrahydro-1,8-naphthyridin-2-yl; R$_2$ is -1,2,3,4-tetrahydro-3-quinolinyl, q is 0, and Z is OH.

38. The compound of claim 1 wherein W is —(CH$_2$)$_2$—R$_1$; R$_1$ is -5,6,7,8-tetrahydro-1,8-naphthyridin-2-yl; R$_2$ is -1,2,3,4-tetrahydro-3-quinolinyl, q is 1 and Z is OH.

39. A compound of Formula (I.3):

Formula (I.3)

wherein
W is —C$_{0-4}$alkyl(R$_1$);
R$_1$ is 5,6,7,8-tetrahydro-1,8-naphthyridin-2-yl;
R$_2$ is selected from the group consisting of hydrogen, -tetrahydropyrimidinyl(R$_8$), -1,3-benzodioxolyl(R$_8$), -dihydrobenzofuranyl(R$_8$), -tetrahydroquinolinyl(R$_8$), -phenyl(R$_8$), -naphthalenyl(R$_8$), -pyridinyl(R$_4$-pyrimidinyl(R$_8$) and -quinolinyl(R$_8$);
R$_8$ is one to four substituents independently selected from the group consisting of hydrogen and —C$_{1-4}$alkyl(R$_9$) when attached to a nitrogen atom; and, wherein R$_8$ is one to four substituents independently selected from the group consisting of hydrogen, —C$_{1-4}$alkyl(R$_9$), —C$_{1-4}$alkoxy(R$_9$), —O-aryl(R$_{10}$) and hydroxy when attached to a carbon atom; and, R$_9$ is selected from the group consisting of hydrogen, —C$_{1-4}$alkoxy, —NH$_2$, —NH—C$_{1-4}$alkyl, —N(C$_{1-4}$alkyl)$_2$, (halo)$_{1-3}$ and hydroxy;

R$_{10}$ is one to four substituents independently selected from the group consisting of hydrogen, —C$_{1-4}$alkyl, —C$_{1-4}$alkoxy, —C(=O)H, —C(=O)—C$_{1-4}$alkyl, —CO$_2$H, —CO$_2$—C$_{1-4}$alkyl, —NH$_2$, —NH—C$_{1-4}$alkyl, —N(C$_{1-4}$alkyl)$_2$, halo, hydroxy, nitro and oxo when attached to a carbon atom;

Z is selected from the group consisting of hydroxy, —NH$_2$, —NH—C$_{1-8}$alkyl, —N(C$_{1-8}$alkyl)$_2$, —O—C$_{1-8}$alkyl, —O—C$_{1-8}$alkyl-OH, —O—C$_{1-8}$alkylC$_{1-8}$alkoxy, —O—C$_{1-8}$alkylcarbonylC$_{1-8}$alkyl, —O—C$_{1-8}$alkyl-CO$_2$H, —O—C$_{1-8}$alkyl-C(O)O—C$_{1-8}$alkyl, —O—C$_{1-8}$alkyl-O—C(O)C$_{1-8}$alkyl, —O—C$_{1-8}$alkyl-NH$_2$, —O—C$_{1-8}$alkyl-NH—C$_{1-8}$alkyl, —O—C$_{1-8}$alkyl-N(C$_{1-8}$alkyl)$_2$, —O—C$_{1-8}$alkylamide, —O—C$_{1-8}$alkyl-C(O)—NH—C$_{1-8}$alkyl, —O—C$_{1-8}$alkyl-C(O)—N(C$_{1-8}$alkyl)$_2$ and NHC(O)C$_{1-8}$alkyl;

and pharmaceutically acceptable salts, racemic mixtures and enantiomers thereof.

40. A compound of Formula (I.4):

Formula (I.4)

wherein R$_2$ is selected from the group consisting of -2-benzofuranyl, -3-benzofuranyl, -4-benzofuranyl, -5-benzofuranyl, -6-benzofuranyl, -7-benzofuranyl, -benzo[b]thien-2-yl, -benzo[b]thien-3-yl, -benzo[b]thien-4-yl, -benzo[b]thien-5-yl, -benzo[b]thien-6-yl, -benzo[b]thien-7-yl, -1H-indol-2-yl, -1H-indol-3-yl, -1H-indol-4-yl, -1H-indol-5-yl, -1H-indol-6-yl, -1H-indol-7-yl, -2-benzoxazolyl, -4-benzoxazolyl, -5-benzoxazolyl, -6-benzoxazolyl, -7-benzoxazolyl, -2-benzothiazolyl, -3-benzothiazolyl, -4-benzothiazolyl, -5-benzothiazolyl, -6-benzothiazolyl, -7-benzothiazolyl, -1H-benzimidazolyl-2-yl, -1H-benzimidazolyl-4-yl, -1H-benzimidazolyl-5-yl, -1H-benzimidazolyl-6-yl, -1H-benzimidazolyl-7-yl, -2-quinolinyl, -3-quinolinyl, -4-quinolinyl, -5-quinolinyl, -6-quinolinyl, -7-quinolinyl, -8-quinolinyl, -2H-1-benzopyran-2-yl, -2H-1-benzopyran-3-yl, -2H-1-benzopyran-4-yl, -2H-1-benzopyran-5-yl, -2H-1-benzopyran-6-yl, -2H-1-benzopyran-7-yl, -2H-1-benzopyran-8-yl, -4H-1-benzopyran-2-yl, -4H-1-benzopyran-3-yl, -4H-1-benzopyran-4-yl, -4H-1-benzopyran-5-yl, -4H-1-benzopyran-6-yl, -4H-1-benzopyran-7-yl, -4H-1-benzopyran-8-yl, -1H-2-benzopyran-1-yl, -1H-2-benzopyran-3-yl, -1H-2-benzopyran-3-yl, -1H-2-benzopyran-5-yl, -1H-2-benzopyran-6-yl, -1H-2-benzopyran-7-yl, -1H-2-benzopyran-8-yl, -1,2,3,4-tetrahydro-1-naphthalenyl, -1,2,3,4-tetrahydro-2-naphthalenyl, -1,2,3,4-tetrahydro-5-naphthalenyl, -1,2,3,4-tetrahydro-6-naphthalenyl, -2,3-dihydro-2-benzofuranyl, -2,3-dihydro-3-benzofuranyl, -2,3-dihydro-4-benzofuranyl, -2,3-dihydro-5-benzofuranyl, -2,3-dihydro-6-benzofuranyl, -2,3-dihydro-7-benzofuranyl, -2,3-dihydrobenzo[b]thien-2-yl, -2,3-dihydrobenzo[b]thien-3-yl, -2,3-dihydrobenzo[b]thien-4-yl, -2,3-dihydrobenzo[b]thien- 5-yl, -2,3-dihydrobenzo[b]thien-6-yl, -2,3-dihydrobenzo[b]thien-7-yl, -2,3-dihydro-1H-indol-2-yl, -2,3-dihydro-1H-indol-3-yl, -2,3-dihydro-1H-indol-4-yl, -2,3-dihydro-1H-indol-5-yl, -2,3-dihydro-1H-indol-6-yl, -2,3-dihydro-1H-indol-7-yl, -2,3-dihydro-2-benzoxazolyl, -2,3-dihydro-4-benzoxazolyl, -2,3-dihydro-5-benzoxazolyl, -2,3-dihydro-6-benzoxazolyl, -2,3-dihydro-7-benzoxazolyl, -2,3-dihydro-1H-benzimidazol-2-yl, -2,3-dihydro-1H-benzimidazol-4-yl, -2,3-dihydro-1H-benzimidazol-5-yl, -2,3-dihydro-1H-benzimidazol-6-yl, -2,3-dihydro-1H-benzimidazol-7-yl, -3,4-dihydro-1 (2H)-quinolinyl, -1,2,3,4-tetrahydro-2-quinolinyl, -1,2,3,4-tetrahydro-3-quinolinyl, -1,2,3,4-tetrahydro-4-quinolinyl, -1,2,3,4-tetrahydro-5-quinolinyl, -1,2,3,4-tetrahydro-6-quinolinyl, -1,2,3,4-tetrahydro-7-quinolinyl, -1,2,3,4-tetrahydro-8-quinolinyl, -3,4-dihydro-2H-1-benzopyran-2-yl, -3,4-dihydro-2H-1-benzopyran-3-yl, -3,4-dihydro-2H-1-benzopyran-4-yl, -3,4-dihydro-2H-1-benzopyran-5-yl, -3,4-dihydro-2H-1-benzopyran-6-yl, -3,4-dihydro-2H-1-benzopyran-7-yl, -3,4-dihydro-2H-1-benzopyran-8-yl, -3,4-dihydro-4H-1-benzopyran-2-yl, -3,4-dihydro-4H-1-benzopyran-3-yl, -3,4-dihydro-4H-1-benzopyran-4-yl, -3,4-dihydro-4H-1-benzopyran-5-yl, -3,4-dihydro-4H-1-benzopyran-6-yl, -3,4-dihydro-4H-1-benzopyran-7-yl, -3,4-dihydro-4H-1-benzopyran-8-yl, -3,4-dihydro-1H-2-benzopyran-2-yl, -3,4-dihydro-1H-2-benzopyran-3-yl, -3,4-dihydro-1H-2-benzopyran-4-yl, -3,4-dihydro-1H-2-benzopyran-5-yl, -3,4-dihydro-1H-2-benzopyran-6-yl, -3,4-dihydro-1H-2-benzopyran-7-yl and -3,4-dihydro-1H-2-benzopyran-8-yi optionally substituted when allowed by available valences with up to 7 substituents independently selected from methyl when attached to a nitrogen atom; and, independently selected from methyl, methoxy or fluoro when attached to a carbon atom;

Z is selected from the group consisting of hydroxy, —NH$_2$, —NH—C$_{1-8}$alkyl, —N(C$_{1-8}$alkyl)$_2$, —O—C$_{1-8}$alkyl, —O—C$_{1-8}$alkyl-OH, —O—C$_{1-8}$alkylC$_{1-8}$alkoxy, —O—C$_{1-8}$alkylcarbonylC$_{1-8}$alkyl, —O—C$_{1-8}$alkyl-CO$_2$H, —O—C$_{1-8}$alkyl-C(O)O—C$_{1-8}$alkyl, —O—C$_{1-8}$alkyl-O—C(O)C$_{1-8}$alkyl, —O—C$_{1-8}$alkyl-NH$_2$, —O—C$_{1-8}$alkyl-NH—C$_{1-8}$alkyl, —O—C$_{1-8}$alkyl-N(C$_{1-8}$alkyl)$_2$, —O—C$_{1-8}$alkylamide, —O—C$_{1-8}$alkyl-C(O)—NH—C$_{1-8}$alkyl, —O—C$_{1-8}$alkyl-C(O)—N(C$_{1-8}$alkyl)$_2$ and NHC(O)C$_{1-8}$alkyl;

and pharmaceutically acceptable salts, racemic mixtures and enantiomers thereof.

41. A composition comprising the compound of claim 1 and a pharmaceutically acceptable carrier.

\* \* \* \* \*